(12) United States Patent
Guo et al.

(10) Patent No.: US 11,987,615 B2
(45) Date of Patent: May 21, 2024

(54) MODIFIED IMMUNOGLOBULINS

(71) Applicant: Biocytogen Pharmaceuticals (Beijing) Co., Ltd., Beijing (CN)

(72) Inventors: Yuan Guo, Beijing (CN); Baihong Liu, Beijing (CN); Yi Yang, Beijing (CN); Yuelei Shen, Beijing (CN)

(73) Assignee: Biocytogen Pharmaceuticals (Beijing) Co., Ltd., Beijing (CN)

( * ) Notice: Subject to any disclaimer, the term of this patent is extended or adjusted under 35 U.S.C. 154(b) by 0 days.

(21) Appl. No.: 17/877,612

(22) Filed: Jul. 29, 2022

(65) Prior Publication Data

US 2023/0041757 A1 Feb. 9, 2023

Related U.S. Application Data

(63) Continuation of application No. PCT/CN2021/089649, filed on Apr. 25, 2021.

(30) Foreign Application Priority Data

Apr. 26, 2020 (WO) ............... PCT/CN2020/087036
Jan. 21, 2021 (WO) ............... PCT/CN2021/073085
Apr. 2, 2021 (WO) ............... PCT/CN2021/085181

(51) Int. Cl.
*C07K 16/00* (2006.01)
*C07K 14/52* (2006.01)

(52) U.S. Cl.
CPC ............. *C07K 16/00* (2013.01); *C07K 14/52* (2013.01); *C07K 2317/24* (2013.01); *C07K 2317/31* (2013.01); *C07K 2317/524* (2013.01); *C07K 2317/526* (2013.01); *C07K 2317/622* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 4,753,894 A | 6/1988 | Frankel et al. | |
| 4,943,533 A | 7/1990 | Mendelsohn et al. | |
| 5,500,362 A | 3/1996 | Robinson et al. | |
| 5,558,864 A | 9/1996 | Bendig et al. | |
| 5,677,171 A | 10/1997 | Hudziak et al. | |
| 5,736,137 A | 4/1998 | Anderson et al. | |
| 5,891,996 A | 4/1999 | Mateo de Acosta del Rio et al. | |
| 6,235,883 B1 | 5/2001 | Jakobovits et al. | |
| 6,506,883 B2 | 11/2003 | Mateo de Acosta del Rio et al. | |
| 7,247,301 B2 | 7/2007 | van de Winkel et al. | |
| 2017/0210818 A1* | 7/2017 | Wang ...................... | C07K 14/47 |
| 2018/0291103 A1 | 10/2018 | Xu et al. | |

FOREIGN PATENT DOCUMENTS

| | | |
|---|---|---|
| CN | 104955953 | 9/2015 |
| EP | 1444268 | 8/2004 |
| WO | WO 1995/20045 | 7/1995 |
| WO | WO 1996/27011 | 9/1996 |
| WO | WO 1996/40210 | 12/1996 |
| WO | WO 2000/034337 | 6/2000 |
| WO | WO 2001/62931 | 8/2001 |
| WO | WO 2001/88138 | 11/2001 |
| WO | WO 2005/111082 | 11/2005 |
| WO | WO 2008/077546 | 7/2008 |
| WO | WO 2011/131746 | 10/2011 |
| WO | WO-2013138643 A1 * | 9/2013 ........... C07K 14/005 |
| WO | WO 2017/034770 | 3/2017 |
| WO | WO 2018/014855 | 1/2018 |
| WO | WO 2018/202649 | 11/2018 |
| WO | WO 2019/057122 | 3/2019 |

OTHER PUBLICATIONS

Ruker et al. "Introducing antigen-binding sites in structural loops of immunoglobulin constant domains: Fc fragments with engineered HER2/neu-binding sites and antibody properties" Protein Engineering Design & Selection, 23(4) pp. 289-297, 2010 (Year: 2010).*
Lobner et al. "Engineered IgG1-Fc-one fragmetn to bind them all" Immunoglogical Reviews 2016, 270 (13-131). (Year: 2016).*
Abhinandan et al., "Analysis and improvements to Kabat and structurally correct numbering of antibody variable domain," Molecular immunology, Aug. 1, 2008, 45(14):3832-3839.
Brinkmann et al., "The making of bispecific antibodies," Mabs, Feb. 17, 2017, 9(2): 182-212.
Chothia et al., "Conformations of immunoglobulin hypervariable regions," Nature, Dec. 1989, 342(6252):877-883.
GenBank Accession No. NP_000563.1, "interleukin-10 isoform 1 precursor [*Homo sapiens*]," dated Jul. 19, 2021, 3 pages.
GenBank Accession No. NP_000580.1, "interleukin-4 isoform 1 precursor [*Homo sapiens*]," dated May 24, 2021, 3 pages.
GenBank Accession No. NP_000591.1, "interleukin-6 isoform 1 precursor [*Homo sapiens*]," dated Jul. 26, 2021, 3 pages.
GenBank Accession No. NP_000651.3, "transforming growth factor beta-1 proprotein preproprotein [*Homo sapiens*]," dated Jul. 19, 2021, 4 pages.
GenBank Accession No. NP_000871.1, "interleukin-7 isoform 1 precursor [*Homo sapiens*]," dated Jun. 26, 2021, 3 pages.
GenBank Accession No. NP_000873.2, "interleukin-12 subunit alpha isoform 1 precursor [*Homo sapiens*]," dated Jul. 5, 2022, 3 pages.
GenBank Accession No. NP_001152896.1, "interleukin-12 subunit alpha isoform 1 [Mus musculus]," dated Jun. 23, 2022, 3 pages.
GenBank Accession No. NP_001290173.1, "interleukin-12 subunit beta precursor [Mus musculus]," dated Jun. 24, 2022, 3 pages.
GenBank Accession No. NP_002249.1 "killer cell lectin-like receptor subfamily B member 1 [*Homo sapiens*]," dated Jul. 5, 2021, 3 pages.
GenBank Accession No. NP_003233.4, "TGF-beta receptor type-2 isoform B precursor [*Homo sapiens*]," dated Jul. 19, 2021, 4 pages.
GenBank Accession No. NP_003799.1, "tumor necrosis factor ligand superfamily member 13 isoform alpha precursor [*Homo sapiens*]," dated Jul. 2, 2022, 3 pages.

(Continued)

*Primary Examiner* — Daniel E Kolker
*Assistant Examiner* — James L Rogers
(74) *Attorney, Agent, or Firm* — Fish & Richardson P.C.

(57) ABSTRACT

This disclosure relates to modified immunoglobulins.

17 Claims, 71 Drawing Sheets

Specification includes a Sequence Listing.

(56) References Cited

OTHER PUBLICATIONS

GenBank Accession No. NP_032377.1, "interleukin-12 subunit alpha isoform 2 precursor [Mus musculus]," dated Jun. 22, 2021, 3 pages.
GenBank Accession No. NP_066546.1, "interferon alpha-4 precursor [Homo sapiens]," dated Dec. 15, 2020, 3 pages.
GenBank Accession No. NP_068575.1, "interleukin-21 isoform 1 precursor [Homo sapiens]," dated Jul. 11, 2021, 3 pages.
GenBank Accession No. NP_078902.2, "V-set domain-containing T-cell activation inhibitor 1 isoform 1 precursor [Homo sapiens]," May 31, 2021, 3 pages.
GenBank Accession No. NP_079513.1, "sclerostin precursor [Homo sapiens]," dated Jun. 25, 2021, 3 pages.
GenBank Accession No. NP_982353.1, "delta-like protein 3 isoform 2 precursor [Homo sapiens]," dated Jun. 7, 2022, 4 pages.
GenBank Accession No. NP_998767.1, "sialic acid-binding Ig-like lectin 15 precursor [Homo sapiens]," dated Jun. 27, 2021, 3 pages.
International Search Report and Written Opinion in International Appln. No. PCT/CN2021/089649, dated Aug. 6, 2021 14 pages.
Irani et al., "Molecular properties of human IgG subclasses and their implications for designing therapeutic monoclonal antibodies against infectious diseases," Molecular immunology, Oct. 1, 2015, 67(2):171-182.
Jungbluth et al., "A monoclonal antibody recognizing human cancers with amplification/overexpression of the human epidermal growth factor receptor," Proceedings of the National Academy of Sciences, Jan. 21, 2003, 100(2): 7 pages.
Karlsson et al., "Kinetic and concentration analysis using BIA technology," Methods, Jun. 1, 1994, 6(2):99-110.
Kettleborough et al., "Humanization of a mouse monoclonal antibody by CDR-grafting: the importance of framework residues on loop conformation," Protein engineering, design and selection, Oct. 1, 1991, 4(7):773-783.
Lefranc et al., "IMGTR® and 30 years of Immunoinformatics insight in antibody V and C domain structure and function," Antibodies, Apr. 11, 2019, 8(2): 21 pages.
Martin et al., "Molecular modeling of antibody combining sites," Methods in enzymology, Jan. 1, 1991, 203:121-153.
Martin, "Protein sequence and structure analysis of antibody variable domains," Antibody engineering, 2001, 31:422-439.
Mateo et al., "Humanization of a mouse monoclonal antibody that blocks the epidermal growth factor receptor: recovery of antagonistic activity," Immunotechnology, Mar. 1, 1997, 3(1):71-81.
Modjtahedi et al., "Antitumor activity of combinations of antibodies directed against different epitopes on the extracellular domain of the human EGF receptor," Cell biophysics, Jan. 1993, 22(1):129-146.
Modjtahedi et al., "Phase I trial and tumour localisation of the anti-EGFR monoclonal antibody ICR62 in head and neck or lung cancer," British Journal of Cancer, Jan. 1, 1996, 73(2):228-235.
Modjtahedi et al., "Targeting of cells expressing wild-type EGFR and type-III mutant EGFR (EGFRvIII) by anti-EGFR MAb ICR62: A two-pronged attack for tumour therapy," International journal of cancer, Jun. 10, 2003, 105(2):273-280.
Modjtahedi et al., "The human EGF receptor as a target for cancer therapy: six new rat mAbs against the receptor on the breast carcinoma MDA-MB 468," British journal of cancer, Feb. 1993, 67(2):247-253.
Morea et al., "Antibody structure, prediction and redesign," Biophysical chemistry, Oct. 1, 1997, 68(1-3):9-16.
Morea et al., "Conformations of the third hypervariable region in the VH domain of immunoglobulins," Journal of molecular biology, Jan. 16, 1998, 275(2):269-294.
Murthy et al., "Binding of an antagonistic monoclonal antibody to an intact and fragmented EGF-receptor polypeptide," Archives of Biochemistry and Biophysics, Feb. 1, 1987, 252(2):549-560.
Ponomarenko et al., "Antibody-protein interactions: benchmark datasets and prediction tools evaluation," BMC structural biology, Dec. 2007, 7(1):1-19.
Ridgway et al., "'Knobs-into-holes' engineering of antibody CH3 domains for heavy chain heterodimerization," Protein Engineering, Design and Selection, Jul. 1, 1996, 9(7):617-621.
Rodeck et al., "Interactions between growth factor receptors and corresponding monoclonal antibodies in human tumors," Journal of Cellular Biochemistry, Dec. 1987, 35(4):315-320.
Silva et al., "The S228P mutation prevents in vivo and in vitro IgG4 Fab-arm exchange as demonstrated using a combination of novel quantitative immunoassays and physiological matrix preparation," Journal of Biological Chemistry, Feb. 27, 2015, 290(9):5462-5469.
Spiess et al., "Alternative molecular formats and therapeutic applications for bispecific antibodies," Molecular immunology, Oct. 1, 2015, ;67(2):95-106.
Vidarsson et al., "IgG subclasses and allotypes: from structure to effector functions," Frontiers in immunology, Oct. 20, 2014, 5(520): 17 pages.
Wolff et al., "Monoclonal antibody homodimers: enhanced antitumor activity in nude mice," Cancer Research, Jun. 1, 1993, 53(11):2560-2565.
Wu et al., "An analysis of the sequences of the variable regions of Bence Jones proteins and myeloma light chains and their implications for antibody complementarity," The Journal of experimental medicine, Aug. 1, 1970, 132(2):211-250.

\* cited by examiner

M: Protein Marker

Line 11 is Protein Marker

| EU numbering | 119 | 128 | 138 | 148 | 158 | 168 | 178 |
|---|---|---|---|---|---|---|---|
| hIgG1-CH | -TKGPSVFPLAPSSKSTSGGTAALGCLVKDYFPEPVTVSWNSGALTSGVHTFPAVLQSSG |
| hIgG2-CH | STKGPSVFPLAPCSRSTSESTAALGCLVKDYFPEPVTVSWNSGALTSGVHTFPAVLQSSG |
| hIgG4-CH | STKGPSVFPLAPCSRSTSESTAALGCLVKDYFPEPVTVSWNSGALTSGVHTFPAVLQSSG |
| hIgG1-CH | LYSLSSVVTVPSSSLGTQTYICNVNHKPSNTKVDKKVEPKSCDKTHTCPPCPAPELLGGP |
| hIgG2-CH | LYSLSSVVTVPSSNFGTQTYTCNVDHKPSNTKVDKTVERKCCVE----CPPCPAPP-VAGP |
| hIgG4-CH | LYSLSSVVTVPSSSLGTKTYTCNVDHKPSNTKVDKRVESKYGPP----CPPCPAPEFLGGP |
| hIgG1-CH | SVFLFPPKPKDTLMISRTPEVTCVVVDVSHEDPEVKFNWYVDGVEVHNAKTKPREEQYNS |
| hIgG2-CH | SVFLFPPKPKDTLMISRTPEVTCVVVDVSHEDPEVQFNWYVDGVEVHNAKTKPREEQFNS |
| hIgG4-CH | SVFLFPPKPKDTLMISRTPEVTCVVVDVSQEDPEVQFNWYVDGVEVHNAKTKPREEQFNS 231 --- --- --- |
| hIgG1-CH | TFRVVSVLTVLHQDWLNGKEYKCKVSNKALPAPIEKTISKAKGQPREPQVYTLPPSREEM |
| hIgG2-CH | TFRVVSVLTVVHQDWLNGKEYKCKVSNKGLPAPIEKTISKTKGQPREPQVYTLPPSREEM |
| hIgG4-CH | TYRVVSVLTVLHQDWLNGKEYKCKVSNKGLPSSIEKTISKAKGQPREPQVYTLPPSQEEM 341 |
| hIgG1-CH | TKNQVSLTCLVKGFYPSDIAVEWESNGQPENNYKTTPPVLDSDGSFFLYSKLTVDKSRWQ |
| hIgG2-CH | TKNQVSLTCLVKGFYPSDIAVEWESNGQPENNYKTTPPMLDSDGSFFLYSKLTVDKSRWQ |
| hIgG4-CH | TKNQVSLTCLVKGFYPSDIAVEWESNGQPENNYKTTPPVLDSDGSFFLYSRLTVDKSRWQ |
| hIgG1-CH | QGNVFSCSVMHEALHNHYTQKSLSLSPGK |
| hIgG2-CH | QGNVFSCSVMHEALHNRFTQKSLSLSPGK |
| hIgG4-CH | EGNVFSCSVMHEALHNHYTQKSLSLSLGK ---- 447 |

CH2 — spanning residues ~231 to 340
CH3 — spanning residues 341 to 447

FIG. 4

| Fc Receptor | Antibody | Analyte Range | KD (M) | Rmax | Legend level |
|---|---|---|---|---|---|
| FcγRIIB-Acro | PDL1-avelumab | 3200nm-25nm | 3.33E-06 | 109.5 | 52.0 |
| FcγRIIB-Acro | PDL1-mIL7-3A-mIFNa4 | 3200nm-50nm | 1.26E-06 | 309.0 | 51.9 |
| FcγRIIB-Acro | PDL1-mIL7-3A | 3200nm-25nm | 2.47E-06 | 150.3 | 54.5 |
| FcγRIIA-H167-Acro | PDL1-avelumab | 800nm-6.25nm | 1.05E-06 | 181.5 | 63.5 |
| FcγRIIA-H167-Acro | PDL1-mIL7-3A-mIFNa4 | 800nm-6.25nm | 1.15E-07 | 287.3 | 63.8 |
| FcγRIIA-H167-Acro | PDL1-mIL7-3A | 800nm-6.25nm | 4.26E-07 | 146.0 | 65.7 |
| FcγRIIIA-V176-Acro | PDL1-avelumab | 400nm-3.125nm | 2.63E-07 | 130.9 | 42.3 |
| FcγRIIIA-V176-Acro | PDL1-mIL7-3A-mIFNa4 | 400nm-3.125nm | 1.73E-08 | 267.9 | 42.3 |
| FcγRIIIA-V176-Acro | PDL1-mIL7-3A | 400nm-3.125nm | 7.55E-08 | 190.6 | 41.9 |
| FcγRIIIB-NA1-Acro | PDL1-avelumab | 800nm-6.25nm | 3.31E-05 | 734.5 | 51.4 |
| FcγRIIIB-NA1-Acro | PDL1-mIL7-3A-mIFNa4 | 800nm-6.25nm | 5.01E-07 | 280.0 | 52.3 |
| FcγRIIIB-NA1-Acro | PDL1-mIL7-3A | 800nm-6.25nm | 4.79E-07 | 173.9 | 52.6 |
| FcγRI-Sino | PDL1-avelumab | 400nm-6.25nm | 1.01E-07 | 77.6 | 56.5 |
| FcγRI-Sino | PDL1-mIL7-3A | 400nm-6.25nm | 1.94E-07 | 97.1 | 56.9 |
| FcγRI-Sino | PDL1-mIL7-3A-mIFNa4 | 400nm-6.25nm | 2.71E-08 | 93.2 | 57.0 |
| FcRn-Acro | PDL1-avelumab | 1000nm-15.625nm | 1.25E-06 | 1011.8 | 217.0 |
| FcRn-Acro | PDL1-mIL7-3A | 1000nm-15.625nm | 5.27E-07 | 1022.4 | 218.0 |
| FcRn-Acro | PDL1-mIL7-3A-mIFNa4 | 1000nm-15.625nm | 1.60E-07 | 1028.3 | 220.6 |

FIG. 8A

| Fc Receptor | PD1-PL1-3F2-FV3A-IgG1 KD (M) | AB-IgG1 KD (M) | PDL1-C40-6A7-FV3A-IgG4 KD (M) | AB-IgG4 KD (M) |
|---|---|---|---|---|
| FcγRI-Sino | 2.94E-09 | 2.31E-10 | 1.22E-09 | 7.56E-10 |
| FcγRIIA-H167-Acro | 6.33E-07 | 4.75E-07 | 1.13E-06 | 1.63E-06 |
| FcγRIIA-R167 | 3.26E-07 | 5.93E-07 | 7.06E-07 | 7.19E-07 |
| FcγRIIB | 2.35E-06 | 2.39E-06 | 7.66E-07 | 1.26E-06 |
| FcγRIIIA-F176 | 8.46E-08 | 3.01E-07 | negative | negative |
| FcγRIIIA-V176-Acro | 1.30E-07 | 1.77E-07 | 7.53E-08 | 6.75E-07 |
| FcγRIIIB-NA1-Acro | 1.18E-06 | 4.42E-07 | negative | negative |

FIG. 8B

| Lane | Name (storage temperature) | Theoretical MW | Apparent MW |
|---|---|---|---|
| 7 | PDL1-mIL7-3A (40°C) | 183KD | ≥180KD |
| 8 | PDL1-mIL7-3A (-20°C) | 183KD | ≥180KD |

| Lane | Name |
|---|---|
| 1 | PDL1-mIL7-3A |
| 2 | PDL1-mIL7-Fab-half-3A-KIH |
| 3 | PDL1-mIL7-3A-hole |
| 4 | PDL1-mIL7-3A-knob |

FIG. 11A
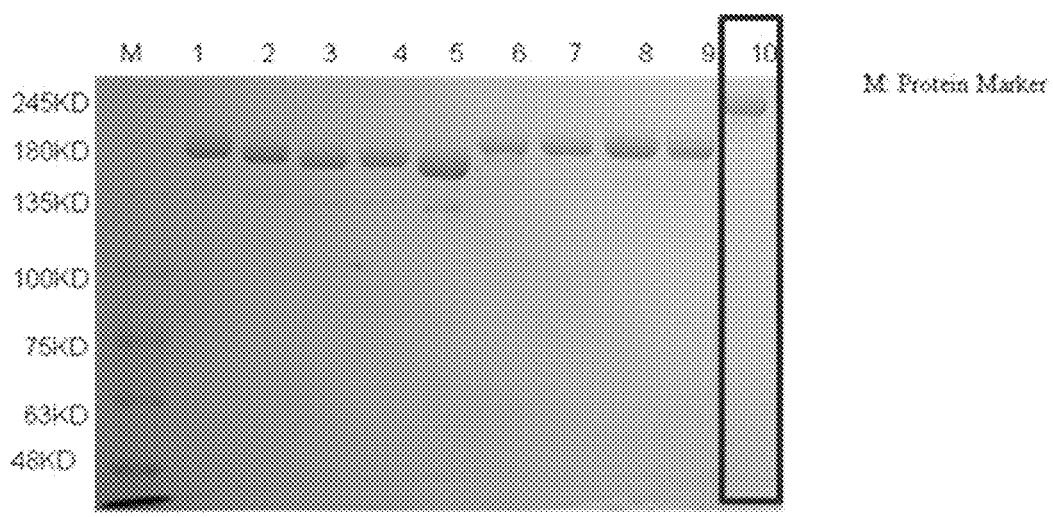
FIG. 11B
| Lane | Name | Theoretical MW |
|------|------|----------------|
| 10 | 3F2-hIL7-3A | About 200KD |
FIG. 11C
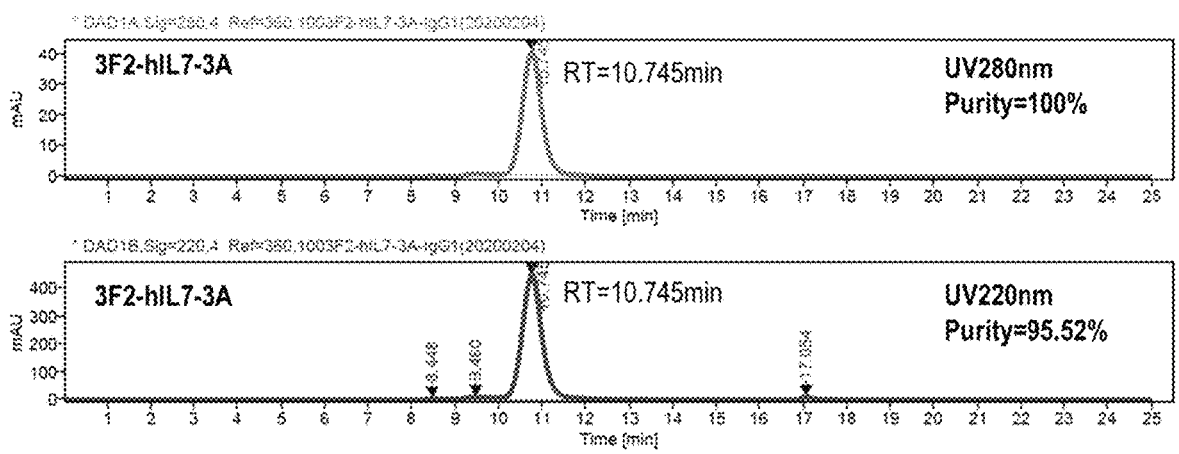

FIG. 12A
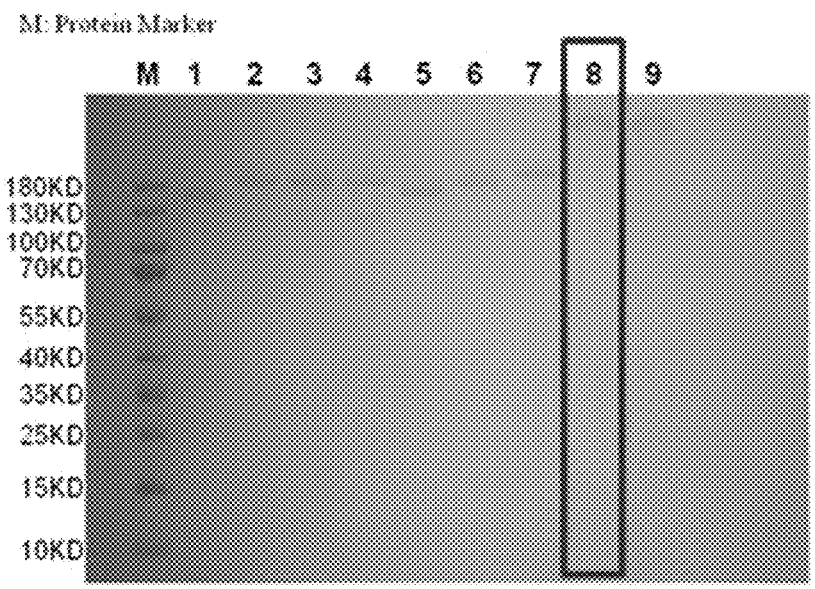
FIG. 12B
| Lane | Name | Theoretical MW | Apparent MW |
|------|------|----------------|-------------|
| 8 | 3F2-hIL7-3A-mIFNa4 | 231KD | ≥180KD |
FIG. 12C
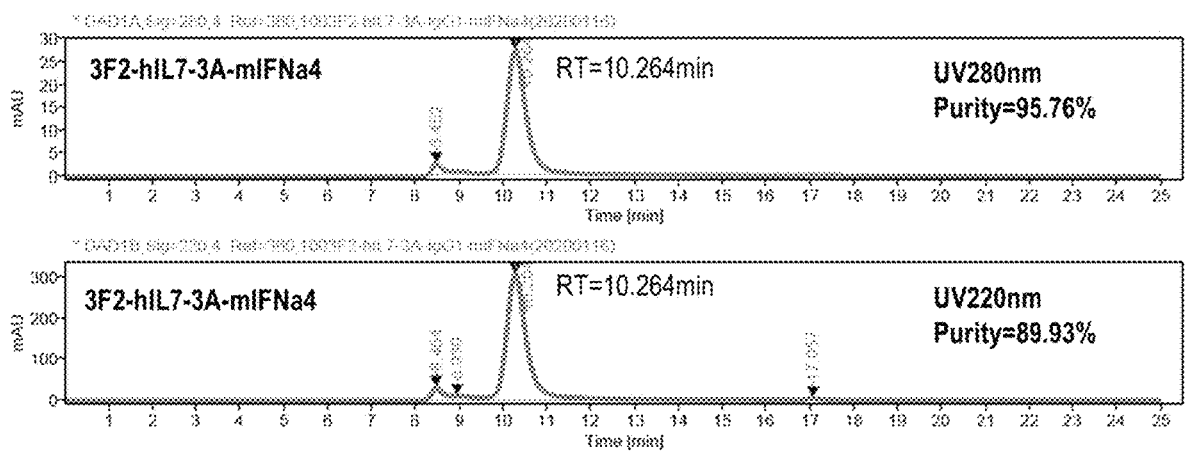

M: Protein Marker

| Lane | Name |
|---|---|
| 13 | PDL1-hIL21-HC |

FIG. 15A
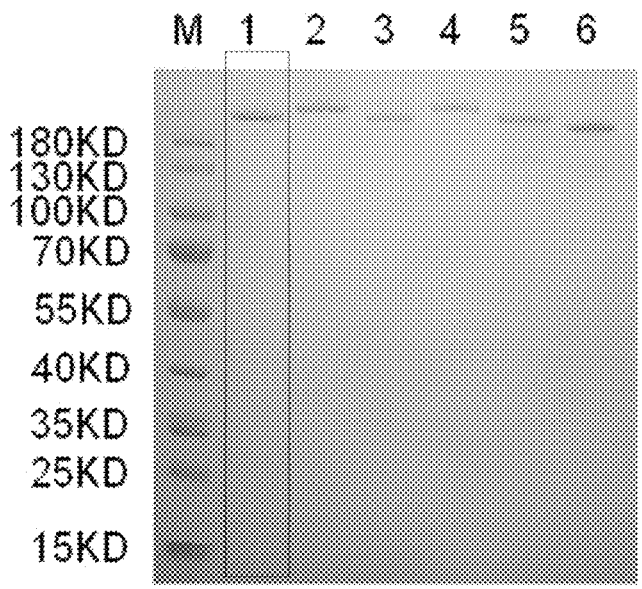
FIG. 15B
| Lane | Name |
|---|---|
| 1 | 3F2-hIL21-3A |
FIG. 15C
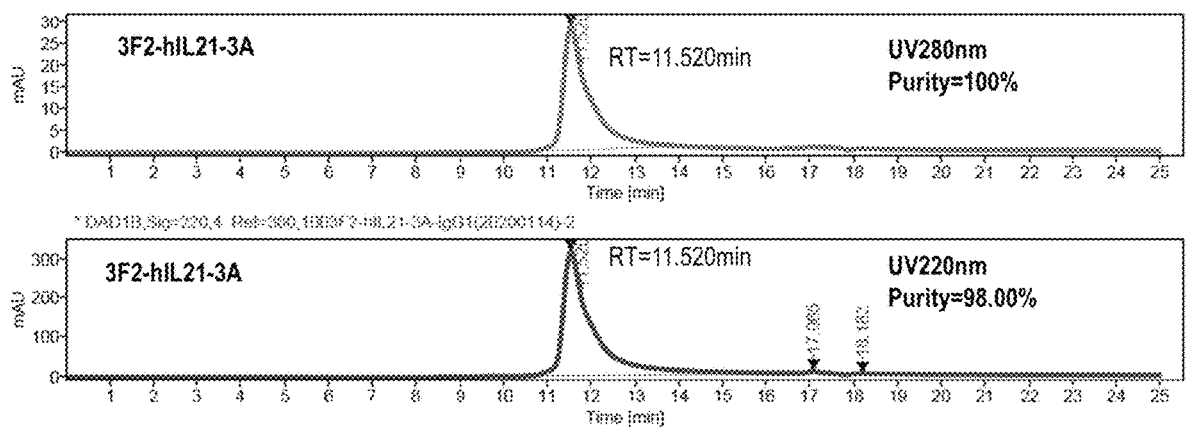

FIG. 16A
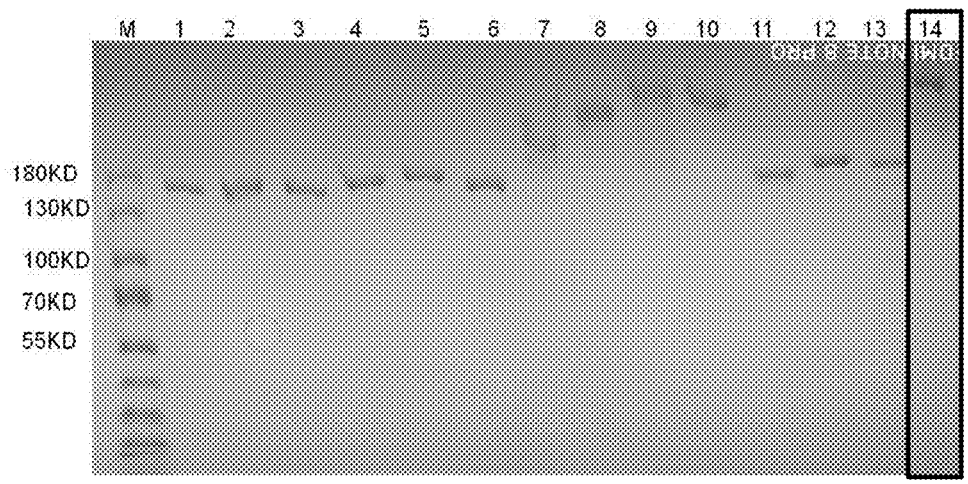
FIG. 16B
| Lane | Name |
|---|---|
| 14 | 3F2-hIL21-3A-mIFNa4 |
FIG. 16C
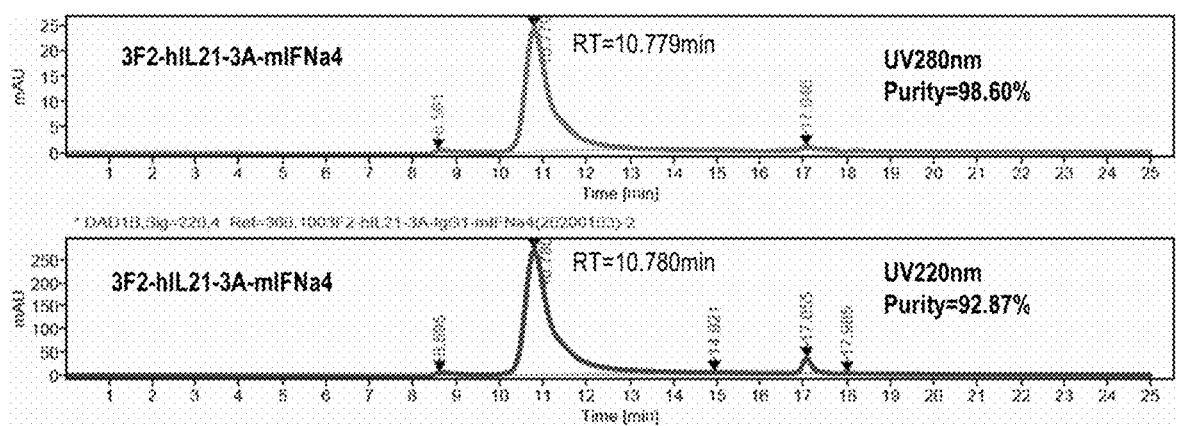

FIG. 18A
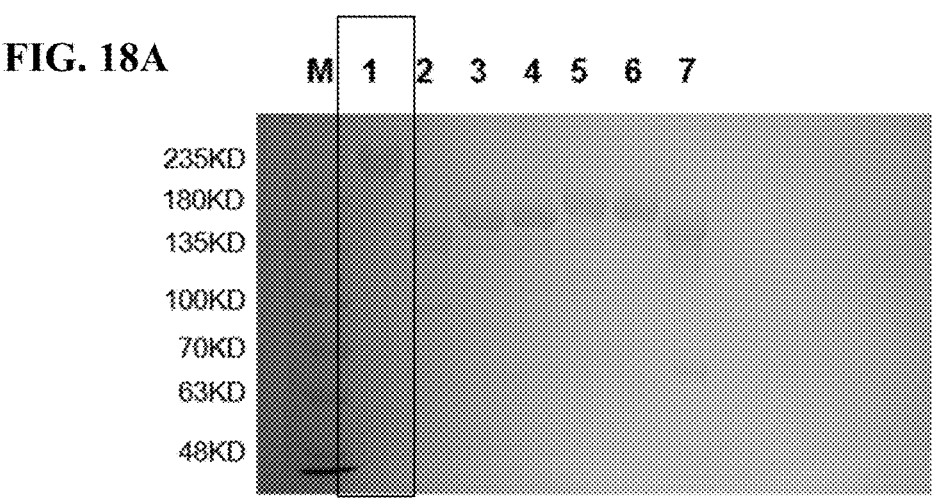
FIG. 18B
| Lane | Name | Theoretical MW | Apparent MW |
|---|---|---|---|
| 1 | PDL1-TGFbR2-3A | About 230KD | About 235KD |
FIG. 18C
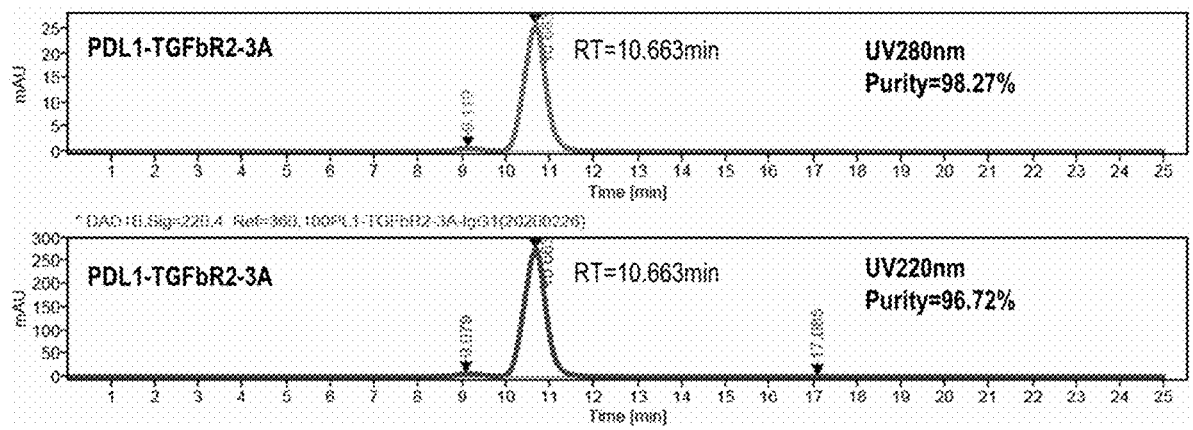

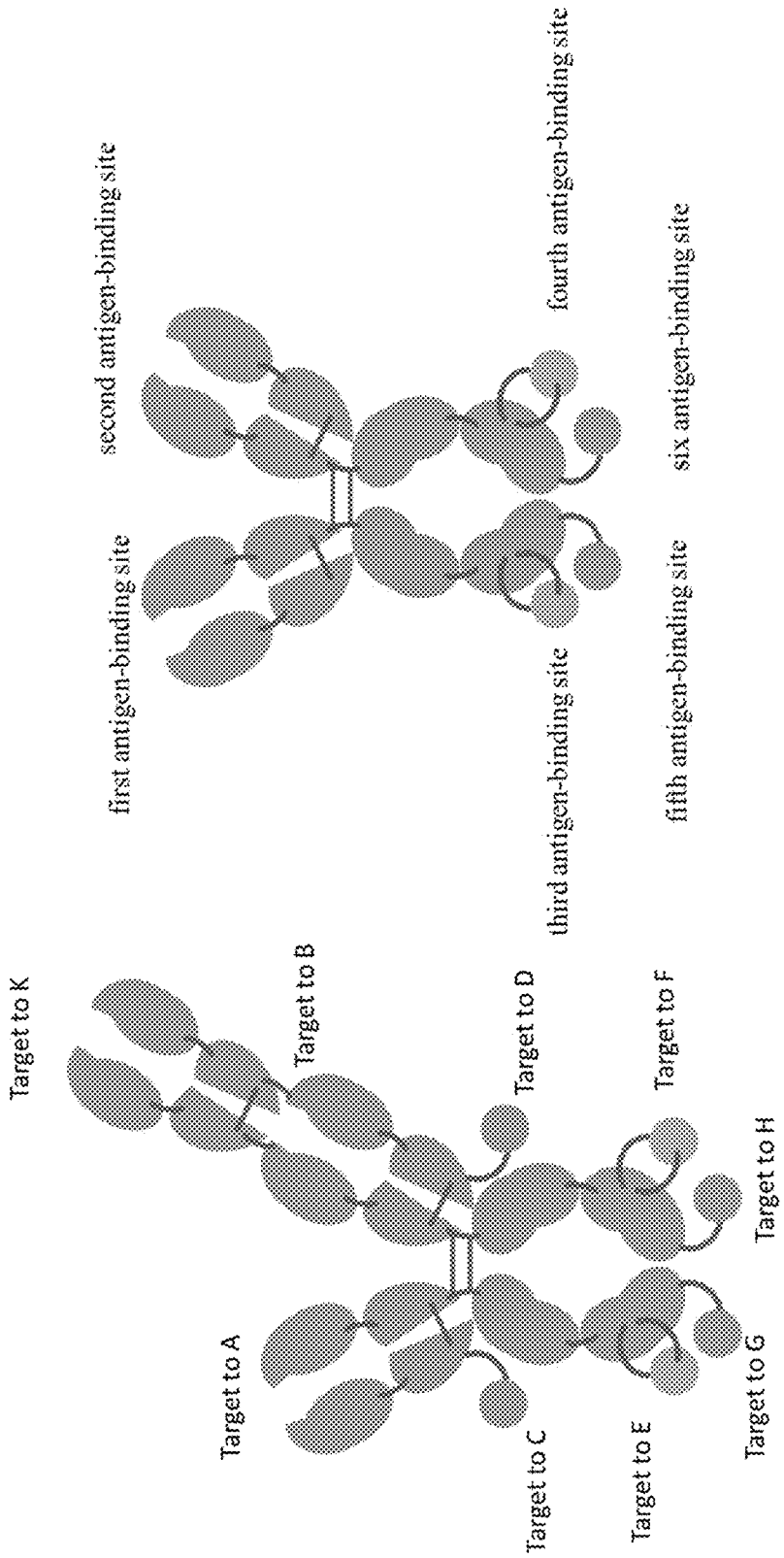

| Lane | Name |
|---|---|
| 1 | PDL1-3F2 |
| 2 | 3F2-hIL3-3A |
| 3 | 3F2-hIL3-HC |
| 4 | 3F2-hIL4-3A |
| 5 | 3F2-hIL4-HC |
| 6 | 3F2-hIL5-3A |
| 7 | 3F2-hIL5-HC |
| 8 | 3F2-hIL6-3A |
| 9 | 3F2-hIL6-HC |

FIG. 33

| | | |
|---|---|---|
| K01316\|IGHC4*01\|Homo | GQPREPQVYTLPPSQEEMTKNQVSLTCLVKGFYPSDIAVEWESNGQPENNYKTTPPVLDS | |
| X03604\|IGHG3*01\|Homo | GQPREPQVYTLPPSREEMTKNQVSLTCLVKGFYPSDIAVEWESSGQPENNYNTTPPMLDS | |
| J00228\|IGHG1*01\|Homo | GQPREPQVYTLPPSRDELTKNQVSLTCLVKGFYPSDIAVEWESNGQPENNYKTTPPVLDS | |
| J00230\|IGHG2*01\|Homo | GQPREPQVYTLPPSREEMTKNQVSLTCLVKGFYPSDIAVEWESNGQPENNYKTTPPMLDS | |
|  | **********.***:** ************,.*;:*** | |
|  | | |
| K01316\|IGHC4*01\|Homo | DGSFFLYSRLTVDKSRWQEGNVFSCSVMHEALHNHYTQKSLSLSLGK | 107 |
| X03604\|IGHG3*01\|Homo | DGSFFLYSKLTVDKSRWQQGNIFSCSVMHEALHNRFTQKSLSLSPGK | 107 |
| J00228\|IGHG1*01\|Homo | DGSFFLYSKLTVDKSRWQQGNVFSCSVMHEALHNHYTQKSLSLSPGK | 107 |
| J00230\|IGHG2*01\|Homo | DGSFFLYSKLTVDKSRWQQGNVFSCSVMHEALHNHYTQKSLSLSPGK | 107 |
|  | ******:***:.:************:*****  | |

```
                                          358  362
RatNor_6_chr6|IGHGC2C*01|Rattus  GKARTPQVYTIPPPRRQMSKNKVSLTCMVTSFYPASISVEWERNGELEQDYKNTLPVLDS
X00915|IGHG9*01|Mus              GRAQTPQVYTIPPPRRQMSKKAVSLTCMVTSFYPASISVEWERNGELEQDYKNTPPILDS
J00228|IGHG1*01|Homo             CQPREPQVYTLPPSRDELTKNQVSLTCLVTNFFSEAISVEWERNGQPENNYKTTPPVLDS
RatNor_6_chr6|IGHGC1*01|Rattus   GRTQVPHVYTMSPTKHEMTQNEVSITCMVKGFYPPDIVVEWQMNGQPQENYKNTPPTMDT
J00453|IGHG1*01|Mus              GTPRGPQVYTMAPPKEEMTQSQVSITCMVKGFYPPDIYTEWKMNGQPQENYKNTPPTMDT
V00703|IGHG2B*01|Mus             GKPKAPQVYTIPPPKEQMAKDKVSLTCMITDFFPEDITVEWQWNGQPAENYKNTQPIMNT
RatNor_6_chr6|IGHGC2B*01|Rattus  GLVRAPQVYTLPPPFAEQLSRKDVSLTCLVVGFNPGDISVEWTSNGHTEENTKDTAPVLDS
V00825|IGHG2A*01|Mus             GLVRKPQVYVMGPPTEQLTEQTVSLTCLTSGFLPMDIGVEWTSNGHIEKNYKNTEPVLDS
J00479|IGHG2C*01|Mus             GSVRAPQVYVLPPPHEEMTKKQVTLTCMVTDFMPEDIYVEWTNNGKTELNYKNTEPVLDS
                                 GPVRAPQVYVLPPPAEEMTKKEPSLTCMITGFLPAEIAVDWTSNGRTEQNYKNTATVLDS
                                 *  : *:**,.; *  ::;:. , ;;**(*; . *     .*;  ,:*  . : .* ::
```

FIG. 35

```
                                                        358   362
J00228|IGHG1*01|Homo           GQPREPQVYTLPPSRDELTKNQVSLTCLVKGFYPSDIAVEWESNGQPENNYKTTPPVLDS   60
AY292512|IGHG3*01|Macaca       GQPREPQVYTLPPQEELTKNQVSLTCLVTGFYPSDIAVEWESNGQPENTYKTTPPVLDS   60
NW_011121238|IGHG1*01|Macaca   GQPREPQVYTLPPSREELTKNQVSLTCLVKGFYPSDIVVEWESSGQPENTYKTTPPVLDS   60
AY292519|IGHG2*01|Macaca       GQPREPQVYTLPPFREELTKNQVSLTCLVKGFYPSDIVVEWASNGQPENTYKTTPPVLDS   60
                               *********** ; :;*********** ****** ** *.******,**********

J00228|IGHG1*01|Homo           DGSFFLYSKLTVDKSRWQQGNVFSCSVMHEALHNHYTQKSLSLSPGK   107
AY292512|IGHG3*01|Macaca       DGSYFLYSKLTVDKSRWQQGNTFSCSVMHEA---------------   91
NW_011121238|IGHG1*01|Macaca   DGSYFLYSKLTVDKSRWQQGNVFSCSVMHEALHNHYTQKSLSVSPGK   107
AY292519|IGHG2*01|Macaca       DGSYFLYSKLTVDKSRWQQGNTFSCSVMHEA---------------   91
                               ***;********************** ***************
```

FIG. 36

```
                                                              57
                                                              59
                                                              59
                                                              60
                                                              60
                            358  362
J00228|IGHG1*01|Homo      CQPREPQVYTLPPSRDELT-KNQVSLTCLVKGFYPSDIAVEWESNGQP--ENNYKTTPPV
IMGT000001|IGHG2*01|Canis CQAHQPSYVVLPPSREELS-KNTVSLTCLIKDFFPPDIDVEWQSNGQQEPESKYRTTPPQ
AF354266|IGHG3*01|Canis   CQAHQPNVYVLPPSRDEMS-KNTVTLTCLVKDFFPPEIDVEWQSNGQQEPESKYRMTPPQ
AF354264|IGHG1*01|Canis   CRAHKPSVYVLPPSPKELSSSDTVSITCLIKDFYPPDIDVEWQSNGQQEPERKHRMTPPQ
AF354267|IGHG4*01|Canis   CQAHQPSVYVLPPSPKELSSSDTVTLTCLIKDFFPPEIDVEWQSNGQQEPESKYHTTAPQ
                          *: :**. **. ***** . .: .:  *:*****:*:.*:* :** ***:****     *  :::

J00228|IGHG1*01|Homo      LDSDGSFFLYSKLTVDKSRWQQGNVFSCSVMHEALHNHYTQKSLSLSPGK           107
IMGT000001|IGHG2*01|Canis LDEDGSYFLYSKLSVDKSRWQRGDTFICAVMHEALHNHYTQKSLSHSPGK           109
AF354266|IGHG3*01|Canis   LDEDGSYFLYSKLSVDKSRWQRGDTFICAVMHEALHNHYTQISLSHSPGK           109
AF354264|IGHG1*01|Canis   LDEDGSYFLYSKLSVDKSRWQQGDPFTTCAVMHETLQMHYTDLSLSHSPGK          110
AF354267|IGHG4*01|Canis   LDEDGSYFLYSKLSVDKSRWQQGDTFTCAVMHERALQMHYTDLSLSHSPGK          110
                          **:***:******:******:* * *.:******:. :. *;****  *** ****
```

FIG. 37

3F2-mIL12-3A

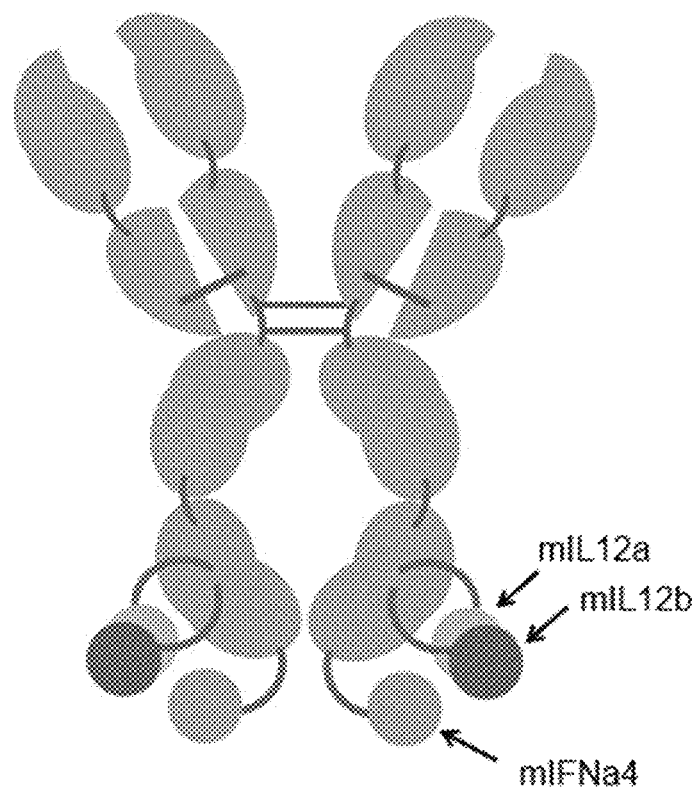
3F2-mIL12-3A-mIFNa4
FIG. 39A
FIG. 39B

FIG. 48

IgG1-heavy chain constant region(CH) (SEQ ID NO: 1)
ASTKGPSVFPLAPSSKSTSGGTAALGCLVKDYFPEPVTVSWNSGALTSGVHTFPAVLQSSGLYSLSSVVTVPSS
SLGTQTYICNVNHKPSNTKVDKKVEPKSCDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALPAPIEKTISKA
KGQPREPQVYTLPPSREEMTKNQVSLTCLVKGFYPSDIAVEWESNGQPENNYKTTPPVLDSDGSFFLYSKLTVD
KSRWQQGNVFSCSVMHEALHNHYTQKSLSLSPGK

IgG2-CH (SEQ ID NO: 2)
STKGPSVFPLAPCSRSTSESTAALGCLVKDYFPEPVTVSWNSGALTSGVHTFPAVLQSSGLYSLSSVVTVPSSN
FGTQTYTCNVDHKPSNTKVDKTVERKCCVECPPCPAPPVAGPSVFLFPPKPKDTLMISRTPEVTCVVVDVSHED
PEVQFNWYVDGVEVHNAKTKPREEQFNSTFRVVSVLTVVHQDWLNGKEYKCKVSNKGLPAPIEKTISKTKGQPR
EPQVYTLPPSREEMTKNQVSLTCLVKGFYPSDIAVEWESNGQPENNYKTTPPMLDSDGSFFLYSKLTVDKSRWQ
QGNVFSCSVMHEALHNHYTQKSLSLSPGK

IgG4-CH (SEQ ID NO: 3)
STKGPSVFPLAPCSRSTSESTAALGCLVKDYFPEPVTVSWNSGALTSGVHTFPAVLQSSGLYSLSSVVTVPSSS
LGTKTYTCNVDHKPSNTKVDKRVESKYGPPCPPCPAPEFLGGPSVFLFPPKPKDTLMISRTPEVTCVVVDVSQE
DPEVQFNWYVDGVEVHNAKTKPREEQFNSTYRVVSVLTVLHQDWLNGKEYKCKVSNKGLPSSIEKTISKAKGQP
REPQVYTLPPSQEEMTKNQVSLTCLVKGFYPSDIAVEWESNGQPENNYKTTPPVLDSDGSFFLYSRLTVDKSRW
QEGNVFSCSVMHEALHNHYTQKSLSLSLGK

PDL1-avelumab antibody light chain (SEQ ID NO: 4)
QSALTQPASVSGSPGQSITISCTGTSSDVGGYNYVSWYQQHPGKAPKLMIYDVSNRPSGVSNRFSGSKSGNTAS
LTISGLQAEDEADYYCSSYTSSSTRVFGTGTKVTVLGQPKANPTVTLFPPSSEELQANKATLVCLISDFYPGAV
TVAWKADGSPVKAGVETTKPSKQSNNKYAASSYLSLTPEQWKSHRSYSCQVTHEGSTVEKTVAPTECS

PDL1-mIL7-3A heavy chain (SEQ ID NO: 5)
EVQLLESGGGLVQPGGSLRLSCAASGFTFSSYIMMWVRQAPGKGLEWVSSIYPSGGITFYADTVKGRFTISRDN
SKNTLYLQMNSLRAEDTAVYYCARIKLGTVTTVDYWGQGTLVTVSSASTKGPSVFPLAPSSKSTSGGTAALGCL
VKDYFPEPVTVSWNSGALTSGVHTFPAVLQSSGLYSLSSVVTVPSSSLGTQTYICNVNHKPSNTKVDKKVEPKS
CDKTHTCPPCPAPELLGGPSVFLFPPKPKDTLMISRTPEVTCVVVDVSHEDPEVKFNWYVDGVEVHNAKTKPRE
EQYNSTYRVVSVLTVLHQDWLNGKEYKCKVSNKALPAPIEKTISKAKGQPREPQVYTLPPSRDEGGGGSGGGGS
<u>ECHIKDKEGKAYESVLMISIDELDKMTGTDSNCPNNEPNFFRKHVCDDTKEAAFLNRAARKLKQFLKMNISEEF</u>
<u>NVHLLTVSQGTQTLVNCTSKEEKNVKEQKKNDACFLKRLLREIKTCWNKILKGSI</u>GGGGSGGGGSVSLTCLVKG
FYPSDIAVEWESNGQPENNYKTTPPVLDSDGSFFLYSKLTVDKSRWQQGNVFSCSVMHEALHNHYTQKSLSLSP
GA*
*The underlined sequence is mIL7 (26-154aa of NP_032397.1). It replaces 358-362 (EU numbering) of the heavy chain.

PDL1-mIL7-3B heavy chain (SEQ ID NO: 6)
EVQLLESGGGLVQPGGSLRLSCAASGFTFSSYIMMWVRQAPGKGLEWVSSIYPSGGITFYADTVKGRFTISRDN
SKNTLYLQMNSLRAEDTAVYYCARIKLGTVTTVDYWGQGTLVTVSSASTKGPSVFPLAPSSKSTSGGTAALGCL
VKDYFPEPVTVSWNSGALTSGVHTFPAVLQSSGLYSLSSVVTVPSSSLGTQTYICNVNHKPSNTKVDKKVEPKS
CDKTHTCPPCPAPELLGGPSVFLFPPKPKDTLMISRTPEVTCVVVDVSHEDPEVKFNWYVDGVEVHNAKTKPRE
EQYNSTYRVVSVLTVLHQDWLNGKEYKCKVSNKALPAPIEKTISKAKGQPREPQVYTLPPSRDELTKNQVSLTC
LVKGFYPSDIAVEWEGGGGSGGGGS<u>ECHIKDKEGKAYESVLMISIDELDKMTGTDSNCPNNEPNFFRKHVCDDT</u>
<u>KEAAFLNRAARKLKQFLKMNISEEFNVHLLTVSQGTQTLVNCTSKEEKNVKEQKKNDACFLKRLLREIKTCWNK</u>
<u>ILKGSI</u>GGGGSGGGGSKTTPPVLDSDGSFFLYSKLTVDKSRWQQGNVFSCSVMHEALHNHYTQKSLSLSPGA*
*The underlined sequence is mIL7 (26-154aa of NP_032397.1). It replaces 383-391 (EU numbering) of the heavy chain.

FIG. 48 (Cont.)

PDL1-mIL7-3C heavy chain (SEQ ID NO: 7)
EVQLLESGGGLVQPGGSLRLSCAASGFTFSSYIMMWVRQAPGKGLEWVSSIYPSGGITFYADTVKGRFTISRDN
SKNTLYLQMNSLRAEDTAVYYCARIKLGTVTTVDYWGQGTLVTVSSASTKGPSVFPLAPSSKSTSGGTAALGCL
VKDYFPEPVTVSWNSGALTSGVHTFPAVLQSSGLYSLSSVVTVPSSSLGTQTYICNVNHKPSNTKVDKKVEPKS
CDKTHTCPPCPAPELLGGPSVFLFPPKPKDTLMISRTPEVTCVVVDVSHEDPEVKFNWYVDGVEVHNAKTKPRE
EQYNSTYRVVSVLTVLHQDWLNGKEYKCKVSNKALPAPIEKTISKAKGQPREPQVYTLPPSRDELTKNQVSLTC
LVKGFYPSDIAVEWESNGGGGSGGGGS<u>ECHIKDKEGKAYESVLMISIDELDKMTGTDSNCPNNEPNFFRKHVCD</u>
<u>DTKEAAFLNRAARKLKQFLKMNISEEFNVHLLTVSQGTQTLVNCTSKEEKNVKEQKKNDACFLKRLLREIKTCW</u>
<u>NKILKGSI</u>GGGGSGGGGSGQPENNYKTTPPVLDSDGSFFLYSKLTVDKSRWQQGNVFSCSVMHEALHNHYTQKS
LSLSPGA*

*The underlined sequence is mIL7 (26-154aa of NP_032397.1). It is inserted between amino acids 384 and 385 (EU numbering) of the heavy chain.

PDL1-mIL7-3D heavy chain (SEQ ID NO: 8)
EVQLLESGGGLVQPGGSLRLSCAASGFTFSSYIMMWVRQAPGKGLEWVSSIYPSGGITFYADTVKGRFTISRDN
SKNTLYLQMNSLRAEDTAVYYCARIKLGTVTTVDYWGQGTLVTVSSASTKGPSVFPLAPSSKSTSGGTAALGCL
VKDYFPEPVTVSWNSGALTSGVHTFPAVLQSSGLYSLSSVVTVPSSSLGTQTYICNVNHKPSNTKVDKKVEPKS
CDKTHTCPPCPAPELLGGPSVFLFPPKPKDTLMISRTPEVTCVVVDVSHEDPEVKFNWYVDGVEVHNAKTKPRE
EQYNSTYRVVSVLTVLHQDWLNGKEYKCKVSNKALPAPIEKTISKAKGQPREPQVYTLPPSRDELTKNQVSLTC
LVKGFYPSDIAVEWESNGQPENNYKTTPPVLDSDGSFFLYSKLTVGGGGSGGGGS<u>ECHIKDKEGKAYESVLMIS</u>
<u>IDELDKMTGTDSNCPNNEPNFFRKHVCDDTKEAAFLNRAARKLKQFLKMNISEEFNVHLLTVSQGTQTLVNCTS</u>
<u>KEEKNVKEQKKNDACFLKRLLREIKTCWNKILKGSI</u>GGGGSGGGGSFSCSVMHEALHNHYTQKSLSLSPGA*

*The underlined sequence is mIL7 (26-154aa of NP_032397.1). It replaces 413-422 (EU numbering) of the heavy chain.

HC linker sequence (SEQ ID NO: 9):
GGGGSGGGGSGGGGSGGGGS mIFNa4 (SEQ ID NO: 10)
CDLPHTYNLGNKRALTVLEEMRRLPPLSCLKDRKDFGFPLEKVDNQQIQKAQAILVLRDLTQQILNLFTSKDLS
ATWNATLLDSFCNDLHQQLNDLKACVMQEPPLTQEDSLLAVRTYFHRITVYLRKKKHSLCAWEVIRAEVWRALS
SSTNLLARLSEEKE* hIL7 NP_000871.1 26 to 177aa (SEQ ID NO: 11)
DCDIEGKDGKQYESVLMVSIDQLLDSMKEIGSNCLNNEFNFFKRHICDANKEGMFLFRAARKLRQFLKMNSTGD
FDLHLLKVSEGTTILLNCTGQVKGRKPAALGEAQPTKSLEENKSLKEQKKLNDLCFLKRLLQEIKTCWNKILMG
TKEH hIL21 NP_068575.1 25 to 162aa (SEQ ID NO: 12)
HKSSSQGQDRHMIRMRQLIDIVDQLKNYVNDLVPEFLPAPEDVETNCEWSAFSCFQKAQLKSANTGNNERIINV
SIKKLKRKPPSTNAGRRQKHRLTCPSCDSYEKKPPKEFLERFKSLLQKMIHQHLSSRTHGSEDS hTGFbR2 NP_003233.4 24 to 159 (SEQ ID NO: 13)
IPPHVQKSVNNDMIVTDNNGAVKFPQLCKFCDVRFSTCDNQKSCMSNCSITSICEKPQEVCVAVWRKNDENITL
ETVCHDPKLPYHDFILEDAASPKCIMKEKKKPGETFFMCSCSSDECNDNIIFSEEYNTSNPD

ATOR1015-CD86 (SEQ ID NO: 14)
APLKIQAYFNETADLPCQFANSQNLSLSELVVFWQDQENLVLNEVYLGKERFDSVDSKYMGRTSFDSDSWTLRL
HNLQIKDKGRYQCIIHHKKPTGMINIHQMNSELSVLA

KN035 VHH (SEQ ID NO: 15)

FIG. 48 (Cont.)

QVQLVESGGGLVQPGGSLRLSCAASGFTFSRRCMAWFRQAPGKERERVAKLLTTSGSTYLADSVKGRFTISRDN
SKNTVYLQMNSLRAEDTAVYYCAADSFEDPTCTLVTSSGAFQYWGQGTLVTVSS

C40-6A7 scFv (SEQ ID NO: 16)
DVVMTQSPLSLPVTLGQPASISCRSSQSLLHSNGNTYLHWYQQRPGQSPNHLIYQVSNRFSGVPDRFSGSGSGT
DFTLKISRVEAEDVGVYFCSQTTHVPWTFGCGTKVEIKGGGGSGGGGSGGGGSGGGGSQVQLVQSGAEVKKPGA
SVKLSCKASGYTFISYYIYWVKQAPGQCLEWIGGINPRNGGTNFNEKFKSRATLTVDTSISTAYMELSRLRSED
TAVYYCTRHGNGVYWGQGTTLTVSS

PDL1-3F2 scFv (SEQ ID NO: 17)
QVQLQESGPGLVKPSETLSLTCTVSGYSITSGYNWHWIRQFPGNCLEWMGYIHHSSITNYNPSLKSRITISRDT
SKNQFSLKLSSVTAADTATYYCAREGYDYDWFAYWGQGTLVTVSSASTGGGGSGGGGSGGGGSGGGGSDIVLTQ
SPDFQSVTPKEKVTLSCRASQSISNNLHWYQQKPDESPKLLIKYASQSISGIPSRFSGSGSGTDFTLTINSVEA
EDFAMYFCQQSKSWPFTFGCGTRLEIK

Linker sequence (SEQ ID NO: 30)
GGGGSGGGGS

Linker sequence (SEQ ID NO: 31)
GGGGS

IGHG1 isoform NCBI Reference No: J00228 (SEQ ID NO: 32)
ASTKGPSVFPLAPSSKSTSGGTAALGCLVKDYFPEPVTVSWNSGALTSGVHTFPAVLQSSGLYSLSSVVTVPSS
SLGTQTYICNVNHKPSNTKVDKKVEPKSCDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALPAPIEKTISKA
KGQPREPQVYTLPPSRDELTKNQVSLTCLVKGFYPSDIAVEWESNGQPENNYKTTPPVLDSDGSFFLYSKLTVD
KSRWQQGNVFSCSVMHEALHNHYTQKSLSLSPGK

IGHG2 isoform NCBI Reference No: J00230 (SEQ ID NO: 33)
ASTKGPSVFPLAPCSRSTSESTAALGCLVKDYFPEPVTVSWNSGALTSGVHTFPAVLQSSGLYSLSSVVTVPSS
NFGTQTYTCNVDHKPSNTKVDKTVERKCCVECPPCPAPPVAGPSVFLFPPKPKDTLMISRTPEVTCVVVDVSHE
DPEVQFNWYVDGVEVHNAKTKPREEQFNSTFRVVSVLTVVHQDWLNGKEYKCKVSNKGLPAPIEKTISKTKGQP
REPQVYTLPPSREEMTKNQVSLTCLVKGFYPSDIAVEWESNGQPENNYKTTPPMLDSDGSFFLYSKLTVDKSRW
QQGNVFSCSVMHEALHNHYTQKSLSLSPGK

IGHG4 isoform NCBI Reference No: K01316 (SEQ ID NO: 34)
ASTKGPSVFPLAPCSRSTSESTAALGCLVKDYFPEPVTVSWNSGALTSGVHTFPAVLQSSGLYSLSSVVTVPSS
SLGTKTYTCNVDHKPSNTKVDKRVESKYGPPCPSCPAPEFLGGPSVFLFPPKPKDTLMISRTPEVTCVVVDVSQ
EDPEVQFNWYVDGVEVHNAKTKPREEQFNSTYRVVSVLTVLHQDWLNGKEYKCKVSNKGLPSSIEKTISKAKGQ
PREPQVYTLPPSQEEMTKNQVSLTCLVKGFYPSDIAVEWESNGQPENNYKTTPPVLDSDGSFFLYSRLTVDKSR
WQEGNVFSCSVMHEALHNHYTQKSLSLSLGK

PDL1-avelumab antibody heavy chain (SEQ ID NO: 35)
EVQLLESGGGLVQPGGSLRLSCAASGFTFSSYIMMWVRQAPGKGLEWVSSIYPSGGITFYADTVKGRFTISRDN
SKNTLYLQMNSLRAEDTAVYYCARIKLGTVTTVDYWGQGTLVTVSSASTKGPSVFPLAPSSKSTSGGTAALGCL
VKDYFPEPVTVSWNSGALTSGVHTFPAVLQSSGLYSLSSVVTVPSSSLGTQTYICNVNHKPSNTKVDKKVEPKS
CDKTHTCPPCPAPELLGGPSVFLFPPKPKDTLMISRTPEVTCVVVDVSHEDPEVKFNWYVDGVEVHNAKTKPRE
EQYNSTYRVVSVLTVLHQDWLNGKEYKCKVSNKALPAPIEKTISKAKGQPREPQVYTLPPSRDELTKNQVSLTC
LVKGFYPSDIAVEWESNGQPENNYKTTPPVLDSDGSFFLYSKLTVDKSRWQQGNVFSCSVMHEALHNHYTQKSL
SLSPGK

PDL1-3F2-IgG1 heavy chain (SEQ ID NO: 36)

FIG. 48 (Cont.)

QVQLQESGPGLVKPSETLSLTCTVSGYSITSGYNWHWIRQFPGNGLEWMGYIHHSSITNYNPSLKSRITISRDT
SKNQFSLKLSSVTAADTATYYCAREGYDYDWFAYWGQGTLVTVSSASTKGPSVFPLAPSSKSTSGGTAALGCLV
KDYFPEPVTVSWNSGALTSGVHTFPAVLQSSGLYSLSSVVTVPSSSLGTQTYICNVNHKPSNTKVDKKVEPKSC
DKTHTCPPCPAPELLGGPSVFLFPPKPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQPREPQVYTLPPSRDELTKNQVSLTCL
VKGFYPSDIAVEWESNGQPENNYKTTPPVLDSDGSFFLYSKLTVDKSRWQQGNVFSCSVMHEALHNHYTQKSLS
LSPGK

PDL1-3F2-IgG1 light chain (SEQ ID NO: 37)
DIVLTQSPDFQSVTPKEKVTITCRASQSISNNLHWYQQKPDESPKLLIKYASQSISGIPSRFSGSGSGTDFTLT
INSVEAEDFAMYFCQQSKSWPFTFGQGTRLEIKRTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

M7824 heavy chain (SEQ ID NO: 38)
EVQLLESGGGLVQPGGSLRLSCAASGFTFSSYIMMWVRQAPGKGLEWVSSIYPSGGITFYADTVKGRFTISRDN
SKNTLYLQMNSLRAEDTAVYYCARIKLGTVTTVDYWGQGTLVTVSSASTKGPSVFPLAPSSKSTSGGTAALGCL
VKDYFPEPVTVSWNSGALTSGVHTFPAVLQSSGLYSLSSVVTVPSSSLGTQTYICNVNHKPSNTKVDKRVEPKS
CDKTHTCPPCPAPELLGGPSVFLFPPKPKDTLMISRTPEVTCVVVDVSHEDPEVKFNWYVDGVEVHNAKTKPRE
EQYNSTYRVVSVLTVLHQDWLNGKEYKCKVSNKALPAPIEKTISKAKGQPREPQVYTLPPSREEMTKNQVSLTC
LVKGFYPSDIAVEWESNGQPENNYKTTPPVLDSDGSFFLYSKLTVDKSRWQQGNVFSCSVMHEALHNHYTQKSL
SLSPGAGGGGSGGGGSGGGGSGGGGSGIPPHVQKSVNNDMIVTDNNGAVKFPQLCKFCDVRFSTCDNQKSCMSN
CSITSICEKPQEVCVAVWRKNDENITLETVCHDPKLPYHDFILEDAASPKCIMKEKKKPGETFFMCSCSSDECN
DNIIFSEEYNTSNPD

M7824 light chain (SEQ ID NO: 39)
QSALTQPASVSGSPGQSITISCTGTSSDVGGYNYVSWYQQHPGKAPKLMIYDVSNRPSGVSNRFSGSKSGNTAS
LTISGLQAEDEADYYCSSYTSSSTRVFGTGTKVTVLGQPKANPTVTLFPPSSEELQANKATLVCLISDFYPGAV
TVAWKADGSPVKAGVETTKPSKQSNNKYAASSYLSLTPEQWKSHRSYSCQVTHEGSTVEKTVAPTECS

PD1-1A7 VH (SEQ ID NO: 40)
EVQLVESGGGLVQPGGSLRLSCAASGFTFSSYSMSWVRQAPGKRLEWVAHISSGGSSTYYPDTVKGRFTISRDN
SKNTLYLQMNSLRAEDTAMYYCTRQFYYGSSFWYFDVWGAGTTVTVSS

PD1-1A7 VL (SEQ ID NO: 41)
DNVLTQSPATLSVSPGERATLSCKASQSVDFDGDSYMNWYQQKPGQPPRLLIYAASNLESGIPARFSGSGSGTD
FTLTISSVEPEDFATYYCQQSNEDPPTFGGGTKVEIK

CT4-4G12-IgG1 heavy chain (SEQ ID NO: 42)
EVQLVESGGGLVQPGGSLRLSCAASGFTFSSYTMSWVRQAPGKGLEWVATISRGGGYTSYPDSVKGRFTISRDN
SKNTLYLQMNSLRAEDTAVYYCAREDYGSSYVHWFAYWGQGTLVTVSAASTKGPSVFPLAPSSKSTSGGTAALG
CLVKDYFPEPVTVSWNSGALTSGVHTFPAVLQSSGLYSLSSVVTVPSSSLGTQTYICNVNHKPSNTKVDKKVEP
KSCDKTHTCPPCPAPELLGGPSVFLFPPKPKDTLMISRTPEVTCVVVDVSHEDPEVKFNWYVDGVEVHNAKTKP
REEQYNSTYRVVSVLTVLHQDWLNGKEYKCKVSNKALPAPIEKTISKAKGQPREPQVYTLPPSREEMTKNQVSL
TCLVKGFYPSDIAVEWESNGQPENNYKTTPPVLDSDGSFFLYSKLTVDKSRWQQGNVFSCSVMHEALHNHYTQK
SLSLSPGK

CT4-4G12-IgG1 light chain (SEQ ID NO: 43)
DIQMTQSPSFLSASVGDRVTITCRAGENIYSYLAWYQQKPGKAPKLLIYNARTLAEGVPSRFSGSGSGTEFTLT
ISSLQPEDFATYYCQHHYGSPRTFGGGTKLEIKRTVAAPSVFIFPPSDEQLKSGTASVVCLLNNFYPREAKVQW
KVDNALQSGNSQESVTEQDSKDSTYSLSSTLTLSKADYEKHKVYACEVTHQGLSSPVTKSFNRGEC

CT4-4G12 VH (SEQ ID NO: 44)
EVQLVESGGGLVQPGGSLRLSCAASGFTFSSYTMSWVRQAPGKGLEWVATISRGGGYTSYPDSVKGRFTISRDN
SKNTLYLQMNSLRAEDTAVYYCAReDYGSSYVHWFAYWGQGTLVTVSA

FIG. 48 (Cont.)

CT4-4G12 VL (SEQ ID NO: 45)
DIQMTQSPSFLSASVGDRVTITCRAGENIYSYLAWYQQKPGKAPKLLIYNARTLAEGVPSRFSGSGSGTEFTLT
ISSLQPEDFATYYCQHHYGSPRTFGGGTKLEIKR

CT4-O40-SCFV-HC heavy chain (SEQ ID NO: 46)
EVQLVESGGGLVQPGGSLRLSCAASGFTFSSYTMSWVRQAPGKGLEWVATISRGGGYTSYPDSVKGRFTISRDN
SKNTLYLQMNSLRAEDTAVYYCAREDYGSSYVHWFAYWGQGTLVTVSAASTKGPSVFPLAPSSKSTSGGTAALG
CLVKDYFPEPVTVSWNSGALTSGVHTFPAVLQSSGLYSLSSVVTVPSSSLGTQTYICNVNHKPSNTKVDKKVEP
KSCDKTHTCPPCPAPELLGGPSVFLFPPKPKDTLMISRTPEVTCVVVDVSHEDPEVKFNWYVDGVEVHNAKTKP
REEQYNSTYRVVSVLTVLHQDWLNGKEYKCKVSNKALPAPIEKTISKAKGQPREPQVYTLPPSREEMTKNQVSL
TCLVKGFYPSDIAVEWESNGQPENNYKTTPPVLDSDGSFFLYSKLTVDKSRWQQGNVFSCSVMHEALHNHYTQK
SLSLSPGGGGSGGGGSGGGGSDIQMTQSPSSLSASVGDRVTITCRASQDINNYLNWYQQKPGGAVKLLIYYTS
RLHTGVPSRFSGSGSGTDFTLTISSLQPEDIATYYCQQTNTLPWTFGCGTKLEVKGGGGSGGGGSGGGGSGGGG
SQVQLVESGGGVVQPGRSLRISCAVSGFSLTSYGVLWVRQAPGKCLEWLGVIWSGGSTDYNAAFISRLTISRDN
SKSTVYFQMNSLRAEDTAVYYCAREEFGYWGQGTLVTVSS

CT4-O40-FV3A heavy chain (SEQ ID NO: 47)
EVQLVESGGGLVQPGGSLRLSCAASGFTFSSYTMSWVRQAPGKGLEWVATISRGGGYTSYPDSVKGRFTISRDN
SKNTLYLQMNSLRAEDTAVYYCAREDYGSSYVHWFAYWGQGTLVTVSAASTKGPSVFPLAPSSKSTSGGTAALG
CLVKDYFPEPVTVSWNSGALTSGVHTFPAVLQSSGLYSLSSVVTVPSSSLGTQTYICNVNHKPSNTKVDKKVEP
KSCDKTHTCPPCPAPELLGGPSVFLFPPKPKDTLMISRTPEVTCVVVDVSHEDPEVKFNWYVDGVEVHNAKTKP
REEQYNSTYRVVSVLTVLHQDWLNGKEYKCKVSNKALPAPIEKTISKAKGQPREPQVYTLPPSREEMTGGGGSG
GGGSDIQMTQSPSSLSASVGDRVTITCRASQDINNYLNWYQQKPGGAVKLLIYYTSRLHTGVPSRFSGSGSGTD
FTLTISSLQPEDIATYYCQQTNTLPWTFGCGTKLEVKGGGGSGGGGSGGGGSGGGGSQVQLVESGGGVVQPGRS
LRISCAVSGFSLTSYGVLWVRQAPGKCLEWLGVIWSGGSTDYNAAFISRLTISRDNSKSTVYFQMNSLRAEDTA
VYYCAREEFGYWGQGTLVTVSSGGGGSGGGGSKNQVSLTCLVKGFYPSDIAVEWESNGQPENNYKTTPPVLDSD
GSFFLYSKLTVDKSRWQQGNVFSCSVMHEALHNHYTQKSLSLSPGK

O40-9H3 VH (SEQ ID NO: 48)
QVQLVESGGGVVQPGRSLRISCAVSGFSLTSYGVLWVRQAPGKGLEWLGVIWSGGSTDYNAAFISRLTISRDNS
KSTVYFQMNSLRAEDTAVYYCAREEFGYWGQGTLVTVSS

O40-9H3 VL (SEQ ID NO: 49)
DIQMTQSPSSLSASVGDRVTITCRASQDINNYLNWYQQKPGGAVKLLIYYTSRLHTGVPSRFSGSGSGTDFTLT
ISSLQPEDIATYYCQQTNTLPWTFGGGTKLEVKR

Mouse CT4-4G12 VH (SEQ ID NO: 50)
DVKLVESGGGLVKPGGSLKLSCTASGFTFSSYTMSWVRQTPEKRLEWVATISRGGGYTSYPDSVKGRFTISRDN
AKNTLYLQMSSLQSEDTAMYYCARDDYGSSYVHWFAYWGQGTLVTVSA

Mouse CT4-4G12 VL (SEQ ID NO: 51)
DIQMTQSPASLSASVGETVTITCRAGENIYSYLAWYQQKQGKSPQLLVYNARTLAEGVPSRFSGSGSGTQFSLK
INSLQPEDFGSYYCQHHYGSPRTFGGGTKLEIK

Mouse OX40 antibody 9H3 VH (SEQ ID NO: 52)
QVQLKQSGPGLVQPSQSLSITCTVSGFSLTSYGVLWVRQPPGKGLEWLGVIWSGGSTDYNAAFISRLSISKDNS
KSQVFFKMNSLQADDTAIYYCAREEFGYWGQGTLVTVSA

Mouse OX40 antibody 9H3 VL (SEQ ID NO: 53)
DIQMTQTTSSLSASLGDRVTISCRASQDINNYLNWYQQKPDGTVKLLIYYTSRLHSGVPSRFSGSGSGTDYSLT
ISNLEQEDIATYFCQQTNTLPWTFGGGTKLEIK

HC Linker sequence (SEQ ID NO: 90)

FIG. 48 (Cont.)

GGGGSGGGGSGGGGSGGGGSG

C40-6A7 VH (SEQ ID NO: 91)
QVQLVQSGAEVKKPGASVKLSCKASGYTFISYYIYWVKQAPGQGLEWIGGINPRNGGTNFNEKFKSRATLTVDT
SISTAYMELSRLRSEDTAVYYCTRHGNGVYWGQGTTLTVSS

C40-6A7 VL (SEQ ID NO: 92)
DVVMTQSPLSLPVTLGQPASISCRSSQSLLHSNGNTYLHWYQQRPGQSPNHLIYQVSNRFSGVPDRFSGSGSGT
DFTLKISRVEAEDVGVYFCSQTTHVPWTFGGGTKVEIK hIL3 (SEQ ID NO: 93)
NCSNMIDEIITHLKQPPLPLLDFNNLNGEDQDILMENNLRRPNLEAFNRAVKSLQNASAIESILKNLLPCLPLA
TAAPTRHPIHIKDGDWNEFRRKLTFYLKTLENAQAQQTTLSLAIF hIL4 (SEQ ID NO: 94)
HKCDITLQEIIKTLNSLTEQKTLCTELTVTDIFAASKNTTEKETFCRAATVLRQFYSHHEKDTRCLGATAQQFH
RHKQLIRFLKRLDRNLWGLAGLNSCPVKEANQSTLENFLERLKTIMREKYSKCSS hIL5 (SEQ ID NO: 95)
IPTEIPTSALVKETLALLSTHRTLLIANETLRIPVPVHKNHQLCTEEIFQGIGTLESQTVQGGTVERLFKNLSL
IKKYIDGQKKKCGEERRRVNQFLDYLQEFLGVMNTEWIIES hIL6 (SEQ ID NO: 96)
VPPGEDSKDVAAPHRQPLTSSERIDKQIRYILDGISALRKETCNKSNMCESSKEALAENNLNLPKMAEKDGCFQ
SGFNEETCLVKIITGLLEFEVYLEYLQNRFESSEEQARAVQMSTKVLIQFLQKKAKNLDAITTPDPTTNASLLT
KLQAQNQWLQDMTTHLILRSFKEFLQSSLRALRQM hIL8 (SEQ ID NO: 97)
PKFIKELRVIESGPHCANTEIIVKLSDGRELCLDPKENWVQRVVEKFLKRAENS hIL9 (SEQ ID NO: 98)
QGCPTLAGILDINFLINKMQEDPASKCHCSANVTSCLCLGIPSDNCTRPCFSERLSQMTNTTMQTRYPLIFSRV
KKSVEVLKNNKCPYFSCEQPCNQTTAGNALTFLKSLLEIFQKEKMRGMRGKI hIL13 (SEQ ID NO: 99)
STALRELIEELVNITQNQKAPLCNGSMVWSINLTAGMYCAALESLINVSGCSAIEKTQRMLSGFCPHKVSAGQF
SSLHVRDTKIEVAQFVKDLLLHLKKLFREG hIL15 (SEQ ID NO: 100)
NWVNVISDLKKIEDLIQSMHIDATLYTESDVHPSCKVTAMKCFLLELQVISLESGDASIHDTVENLIILANNSL
SSNGNVTESGCKECEELEEKNIKEFLQSFVHIVQMFINTS

Amino acids 224-333 of human IgA (SEQ ID NO: 101)
NTFRPEVHLLPPPSEELALNELVTLTCLARGFSPKDVLVRWLQGSQELPREKYLTWASRQEPSQGTTTFA
VTSILRVAAEDWKKGDTFSCMVGHEALPLAFTQKTIDRLA

Amino acids 269-375 of human IgD (SEQ ID NO: 102)
AQAPVKLSLNLLASSDPPEAASWLLCEVSGFSPPNILLMWLEDQREVNTSGFAPARPPPQPRSTTFWAWS
VLRVPAPPSPQPATYTCVVSHEDSRTLLNASRSLEVS

Amino acids 324-433 of human IgM (SEQ ID NO: 103)
VALHRPDVYLLPPAREQLNLRESATITCLVTGFSPADVFVQWMQRGQPLSPEKYVTSAPMPEPQAPGRYF
AHSILTVSEEEWNTGETYTCVAHEALPNRVTERTVDKST

FIG. 48 (Cont.)

**CH3-CHS region of human IgG1 (J00228|IGHG1*01|Homo sapiens)(SEQ ID NO: 104)**
GQPREPQVYTLPPSRDELTKNQVSLTCLVKGFYPSDIAVEWESNGQPENNYKTTPPVLDSDGSFFLYSKLTVDK
SRWQQGNVFSCSVMHEALHNHYTQKSLSLSPGK

**CH3-CHS region of human IgG2 (J00230|IGHG2*01|Homo sapiens) (SEQ ID NO: 105)**
GQPREPQVYTLPPSREEMTKNQVSLTCLVKGFYPSDIAVEWESNGQPENNYKTTPPMLDSDGSFFLYSKLTVDK
SRWQQGNVFSCSVMHEALHNHYTQKSLSLSPGK

**CH3-CHS region of human IgG3 (X03604|IGHG3*01|Homo sapiens)(SEQ ID NO: 106)**
GQPREPQVYTLPPSREEMTKNQVSLTCLVKGFYPSDIAVEWESSGQPENNYNTTPPMLDSDGSFFLYSKLTVDK
SRWQQGNIFSCSVMHEALHNRFTQKSLSLSPGK

**CH3-CHS region of human IgG4 (K01316|IGHG4*01|Homo sapiens) (SEQ ID NO: 107)**
GQPREPQVYTLPPSQEEMTKNQVSLTCLVKGFYPSDIAVEWESNGQPENNYKTTPPVLDSDGSFFLYSRLTVDK
SRWQEGNVFSCSVMHEALHNHYTQKSLSLSLGK

**CH3-CHS region of rat IgG1 (RatNor_6_chr6|IGHG1*01|Rattus norvegicus) (SEQ ID NO: 108)**
GRTQVPHVYTMSPTKEEMTQNEVSITCMVKGFYPPDIYVEWQMNGQPQENYKNTPPTMDTDGSYFLYSKLNVKK
EKWQQGNTFTCSVLHEGLHNHHTEKSLSHSPGK

**CH3-CHS region of rat IgG2A (RatNor_6_chr6|IGHG2A*01|Rattus norvegicus) (SEQ ID NO: 109)**
GTPRGPQVYTMAPPKEEMTQSQVSITCMVKGFYPPDIYTEWKMNGQPQENYKNTPPTMDTDGSYFLYSKLNVKK
ETWQQGNTFTCSVLHEGLHNHHTEKSLSHSPGK

**CH3-CHS region of rat IgG2B (RatNor_6_chr6|IGHG2B*01|Rattus norvegicus) (SEQ ID NO: 110)**
GLVRKPQVYVMGPPTEQLTEQTVSLTCLTSGFLPNDIGVEWTSNGHIEKNYKNTEPVMDSDGSFFMYSKLNVER
SRWDSRAPFVCSVVHEGLHNHHVEKSISRPPGK

**CH3-CHS region of rat IgG2C (RatNor_6_chr6|IGHG2C*01|Rattus norvegicus) (SEQ ID NO: 111)**
GKARTPQVYTIPPPREQMSKNKVSLTCMVTSFYPASISVEWERNGELEQDYKNTLPVLDSDESYFLYSKLSVDT
DSWMRGDIYTCSVVHEALHNHHTQKNLSRSPGK

**CH3-CHS region of mouse IgG1 (J00453|IGHG1*01|Mus musculus) (SEQ ID NO: 112)**
GRPKAPQVYTIPPPKEQMAKDKVSLTCMITDFFPEDITVEWQWNGQPAENYKNTQPIMNTNGSYFVYSKLNVQK
SNWEAGNTFTCSVLHEGLHNHHTEKSLSHSPGK

**CH3-CHS region of mouse IgG2A (V00825|IGHG2A*01|Mus musculus) (SEQ ID NO: 113)**
GSVRAPQVYVLPPPEEEMTKKQVTLTCMVTDFMPEDIYVEWTNNGKTELNYKNTEPVLDSDGSYFMYSKLRVEK
KNWVERNSYSCSVVHEGLHNHHTTKSFSRTPGK

**CH3-CHS region of mouse IgG2B (V00763|IGHG2B*01|Mus musculus) (SEQ ID NO: 114)**
GLVRAPQVYTLPPPAEQLSRKDVSLTCLVVGFNPGDISVEWTSNGHTEENYKDTAPVLDSDGSYFIYSKLNMKT
SKWEKTDSFSCNVRHEGLKNYYLKKTISRSPGK

FIG. 48 (Cont.)

CH3-CHS region of mouse IgG2C (J00479|IGHG2C*01|Mus musculus) (SEQ ID NO: 115)
GPVRAPQVYVLPPPAEEMTKKEFSLTCMITGFLPAEIAVDWTSNGRTEQNYKNTATVLDSDGSYFMYSKLRVQK
STWERGSLFACSVVHEVLHNHLTTKTISRSLGK CH3-CHS region of mouse IgG3 (X00915|IGHG3*01|Mus musculus) (SEQ ID NO: 116)
GRAQTPQVYTIPPPREQMSKKKVSLTCLVTNFFSEAISVEWERNGELEQDYKNTPPILDSDGTYFLYSKLTVDT
DSWLQGEIFTCSVVHEALHNHHTQKNLSRSPGK CH3-CHS region of monkey IgG1 (NW_001121238|IGHG1*01|Macaca mulatta) (SEQ ID NO: 117)
GQPREPQVYTLPPSREELTKNQVSLTCLVKGFYPSDIVVEWESSGQPENTYKTTPPVLDSDGSYFLYSKLTVDK
SRWQQGNVFSCSVMHEALHNHYTQKSLSVSPGK CH3-CHS region of monkey IgG2 (AY292519|IGHG2*01|Macaca mulatta) (SEQ ID NO: 118)
GQPREPQVYTLPPPREELTKNQVSLTCLVKGFYPSDIVVEWASNGQPENTYKTTPPVLDSDGSYFLYSKLTVDK
SRWQQGNTFSCSVMHEA CH3 region of monkey IgG3 (AY292512|IGHG3*01|Macaca mulatta) (SEQ ID NO: 119)
GQPREPQVYILPPPQEELTKNQVSLTCLVTGFYPSDIAVEWESNGQPENTYKTTPPVLDSDGSYFLYSKLTVDK
SRWQQGNTFSCSVMHEA CH3-CHS region of dog IgG1 (AF354264|IGHG1*01|Canis lupus familiaris) (SEQ ID NO: 120)
GRAHKPSVYVLPPSPKELSSSDTVSITCLIKDFYPPDIDVEWQSNGQQEPERKHRMTPPQLDEDGSYFLYSKLS
VDKSRWQQGDPFTCAVMHETLQNHYTDLSLSHSPGK CH3-CHS region of dog IgG2 (IMGT000001|IGHG2*01|Canis lupus familiaris) (SEQ ID NO: 121)
GQAHQPSVYVLPPSREELSKNTVSLTCLIKDFFPPDIDVEWQSNGQQEPESKYRTTPPQLDEDGSYFLYSKLSV
DKSRWQRGDTFICAVMHEALHNHYTQKSLSHSPGK CH3-CHS region of dog IgG3 (AF354266|IGHG3*01|Canis lupus familiaris) (SEQ ID NO: 122)
GQAHQPNVYVLPPSRDEMSKNTVTLTCLVKDFFPPEIDVEWQSNGQQEPESKYRMTPPQLDEDGSYFLYSKLSV
DKSRWQRGDTFICAVMHEALHNHYTQISLSHSPGK CH3-CHS region of dog IgG4 (AF354267|IGHG4*01|Canis lupus familiaris) (SEQ ID NO: 123)
GQAHQPSVYVLPPSPKELSSSDTVTLTCLIKDFFPPEIDVEWQSNGQPEPESKYHTTAPQLDEDGSYFLYSKLS
VDKSRWQQGDTFTCAVMHEALQNHYTDLSLSHSPGK Linker sequence3 (SEQ ID NO: 124)
GGGGSGGGGSGGGGS mIL12a (SEQ ID NO: 125)
VIPVSGPARCLSQSRNLLKTTDDMVKTAREKLKHYSCTAEDIDHEDITRDQTSTLKTCLPLELHKNESCLATRE
TSSTTRGSCLPPQKTSLMMTLCLGSIYEDLKMYQTEFQAINAALQNHNHQQIILDKGMLVAIDELMQSLNHNGE
TLRQKPPVGEADPYRVKMKLCILLHAFSTRVVTINRVMGYLSSA mIL12b (SEQ ID NO: 126)

FIG. 48 (Cont.)

MWELEKDVYVVEVDWTPDAPGETVNLTCDTPEEDDITWTSDQRHGVIGSGKTLTITVKEFLDAGQYTCHKGGET
LSHSHLLLHKKENGIWSTEILKNFKNKTFLKCEAPNYSGRFTCSWLVQRNMDLKFNIKSSSSSPDSRAVTCGMA
SLSAEKVTLDQRDYEKYSVSCQEDVTCPTAEEETLPIELALEARQQNKYENYSTSFFIRDIIKPDPPKNLQMKPL
KNSQVEVSWEYPDSWSTPHSYFSLKFFVRIQRKKEKMKETEEGCNQKGAFLVEKTSTEVQCKGGNVCVQAQDRY
YNSSCSKWACVPCRVRS hIL12a (SEQ ID NO: 127)
ARNLPVATPDPGMFPCLHHSQNLLRAVSNMLQKARQTLEFYPCTSEEIDHEDITKDKTSTVEACLPLELTKNES
CLNSRETSFITNGSCLASRKTSFMMALCLSSIYEDLKMYQVEFKTMNAKLLMDPKRQIFLDQNMLAVIDELMQA
LNFNSETVPQKSSLEEPDFYKTKIKLCILLHAFRIRAVTIDRVMSYLNAS hIL12b (SEQ ID NO: 128)
IWELKKDVYVVELDWYPDAPGEMVVLTCDTPEEDGITWTLDQSSEVLGSGKTLTIQVKEFGDAGQYTCHKGGEV
LSHSLLLLHKKEDGIWSTDILKDQKEPKNKTFLRCEAKNYSGRFTCWWLTTISTDLTFSVKSSRGSSDPQGVTC
GAATLSAERVRGDNKEYEYSVECQEDSACPAAEESLPIEVMVDAVHKLKYENYTSSFFIRDIIKPDPPKNLQLK
PLKNSRQVEVSWEYPDTWSTPHSYFSLTFCVQVQGKSKREKKDRVFTDKTSATVICRKNASISVRAQDRYYSSS
WSEWASVPCS hIFNa4 (SEQ ID NO: 129)
CDLPQTHSLGNRRALILLAQMGRISHFSCLKDRHDFGFPEEEFDGHQFQKAQAISVLHEMIQQTFNLFSTEDSS
AAWEQSLLEKFSTELYQQLNDLEACVIQEVGVEETPLMNEDSILAVRKYFQRITLYLTEKKYSPCAWEVVRAEI
MRSLSFSTNLQKRLRRKD selicrelumab VH (SEQ ID NO: 130)
QVQLVQSGAEVKKPGASVKVSCKASGYTFTGYYMHWVRQAPGQGLEWMGWINPDSGGTNYAQKFQGRVTMTRDT
SISTAYMELNRLRSDDTAVYYCARDQPLGYCTNGVCSYFDYWGQGTLVTVSS selicrelumab VL (SEQ ID NO: 131)
DIQMTQSPSSVSASVGDRVTITCRASQGIYSWLAWYQQKPGKAPNLLIYTASTLQSGVPSRFSGSGSGTDFTLT
ISSLQPEDFATYYCQQANIFPLTFGGGTKVEIK selicrelumab scFV (SEQ ID NO: 132)
DIQMTQSPSSVSASVGDRVTITCRASQGIYSWLAWYQQKPGKAPNLLIYTASTLQSGVPSRFSGSGSGTDFTLT
ISSLQPEDFATYYCQQANIFPLTFGGGTKVEIKGGGGSGGGGSGGGGSQVQLVQSGAEVKKPGASVKVS
CKASGYTFTGYYMHWVRQAPGQGLEWMGWINPDSGGTNYAQKFQGRVTMTRDTSISTAYMELNRLRSDDTAVYY
CARDQPLGYCTNGVCSYFDYWGQGTLVTVSS

1A7-selicrelumab-FV3A-IgG4 (heavy chain) (SEQ ID NO: 133)
EVQLVESGGGLVQPGGSLRLSCAASGFTFSSYSMSWVRQAPGKRLEWVAHISSGGSSTYYPDTVKGRFTISRDN
SKNTLYLQMNSLRAEDTAMYYCTRQFYYGSSFWYFDVWGAGTTVTVSSASTKGPSVFPLAPCSRSTSESTAALG
CLVKDYFPEPVTVSWNSGALTSGVHTFPAVLQSSGLYSLSSVVTVPSSSLGTKTYTCNVDHKPSNTKVDKRVES
KYGPPCPPCPAPEFLGGPSVFLFPPKPKDTLMISRTPEVTCVVVDVSQEDPEVQFNWYVDGVEVHNAKTKPREE
QFNSTYRVVSVLTVLHQDWLNGKEYKCKVSNKGLPSSIEKTISKAKGQPREPQVYTLPPSQEEGGGSGGGGSD
IQMTQSPSSVSASVGDRVTITCRASQGIYSWLAWYQQKPGKAPNLLIYTASTLQSGVPSRFSGSGSGTDFTLTI
SSLQPEDFATYYCQQANIFPLTFGGGTKVEIKGGGGSGGGGSGGGGSQVQLVQSGAEVKKPGASVKVSC
KASGYTFTGYYMHWVRQAPGQGLEWMGWINPDSGGTNYAQKFQGRVTMTRDTSISTAYMELNRLRSDDTAVYYC
ARDQPLGYCTNGVCSYFDYWGQGTLVTVSSGGGGSGGGGSVSLTCLVKGFYPSDIAVEWESNGQPENNYKTTPP
VLDSDGSFFLYSRLTVDKSRWQEGNVFSCSVMHEALHNHYTQKSLSLSPGK

1A7-selicrelumab-FV3A-IgG4 (light chain) (SEQ ID NO: 134)
DNVLTQSPATLSVSPGERATLSCKASQSVDFDGDSYMNWYQQKPGQPPRLLIYAASNLESGIPARFSGSGSGTD
FTLTISSVEPEDFATYYCQQSNEDPPTFGGGTKVEIKRTVAAPSVFIFPPSDEQLKSGTASVVCLLNNFYPREA
KVQWKVDNALQSGNSQESVTEQDSKDSTYSLSSTLTLSKADYEKHKVYACEVTHQGLSSPVTKSFNRGEC

1A7-selicrelumab-FVHC-IgG4 heavy chain (SEQ ID NO: 135)

FIG. 48 (Cont.)

EVQLVESGGGLVQPGGSLRLSCAASGFTFSSYSMSWVRQAPGKRLEWVAHISSGGSSTYYPDTVKGRFTISRDN
SKNTLYLQMNSLRAEDTAMYYCTRQFYYGSSFWYFDVWGAGTTVTVSSASTKGPSVFPLAPCSRSTSESTAALG
CLVKDYFPEPVTVSWNSGALTSGVHTFPAVLQSSGLYSLSSVVTVPSSSLGTKTYTCNVDHKPSNTKVDKRVES
KYGPPCPPCPAPEFLGGPSVFLFPPKPKDTLMISRTPEVTCVVVDVSQEDPEVQFNWYVDGVEVHNAKTKPREE
QFNSTYRVVSVLTVLHQDWLNGKEYKCKVSNKGLPSSIEKTISKAKGQPREPQVYTLPPSQEEMTKNQVSLTCL
VKGFYPSDIAVEWESNGQPENNYKTTPPVLDSDGSFFLYSRLTVDKSRWQEGNVFSCSVMHEALHNHYTQKSLS
LSPGGGGSGGGGSGGGGSDIQMTQSPSSVSASVGDRVTITCRASQGIYSWLAWYQQKPGKAPNLLIYTASTLQ
SGVPSRFSGSGSGTDFTLTISSLQPEDFATYYCQQANIFPLTFGGGTKVEIKGGGGSGGGGSGGGGSGGGGSQV
QLVQSGAEVKKPGASVKVSCKASGYTFTGYYMHWVRQAPGQGLEWMGWINPDSGGTNYAQKFQGRVTMTRDTSI
STAYMELNRLRSDDTAVYYCARDQPLGYCTNGVCSYFDYWGQGTLVTVSS

1A7-selicrelumab-FVHC-IgG4 light chain (SEQ ID NO: 136)
DNVLTQSPATLSVSPGERATLSCKASQSVDFDGDSYMNWYQQKPGQPPRLLIYAASNLESGIPARFSGSGSGTD
FTLTISSVEPEDFATYYCQQSNEDPPTFGGGTKVEIKGGGSGGGGQVQLVQSGAEVKKPGASVKVSCKASGYTF
TGYYMHWVRQAPGQGLEWMGWINPDSGGTNYAQKFQGRVTMTRDTSISTAYMELNRLRSDDTAVYYCARDQPLG
YCTNGVCSYFDYWGQGTLVTVSSRTVAAPSVFIFPPSDEQLKSGTASVVCLLNNFYPREAKVQWKVDNALQSGN
SQESVTEQDSKDSTYSLSSTLTLSKADYEKHKVYACEVTHQGLSSPVTKSFNRGEC

FIG. 49
Kabat CDR

| Ab | VH CDR1 | SEQ ID: | VH CDR2 | SEQ ID: | VH CDR3 | SEQ ID: | VL CDR1 | SEQ ID: | VL CDR2 | SEQ ID: | VL CDR3 | SEQ ID: |
|---|---|---|---|---|---|---|---|---|---|---|---|---|
| 4G12 or humanized 4G12 (CTLA4) | SYTMS | 54 | TISRGGGYTSYPDSVKG | 55 | EDYGSSYVHWFAY | 56 | RAGENIYSYLA | 57 | NARTLAE | 58 | QHHYGSPRT | 59 |
| 9H3 or humanized 9H3 (OX40) | SYGVL | 60 | VIWSGGSTDYNAAFIS | 61 | EEFGY | 62 | RASQDINNYLN | 63 | YTSRLHS | 64 | QQTNTLPWT | 65 |
| 3F2 or humanized 3F2 (PD-L1) | SGYNWH | 18 | YIHHSSITNYNPSLKS | 19 | EGYDYDWFAY | 20 | RASQSISNNLH | 21 | YASQSIS | 22 | QQSKSWPFT | 23 |
| 1A7 or humanized 1A7 (PD-1) | SYSMS | 24 | HISSGGSSTYYPDTVKG | 25 | QFYYGSSFWYFDV | 26 | KASQSVDFDGDSYMN | 27 | AASNLES | 28 | QQSNEDPPT | 29 |

FIG. 50
Chothia CDR

| Ab | VH CDR1 | SEQ ID: | VH CDR2 | SEQ ID: | VH CDR3 | SEQ ID: | VL CDR1 | SEQ ID: | VL CDR2 | SEQ ID: | VL CDR3 | SEQ ID: |
|---|---|---|---|---|---|---|---|---|---|---|---|---|
| 4G12 or humanized 4G12 (CTLA4) | GFTFS SYTMS | 66 | SRGGGY | 67 | EDYGSSYVH WFAY | 68 | RAGENIYSYLA | 69 | NARTLAE | 70 | QHHYGSP RT | 71 |
| 9H3 or humanized 9H3 (OX40) | GFSLT SYGVL | 72 | WSGGS | 73 | EEFGY | 74 | RASQDINNYLN | 75 | YTSRLHS | 76 | QQTNTLP WT | 77 |
| 3F2 or humanized 3F2 (PD-L1) | GYSIT SGYN WH | 78 | HHSSI | 79 | EGYDYDW FAY | 80 | RASQSISNNL H | 81 | YASQSIS | 82 | QQSKS WPFT | 83 |
| 1A7 or humanized 1A7 (PD-1) | GFTFS SYSMS | 84 | SSGGSS | 85 | QFYYGSSFW YFDV | 86 | KASQSVDFDG DSYMN | 87 | AASNLES | 88 | QQSNED PPT | 89 |

SEQUENCE LISTING

```
Sequence total quantity: 136
SEQ ID NO: 1              moltype = AA  length = 330
FEATURE                   Location/Qualifiers
REGION                    1..330
                          note = IgG1-heavy chain constant region(CH)
source                    1..330
                          mol_type = protein
                          organism = synthetic construct
SEQUENCE: 1
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 2              moltype = AA  length = 325
FEATURE                   Location/Qualifiers
REGION                    1..325
                          note = IgG2-CH
source                    1..325
                          mol_type = protein
                          organism = synthetic construct
SEQUENCE: 2
STKGPSVFPL APCSRSTSES TAALGCLVKD YFPEPVTVSW NSGALTSGVH TFPAVLQSSG   60
LYSLSSVVTV PSSNFGTQTY TCNVDHKPSN TKVDKTVERK CCVECPPCPA PPVAGPSVFL  120
FPPKPKDTLM ISRTPEVTCV VVDVSHEDPE VQFNWYVDGV EVHNAKTKPR EEQFNSTFRV  180
VSVLTVVHQD WLNGKEYKCK VSNKGLPAPI EKTISKTKGQ PREPQVYTLP PSREEMTKNQ  240
VSLTCLVKGF YPSDIAVEWE SNGQPENNYK TTPPMLDSDG SFFLYSKLTV DKSRWQQGNV  300
FSCSVMHEAL HNHYTQKSLS LSPGK                                       325

SEQ ID NO: 3              moltype = AA  length = 326
FEATURE                   Location/Qualifiers
REGION                    1..326
                          note = IgG4-CH
source                    1..326
                          mol_type = protein
                          organism = synthetic construct
SEQUENCE: 3
STKGPSVFPL APCSRSTSES TAALGCLVKD YFPEPVTVSW NSGALTSGVH TFPAVLQSSG   60
LYSLSSVVTV PSSSLGTKTY TCNVDHKPSN TKVDKRVESK YGPPCPPCPA PEFLGGPSVF  120
LFPPKPKDTL MISRTPEVTC VVVDVSQEDP EVQFNWYVDG VEVHNAKTKP REEQFNSTYR  180
VVSVLTVLHQ DWLNGKEYKC KVSNKGLPSS IEKTISKAKG QPREPQVYTL PPSQEEMTKN  240
QVSLTCLVKG FYPSDIAVEW ESNGQPENNY KTTPPVLDSD GSFFLYSRLT VDKSRWQEGN  300
VFSCSVMHEA LHNHYTQKSL SLSLGK                                      326

SEQ ID NO: 4              moltype = AA  length = 216
FEATURE                   Location/Qualifiers
REGION                    1..216
                          note = PDL1-avelumab antibody light chain
source                    1..216
                          mol_type = protein
                          organism = synthetic construct
SEQUENCE: 4
QSALTQPASV SGSPGQSITI SCTGTSSDVG GYNYVSWYQQ HPGKAPKLMI YDVSNRPSGV   60
SNRFSGSKSG NTASLTISGL QAEDEADYYC SSYTSSSTRV FGTGTKVTVL GQPKANPTVT  120
```

```
LFPPSSEELQ ANKATLVCLI SDFYPGAVTV AWKADGSPVK AGVETTKPSK QSNNKYAASS   180
YLSLTPEQWK SHRSYSCQVT HEGSTVEKTV APTECS                             216

SEQ ID NO: 5            moltype = AA  length = 594
FEATURE                 Location/Qualifiers
REGION                  1..594
                        note = PDL1-mIL7-3A heavy chain
source                  1..594
                        mol_type = protein
                        organism = synthetic construct
SEQUENCE: 5
EVQLLESGGG LVQPGGSLRL SCAASGFTFS SYIMMWVRQA PGKGLEWVSS IYPSGGITFY    60
ADTVKGRFTI SRDNSKNTLY LQMNSLRAED TAVYYCARIK LGTVTTVDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPELLGG   240
PSVFLFPPKP KDTLMISRTP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSRDE   360
GGGGSGGGGS ECHIKDKEGK AYESVLMISI DELDKMTGTD SNCPNNEPNF FRKHVCDDTK   420
EAAFLNRAAR KLKQFLKMNI SEEFNVHLLT VSQGTQTLVN CTSKEEKNVK EQKKNDACFL   480
KRLLREIKTC WNKILKGSIG GGGSGGGGSV SLTCLVKGFY PSDIAVEWES NGQPENNYKT   540
TPPVLDSDGS FFLYSKLTVD KSRWQQGNVF SCSVMHEALH NHYTQKSLSL SPGA         594

SEQ ID NO: 6            moltype = AA  length = 590
FEATURE                 Location/Qualifiers
REGION                  1..590
                        note = PDL1-mIL7-3B heavy chain
source                  1..590
                        mol_type = protein
                        organism = synthetic construct
SEQUENCE: 6
EVQLLESGGG LVQPGGSLRL SCAASGFTFS SYIMMWVRQA PGKGLEWVSS IYPSGGITFY    60
ADTVKGRFTI SRDNSKNTLY LQMNSLRAED TAVYYCARIK LGTVTTVDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPELLGG   240
PSVFLFPPKP KDTLMISRTP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSRDE   360
LTKNQVSLTC LVKGFYPSDI AVEWEGGGGS GGGGSECHIK DKEGKAYESV LMISIDELDK   420
MTGTDSNCPN NEPNFFRKHV CDDTKEAAFL NRAARKLKQF LKMNISEEFN VHLLTVSQGT   480
QTLVNCTSKE EKNVKEQKKN DACFLKRLLR EIKTCWNKIL KGSIGGGGSG GGGSKTTPPV   540
LDSDGSFFLY SKLTVDKSRW QQGNVFSCSV MHEALHNHYT QKSLSLSPGA              590

SEQ ID NO: 7            moltype = AA  length = 599
FEATURE                 Location/Qualifiers
REGION                  1..599
                        note = PDL1-mIL7-3C heavy chain
source                  1..599
                        mol_type = protein
                        organism = synthetic construct
SEQUENCE: 7
EVQLLESGGG LVQPGGSLRL SCAASGFTFS SYIMMWVRQA PGKGLEWVSS IYPSGGITFY    60
ADTVKGRFTI SRDNSKNTLY LQMNSLRAED TAVYYCARIK LGTVTTVDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPELLGG   240
PSVFLFPPKP KDTLMISRTP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSRDE   360
LTKNQVSLTC LVKGFYPSDI AVEWESNGGG GSGGGGSECH IKDKEGKAYE SVLMISIDEL   420
DKMTGTDSNC PNNEPNFFRK HVCDDTKEAA FLNRAARKLK QFLKMNISEE FNVHLLTVSQ   480
GTQTLVNCTS KEEKNVKEQK KNDACFLKRL LREIKTCWNK ILKGSIGGGG SGGGGSGQPE   540
NNYKTTPPVL DSDGSFFLYS KLTVDKSRWQ QGNVFSCSVM HEALHNHYTQ KSLSLSPGA    599

SEQ ID NO: 8            moltype = AA  length = 589
FEATURE                 Location/Qualifiers
REGION                  1..589
                        note = PDL1-mIL7-3D heavy chain
source                  1..589
                        mol_type = protein
                        organism = synthetic construct
SEQUENCE: 8
EVQLLESGGG LVQPGGSLRL SCAASGFTFS SYIMMWVRQA PGKGLEWVSS IYPSGGITFY    60
ADTVKGRFTI SRDNSKNTLY LQMNSLRAED TAVYYCARIK LGTVTTVDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPELLGG   240
PSVFLFPPKP KDTLMISRTP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSRDE   360
LTKNQVSLTC LVKGFYPSDI AVEWESNGQP ENNYKTTPPV LDSDGSFFLY SKLTVGGGGS   420
GGGGSECHIK DKEGKAYESV LMISIDELDK MTGTDSNCPN NEPNFFRKHV CDDTKEAAFL   480
NRAARKLKQF LKMNISEEFN VHLLTVSQGT QTLVNCTSKE EKNVKEQKKN DACFLKRLLR   540
EIKTCWNKIL KGSIGGGGSG GGGSFSCSVM HEALHNHYTQ KSLSLSPGA               589
```

```
SEQ ID NO: 9            moltype = AA  length = 20
FEATURE                 Location/Qualifiers
REGION                  1..20
                        note = HC linker sequence
source                  1..20
                        mol_type = protein
                        organism = synthetic construct
SEQUENCE: 9
GGGGSGGGGS GGGGSGGGGS                                                 20

SEQ ID NO: 10           moltype = AA  length = 162
FEATURE                 Location/Qualifiers
source                  1..162
                        mol_type = protein
                        organism = Mus musculus
SEQUENCE: 10
CDLPHTYNLG NKRALTVLEE MRRLPPLSCL KDRKDFGFPL EKVDNQQIQK AQAILVLRDL     60
TQQILNLFTS KDLSATWNAT LLDSFCNDLH QQLNDLKACV MQEPPLTQED SLLAVRTYFH    120
RITVYLRKKK HSLCAWEVIR AEVWRALSSS TNLLARLSEE KE                       162

SEQ ID NO: 11           moltype = AA  length = 152
FEATURE                 Location/Qualifiers
source                  1..152
                        mol_type = protein
                        organism = Homo sapiens
SEQUENCE: 11
DCDIEGKDGK QYESVLMVSI DQLLDSMKEI GSNCLNNEFN FFKRHICDAN KEGMFLFRAA     60
RKLRQFLKMN STGDFDLHLL KVSEGTTILL NCTGQVKGRK PAALGEAQPT KSLEENKSLK    120
EQKKLNDLCF LKRLLQEIKT CWNKILMGTK EH                                  152

SEQ ID NO: 12           moltype = AA  length = 138
FEATURE                 Location/Qualifiers
source                  1..138
                        mol_type = protein
                        organism = Homo sapiens
SEQUENCE: 12
HKSSSQGQDR HMIRMRQLID IVDQLKNYVN DLVPEFLPAP EDVETNCEWS AFSCFQKAQL     60
KSANTGNNER IINVSIKKLK RKPPSTNAGR RQKHRLTCPS CDSYEKKPPK EFLERFKSLL    120
QKMIHQHLSS RTHGSEDS                                                  138

SEQ ID NO: 13           moltype = AA  length = 136
FEATURE                 Location/Qualifiers
source                  1..136
                        mol_type = protein
                        organism = Homo sapiens
SEQUENCE: 13
IPPHVQKSVN NDMIVTDNNG AVKFPQLCKF CDVRFSTCDN QKSCMSNCSI TSICEKPQEV     60
CVAVWRKNDE NITLETVCHD PKLPYHDFIL EDAASPKCIM KEKKKPGETF FMCSCSSDEC    120
NDNIIFSEEY NTSNPD                                                    136

SEQ ID NO: 14           moltype = AA  length = 111
FEATURE                 Location/Qualifiers
REGION                  1..111
                        note = ATOR1015-CD86
source                  1..111
                        mol_type = protein
                        organism = synthetic construct
SEQUENCE: 14
APLKIQAYFN ETADLPCQFA NSQNLSLSEL VVFWQDQENL VLNEVYLGKE RFDSVDSKYM     60
GRTSFDSDSW TLRLHNLQIK DKGRYQCIIH HKKPTGMINI HQMNSELSVL A             111

SEQ ID NO: 15           moltype = AA  length = 128
FEATURE                 Location/Qualifiers
REGION                  1..128
                        note = KN035 VHH
source                  1..128
                        mol_type = protein
                        organism = synthetic construct
SEQUENCE: 15
QVQLVESGGG LVQPGGSLRL SCAASGFTFS RRCMAWFRQA PGKERERVAK LLTTSGSTYL     60
ADSVKGRFTI SRDNSKNTVY LQMNSLRAED TAVYYCAADS FEDPTCTLVT SSGAFQYWGQ    120
GTLVTVSS                                                             128

SEQ ID NO: 16           moltype = AA  length = 247
FEATURE                 Location/Qualifiers
REGION                  1..247
                        note = C40-6A7 scFv
source                  1..247
                        mol_type = protein
```

-continued

```
                         organism = synthetic construct
SEQUENCE: 16
DVVMTQSPLS LPVTLGQPAS ISCRSSQSLL HSNGNTYLHW YQQRPGQSPN HLIYQVSNRF    60
SGVPDRFSGS GSGTDFTLKI SRVEAEDVGV YFCSQTTHVP WTFGCGTKVE IKGGGGSGGG   120
GSGGGGSGGG GSQVQLVQSG AEVKKPGASV KLSCKASGYT FISYYIYWVK QAPGQCLEWI   180
GGINPRNGGT NFNEKFKSRA TLTVDTSIST AYMELSRLRS EDTAVYYCTR HGNGVYWGQG   240
TTLTVSS                                                             247

SEQ ID NO: 17             moltype = AA   length = 249
FEATURE                   Location/Qualifiers
REGION                    1..249
                          note = PDL1-3F2 scFv
source                    1..249
                          mol_type = protein
                          organism = synthetic construct
SEQUENCE: 17
QVQLQESGPG LVKPSETLSL TCTVSGYSIT SGYNWHWIRQ FPGNCLEWMG YIHHSSITNY    60
NPSLKSRITI SRDTSKNQFS LKLSSVTAAD TATYYCAREG YDYDWFAYWG QGTLVTVSSA   120
STGGGGSGGG GSGGGGSGGG GSDIVLTQSP DFQSVTPKEK VTLSCRASQS ISNNLHWYQQ   180
KPDESPKLLI KYASQSISGI PSRFSGSGSG TDFTLTINSV EAEDFAMYFC QQSKSWPFTF   240
GCGTRLEIK                                                           249

SEQ ID NO: 18             moltype = AA   length = 6
FEATURE                   Location/Qualifiers
REGION                    1..6
                          note = CDR sequence
source                    1..6
                          mol_type = protein
                          organism = synthetic construct
SEQUENCE: 18
SGYNWH                                                                6

SEQ ID NO: 19             moltype = AA   length = 16
FEATURE                   Location/Qualifiers
REGION                    1..16
                          note = CDR sequence
source                    1..16
                          mol_type = protein
                          organism = synthetic construct
SEQUENCE: 19
YIHHSSITNY NPSLKS                                                    16

SEQ ID NO: 20             moltype = AA   length = 10
FEATURE                   Location/Qualifiers
REGION                    1..10
                          note = CDR sequence
source                    1..10
                          mol_type = protein
                          organism = synthetic construct
SEQUENCE: 20
EGYDYDWFAY                                                           10

SEQ ID NO: 21             moltype = AA   length = 11
FEATURE                   Location/Qualifiers
REGION                    1..11
                          note = CDR sequence
source                    1..11
                          mol_type = protein
                          organism = synthetic construct
SEQUENCE: 21
RASQSISNNL H                                                         11

SEQ ID NO: 22             moltype = AA   length = 7
FEATURE                   Location/Qualifiers
REGION                    1..7
                          note = CDR sequence
source                    1..7
                          mol_type = protein
                          organism = synthetic construct
SEQUENCE: 22
YASQSIS                                                               7

SEQ ID NO: 23             moltype = AA   length = 9
FEATURE                   Location/Qualifiers
REGION                    1..9
                          note = CDR sequence
source                    1..9
                          mol_type = protein
                          organism = synthetic construct
```

-continued

```
SEQUENCE: 23
QQSKSWPFT                                                                    9

SEQ ID NO: 24           moltype = AA   length = 5
FEATURE                 Location/Qualifiers
REGION                  1..5
                        note = CDR sequence
source                  1..5
                        mol_type = protein
                        organism = synthetic construct
SEQUENCE: 24
SYSMS                                                                        5

SEQ ID NO: 25           moltype = AA   length = 17
FEATURE                 Location/Qualifiers
REGION                  1..17
                        note = CDR sequence
source                  1..17
                        mol_type = protein
                        organism = synthetic construct
SEQUENCE: 25
HISSGGSSTY YPDTVKG                                                          17

SEQ ID NO: 26           moltype = AA   length = 13
FEATURE                 Location/Qualifiers
REGION                  1..13
                        note = CDR sequence
source                  1..13
                        mol_type = protein
                        organism = synthetic construct
SEQUENCE: 26
QFYYGSSFWY FDV                                                              13

SEQ ID NO: 27           moltype = AA   length = 15
FEATURE                 Location/Qualifiers
REGION                  1..15
                        note = CDR sequence
source                  1..15
                        mol_type = protein
                        organism = synthetic construct
SEQUENCE: 27
KASQSVDFDG DSYMN                                                            15

SEQ ID NO: 28           moltype = AA   length = 7
FEATURE                 Location/Qualifiers
REGION                  1..7
                        note = CDR sequence
source                  1..7
                        mol_type = protein
                        organism = synthetic construct
SEQUENCE: 28
AASNLES                                                                      7

SEQ ID NO: 29           moltype = AA   length = 9
FEATURE                 Location/Qualifiers
REGION                  1..9
                        note = CDR sequence
source                  1..9
                        mol_type = protein
                        organism = synthetic construct
SEQUENCE: 29
QQSNEDPPT                                                                    9

SEQ ID NO: 30           moltype = AA   length = 10
FEATURE                 Location/Qualifiers
REGION                  1..10
                        note = Linker sequence 1
source                  1..10
                        mol_type = protein
                        organism = synthetic construct
SEQUENCE: 30
GGGGSGGGGS                                                                  10

SEQ ID NO: 31           moltype = AA   length = 5
FEATURE                 Location/Qualifiers
REGION                  1..5
                        note = Linker sequence 2
source                  1..5
                        mol_type = protein
```

-continued

```
                              organism = synthetic construct
SEQUENCE: 31
GGGGS                                                                  5

SEQ ID NO: 32           moltype = AA   length = 330
FEATURE                 Location/Qualifiers
source                  1..330
                        mol_type = protein
                        organism = Homo sapiens
SEQUENCE: 32
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                    330

SEQ ID NO: 33           moltype = AA   length = 326
FEATURE                 Location/Qualifiers
source                  1..326
                        mol_type = protein
                        organism = Homo sapiens
SEQUENCE: 33
ASTKGPSVFP LAPCSRSTSE STAALGCLVK DYFPEPVTVS WNSGALTSGV HTFPAVLQSS    60
GLYSLSSVVT VPSSNFGTQT YTCNVDHKPS NTKVDKTVER KCCVECPPCP APPVAGPSVF   120
LFPPKPKDTL MISRTPEVTC VVVDVSHEDP EVQFNWYVDG VEVHNAKTKP REEQFNSTFR   180
VVSVLTVVHQ DWLNGKEYKC KVSNKGLPAP IEKTISKTKG QPREPQVYTL PPSREEMTKN   240
QVSLTCLVKG FYPSDIAVEW ESNGQPENNY KTTPPMLDSD GSFFLYSKLT VDKSRWQQGN   300
VFSCSVMHEA LHNHYTQKSL SLSPGK                                        326

SEQ ID NO: 34           moltype = AA   length = 327
FEATURE                 Location/Qualifiers
source                  1..327
                        mol_type = protein
                        organism = Homo sapiens
SEQUENCE: 34
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPSCP APEFLGGPSV   120
FLFPPKPKDT LMISRTPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVMHE ALHNHYTQKS LSLSLGK                                       327

SEQ ID NO: 35           moltype = AA   length = 450
FEATURE                 Location/Qualifiers
REGION                  1..450
                        note = PDL1-avelumab antibody heavy chain
source                  1..450
                        mol_type = protein
                        organism = synthetic construct
SEQUENCE: 35
EVQLLESGGG LVQPGGSLRL SCAASGFTFS SYIMMWVRQA PGKGLEWVSS IYPSGGITFY    60
ADTVKGRFTI SRDNSKNTLY LQMNSLRAED TAVYYCARIK LGTVTTVDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPELLGG   240
PSVFLFPPKP KDTLMISRTP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VYTLPPSRDE   360
LTKNQVSLTC LVKGFYPSDI AVEWESNGQP ENNYKTTPPV LDSDGSFFLY SKLTVDKSRW   420
QQGNVFSCSV MHEALHNHYT QKSLSLSPGK                                    450

SEQ ID NO: 36           moltype = AA   length = 449
FEATURE                 Location/Qualifiers
REGION                  1..449
                        note = PDL1-3F2-IgG1 heavy chain
source                  1..449
                        mol_type = protein
                        organism = synthetic construct
SEQUENCE: 36
QVQLQESGPG LVKPSETLSL TCTVSGYSIT SGYNWHWIRQ FPGNGLEWMG YIHHSSITNY    60
NPSLKSRITI SRDTSKNQFS LKLSSVTAAD TATYYCAREG YDYDWFAYWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKKVEPK SCDKTHTCPP CPAPELLGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSRDEL   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGK                                     449

SEQ ID NO: 37           moltype = AA   length = 214
FEATURE                 Location/Qualifiers
```

```
REGION                  1..214
                        note = PDL1-3F2-IgG1 light chain
source                  1..214
                        mol_type = protein
                        organism = synthetic construct
SEQUENCE: 37
DIVLTQSPDF QSVTPKEKVT ITCRASQSIS NNLHWYQQKP DESPKLLIKY ASQSISGIPS   60
RFSGSGSGTD FTLTINSVEA EDFAMYFCQQ SKSWPFTFGQ GTRLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 38           moltype = AA  length = 607
FEATURE                 Location/Qualifiers
REGION                  1..607
                        note = M7824 heavy chain
source                  1..607
                        mol_type = protein
                        organism = synthetic construct
SEQUENCE: 38
EVQLLESGGG LVQPGGSLRL SCAASGFTFS SYIMMWVRQA PGKGLEWVSS IYPSGGITFY   60
ADTVKGRFTI SRDNSKNTLY LQMNSLRAED TAVYYCARIK LGTVTTVDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKRVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFFLY SKLTVDKSRW  420
QQGNVFSCSV MHEALHNHYT QKSLSLSPGA GGGGSGGGGS GGGGSGGGGS GIPPHVQKSV  480
NNDMIVTDNN GAVKFPQLCK FCDVRFSTCD NQKSCMSNCS ITSICEKPQE VCVAVWRKND  540
ENITLETVCH DPKLPYHDFI LEDAASPKCI MKEKKKPGET FFMCSCSSDE CNDNIIFSEE  600
YNTSNPD                                                            607

SEQ ID NO: 39           moltype = AA  length = 216
FEATURE                 Location/Qualifiers
REGION                  1..216
                        note = M7824 light chain
source                  1..216
                        mol_type = protein
                        organism = synthetic construct
SEQUENCE: 39
QSALTQPASV SGSPGQSITI SCTGTSSDVG GYNYVSWYQQ HPGKAPKLMI YDVSNRPSGV   60
SNRFSGSKSG NTASLTISGL QAEDEADYYC SSYTSSSTRV FGTGTKVTVL GQPKANPTVT  120
LFPPSSEELQ ANKATLVCLI SDFYPGAVTV AWKADGSPVK AGVETTKPSK QSNNKYAASS  180
YLSLTPEQWK SHRSYSCQVT HEGSTVEKTV APTECS                            216

SEQ ID NO: 40           moltype = AA  length = 122
FEATURE                 Location/Qualifiers
REGION                  1..122
                        note = PD1-1A7 VH
source                  1..122
                        mol_type = protein
                        organism = synthetic construct
SEQUENCE: 40
EVQLVESGGG LVQPGGSLRL SCAASGFTFS SYSMSWVRQA PGKRLEWVAH ISSGGSSTYY   60
PDTVKGRFTI SRDNSKNTLY LQMNSLRAED TAMYYCTRQF YYGSSFWYFD VWGAGTTVTV  120
SS                                                                 122

SEQ ID NO: 41           moltype = AA  length = 111
FEATURE                 Location/Qualifiers
REGION                  1..111
                        note = PD1-1A7 VL
source                  1..111
                        mol_type = protein
                        organism = synthetic construct
SEQUENCE: 41
DNVLTQSPAT LSVSPGERAT LSCKASQSVD FDGDSYMNWY QQKPGQPPRL LIYAASNLES   60
GIPARFSGSG SGTDFTLTIS SVEPEDFATY YCQQSNEDPP TFGGGTKVEI K            111

SEQ ID NO: 42           moltype = AA  length = 452
FEATURE                 Location/Qualifiers
REGION                  1..452
                        note = CT4-4G12-IgG1 heavy chain
source                  1..452
                        mol_type = protein
                        organism = synthetic construct
SEQUENCE: 42
EVQLVESGGG LVQPGGSLRL SCAASGFTFS SYTMSWVRQA PGKGLEWVAT ISRGGGYTSY   60
PDSVKGRFTI SRDNSKNTLY LQMNSLRAED TAVYYCARED YGSSYVHWFA YWGQTLVTV   120
SAASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKKV EPKSCDKTHT CPPCPAPELL  240
```

```
GGPSVFLFPP KPKDTLMISR TPEVTCVVVD VSHEDPEVKF NWYVDGVEVH NAKTKPREEQ    300
YNSTYRVVSV LTVLHQDWLN GKEYKCKVSN KALPAPIEKT ISKAKGQPRE PQVYTLPPSR    360
EEMTKNQVSL TCLVKGFYPS DIAVEWESNG QPENNYKTTP PVLDSDGSFF LYSKLTVDKS    420
RWQQGNVFSC SVMHEALHNH YTQKSLSLSP GK                                  452

SEQ ID NO: 43           moltype = AA   length = 214
FEATURE                 Location/Qualifiers
REGION                  1..214
                        note = CT4-4G12-IgG1 light chain
source                  1..214
                        mol_type = protein
                        organism = synthetic construct
SEQUENCE: 43
DIQMTQSPSF LSASVGDRVT ITCRAGENIY SYLAWYQQKP GKAPKLLIYN ARTLAEGVPS    60
RFSGSGSGTE FTLTISSLQP EDFATYYCQH HYGSPRTFGG GTKLEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 44           moltype = AA   length = 122
FEATURE                 Location/Qualifiers
REGION                  1..122
                        note = CT4-4G12 VH
source                  1..122
                        mol_type = protein
                        organism = synthetic construct
SEQUENCE: 44
EVQLVESGGG LVQPGGSLRL SCAASGFTFS SYTMSWVRQA PGKGLEWVAT ISRGGGYTSY    60
PDSVKGRFTI SRDNSKNTLY LQMNSLRAED TAVYYCARED YGSSYVHWFA YWGQGTLVTV    120
SA                                                                   122

SEQ ID NO: 45           moltype = AA   length = 108
FEATURE                 Location/Qualifiers
REGION                  1..108
                        note = CT4-4G12 VL
source                  1..108
                        mol_type = protein
                        organism = synthetic construct
SEQUENCE: 45
DIQMTQSPSF LSASVGDRVT ITCRAGENIY SYLAWYQQKP GKAPKLLIYN ARTLAEGVPS    60
RFSGSGSGTE FTLTISSLQP EDFATYYCQH HYGSPRTFGG GTKLEIKR                 108

SEQ ID NO: 46           moltype = AA   length = 706
FEATURE                 Location/Qualifiers
REGION                  1..706
                        note = CT4-040-SCFV-HC heavy chain
source                  1..706
                        mol_type = protein
                        organism = synthetic construct
SEQUENCE: 46
EVQLVESGGG LVQPGGSLRL SCAASGFTFS SYTMSWVRQA PGKGLEWVAT ISRGGGYTSY    60
PDSVKGRFTI SRDNSKNTLY LQMNSLRAED TAVYYCARED YGSSYVHWFA YWGQGTLVTV    120
SAASTKGPSV FPLAPSSKST SGGTAALGCL VKDYFPEPVT VSWNSGALTS GVHTFPAVLQ    180
SSGLYSLSSV VTVPSSSLGT QTYICNVNHK PSNTKVDKKV EPKSCDKTHT CPPCPAPELL    240
GGPSVFLFPP KPKDTLMISR TPEVTCVVVD VSHEDPEVKF NWYVDGVEVH NAKTKPREEQ    300
YNSTYRVVSV LTVLHQDWLN GKEYKCKVSN KALPAPIEKT ISKAKGQPRE PQVYTLPPSR    360
EEMTKNQVSL TCLVKGFYPS DIAVEWESNG QPENNYKTTP PVLDSDGSFF LYSKLTVDKS    420
RWQQGNVFSC SVMHEALHNH YTQKSLSLSP GGGGSGGGG SGGGGSDIQM TQSPSSLSAS    480
VGDRVTITCR ASQDINNYLN WYQQKPGGAV KLLIYYTSRL HTGVPSRFSG SGSGTDFTLT    540
ISSLQPEDIA TYYCQQTNTL PWTFGCGTKL EVKGGGGSGG GGSGGGGSGG GGSQVQLVES    600
GGGVVQPGRS LRISCAVSGF SLTSYGVLWV RQAPGKCLEW LGVIWSGGST DYNAAFISRL    660
TISRDNSKST VYFQMNSLRA EDTAVYYCAR EEFGYWGQGT LVTVSS                   706

SEQ ID NO: 47           moltype = AA   length = 712
FEATURE                 Location/Qualifiers
REGION                  1..712
                        note = CT4-040-FV3A heavy chain
source                  1..712
                        mol_type = protein
                        organism = synthetic construct
SEQUENCE: 47
EVQLVESGGG LVQPGGSLRL SCAASGFTFS SYTMSWVRQA PGKGLEWVAT ISRGGGYTSY    60
PDSVKGRFTI SRDNSKNTLY LQMNSLRAED TAVYYCARED YGSSYVHWFA YWGQGTLVTV    120
SAASTKGPSV FPLAPSSKST SGGTAALGCL VKDYFPEPVT VSWNSGALTS GVHTFPAVLQ    180
SSGLYSLSSV VTVPSSSLGT QTYICNVNHK PSNTKVDKKV EPKSCDKTHT CPPCPAPELL    240
GGPSVFLFPP KPKDTLMISR TPEVTCVVVD VSHEDPEVKF NWYVDGVEVH NAKTKPREEQ    300
YNSTYRVVSV LTVLHQDWLN GKEYKCKVSN KALPAPIEKT ISKAKGQPRE PQVYTLPPSR    360
EEMTGGGGSG GGGSDIQMTQ SPSSLSASVG DRVTITCRAS QDINNYLNWY QQKPGGAVKL    420
LIYYTSRLHT GVPSRFSGSG SGTDFTLTIS SLQPEDIATY YCQQTNTLPW TFGCGTKLEV    480
KGGGGSGGGG SGGGGSGGGG SQVQLVESGG GVVQPGRSLR ISCAVSGFSL TSYGVLWVRQ    540
```

```
APGKCLEWLG VIWSGGSTDY NAAFISRLTI SRDNSKSTVY FQMNSLRAED TAVYYCAREE    600
FGYWGQGTLV TVSSGGGGSG GGGSKNQVSL TCLVKGFYPS DIAVEWESNG QPENNYKTTP    660
PVLDSDGSFF LYSKLTVDKS RWQQGNVFSC SVMHEALHNH YTQKSLSLSP GK            712

SEQ ID NO: 48           moltype = AA   length = 113
FEATURE                 Location/Qualifiers
REGION                  1..113
                        note = O40-9H3 VH
source                  1..113
                        mol_type = protein
                        organism = synthetic construct
SEQUENCE: 48
QVQLVESGGG VVQPGRSLRI SCAVSGFSLT SYGVLWVRQA PGKGLEWLGV IWSGGSTDYN    60
AAFISRLTIS RDNSKSTVYF QMNSLRAEDT AVYYCAREEF GYWGQGTLVT VSS           113

SEQ ID NO: 49           moltype = AA   length = 108
FEATURE                 Location/Qualifiers
REGION                  1..108
                        note = O40-9H3 VL
source                  1..108
                        mol_type = protein
                        organism = synthetic construct
SEQUENCE: 49
DIQMTQSPSS LSASVGDRVT ITCRASQDIN NYLNWYQQKP GGAVKLLIYY TSRLHTGVPS    60
RFSGSGSGTD FTLTISSLQP EDIATYYCQQ TNTLPWTFGG GTKLEVKR                 108

SEQ ID NO: 50           moltype = AA   length = 122
FEATURE                 Location/Qualifiers
REGION                  1..122
                        note = Mouse CT4-4G12 VH
source                  1..122
                        mol_type = protein
                        organism = synthetic construct
SEQUENCE: 50
DVKLVESGGG LVKPGGSLKL SCTASGFTFS SYTMSWVRQT PEKRLEWVAT ISRGGGYTSY    60
PDSVKGRFTI SRDNAKNTLY LQMSSLQSED TAMYYCARDD YGSSYVHWFA YWGQGTLVTV    120
SA                                                                  122

SEQ ID NO: 51           moltype = AA   length = 107
FEATURE                 Location/Qualifiers
REGION                  1..107
                        note = Mouse CT4-4G12 VL
source                  1..107
                        mol_type = protein
                        organism = synthetic construct
SEQUENCE: 51
DIQMTQSPAS LSASVGETVT ITCRAGENIY SYLAWYQQKQ GKSPQLLVYN ARTLAEGVPS    60
RFSGSGSGTQ FSLKINSLQP EDFGSYYCQH HYGSPRTFGG GTKLEIK                  107

SEQ ID NO: 52           moltype = AA   length = 113
FEATURE                 Location/Qualifiers
REGION                  1..113
                        note = Mouse OX40 antibody 9H3 VH
source                  1..113
                        mol_type = protein
                        organism = synthetic construct
SEQUENCE: 52
QVQLKQSGPG LVQPSQSLSI TCTVSGFSLT SYGVLWVRQP PGKGLEWLGV IWSGGSTDYN    60
AAFISRLSIS KDNSKSQVFF KMNSLQADDT AIYYCAREEF GYWGQGTLVT VSA           113

SEQ ID NO: 53           moltype = AA   length = 107
FEATURE                 Location/Qualifiers
REGION                  1..107
                        note = Mouse OX40 antibody 9H3 VL
source                  1..107
                        mol_type = protein
                        organism = synthetic construct
SEQUENCE: 53
DIQMTQTTSS LSASLGDRVT ISCRASQDIN NYLNWYQQKP DGTVKLLIYY TSRLHSGVPS    60
RFSGSGSGTD YSLTISNLEQ EDIATYFCQQ TNTLPWTFGG GTKLEIK                  107

SEQ ID NO: 54           moltype = AA   length = 5
FEATURE                 Location/Qualifiers
REGION                  1..5
                        note = CDR sequence
source                  1..5
                        mol_type = protein
                        organism = synthetic construct
SEQUENCE: 54
```

```
SYTMS                                                                        5

SEQ ID NO: 55          moltype = AA  length = 17
FEATURE                Location/Qualifiers
REGION                 1..17
                       note = CDR sequence
source                 1..17
                       mol_type = protein
                       organism = synthetic construct
SEQUENCE: 55
TISRGGGYTS YPDSVKG                                                          17

SEQ ID NO: 56          moltype = AA  length = 13
FEATURE                Location/Qualifiers
REGION                 1..13
                       note = CDR sequence
source                 1..13
                       mol_type = protein
                       organism = synthetic construct
SEQUENCE: 56
EDYGSSYVHW FAY                                                              13

SEQ ID NO: 57          moltype = AA  length = 11
FEATURE                Location/Qualifiers
REGION                 1..11
                       note = CDR sequence
source                 1..11
                       mol_type = protein
                       organism = synthetic construct
SEQUENCE: 57
RAGENIYSYL A                                                                11

SEQ ID NO: 58          moltype = AA  length = 7
FEATURE                Location/Qualifiers
REGION                 1..7
                       note = CDR sequence
source                 1..7
                       mol_type = protein
                       organism = synthetic construct
SEQUENCE: 58
NARTLAE                                                                      7

SEQ ID NO: 59          moltype = AA  length = 9
FEATURE                Location/Qualifiers
REGION                 1..9
                       note = CDR sequence
source                 1..9
                       mol_type = protein
                       organism = synthetic construct
SEQUENCE: 59
QHHYGSPRT                                                                    9

SEQ ID NO: 60          moltype = AA  length = 5
FEATURE                Location/Qualifiers
REGION                 1..5
                       note = CDR sequence
source                 1..5
                       mol_type = protein
                       organism = synthetic construct
SEQUENCE: 60
SYGVL                                                                        5

SEQ ID NO: 61          moltype = AA  length = 16
FEATURE                Location/Qualifiers
REGION                 1..16
                       note = CDR sequence
source                 1..16
                       mol_type = protein
                       organism = synthetic construct
SEQUENCE: 61
VIWSGGSTDY NAAFIS                                                           16

SEQ ID NO: 62          moltype = AA  length = 5
FEATURE                Location/Qualifiers
REGION                 1..5
                       note = CDR sequence
source                 1..5
                       mol_type = protein
                       organism = synthetic construct
```

```
SEQUENCE: 62
EEFGY                                                                    5

SEQ ID NO: 63           moltype = AA   length = 11
FEATURE                 Location/Qualifiers
REGION                  1..11
                        note = CDR sequence
source                  1..11
                        mol_type = protein
                        organism = synthetic construct
SEQUENCE: 63
RASQDINNYL N                                                            11

SEQ ID NO: 64           moltype = AA   length = 7
FEATURE                 Location/Qualifiers
REGION                  1..7
                        note = CDR sequence
source                  1..7
                        mol_type = protein
                        organism = synthetic construct
SEQUENCE: 64
YTSRLHS                                                                  7

SEQ ID NO: 65           moltype = AA   length = 9
FEATURE                 Location/Qualifiers
REGION                  1..9
                        note = CDR sequence
source                  1..9
                        mol_type = protein
                        organism = synthetic construct
SEQUENCE: 65
QQTNTLPWT                                                                9

SEQ ID NO: 66           moltype = AA   length = 10
FEATURE                 Location/Qualifiers
REGION                  1..10
                        note = CDR sequence
source                  1..10
                        mol_type = protein
                        organism = synthetic construct
SEQUENCE: 66
GFTFSSYTMS                                                              10

SEQ ID NO: 67           moltype = AA   length = 6
FEATURE                 Location/Qualifiers
REGION                  1..6
                        note = CDR sequence
source                  1..6
                        mol_type = protein
                        organism = synthetic construct
SEQUENCE: 67
SRGGGY                                                                   6

SEQ ID NO: 68           moltype = AA   length = 13
FEATURE                 Location/Qualifiers
REGION                  1..13
                        note = CDR sequence
source                  1..13
                        mol_type = protein
                        organism = synthetic construct
SEQUENCE: 68
EDYGSSYVHW FAY                                                          13

SEQ ID NO: 69           moltype = AA   length = 11
FEATURE                 Location/Qualifiers
REGION                  1..11
                        note = CDR sequence
source                  1..11
                        mol_type = protein
                        organism = synthetic construct
SEQUENCE: 69
RAGENIYSYL A                                                            11

SEQ ID NO: 70           moltype = AA   length = 7
FEATURE                 Location/Qualifiers
REGION                  1..7
                        note = CDR sequence
source                  1..7
                        mol_type = protein
```

```
                        organism = synthetic construct
SEQUENCE: 70
NARTLAE                                                                          7

SEQ ID NO: 71           moltype = AA   length = 9
FEATURE                 Location/Qualifiers
REGION                  1..9
                        note = CDR sequence
source                  1..9
                        mol_type = protein
                        organism = synthetic construct
SEQUENCE: 71
QHHYGSPRT                                                                        9

SEQ ID NO: 72           moltype = AA   length = 10
FEATURE                 Location/Qualifiers
REGION                  1..10
                        note = CDR sequence
source                  1..10
                        mol_type = protein
                        organism = synthetic construct
SEQUENCE: 72
GFSLTSYGVL                                                                      10

SEQ ID NO: 73           moltype = AA   length = 5
FEATURE                 Location/Qualifiers
REGION                  1..5
                        note = CDR sequence
source                  1..5
                        mol_type = protein
                        organism = synthetic construct
SEQUENCE: 73
WSGGS                                                                            5

SEQ ID NO: 74           moltype = AA   length = 5
FEATURE                 Location/Qualifiers
REGION                  1..5
                        note = CDR sequence
source                  1..5
                        mol_type = protein
                        organism = synthetic construct
SEQUENCE: 74
EEFGY                                                                            5

SEQ ID NO: 75           moltype = AA   length = 11
FEATURE                 Location/Qualifiers
REGION                  1..11
                        note = CDR sequence
source                  1..11
                        mol_type = protein
                        organism = synthetic construct
SEQUENCE: 75
RASQDINNYL N                                                                    11

SEQ ID NO: 76           moltype = AA   length = 7
FEATURE                 Location/Qualifiers
REGION                  1..7
                        note = CDR sequence
source                  1..7
                        mol_type = protein
                        organism = synthetic construct
SEQUENCE: 76
YTSRLHS                                                                          7

SEQ ID NO: 77           moltype = AA   length = 9
FEATURE                 Location/Qualifiers
REGION                  1..9
                        note = CDR sequence
source                  1..9
                        mol_type = protein
                        organism = synthetic construct
SEQUENCE: 77
QQTNTLPWT                                                                        9

SEQ ID NO: 78           moltype = AA   length = 11
FEATURE                 Location/Qualifiers
REGION                  1..11
                        note = CDR sequence
source                  1..11
```

```
                        mol_type = protein
                        organism = synthetic construct
SEQUENCE: 78
GYSITSGYNW H                                                                11

SEQ ID NO: 79           moltype = AA   length = 5
FEATURE                 Location/Qualifiers
REGION                  1..5
                        note = CDR sequence
source                  1..5
                        mol_type = protein
                        organism = synthetic construct
SEQUENCE: 79
HHSSI                                                                        5

SEQ ID NO: 80           moltype = AA   length = 10
FEATURE                 Location/Qualifiers
REGION                  1..10
                        note = CDR sequence
source                  1..10
                        mol_type = protein
                        organism = synthetic construct
SEQUENCE: 80
EGYDYDWFAY                                                                  10

SEQ ID NO: 81           moltype = AA   length = 11
FEATURE                 Location/Qualifiers
REGION                  1..11
                        note = CDR sequence
source                  1..11
                        mol_type = protein
                        organism = synthetic construct
SEQUENCE: 81
RASQSISNNL H                                                                11

SEQ ID NO: 82           moltype = AA   length = 7
FEATURE                 Location/Qualifiers
REGION                  1..7
                        note = CDR sequence
source                  1..7
                        mol_type = protein
                        organism = synthetic construct
SEQUENCE: 82
YASQSIS                                                                      7

SEQ ID NO: 83           moltype = AA   length = 9
FEATURE                 Location/Qualifiers
REGION                  1..9
                        note = CDR sequence
source                  1..9
                        mol_type = protein
                        organism = synthetic construct
SEQUENCE: 83
QQSKSWPFT                                                                    9

SEQ ID NO: 84           moltype = AA   length = 10
FEATURE                 Location/Qualifiers
REGION                  1..10
                        note = CDR sequence
source                  1..10
                        mol_type = protein
                        organism = synthetic construct
SEQUENCE: 84
GFTFSSYSMS                                                                  10

SEQ ID NO: 85           moltype = AA   length = 6
FEATURE                 Location/Qualifiers
REGION                  1..6
                        note = CDR sequence
source                  1..6
                        mol_type = protein
                        organism = synthetic construct
SEQUENCE: 85
SSGGSS                                                                       6

SEQ ID NO: 86           moltype = AA   length = 13
FEATURE                 Location/Qualifiers
REGION                  1..13
                        note = CDR sequence
```

```
source                    1..13
                          mol_type = protein
                          organism = synthetic construct
SEQUENCE: 86
QFYYGSSFWY FDV                                                          13

SEQ ID NO: 87             moltype = AA  length = 15
FEATURE                   Location/Qualifiers
REGION                    1..15
                          note = CDR sequence
source                    1..15
                          mol_type = protein
                          organism = synthetic construct
SEQUENCE: 87
KASQSVDFDG DSYMN                                                        15

SEQ ID NO: 88             moltype = AA  length = 7
FEATURE                   Location/Qualifiers
REGION                    1..7
                          note = CDR sequence
source                    1..7
                          mol_type = protein
                          organism = synthetic construct
SEQUENCE: 88
AASNLES                                                                 7

SEQ ID NO: 89             moltype = AA  length = 9
FEATURE                   Location/Qualifiers
REGION                    1..9
                          note = CDR sequence
source                    1..9
                          mol_type = protein
                          organism = synthetic construct
SEQUENCE: 89
QQSNEDPPT                                                               9

SEQ ID NO: 90             moltype = AA  length = 21
FEATURE                   Location/Qualifiers
REGION                    1..21
                          note = HC Linker sequence
source                    1..21
                          mol_type = protein
                          organism = synthetic construct
SEQUENCE: 90
GGGGSGGGGS GGGGSGGGGS G                                                 21

SEQ ID NO: 91             moltype = AA  length = 115
FEATURE                   Location/Qualifiers
REGION                    1..115
                          note = C40-6A7 VH
source                    1..115
                          mol_type = protein
                          organism = synthetic construct
SEQUENCE: 91
QVQLVQSGAE VKKPGASVKL SCKASGYTFI SYYIYWVKQA PGQGLEWIGG INPRNGGTNF        60
NEKFKSRATL TVDTSISTAY MELSRLRSED TAVYYCTRHG NGVYWGQGTT LTVSS            115

SEQ ID NO: 92             moltype = AA  length = 112
FEATURE                   Location/Qualifiers
REGION                    1..112
                          note = C40-6A7 VL
source                    1..112
                          mol_type = protein
                          organism = synthetic construct
SEQUENCE: 92
DVVMTQSPLS LPVTLGQPAS ISCRSSQSLL HSNGNTYLHW YQQRPGQSPN HLIYQVSNRF        60
SGVPDRFSGS GSGTDFTLKI SRVEAEDVGV YFCSQTTHVP WTFGGGTKVE IK               112

SEQ ID NO: 93             moltype = AA  length = 119
FEATURE                   Location/Qualifiers
source                    1..119
                          mol_type = protein
                          organism = Homo sapiens
SEQUENCE: 93
NCSNMIDEII THLKQPPLPL LDFNNLNGED QDILMENNLR RPNLEAFNRA VKSLQNASAI        60
ESILKNLLPC LPLATAAPTR HPIHIKDGDW NEFRRKLTFY LKTLENAQAQ QTTLSLAIF        119

SEQ ID NO: 94             moltype = AA  length = 129
FEATURE                   Location/Qualifiers
```

```
source                      1..129
                            mol_type = protein
                            organism = Homo sapiens
SEQUENCE: 94
HKCDITLQEI IKTLNSLTEQ KTLCTELTVT DIFAASKNTT EKETFCRAAT VLRQFYSHHE      60
KDTRCLGATA QQFHRHKQLI RFLKRLDRNL WGLAGLNSCP VKEANQSTLE NFLERLKTIM     120
REKYSKCSS                                                             129

SEQ ID NO: 95               moltype = AA   length = 115
FEATURE                     Location/Qualifiers
source                      1..115
                            mol_type = protein
                            organism = Homo sapiens
SEQUENCE: 95
IPTEIPTSAL VKETLALLST HRTLLIANET LRIPVPVHKN HQLCTEEIFQ GIGTLESQTV      60
QGGTVERLFK NLSLIKKYID GQKKKCGEER RRVNQFLDYL QEFLGVMNTE WIIES          115

SEQ ID NO: 96               moltype = AA   length = 183
FEATURE                     Location/Qualifiers
source                      1..183
                            mol_type = protein
                            organism = Homo sapiens
SEQUENCE: 96
VPPGEDSKDV AAPHRQPLTS SERIDKQIRY ILDGISALRK ETCNKSNMCE SSKEALAENN      60
LNLPKMAEKD GCFQSGFNEE TCLVKIITGL LEFEVYLEYL QNRFESSEEQ ARAVQMSTKV     120
LIQFLQKKAK NLDAITTPDP TTNASLLTKL QAQNQWLQDM TTHLILRSFK EFLQSSLRAL     180
RQM                                                                   183

SEQ ID NO: 97               moltype = AA   length = 54
FEATURE                     Location/Qualifiers
source                      1..54
                            mol_type = protein
                            organism = Homo sapiens
SEQUENCE: 97
PKFIKELRVI ESGPHCANTE IIVKLSDGRE LCLDPKENWV QRVVEKFLKR AENS            54

SEQ ID NO: 98               moltype = AA   length = 126
FEATURE                     Location/Qualifiers
source                      1..126
                            mol_type = protein
                            organism = Homo sapiens
SEQUENCE: 98
QGCPTLAGIL DINFLINKMQ EDPASKCHCS ANVTSCLCLG IPSDNCTRPC FSERLSQMTN      60
TTMQTRYPLI FSRVKKSVEV LKNNKCPYFS CEQPCNQTTA GNALTFLKSL LEIFQKEKMR     120
GMRGKI                                                                126

SEQ ID NO: 99               moltype = AA   length = 104
FEATURE                     Location/Qualifiers
source                      1..104
                            mol_type = protein
                            organism = Homo sapiens
SEQUENCE: 99
STALRELIEE LVNITQNQKA PLCNGSMVWS INLTAGMYCA ALESLINVSG CSAIEKTQRM      60
LSGFCPHKVS AGQFSSLHVR DTKIEVAQFV KDLLLHLKKL FREG                      104

SEQ ID NO: 100              moltype = AA   length = 114
FEATURE                     Location/Qualifiers
source                      1..114
                            mol_type = protein
                            organism = Homo sapiens
SEQUENCE: 100
NWVNVISDLK KIEDLIQSMH IDATLYTESD VHPSCKVTAM KCFLLELQVI SLESGDASIH      60
DTVENLIILA NNSLSSNGNV TESGCKECEE LEEKNIKEFL QSFVHIVQMF INTS           114

SEQ ID NO: 101              moltype = AA   length = 110
FEATURE                     Location/Qualifiers
source                      1..110
                            mol_type = protein
                            organism = Homo sapiens
SEQUENCE: 101
NTFRPEVHLL PPPSEELALN ELVTLTCLAR GFSPKDVLVR WLQGSQELPR EKYLTWASRQ      60
EPSQGTTTFA VTSILRVAAE DWKKGDTFSC MVGHEALPLA FTQKTIDRLA                110

SEQ ID NO: 102              moltype = AA   length = 107
FEATURE                     Location/Qualifiers
source                      1..107
                            mol_type = protein
                            organism = Homo sapiens
SEQUENCE: 102
```

```
AQAPVKLSLN LLASSDPPEA ASWLLCEVSG FSPPNILLMW LEDQREVNTS GFAPARPPPQ    60
PRSTTFWAWS VLRVPAPPSP QPATYTCVVS HEDSRTLLNA SRSLEVS                107

SEQ ID NO: 103          moltype = AA   length = 109
FEATURE                 Location/Qualifiers
source                  1..109
                        mol_type = protein
                        organism = Homo sapiens
SEQUENCE: 103
VALHRPDVYL LPPAREQLNL RESATITCLV TGFSPADVFV QWMQRGQPLS PEKYVTSAPM    60
PEPQAPGRYF AHSILTVSEE EWNTGETYTC VAHEALPNRV TERTVDKST              109

SEQ ID NO: 104          moltype = AA   length = 107
FEATURE                 Location/Qualifiers
source                  1..107
                        mol_type = protein
                        organism = Homo sapiens
SEQUENCE: 104
GQPREPQVYT LPPSRDELTK NQVSLTCLVK GFYPSDIAVE WESNGQPENN YKTTPPVLDS    60
DGSFFLYSKL TVDKSRWQQG NVFSCSVMHE ALHNHYTQKS LSLSPGK                107

SEQ ID NO: 105          moltype = AA   length = 107
FEATURE                 Location/Qualifiers
source                  1..107
                        mol_type = protein
                        organism = Homo sapiens
SEQUENCE: 105
GQPREPQVYT LPPSREEMTK NQVSLTCLVK GFYPSDIAVE WESNGQPENN YKTTPPMLDS    60
DGSFFLYSKL TVDKSRWQQG NVFSCSVMHE ALHNHYTQKS LSLSPGK                107

SEQ ID NO: 106          moltype = AA   length = 107
FEATURE                 Location/Qualifiers
source                  1..107
                        mol_type = protein
                        organism = Homo sapiens
SEQUENCE: 106
GQPREPQVYT LPPSREEMTK NQVSLTCLVK GFYPSDIAVE WESSGQPENN YNTTPPMLDS    60
DGSFFLYSKL TVDKSRWQQG NIFSCSVMHE ALHNRFTQKS LSLSPGK                107

SEQ ID NO: 107          moltype = AA   length = 107
FEATURE                 Location/Qualifiers
source                  1..107
                        mol_type = protein
                        organism = Homo sapiens
SEQUENCE: 107
GQPREPQVYT LPPSQEEMTK NQVSLTCLVK GFYPSDIAVE WESNGQPENN YKTTPPVLDS    60
DGSFFLYSRL TVDKSRWQEG NVFSCSVMHE ALHNHYTQKS LSLSLGK                107

SEQ ID NO: 108          moltype = AA   length = 107
FEATURE                 Location/Qualifiers
source                  1..107
                        mol_type = protein
                        organism = Rattus norvegicus
SEQUENCE: 108
GRTQVPHVYT MSPTKEEMTQ NEVSITCMVK GFYPPDIYVE WQMNGQPQEN YKNTPPTMDT    60
DGSYFLYSKL NVKKEKWQQG NTFTCSVLHE GLHNHHTEKS LSHSPGK                107

SEQ ID NO: 109          moltype = AA   length = 107
FEATURE                 Location/Qualifiers
source                  1..107
                        mol_type = protein
                        organism = Rattus norvegicus
SEQUENCE: 109
GTPRGPQVYT MAPPKEEMTQ SQVSITCMVK GFYPPDIYTE WKMNGQPQEN YKNTPPTMDT    60
DGSYFLYSKL NVKKETWQQG NTFTCSVLHE GLHNHHTEKS LSHSPGK                107

SEQ ID NO: 110          moltype = AA   length = 107
FEATURE                 Location/Qualifiers
source                  1..107
                        mol_type = protein
                        organism = Rattus norvegicus
SEQUENCE: 110
GLVRKPQVYV MGPPTEQLTE QTVSLTCLTS GFLPNDIGVE WTSNGHIEKN YKNTEPVMDS    60
DGSFFMYSKL NVERSRWDSR APFVCSVVHE GLHNHHVEKS ISRPPGK                107

SEQ ID NO: 111          moltype = AA   length = 107
FEATURE                 Location/Qualifiers
source                  1..107
                        mol_type = protein
```

```
                            organism = Rattus norvegicus
SEQUENCE: 111
GKARTPQVYT IPPPREQMSK NKVSLTCMVT SFYPASISVE WERNGELEQD YKNTLPVLDS    60
DESYFLYSKL SVDTDSWMRG DIYTCSVVHE ALHNHHTQKN LSRSPGK                 107

SEQ ID NO: 112              moltype = AA   length = 107
FEATURE                     Location/Qualifiers
source                      1..107
                            mol_type = protein
                            organism = Mus musculus
SEQUENCE: 112
GRPKAPQVYT IPPPKEQMAK DKVSLTCMIT DFFPEDITVE WQWNGQPAEN YKNTQPIMNT    60
NGSYFVYSKL NVQKSNWEAG NTFTCSVLHE GLHNHHTEKS LSHSPGK                 107

SEQ ID NO: 113              moltype = AA   length = 107
FEATURE                     Location/Qualifiers
source                      1..107
                            mol_type = protein
                            organism = Mus musculus
SEQUENCE: 113
GSVRAPQVYV LPPPEEEMTK KQVTLTCMVT DFMPEDIYVE WTNNGKTELN YKNTEPVLDS    60
DGSYFMYSKL RVEKKNWVER NSYSCSVVHE GLHNHHTTKS FSRTPGK                 107

SEQ ID NO: 114              moltype = AA   length = 107
FEATURE                     Location/Qualifiers
source                      1..107
                            mol_type = protein
                            organism = Mus musculus
SEQUENCE: 114
GLVRAPQVYT LPPPAEQLSR KDVSLTCLVV GFNPGDISVE WTSNGHTEEN YKDTAPVLDS    60
DGSYFIYSKL NMKTSKWEKT DSFSCNVRHE GLKNYYLKKT ISRSPGK                 107

SEQ ID NO: 115              moltype = AA   length = 107
FEATURE                     Location/Qualifiers
source                      1..107
                            mol_type = protein
                            organism = Mus musculus
SEQUENCE: 115
GPVRAPQVYV LPPPAEEMTK KEFSLTCMIT GFLPAEIAVD WTSNGRTEQN YKNTATVLDS    60
DGSYFMYSKL RVQKSTWERG SLFACSVVHE VLHNHLTTKT ISRSLGK                 107

SEQ ID NO: 116              moltype = AA   length = 107
FEATURE                     Location/Qualifiers
source                      1..107
                            mol_type = protein
                            organism = Mus musculus
SEQUENCE: 116
GRAQTPQVYT IPPPREQMSK KKVSLTCLVT NFFSEAISVE WERNGELEQD YKNTPPILDS    60
DGTYFLYSKL TVDTDSWLQG EIFTCSVVHE ALHNHHTQKN LSRSPGK                 107

SEQ ID NO: 117              moltype = AA   length = 107
FEATURE                     Location/Qualifiers
source                      1..107
                            mol_type = protein
                            organism = Macaca mulatta
SEQUENCE: 117
GQPREPQVYT LPPSREELTK NQVSLTCLVK GFYPSDIVVE WESSGQPENT YKTTPPVLDS    60
DGSYFLYSKL TVDKSRWQQG NVFSCSVMHE ALHNHYTQKS LSVSPGK                 107

SEQ ID NO: 118              moltype = AA   length = 91
FEATURE                     Location/Qualifiers
source                      1..91
                            mol_type = protein
                            organism = Macaca mulatta
SEQUENCE: 118
GQPREPQVYT LPPPREELTK NQVSLTCLVK GFYPSDIVVE WASNGQPENT YKTTPPVLDS    60
DGSYFLYSKL TVDKSRWQQG NTFSCSVMHE A                                   91

SEQ ID NO: 119              moltype = AA   length = 91
FEATURE                     Location/Qualifiers
source                      1..91
                            mol_type = protein
                            organism = Macaca mulatta
SEQUENCE: 119
GQPREPQVYI LPPPQEELTK NQVSLTCLVT GFYPSDIAVE WESNGQPENT YKTTPPVLDS    60
DGSYFLYSKL TVDKSRWQQG NTFSCSVMHE A                                   91

SEQ ID NO: 120              moltype = AA   length = 110
FEATURE                     Location/Qualifiers
```

```
source                  1..110
                        mol_type = protein
                        organism = Canis lupus familiaris
SEQUENCE: 120
GRAHKPSVYV LPPSPKELSS SDTVSITCLI KDFYPPDIDV EWQSNGQQEP ERKHRMTPPQ    60
LDEDGSYFLY SKLSVDKSRW QQGDPFTCAV MHETLQNHYT DLSLSHSPGK              110

SEQ ID NO: 121          moltype = AA  length = 109
FEATURE                 Location/Qualifiers
source                  1..109
                        mol_type = protein
                        organism = Canis lupus familiaris
SEQUENCE: 121
GQAHQPSVYV LPPSREELSK NTVSLTCLIK DFFPPDIDVE WQSNGQQEPE SKYRTTPPQL    60
DEDGSYFLYS KLSVDKSRWQ RGDTFICAVM HEALHNHYTQ KSLSHSPGK               109

SEQ ID NO: 122          moltype = AA  length = 109
FEATURE                 Location/Qualifiers
source                  1..109
                        mol_type = protein
                        organism = Canis lupus familiaris
SEQUENCE: 122
GQAHQPNVYV LPPSRDEMSK NTVTLTCLVK DFFPPEIDVE WQSNGQQEPE SKYRMTPPQL    60
DEDGSYFLYS KLSVDKSRWQ RGDTFICAVM HEALHNHYTQ ISLSHSPGK               109

SEQ ID NO: 123          moltype = AA  length = 110
FEATURE                 Location/Qualifiers
source                  1..110
                        mol_type = protein
                        organism = Canis lupus familiaris
SEQUENCE: 123
GQAHQPSVYV LPPSPKELSS SDTVTLTCLI KDFFPPEIDV EWSNGQPEP ESKYHTTAPQ     60
LDEDGSYFLY SKLSVDKSRW QQGDTFTCAV MHEALQNHYT DLSLSHSPGK              110

SEQ ID NO: 124          moltype = AA  length = 15
FEATURE                 Location/Qualifiers
REGION                  1..15
                        note = Linker sequence 3
source                  1..15
                        mol_type = protein
                        organism = synthetic construct
SEQUENCE: 124
GGGGSGGGGS GGGGS                                                     15

SEQ ID NO: 125          moltype = AA  length = 192
FEATURE                 Location/Qualifiers
source                  1..192
                        mol_type = protein
                        organism = Mus musculus
SEQUENCE: 125
VIPVSGPARC LSQSRNLLKT TDDMVKTARE KLKHYSCTAE DIDHEDITRD QTSTLKTCLP    60
LELHKNESCL ATRETSSTTR GSCLPPQKTS LMMTLCLGSI YEDLKMYQTE FQAINAALQN   120
HNHQQIILDK GMLVAIDELM QSLNHNGETL RQKPPVGEAD PYRVKMKLCI LLHAFSTRVV   180
TINRVMGYLS SA                                                      192

SEQ ID NO: 126          moltype = AA  length = 313
FEATURE                 Location/Qualifiers
source                  1..313
                        mol_type = protein
                        organism = Mus musculus
SEQUENCE: 126
MWELEKDVYV VEVDWTPDAP GETVNLTCDT PEEDDITWTS DQRHGVIGSG KTLTITVKEF    60
LDAGQYTCHK GGETLSHSHL LLHKKENGIW STEILKNFKN KTFLKCEAPN YSGRFTCSWL   120
VQRNMDLKFN IKSSSSSPDS RAVTCGMASL SAEKVTLDQR DYEKYSVSCQ EDVTCPTAEE   180
TLPIELALEA RQQNKYENYS TSFFIRDIIK PDPPKNLQMK PLKNSQVEVS WEYPDSWSTP   240
HSYFSLKFFV RIQRKKEKMK ETEEGCNQKG AFLVEKTSTE VQCKGGNVCV QAQDRYYNSS   300
CSKWACVPCR VRS                                                     313

SEQ ID NO: 127          moltype = AA  length = 198
FEATURE                 Location/Qualifiers
source                  1..198
                        mol_type = protein
                        organism = Homo sapiens
SEQUENCE: 127
ARNLPVATPD PGMFPCLHHS QNLLRAVSNM LQKARQTLEF YPCTSEEIDH EDITKDKTST    60
VEACLPLELT KNESCLNSRE TSFITNGSCL ASRKTSFMMA LCLSSIYEDL KMYQVEFKTM   120
NAKLLMDPKR QIFLDQNMLA VIDELMQALN FNSETVPQKS SLEEPDFYKT KIKLCILLHA   180
FRIRAVTIDR VMSYLNAS                                                198
```

```
SEQ ID NO: 128         moltype = AA   length = 306
FEATURE                Location/Qualifiers
source                 1..306
                       mol_type = protein
                       organism = Homo sapiens
SEQUENCE: 128
IWELKKDVYV VELDWYPDAP GEMVVLTCDT PEEDGITWTL DQSSEVLGSG KTLTIQVKEF    60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSACPAA   180
EESLPIEVMV DAVHKLKYEN YTSSFFIRDI IKPDPPKNLQ LKPKLNSRQV EVSWEYPDTW   240
STPHSYFSLT FCVQVQGKSK REKKDRVFTD KTSATVICRK NASISVRAQD RYYSSSWSEW   300
ASVPCS                                                              306

SEQ ID NO: 129         moltype = AA   length = 166
FEATURE                Location/Qualifiers
source                 1..166
                       mol_type = protein
                       organism = Homo sapiens
SEQUENCE: 129
CDLPQTHSLG NRRALILLAQ MGRISHFSCL KDRHDFGFPE EEFDGHQFQK AQAISVLHEM    60
IQQTFNLFST EDSSAAWEQS LLEKFSTELY QQLNDLEACV IQEVGVEETP LMNEDSILAV   120
RKYFQRITLY LTEKKYSPCA WEVVRAEIMR SLSFSTNLQK RLRRKD                  166

SEQ ID NO: 130         moltype = AA   length = 126
FEATURE                Location/Qualifiers
REGION                 1..126
                       note = SelicrelumabVH
source                 1..126
                       mol_type = protein
                       organism = synthetic construct
SEQUENCE: 130
QVQLVQSGAE VKKPGASVKV SCKASGYTFT GYYMHWVRQA PGQGLEWMGW INPDSGGTNY    60
AQKFQGRVTM TRDTSISTAY MELNRLRSDD TAVYYCARDQ PLGYCTNGVC SYFDYWGQGT   120
LVTVSS                                                              126

SEQ ID NO: 131         moltype = AA   length = 107
FEATURE                Location/Qualifiers
REGION                 1..107
                       note = SelicrelumabVL
source                 1..107
                       mol_type = protein
                       organism = synthetic construct
SEQUENCE: 131
DIQMTQSPSS VSASVGDRVT ITCRASQGIY SWLAWYQQKP GKAPNLLIYT ASTLQSGVPS    60
RFSGSGSGTD FTLTISSLQP EDFATYYCQQ ANIFPLTFGG GTKVEIK                 107

SEQ ID NO: 132         moltype = AA   length = 253
FEATURE                Location/Qualifiers
REGION                 1..253
                       note = SelicrelumabscFV
source                 1..253
                       mol_type = protein
                       organism = synthetic construct
SEQUENCE: 132
DIQMTQSPSS VSASVGDRVT ITCRASQGIY SWLAWYQQKP GKAPNLLIYT ASTLQSGVPS    60
RFSGSGSGTD FTLTISSLQP EDFATYYCQQ ANIFPLTFGG GTKVEIKGGG GSGGGGSGGG   120
GSGGGGSQVQ LVQSGAEVKK PGASVKVSCK ASGYTFTGYY MHWVRQAPGQ GLEWMGWINP   180
DSGGTNYAQK FQGRVTMTRD TSISTAYMEL NRLRSDDTAV YYCARDQPLG YCTNGVCSYF   240
DYWGQGTLVT VSS                                                      253

SEQ ID NO: 133         moltype = AA   length = 717
FEATURE                Location/Qualifiers
REGION                 1..717
                       note = 1A7-selicrelumab-FV3A-IgG4 heavy chain
source                 1..717
                       mol_type = protein
                       organism = synthetic construct
SEQUENCE: 133
EVQLVESGGG LVQPGGSLRL SCAASGFTFS SYSMSWVRQA PGKRLEWVAH ISSGGSSTYY    60
PDTVKGRFTI SRDNSKNTLY LQMNSLRAED TAMYYCTRQF YYGSSFWYFD VWGAGTTVTV   120
SSASTKGPSV FPLAPCSRST SESTAALGCL VKDYFPEPVT VSWNSGALTS GVHTFPAVLQ   180
SSGLYSLSSV VTVPSSSLGT KTYTCNVDHK PSNTKVDKRV ESKYGPPCPP CPAPEFLGGP   240
SVFLFPPKPK DTLMISRTPE VTCVVVDVSQ EDPEVQFNWY VDGVEVHNAK TKPREEQFNS   300
TYRVVSVLTV LHQDWLNGKE YKCKVSNKGL PSSIEKTISK AKGQPREPQV YTLPPSQEEG   360
GGGSGGGGSD IQMTQSPSSV SASVGDRVTI TCRASQGIYS WLAWYQQKPG KAPNLLIYTA   420
STLQSGVPSR FSGSGSGTDF TLTISSLQPE DFATYYCQQA NIFPLTFGGG TKVEIKGGGG   480
SGGGGSGGGG SGGGGSQVQL VQSGAEVKKP GASVKVSCKA SGYTFTGYYM HWVRQAPGQG   540
LEWMGWINPS GGTNYAQKF QGRVTMTRDT SISTAYMELN RLRSDDTAVY YCARDQPLGY   600
CTNGVCSYFD YWGQGTLVTV SSGGGGSGGG GSVSLTCLVK GFYPSDIAVE WESNGQPENN   660
```

```
YKTTPPVLDS DGSFFLYSRL TVDKSRWQEG NVFSCSVMHE ALHNHYTQKS LSLSPGK          717

SEQ ID NO: 134          moltype = AA  length = 218
FEATURE                 Location/Qualifiers
REGION                  1..218
                        note = 1A7-selicrelumab-FV3A-IgG4 light chain
source                  1..218
                        mol_type = protein
                        organism = synthetic construct
SEQUENCE: 134
DNVLTQSPAT LSVSPGERAT LSCKASQSVD FDGDSYMNWY QQKPGQPPRL LIYAASNLES      60
GIPARFSGSG SGTDFTLTIS SVEPEDFATY YCQQSNEDPP TFGGGTKVEI KRTVAAPSVF      120
IFPPPSDEQLK SGTASVVCLL NNFYPREAKV QWKVDNALQS GNSQESVTEQ DSKDSTYSLS     180
STLTLSKADY EKHKVYACEV THQGLSSPVT KSFNRGEC                              218

SEQ ID NO: 135          moltype = AA  length = 716
FEATURE                 Location/Qualifiers
REGION                  1..716
                        note = 1A7-selicrelumab-FVHC-IgG4 heavy chain
source                  1..716
                        mol_type = protein
                        organism = synthetic construct
SEQUENCE: 135
EVQLVESGGG LVQPGGSLRL SCAASGFTFS SYSMSWVRQA PGKRLEWVAH ISSGGSSTYY      60
PDTVKGRFTI SRDNSKNTLY LQMNSLRAED TAMYYCTRQF YYGSSFWYFD VWGAGTTVTV      120
SSASTKGPSV FPLAPCSRST SESTAALGCL VKDYFPEPVT VSWNSGALTS GVHTFPAVLQ      180
SSGLYSLSSV VTVPSSSLGT KTYTCNVDHK PSNTKVDKRV ESKYGPPCPP CPAPEFLGGP      240
SVFLFPPKPK DTLMISRTPE VTCVVVDVSQ EDPEVQFNWY VDGVEVHNAK TKPREEQFNS      300
TYRVVSVLTV LHQDWLNGKE YKCKVSNKGL PSSIEKTISK AKGQPREPQV YTLPPSQEEM      360
TKNQVSLTCL VKGFYPSDIA VEWESNGQPE NNYKTTPPVL DSDGSFFLYS RLTVDKSRWQ      420
EGNVFSCSVM HEALHNHYTQ KSLSLSPGGG GGSGGGGSGG GGSDIQMTQS PSSVSASVGD      480
RVTITCRASQ GIYSWLAWYQ QKPGKAPNLL IYTASTLQSG VPSRFSGSGS GTDFTLTISS      540
LQPEDFATYY CQQANIFPLT FGGGTKVEIK GGGGSGGGGS GGGGSGGGGS QVQLVQSGAE      600
VKKKPGASVKV SCKASGYTFT GYYMHWVRQA PGQGLEWMGW INPDSGGTNY AQKFQGRVTM     660
TRDTSISTAY MELNRLRSDD TAVYYCARDQ PLGYCTNGVC SYFDYWGQGT LVTVSS          716

SEQ ID NO: 136          moltype = AA  length = 352
FEATURE                 Location/Qualifiers
REGION                  1..352
                        note = 1A7-selicrelumab-FVHC-IgG4 light chain
source                  1..352
                        mol_type = protein
                        organism = synthetic construct
SEQUENCE: 136
DNVLTQSPAT LSVSPGERAT LSCKASQSVD FDGDSYMNWY QQKPGQPPRL LIYAASNLES      60
GIPARFSGSG SGTDFTLTIS SVEPEDFATY YCQQSNEDPP TFGGGTKVEI KGGGSGGGGQ      120
VQLVQSGAEV KKKPGASVKVS CKASGYTFTG YYMHWVRQA GQGLEWMGWI NPDSGGTNYA      180
QKFQGRVTMT RDTSISTAYM ELNRLRSDDT AVYYCARDQP LGYCTNGVCS YFDYWGQGTL      240
VTVSSRTVAA PSVFIFPPSD EQLKSGTASV VCLLNNFYPR EAKVQWKVDN ALQSGNSQES      300
VTEQDSKDST YSLSSTLTLS KADYEKHKVY ACEVTHQGLS SPVTKSFNRG EC              352
```

MODIFIED IMMUNOGLOBULINS

CLAIM OF PRIORITY

Pursuant to 35 U.S.C. § 119(e), this application is a continuation of International Application No. PCT/CN2021/089649, filed on Apr. 25, 2021, which claims the benefit of International Application Nos. PCT/CN2021/085181, filed Apr. 2, 2021, PCT/CN2021/073085, filed Jan. 21, 2021, and PCT/CN2020/087036, filed Apr. 26, 2020, the contents of which are hereby incorporated by reference in their entirety.

SEQUENCE LISTING

This application contains a sequence listing that has been submitted electronically in XML format and is hereby incorporated by reference in its entirety. Said XML file is named 44835-0060001_PatentCenter. The XML file, created on Jul. 29, 2022, is 171,173 bytes in size.

TECHNICAL FIELD

This disclosure relates to modified immunoglobulins.

BACKGROUND

Antibodies are immunological proteins that bind a specific antigen. Generally, antibodies are specific for targets, have the ability to mediate immune effector mechanisms, and have a long half-life in serum. Such properties make antibodies powerful therapeutics. Monoclonal antibodies are used therapeutically for the treatment of a variety of conditions including cancer, infectious disease, autoimmune disease, and inflammatory disorders.

Many new antibody formats are proposed for various treatment purposes. For example, bispecific antibodies can bind to two different targets or two different epitopes on a target, creating additive or synergistic effect superior to the effect of individual antibodies. Immunocytokines are antibody-cytokine fusion proteins, with the potential to preferentially localize on tumor lesions and to activate anticancer immunity at the site of disease. Despite their conceptual advantages, these antibody formats are challenging to manufacture and it is difficult to develop them as drugs. Many existing manufacturing approaches for these antibody formats suffer from low efficiency and are limited by the complicated purification processes. Many other protein engineering and molecular biology techniques have been proposed. However, once these known engineered antibody formats are adopted, these molecules usually lose their favorable biochemical and/or biophysical properties, serum half-life, and/or stability, resulting in poor efficacy, instability and high immunogenicity. Particularly, it is widely known that many bispecific antibody formats are associated with low expression levels. There remains a need to provide an improved antibody format that is stable and suitable for pharmaceutical use and can be stably expressed at a high expression level.

SUMMARY

The present disclosure provides modified immunoglobulins. This disclosure is based on, in part, the unexpected discovery that an entire functional protein can be fused to a particular region in the CH3 domain of an immunoglobulin, and the modified immunoglobulin is stable and can be stably expressed at a high level.

In one aspect, provided herein is a polypeptide complex comprising: a first polypeptide comprising a first CH3 domain, a second polypeptide comprising a second CH3 domain. In some embodiments, a third polypeptide is fused to the first CH3 domain at a region from position 344 to position 382 of the first CH3 domain according to EU numbering.

In some embodiments, the third polypeptide is linked to a first amino acid residue and a second amino acid residue of the first CH3 domain.

In some embodiments, the first and the second amino acid residues are selected from the group consisting of amino acid residues at positions 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, and 383 of the first CH3 domain according to EU numbering.

In some embodiments, the third polypeptide is fused to the first CH3 domain at a region from position 351 to position 362 of the first CH3 domain according to EU numbering.

In some embodiments, the first and the second amino acid residues are selected from the group consisting of amino acid residues at positions 350, 351, 352, 353, 354, 355, 356, 357, 358, 359, 360, 361, 362, and 363 of the first CH3 domain according to EU numbering.

In some embodiments, the third polypeptide is fused to the first CH3 domain at a region from position 358 to position 362 of the first CH3 domain according to EU numbering.

In some embodiments, the first and the second amino acid residues are selected from the group consisting of amino acid residues at positions 357, 358, 359, 360, 361, 362, and 363 of the first CH3 domain according to EU numbering.

In some embodiments, one or more amino acid residues in a wildtype CH3 domain between the first and the second amino acid residues in the first CH3 domain are deleted.

In some embodiments, the first polypeptide further comprises a CH2 domain.

In some embodiments, the second polypeptide further comprises a CH2 domain.

In some embodiments, the first polypeptide further comprises a heavy chain variable domain and/or a heavy chain CH1 domain.

In some embodiments, the second polypeptide further comprises a heavy chain variable domain and/or a heavy chain CH1 domain.

In some embodiments, the polypeptide complex comprises two light chain polypeptides.

In some embodiments, the polypeptide complex is an IgG-like antibody.

In some embodiments, the third polypeptide is linked to the first polypeptide through a linker sequence.

In some embodiments, the linker sequence comprises 5-20 amino acid residues.

In some embodiments, the linker sequence comprises at least four glycine residues.

In some embodiments, the linker sequence comprises a sequence that is at least 80% identical to GGGGSGGGGS (SEQ ID NO: 30).

In some embodiments, the third polypeptide has about or at least 6, 7, 8, 9, 10, 20, 30, 40, or 50 amino acid residues.

In some embodiments, the third polypeptide has about 6 to 500 amino acid residues (e.g., 10 to 500, or 20 to 300 amino acid residues).

In some embodiments, the third polypeptide is a soluble polypeptide.

In some embodiments, the soluble protein is a cytokine (e.g., IL-1, IL-2, IL-3, IL-4, IL-5, IL-6, IL-7, IL-8, IL-9, IL-10, IL-11, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-35, or IL-36).

In some embodiments, the third polypeptide is IL3, IL4, IL5, IL6, IL-7, IL8, IL9, IL13, IL15, or IL-21.

In some embodiments, the third polypeptide comprises a single chain antigen-binding polypeptide (e.g., a single chain variable fragment (scFv) or a single-domain antibody (nanobody)).

In some embodiments, the single chain antigen-binding polypeptide specifically binds to a cell antigen (e.g., an effector cell antigen).

In some embodiments, the third polypeptide comprises a soluble portion (e.g., an extracellular region) of a transmembrane protein (e.g., transforming growth factor beta receptor 2 (TGFbR2)) or a secretory protein.

In some embodiments, the third polypeptide is a ligand (e.g., ATOR1015-CD86). In some embodiments, the third polypeptide is a nanobody (e.g., KN035) or a VHH.

In some embodiments, the third polypeptide in the polypeptide complex has about the same or a higher level of biological activity as compared to an isolated third polypeptide.

In some embodiments, the polypeptide complex has about the same or a higher level of binding affinity to a target as compared to a parent polypeptide complex.

In some embodiments, the polypeptide complex specifically binds to two antigens, and the polypeptide complex has about the same or a higher expression level as compared to that of a bispecific antibody that specifically binds to the same two antigens.

In some embodiments, the polypeptide complex does not form aggregates (e.g., in a purified form).

In some embodiments, the polypeptide complex can bind to an Fc receptor, when the third polypeptide in the polypeptide complex does not interact with a target protein. In some embodiments, the polypeptide complex in an isolated form can bind to an Fc receptor.

In some embodiments, the third polypeptide comprises a scFv. In some embodiments, the scFv has about the same or a higher level of binding affinity as compared to that of an isolated scFv.

In some embodiments, provided herein is the polypeptide complex further comprising: a fourth polypeptide. In some embodiments, the fourth polypeptide is fused to the second CH3 domain at a region from position 344 to position 382 of the second CH3 domain according to EU numbering.

In some embodiments, the fourth polypeptide is linked to a first amino acid residue and a second amino acid residue of the second CH3 domain.

In some embodiments, the first and the second amino acid residues are selected from the group consisting of amino acid residues at positions 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, and 383 of the second CH3 domain according to EU numbering.

In some embodiments, the fourth polypeptide is fused to the second CH3 domain at a region from position 351 to position 362 of the second CH3 domain according to EU numbering.

In some embodiments, the fourth polypeptide is linked to a first amino acid residue and a second amino acid residue of the second CH3 domain.

In some embodiments, the first and the second amino acid residues are selected from the group consisting of amino acid residues at positions 350, 351, 352, 353, 354, 355, 356, 357, 358, 359, 360, 361, 362, and 363 of the second CH3 domain according to EU numbering.

In some embodiments, the fourth polypeptide is fused to the second CH3 domain at a region from position 358 to position 362 of the second CH3 domain according to EU numbering.

In some embodiments, the fourth polypeptide is linked to a first amino acid residue and a second amino acid residue of the second CH3 domain.

In some embodiments, the first and the second amino acid residues are selected from the group consisting of amino acid residues at positions 357, 358, 359, 360, 361, 362, and 363 of the second CH3 domain according to EU numbering.

In some embodiments, provided herein is the polypeptide complex further comprising a fifth polypeptide. In some embodiments, the fifth polypeptide is fused to the C-terminus of the first polypeptide.

In some embodiments, the fifth polypeptide is fused to the C-terminus of the first polypeptide through a linker sequence.

In some embodiments, the linker sequence comprises 10-40 amino acid residues.

In some embodiments, the linker sequence comprises a sequence that is at least 80% identical to GGGGSGGGGSGGGGSGGGGS (SEQ ID NO: 9).

In some embodiments, the fifth polypeptide has more than 10 amino acid residues.

In some embodiments, the fifth polypeptide has about 10 to 500 amino acid residues.

In some embodiments, the fifth polypeptide is a cytokine.

In some embodiments, the cytokine is IFNa4.

In some embodiments, provided herein is the polypeptide complex further comprising a sixth polypeptide. In some embodiments, the sixth polypeptide is fused to the C-terminus of the second polypeptide.

In some embodiments, the first polypeptide and the second polypeptide form a heterodimer through knobs-in-holes (KIH) technique.

In some embodiments, the first polypeptide interacts with a light chain polypeptide, forming an antigen-binding site. In some embodiments, the second polypeptide does not interact with the light chain polypeptide.

In some embodiments, the first polypeptide interacts with a first light chain polypeptide, forming a first antigen-binding site. In some embodiments, the second polypeptide interacts with a second light chain polypeptide, forming a second antigen-binding site. In some embodiments, the first antigen-binding site and the second antigen-binding site specifically binds to same or different antigens.

In some embodiments, the polypeptide complex can bind to an Fc receptor when the third polypeptide in the polypeptide complex does not interact with a binding partner for the third polypeptide.

In one aspect, provided herein is a protein comprising a variant Fc. In some embodiments, a polypeptide is fused to the variant Fc at a region from position 344 to position 382 of the variant Fc according to EU numbering.

In some embodiments, the polypeptide is linked to a first amino acid residue and a second amino acid residue of the variant Fc. In some embodiments, the first and the second amino acid residues are selected from the group consisting of amino acid residues at positions 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, and 383 of the variant Fc according to EU numbering.

In some embodiments, the polypeptide is fused to the variant Fc at a region from position 351 to position 362 of the variant Fc according to EU numbering.

In some embodiments, the polypeptide is linked to a first amino acid residue and a second amino acid residue of the variant Fc. In some embodiments, the first and the second amino acid residues are selected from the group consisting of amino acid residues at positions 350, 351, 352, 353, 354, 355, 356, 357, 358, 359, 360, 361, 362, and 363 of the variant Fc according to EU numbering.

In some embodiments, the polypeptide is fused to the variant Fc at a region from position 358 to position 362 of the variant Fc according to EU numbering.

In some embodiments, the polypeptide is linked to a first amino acid residue and a second amino acid residue of the variant Fc. In some embodiments, the first and the second amino acid residues are selected from the group consisting of amino acid residues at positions 357, 358, 359, 360, 361, 362, and 363 of the variant Fc according to EU numbering.

In one aspect, provided herein is a protein comprising a variant Fc. In some embodiments, a polypeptide is fused to the variant Fc at a region from position 383 to position 391 of the variant Fc according to EU numbering.

In some embodiments, the polypeptide is linked to a first amino acid residue and a second amino acid residue of the variant Fc. In some embodiments, the first and the second amino acid residues are selected from the group consisting of amino acid residues at positions 382, 383, 384, 385, 386, 387, 388, 389, 390, 391, and 392 of the variant Fc according to EU numbering.

In one aspect, provided herein is a protein comprising a variant Fc. In some embodiments, a polypeptide is fused to the variant Fc at a region from position 383 to position 385 of the variant Fc according to EU numbering.

In some embodiments, the polypeptide is linked to a first amino acid residue and a second amino acid residue of the variant Fc. In some embodiments, the first and the second amino acid residues are selected from the group consisting of amino acid residues at positions 382, 383, 384, 385, and 386 of the variant Fc according to EU numbering.

In one aspect, provided herein is a protein comprising a variant Fc. In some embodiments, a polypeptide is fused to the variant Fc at a region from position 413 to position 422 of the variant Fc according to EU numbering.

In some embodiments, the polypeptide is linked to a first amino acid residue and a second amino acid residue of the variant Fc. In some embodiments, the first and the second amino acid residues are selected from the group consisting of amino acid residues at positions 412, 413, 414, 415, 416, 417, 418, 419, 420, 421, 422, and 423 of the variant Fc according to EU numbering.

In some embodiments, the Fc is an IgG Fc. In some embodiments, the Fc is an IgG1, IgG2, or IgG4 Fc. In some embodiments, the protein is an IgG-like antibody or an immunoglobulin (e.g., IgM, IgD, IgE, IgA, or IgG). In some embodiments, the protein is a multispecific antibody (e.g., a bispecific antibody).

In one aspect, provided herein is a polypeptide complex comprising a first polypeptide comprising a first CH3 domain, a second polypeptide comprising a second CH3 domain. In some embodiments, a third polypeptide is fused to the first CH3 domain at a region from position 383 to position 391 of the first CH3 domain according to EU numbering.

In some embodiments, the third polypeptide is linked to a first amino acid residue and a second amino acid residue of the first CH3 domain. In some embodiments, the first and the second amino acid residues are selected from the group consisting of amino acid residues at positions 382, 383, 384, 385, 386, 387, 388, 389, 390, 391, and 392 of the first CH3 domain according to EU numbering.

In one aspect, provided herein is a polypeptide complex comprising a first polypeptide comprising a first CH3 domain, a second polypeptide comprising a second CH3 domain. In some embodiments, a third polypeptide is fused to the first CH3 domain at a region from position 383 to position 385 of the first CH3 domain according to EU numbering.

In some embodiments, the third polypeptide is linked to a first amino acid residue and a second amino acid residue of the first CH3 domain. In some embodiments, the first and the second amino acid residues are selected from the group consisting of amino acid residues at positions 382, 383, 384, 385, and 386 of the first CH3 domain according to EU numbering. In one aspect, provided herein is a polypeptide complex comprising a first polypeptide comprising a first CH3 domain, a second polypeptide comprising a second CH3 domain. In some embodiments, a third polypeptide is fused to the first CH3 domain at a region from position 413 to position 422 of the first CH3 domain according to EU numbering.

In some embodiments, the third polypeptide is linked to a first amino acid residue and a second amino acid residue of the first CH3 domain. In some embodiments, the first and the second amino acid residues are selected from the group consisting of amino acid residues at positions 412, 413, 414, 415, 416, 417, 418, 419, 420, 421, 422, and 423 of the first CH3 domain according to EU numbering.

In one aspect, provided herein is a modified antibody, comprising a first heavy chain polypeptide comprising a first non-native polypeptide sequence; a second heavy chain polypeptide; a first light chain polypeptide; and a second light chain polypeptide. In some embodiments, the first heavy chain polypeptide and the first light chain polypeptide associate with each other, forming a first antigen binding region.

In some embodiments, the second heavy chain polypeptide and the second light chain polypeptide associate with each other, forming a second antigen binding region. In some embodiments, the first non-native polypeptide sequence is fused to the first heavy chain polypeptide at a region from position 344 to position 382 of the first heavy chain polypeptide according to EU numbering.

In some embodiments, the second heavy chain polypeptide comprises a second non-native polypeptide sequence. In some embodiments, the second non-native polypeptide sequence is fused to the second heavy chain polypeptide at a region from position 344 to position 382 of the second heavy chain polypeptide according to EU numbering.

In some embodiments, the first antigen binding region and the second antigen binding region specifically bind to a same antigen.

In some embodiments, the first antigen binding region and the second antigen binding region specifically bind to different antigens.

In some embodiments, the first antigen binding region and/or the second antigen binding region specifically bind to a tumor associated antigen.

In some embodiments, the first non-native polypeptide sequence and/or the second non-native polypeptide sequence (e.g., a scFV or a nanobody) comprising an antigen-binding site that specifically binds to a cell antigen (e.g., an effector cell antigen).

In some embodiments, a functional polypeptide is linked to the C-terminus of the first heavy chain polypeptide.

In some embodiments, a functional polypeptide is linked to the C-terminus of the second heavy chain polypeptide.

In one aspect, provided herein is a fusion polypeptide, comprising a first region comprising CH2, and a first portion of CH3; a second region comprising a non-native polypeptide sequence; a third region comprising a second portion of CH3. In some embodiments, the first portion of CH3 comprises amino acid residues 341-343 of a CH3 domain according to EU numbering, and the second portion of CH3 comprises amino acid residues 383-447 of a CH3 domain according to EU numbering.

In some embodiments, the first portion of CH3 comprises amino acid residues 341-350 of a CH3 domain according to EU numbering, and the second portion of CH3 comprises amino acid residues 363-447 of a CH3 domain according to EU numbering. In some embodiments, the first portion of CH3 comprises amino acid residues 341-357 of a CH3 domain according to EU numbering, and the second portion of CH3 comprises amino acid residues 363-447 of a CH3 domain according to EU numbering.

In some embodiments, the first region further comprises VH and/or CH1.

In one aspect, provided herein is a modified antibody comprising two light chain polypeptides; and two of the fusion heavy chain polypeptides as described herein.

In one aspect, provided herein is a multispecific antibody comprising a first antigen binding site that specifically binds a first antigen, a second antigen binding site that specifically binds to a second antigen. In some embodiments, the second antigen binding site is located within a polypeptide fused to the multispecific antibody. In some embodiments, when the second antigen binding site specifically binds to the second antigen, effector function of the multispecific antibody is inhibited or reduced.

In some embodiments, the multispecific antibody comprises a CH3 domain and the polypeptide is fused to the CH3 domain at a region from position 344 to position 382 of the CH3 domain according to EU numbering.

In some embodiments, the multispecific antibody comprises a CH3 domain and the polypeptide is fused to the CH3 domain at a region from position 351 to position 362 of the CH3 domain according to EU numbering.

In some embodiments, the multispecific antibody comprises a CH3 domain and the polypeptide is fused to the CH3 domain at a region from position 358 to position 362 of the CH3 domain according to EU numbering.

In some embodiments, the first antigen is from a tumor cell and the second antigen is from an effector cell. In some embodiments, the effector cell is a NK cell, a T cell, a B cell, a monocyte, a microphage, a dendritic cell, or a neutrophil.

In some embodiments, when the first antigen binding site specifically binds a first antigen and the second antigen binding site does not bind to the second antigen, the multispecific antibody induces the effector function.

In some embodiments, the effector function is ADCC or ADCP.

In some embodiments, the second antigen binding site is located within the polypeptide comprising a single chain antigen-binding polypeptide (e.g., a scFv or a nanobody).

In some embodiments, the second antigen binding site is located within a scFv or a nanobody that is fused at a CH3 domain of the multispecific antibody.

In some embodiments, the first antigen binding site is a scFv or a nanobody that is linked to N terminal of a CH1 domain or a CH2 domain.

In some embodiments, the first antigen binding site is formed by a VH and a VL.

In some embodiments, the multispecific antibody is a bispecific antibody.

In one aspect, provided herein is a modified antibody comprising an antigen binding site that specifically binds an antigen, and a receptor (e.g., a cytokine receptor) binding site that specifically binds to a receptor, wherein the receptor binding site is located within a polypeptide fused to the modified antibody, wherein when the receptor binding site specifically binds to the receptor, effector function of the modified antibody is inhibited or reduced.

In one aspect, provided herein is a modified antibody comprising an antigen binding site that specifically binds an antigen, and a ligand (e.g., a cytokine ligand or a receptor ligand) binding site that specifically binds to a ligand, wherein the ligand binding site is located within a polypeptide fused to the modified antibody, wherein when the ligand binding site specifically binds to the ligand receptor, effector function of the modified antibody is inhibited.

In one aspect, the disclosure provides a modified antibody comprising an antigen binding site that specifically binds an antigen, a binding polypeptide that specifically interacts with its binding partner, wherein the receptor binding site is located within a polypeptide fused to the modified antibody, wherein when the receptor binding site specifically binds to the receptor, effector function of the modified antibody is inhibited. In some embodiments, the binding polypeptide is a ligand and the binding partner is a receptor for the ligand. In some embodiments, the binding polypeptide is a soluble portion of a receptor and the binding partner is a ligand that specifically interacts with the receptor.

In some embodiments, the modified antibody comprises a CH3 domain and the polypeptide is fused to the CH3 domain at a region from position 344 to position 382 of the CH3 domain according to EU numbering.

In some embodiments, the modified antibody comprises a CH3 domain and the polypeptide is fused to the CH3 domain at a region from position 351 to position 362 of the CH3 domain according to EU numbering.

In some embodiments, the modified antibody comprises a CH3 domain and the polypeptide is fused to the CH3 domain at a region from position 358 to position 362 of the CH3 domain according to EU numbering.

In one aspect, provided herein is a pharmaceutical composition comprising the polypeptide, the polypeptide complex, or the antibody as described herein.

In one aspect, provided herein is a nucleic acid encoding the polypeptide, the polypeptide complex, or the antibody as described herein.

In one aspect, provided herein is a vector comprising the nucleic acid as described herein.

In one aspect, provided herein is a host cell comprising the nucleic acid as described herein.

In one aspect, provided herein is a method for producing a polypeptide, a polypeptide complex, or an antibody, the method comprising culturing the host cell as described herein under conditions suitable to produce the polypeptide, the polypeptide complex, or the antibody.

As used herein, the term “antibody” or “immunoglobulin” refers to any antigen-binding molecule that contains at least one (e.g., one, two, three, four, five, or six) complementary determining region (CDR) (e.g., any of the three CDRs from an immunoglobulin light chain or any of the three CDRs from an immunoglobulin heavy chain) and is capable of specifically binding to an epitope. Non-limiting examples of antibodies include: monoclonal antibodies, polyclonal antibodies, multi-specific antibodies (e.g., bi-specific antibodies), single-chain antibodies, chimeric antibodies, human antibodies, and humanized antibodies. In some embodiments, an antibody contains an Fc region of a human antibody. The term antibody also includes derivatives, e.g., bi-specific antibodies, single-chain antibodies, diabodies, linear antibodies, and multi-specific antibodies formed from antibody fragments.

As used herein, the term "IgG-like" refers to a molecule that is largely similar to an IgG antibody. Non-limiting examples of IgG-like molecules include an IgG antibody with one or more non-native polypeptides that are added to the IgG antibody. In some embodiments, the polypeptide complex comprises or consists of an IgG-like molecule.

As used herein, the term "antigen-binding fragment" refers to a portion of a full-length antibody, wherein the portion of the antibody is capable of specifically binding to an antigen. In some embodiments, the antigen-binding fragment contains at least one variable domain (e.g., a variable domain of a heavy chain or a variable domain of light chain). Non-limiting examples of antibody fragments include, e.g., Fab, Fab', F(ab')2, and Fv fragments.

As used herein, the term "human antibody" refers to an antibody that is encoded by an endogenous nucleic acid (e.g., rearranged human immunoglobulin heavy or light chain locus) present in a human. In some embodiments, a human antibody is collected from a human or produced in a human cell culture (e.g., human hybridoma cells). In some embodiments, a human antibody is produced in a non-human cell (e.g., a mouse or hamster cell line).

As used herein, the term "chimeric antibody" refers to an antibody that contains a sequence present in at least two different antibodies (e.g., antibodies from two different mammalian species such as a human and a mouse antibody). A non-limiting example of a chimeric antibody is an antibody containing the variable domain sequences (e.g., all or part of a light chain and/or heavy chain variable domain sequence) of a non-human (e.g., mouse) antibody and the constant domains of a human antibody. Additional examples of chimeric antibodies are described herein and are known in the art.

As used herein, the term "humanized antibody" refers to a non-human antibody which contains minimal sequence derived from a non-human (e.g., mouse) immunoglobulin and contains sequences derived from a human immunoglobulin. In non-limiting examples, humanized antibodies are human antibodies (recipient antibody) in which hypervariable (e.g., CDR) region residues of the recipient antibody are replaced by hypervariable (e.g., CDR) region residues from a non-human antibody (e.g., a donor antibody), e.g., a mouse, rat, or rabbit antibody, having the desired specificity, affinity, and capacity. In some embodiments, the Fv framework residues of the human immunoglobulin are replaced by corresponding non-human (e.g., mouse) immunoglobulin residues. In some embodiments, humanized antibodies may contain residues which are not found in the recipient antibody or in the donor antibody. These modifications can be made to further refine antibody performance.

As used herein, the term "single-chain antibody" refers to a single polypeptide that contains at least two immunoglobulin variable domains (e.g., a variable domain of a mammalian immunoglobulin heavy chain or light chain) that is capable of specifically binding to an antigen. Non-limiting examples of single-chain antibodies are described herein.

As used herein, the term "multispecific antibody" refers to an antibody that can specifically bind to two or more different antigens or epitopes. In some embodiments, the multispecific antibody is able to crosslink one target molecule (e.g., PD-1) to at least one second target molecule (e.g., CTLA-4) on the surface of a mammalian cell (e.g., a human T-cell). In some embodiments, a multispecific antibody is a bispecific antibody.

As used herein, when referring to an antibody, the phrases "specifically binding" and "specifically binds" mean that the antibody interacts with its target molecule (e.g., PD-1) preferably to other molecules, because the interaction is dependent upon the presence of a particular structure (i.e., the antigenic determinant or epitope) on the target molecule; in other words, the reagent is recognizing and binding to molecules that include a specific structure rather than to all molecules in general. An antibody that specifically binds to the target molecule may be referred to as a target-specific antibody. For example, an antibody that specifically binds to a PD-1 molecule may be referred to as a PD-1-specific antibody or an anti-PD-1 antibody.

As used herein, the terms "subject" and "patient" are used interchangeably throughout the specification and describe an animal, human or non-human, to whom treatment according to the methods of the present invention is provided. Veterinary and non-veterinary applications are contemplated by the present invention. Human patients can be adult humans or juvenile humans (e.g., humans below the age of 18 years old). In addition to humans, patients include but are not limited to mice, rats, hamsters, guinea-pigs, rabbits, ferrets, cats, dogs, and primates. Included are, for example, non-human primates (e.g., monkey, chimpanzee, gorilla, and the like), rodents (e.g., rats, mice, gerbils, hamsters, ferrets, rabbits), lagomorphs, swine (e.g., pig, miniature pig), equine, canine, feline, bovine, and other domestic, farm, and zoo animals.

As used herein, the terms "polypeptide," "peptide," and "protein" are used interchangeably to refer to polymers of amino acids of any length of at least two amino acids.

As used herein, the term "polypeptide complex" refers to a complex comprising one or more polypeptides that are associated to perform certain functions. In certain embodiments, the polypeptides are antibody heavy chains and/or light chains or derived from antibodies.

As used herein, the terms "polynucleotide," "nucleic acid molecule," and "nucleic acid sequence" are used interchangeably herein to refer to polymers of nucleotides of any length of at least two nucleotides, and include, without limitation, DNA, RNA, DNA/RNA hybrids, and modifications thereof.

As used herein, the term "fusion" or "fused" when used with respect to amino acid sequences (e.g. peptide, polypeptide or protein) refers to combination of two or more amino acid sequences, for example by chemical bonding or recombinant means, into a single amino acid sequence which does not exist naturally. A fusion amino acid sequence can be produced by genetic recombination of two encoding polynucleotide sequences, and can be expressed by a method of introducing a construct containing the recombinant polynucleotides into a host cell.

As used herein, the term "linked" when used with respect to amino acid sequences (e.g. peptide, polypeptide or protein) refers to combination of two or more amino acid sequences by chemical bonds (e.g., a peptide bond, a disulfide bond, bis-sulfone linker).

As used herein, the term "full length antibody" refers to an antibody that has an intact structure as compared to a wildtype antibody. In some embodiments, a full length antibody is an antibody having two full-length heavy chains and two full length light chains.

As used herein, the term "about" or "approximately" refers to a quantity, level, value, number, frequency, percentage, dimension, size, amount, weight or length that varies by as much as 30%, 25%, 20%, 25%, 10%, 9%, 8%, 7%, 6%, 5%, 4%, 3%, 2% or 1% to a reference quantity, level, value, number, frequency, percentage, dimension, size, amount, weight or length. In some embodiments, the terms "about" or "approximately" when preceding a numerical value or a level indicates the value plus or minus a range of 15%, 10%, 5%, or 1%. The term "about the same level" indicates the level plus or minus a range of 15%, 10%, 5%, or 1%.

As used herein, the term "operably link" or "operably linked" refers to a juxtaposition, with or without a spacer or linker sequence, of two or more biological sequences of interest in such a way that they are in a relationship permitting them to function in an intended manner. When used with respect to polypeptides, it is intended to mean that the polypeptide sequences are linked in such a way that permits the linked product to have the intended biological function. For example, an antibody variable region may be operably linked to a constant region so as to provide for a stable product with antigen-binding activity. The term can also be used with respect to polynucleotides. For one instance, when a polynucleotide encoding a polypeptide is operably linked to a regulatory sequence (e.g., promoter, enhancer, silencer sequence, etc.), it is intended to mean that the polynucleotide sequences are linked in such a way that permits regulated expression of the polypeptide from the polynucleotide.

As used herein, the term "binding partner" refers to a member of a pair of molecules capable of recognizing a specific structural aspect of another molecule, wherein the binding partners interact with each other by means of a specific, noncovalent or covalent interaction. Examples of such binding partners and corresponding molecules or compositions include, but are not limited to, any of the class of immune-type binding pairs, such as antigen/antibody; and also any of the class of nonimmune-type binding pairs, such as ligand/receptor, biotin/avidin, biotin/streptavidin, digoxigenin/anti-digoxigenin F(ab')2, folic acid/folate binding protein, complementary nucleic acid segments, protein A or G/immunoglobulins, lectin/carbohydrate, substrate/enzyme, inhibitor/enzyme, or virus/cellular receptor.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 4 is a sequence alignment of human IgG1 heavy chain constant regions (hIgG1-CH; SEQ ID NO: 1), human IgG2 heavy chain constant regions (hIgG2-CH; SEQ ID NO: 2) and human IgG4 heavy chain constant regions (hIgG4-CH; SEQ ID NO: 3). CH2 region is marked by dash lines and CH3 region is marked by solid lines.

FIG. 8A summarizes binding affinities of PDL1-avelumab, PDL1-mIL7-3A-mIFNa4, and PDL1-mIL7-3A against various Fc receptors.

FIG. 8B summarizes binding affinities of PD1-PL1-3F2-FV3A-IgG1, AB-IgG1, PDL1-C40-6A7-FV3A-IgG4, and AB-IgG4 against various Fc receptors.

FIG. 11A is a gel image showing 3F2-hIL7-3A in Lane 10.

FIG. 11B is a table showing lane number, corresponding protein name and theoretical molecular weight (MW).

FIG. 11C is the SEC-HPLC result of 3F2-hIL7-3A.

FIG. 12A is a gel image showing 3F2-hIL7-3A-mIFNa4 in Lane 8.

FIG. 12B is a table showing lane number, corresponding protein name, theoretical molecular weight (MW) and apparent molecular weight.

FIG. 12C is the SEC-HPLC result of 3F2-hIL7-3A-mIFNa4.

FIG. 15A is a gel image showing 3F2-hIL21-3A in Lane 1.

FIG. 15B is a table showing lane numbers and the corresponding protein name.

FIG. 15C is the SEC-HPLC result of 3F2-hIL21-3A.

FIG. 16A is a gel image showing 3F2-hIL21-3A-mIFNa4 in Lane 14.

FIG. 16B is a table showing lane number and corresponding protein name.

FIG. 16C is the SEC-HPLC result of 3F2-hIL21-3A-mIFNa4.

FIG. 18A is a gel image showing PDL1-TGFbR2-3A in Lane 1.

FIG. 18B is a table showing lane numbers, corresponding protein names, theoretical molecular weights (MW) and apparent molecular weights.

FIG. 18C is the SEC-HPLC result of PDL1-TGFbR2-3A.

FIGS. 20A-20D shows different modified immunoglobulin formats.

FIG. 33 shows a sequence alignment result between human IgD, human IgG4, human IgG3, human IgG1, human IgG2, human IgA, and human IgM. The asterisk mark ("*") indicates positions which have a single, fully conserved residue. The period mark (".") indicates conservation between groups of weakly similar properties—roughly equivalent to scoring ≤0.5 and >0 in the Gonnet PAM 250 matrix. The colon mark (":") indicates conservation between groups of strongly similar properties—roughly equivalent to scoring >0.5 in the Gonnet PAM 250 matrix.

FIG. 34 shows a sequence alignment result between human IgG4, human IgG3, human IgG1, and human IgG2.

FIG. 35 shows a sequence alignment result between rat IgG2C, mouse IgG3, human IgG1, rat IgG1, rat IgG2A, mouse IgG1, mouse IgG2B, rat IgG2B, mouse IgG2A, and mouse IgG2C.

FIG. 36 shows a sequence alignment result between human IgG1, monkey IgG3, monkey IgG1, and monkey IgG2.

FIG. 37 shows a sequence alignment result between human IgG1, dog IgG2, dog IgG3, dog IgG1, and dog IgG4.

FIG. 39A shows a schematic structure of 3F2-mIL12-3A-mIFNa4.

FIG. 39B shows schematic diagrams of plasmids encoding the modified heavy chain, light chain and IL12b of 3F2-mIL12-3A-mIFNa4. L indicates a linker sequence.

FIG. 48 provides several sequences discussed in the disclosure.

FIG. 49 provides CDR sequences for anti-CTLA4 antibody 4G12, anti-OX40 antibody 9H3, anti-PD-L1 antibody 3F2 and anti-PD-1 antibody 1A7 according to Kabat numbering.

FIG. 50 provides CDR sequences for anti-CTLA4 antibody 4G12, anti-OX40 antibody 9H3, anti-PD-L1 antibody 3F2 and anti-PD-1 antibody 1A7 according to Chothia numbering.

DETAILED DESCRIPTION

Figure 1:
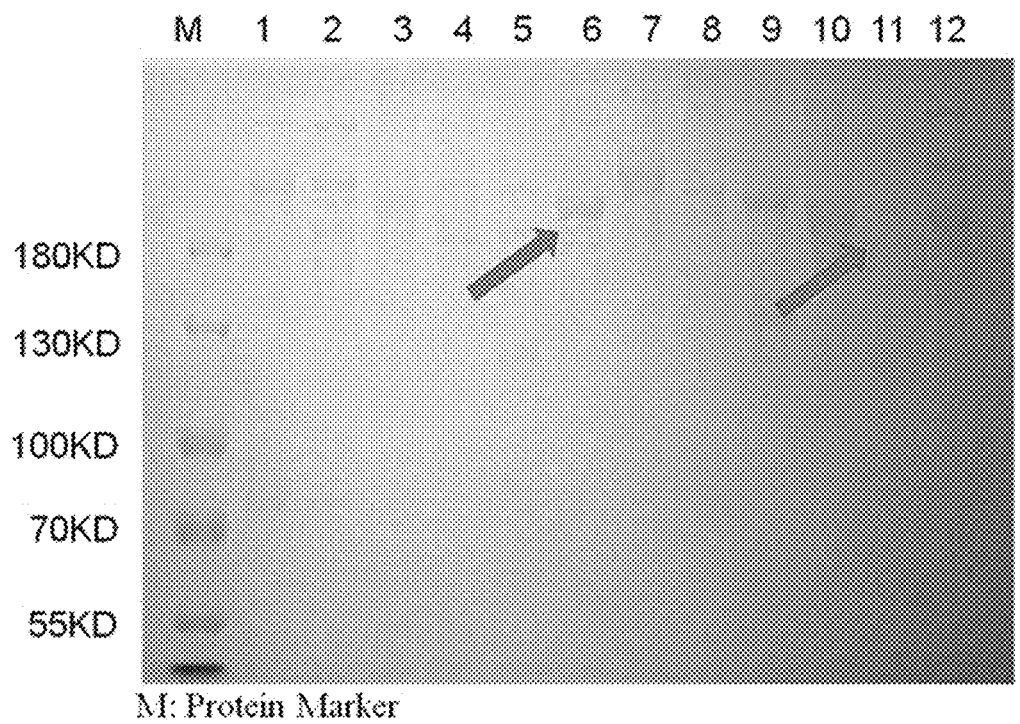
FIG. 1 is an image of electrophoresis showing PDL1-mIL7-HC in Lane 6 and PDL1-mIL7-LC in Lane 11.

Bispecific antibodies are growing to be the new category of therapeutic antibodies. They can bind two different targets or two different epitopes on a target, creating additive or synergistic effect superior to the effect of individual antibodies. Immunocytokines are antibody-cytokine fusion proteins, with the potential to preferentially localize on tumor lesions and to activate anticancer immunity at the site of disease. Many existing manufacturing approaches for bispecific antibodies and immunocytokines have the problems of low efficiency, instability, and aggregation.

The present disclosure shows that immunoglobulins with a fusion polypeptide that is fused to a selected region in the Fc region is very stable and can be stably expressed at a high level. In addition, the fusion of the polypeptide into the immunoglobulins does not affect the binding affinity of the immunoglobulins or the biological activity of the fused polypeptide. Moreover, the modified immunoglobulins are compatible with knobs-in-holes (KIH) modifications and can be further modified by many other antibody-engineering techniques. This modification provides an improved antibody format that can be used to generate various bispecific antibodies, multi-specific antibodies, and immunocytokines.

Modified Immunoglobulins

The present disclosure provides modified immunoglobulins, wherein a polypeptide is fused to a selected region in the Fc region of the immunoglobulins. In one aspect, the disclosure provides a modified Fc region, wherein a functional protein is fused to the selected region in the Fc region.

In general, immunoglobulins (also called antibodies) are made up of two classes of polypeptide chains, light chains and heavy chains. A non-limiting examples of antibody of the present disclosure can be an intact, four immunoglobulin chain antibody comprising two heavy chains and two light chains.

The heavy chains, which each contain one variable domain (or variable region, VH) and multiple constant domains (or constant regions), bind to one another via disulfide bonding within their constant domains to form the "stem" of the antibody. The light chains, which each contain one variable domain (or variable region, VL) and one constant domain (or constant region), each bind to one heavy chain via disulfide binding. The variable region of each light chain is aligned with the variable region of the heavy chain to which it is bound. The variable regions of both the light chains and heavy chains contain three hypervariable regions sandwiched between more conserved framework regions (FR). These hypervariable regions, known as the complementary determining regions (CDRs), form loops that comprise the antigen binding surface of the antibody. The four framework regions largely adopt a beta-sheet conformation and the CDRs form loops connecting the beta-sheet structure, and in some cases forming part of, the beta-sheet structure. The CDRs in each chain are held in close proximity by the framework regions and, with the CDRs from the other chain, contribute to the formation of the antigen-binding region.

The heavy chain has four to five domains, depending on the isotype, including a variable (VH) domain and several constant (CH) domains: three CH domains (CH1, CH2, CH3) in IgG, IgA and IgD and four CH domains (CH1, CH2, CH3, CH4) in IgM and IgE. The antigen-binding fragment (Fab) is formed by the light chain (VL and CL) and the first two domains of the heavy chain (VH and CH1) and is specifically involved in antigen binding. The Ig Fc (fragment crystallizable) portion is formed by the CH2 and CH3 constant domains, and optionally with CH4 constant domain, from each heavy chain. The Fc region ensures that each antibody generates an appropriate immune response for a given antigen, by binding to a specific class of Fc receptors, and other immune molecules, such as complement proteins. By doing this, it mediates different physiological effects, including recognition of opsonized particles (binding to FcγR), lysis of cells (binding to complement), and degranulation of mast cells, basophils, and eosinophils (binding to FcεR).

All domains in immunoglobulins have a similar structure and are constructed from two β sheets. The sheets are linked by a disulfide bridge and together form a roughly barrel-shaped structure, known as a β barrel. The distinctive folded structure of the immunoglobulin protein domain is known as the immunoglobulin fold. The constant domains are built up from seven β strands arranged such that four strands form one β sheet and three strands form a second sheet. The loops connecting the β strands are relatively short and, as a result, a majority of the residues of the domain are contained in the two β sheets. These strands include A-strand, B-strand, C-strand, D-strand, E-strand, F-Strand, and G-strand. The sequence connecting the β strands include AB-turn, BC-loop, CD-strand, DE-turn, and EF-turn. A detailed description of the structure of the constant domain can be found e.g., in Lefranc et al., "IMGT® and 30 years of Immunoinformatics Insight in antibody V and C domain structure and function." Antibodies 8.2 (2019): 29, which is incorporated herein by reference in its entirety.

The present disclosure demonstrates that a non-native polypeptide can be fused to a particular region in the Fc region of the immunoglobulins. As used herein, a "non-native" polypeptide refers to a polypeptide which cannot be found in the Fc region of a wildtype immunoglobulin. This particular region in the present disclosure is referred as the "3A site." The 3A site is located in the CH3 domain, and starts from position 344 to position 382 (EU numbering). The fusion of a non-native polypeptide can provide superior results. As compared to some other modified immunoglobulins, the immunoglobulins with this modification is very stable, and the immunoglobulins with a non-native polypeptide fused at this site can be expressed at a high level and they do not form aggregates. The property of this fusion site is also unexpected, as the 3A site is located in the A-strand and B-strand, which seems to be important for the function and stability of the CH3 domain. The results in the present disclosure demonstrated that the immunoglobulins have a much higher tolerance for non-native sequence at the 3A site as compared to some other locations in the CH3 domain.

Figure 21:
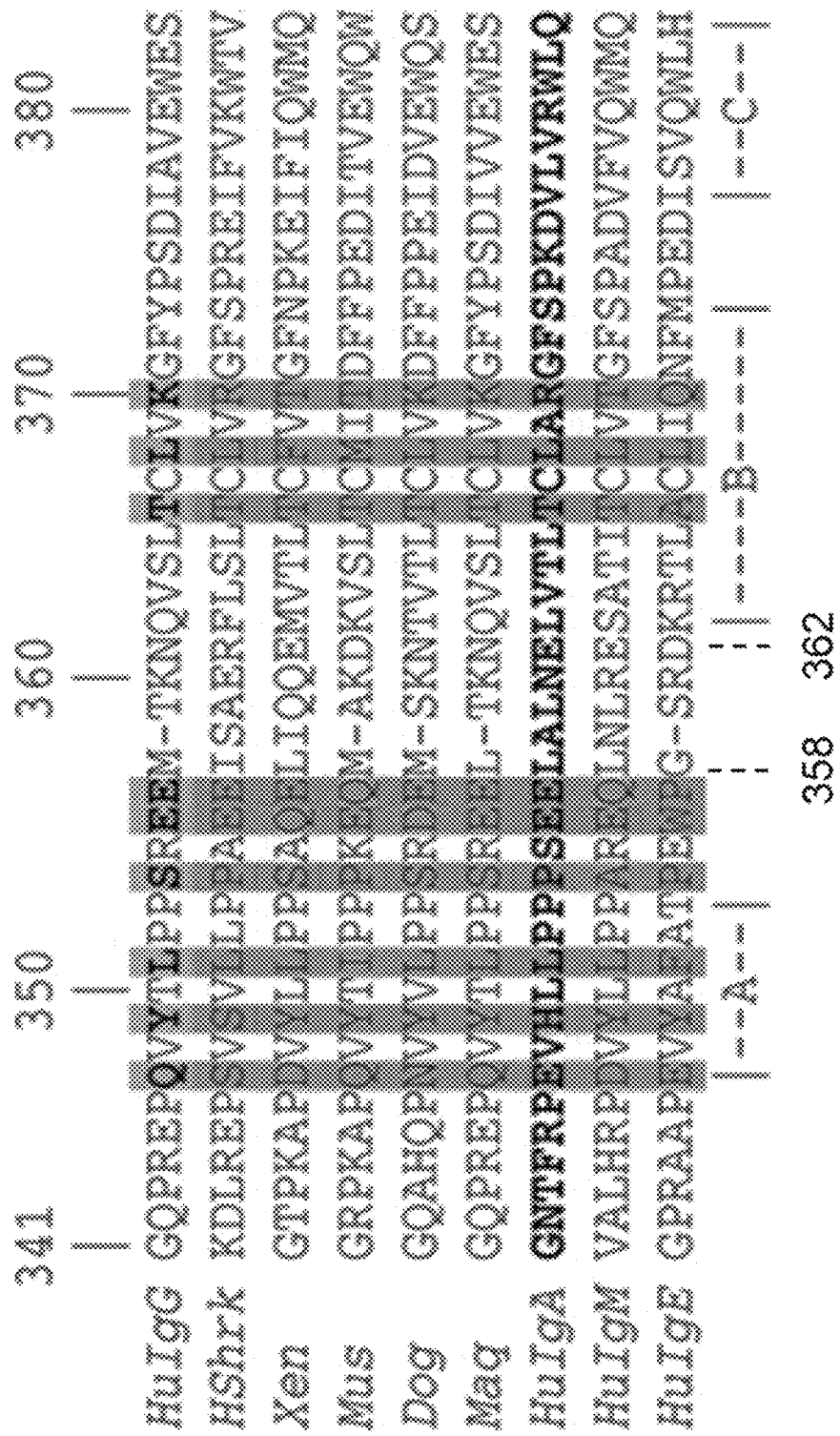
FIG. 21 shows sequence alignment results for a portion of CH3 domain of Human IgG (HuIgG), human IgA (HuIgA), human IgM (HuIgM), human IgE (HuIgE), horn shark (HShrk; *Heterodontus franscisci*), *Xenopus laevis* (Xen), *Mus musculus* (Mus), *Canis familiaris* (dog), and rhesus monkey (Maq; *Macaca* mulatta).
Figure 22:
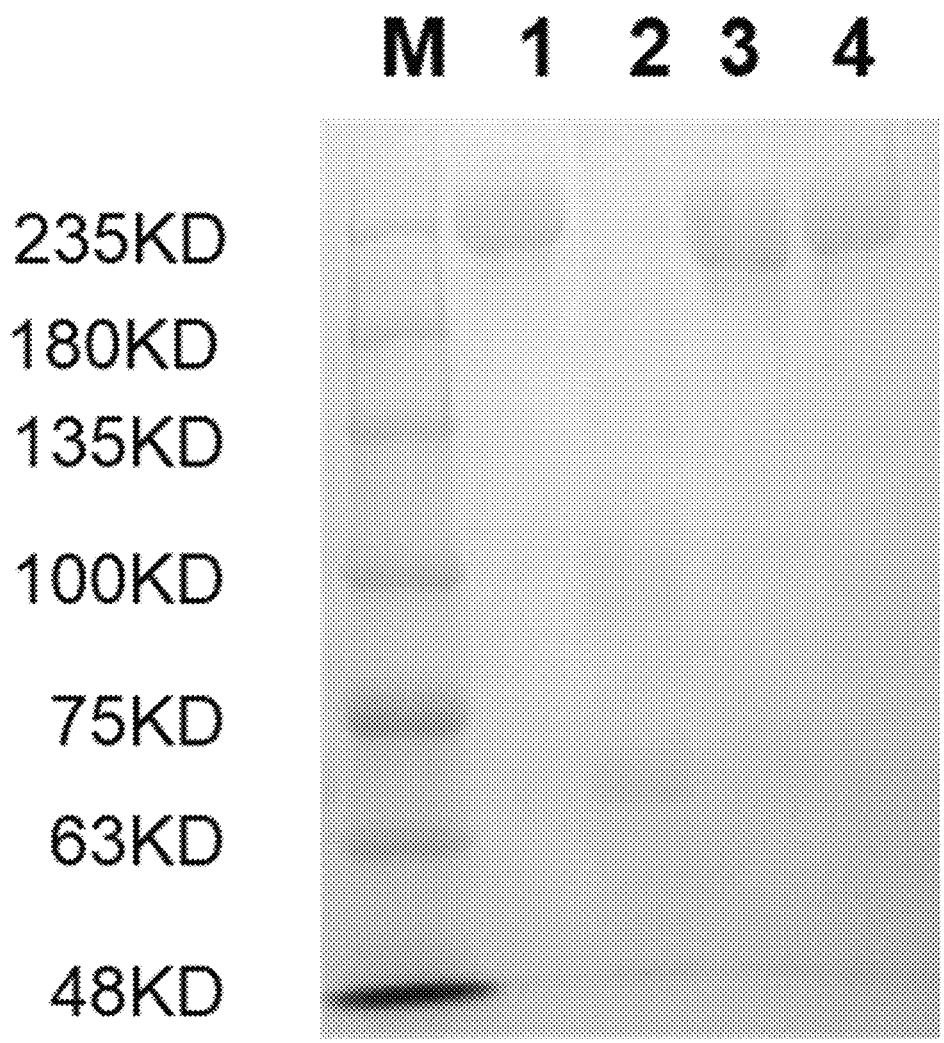
FIG. 22 is a gel image showing purified PDL1-TGFbR2-3A (lane 1), PDL1-TGFbR2-3B (lane 2), PDL1-TGFbR2-3C (lane 3), and PDL1-TGFbR2-3D (lane 4). M is protein marker.
Figure 23:
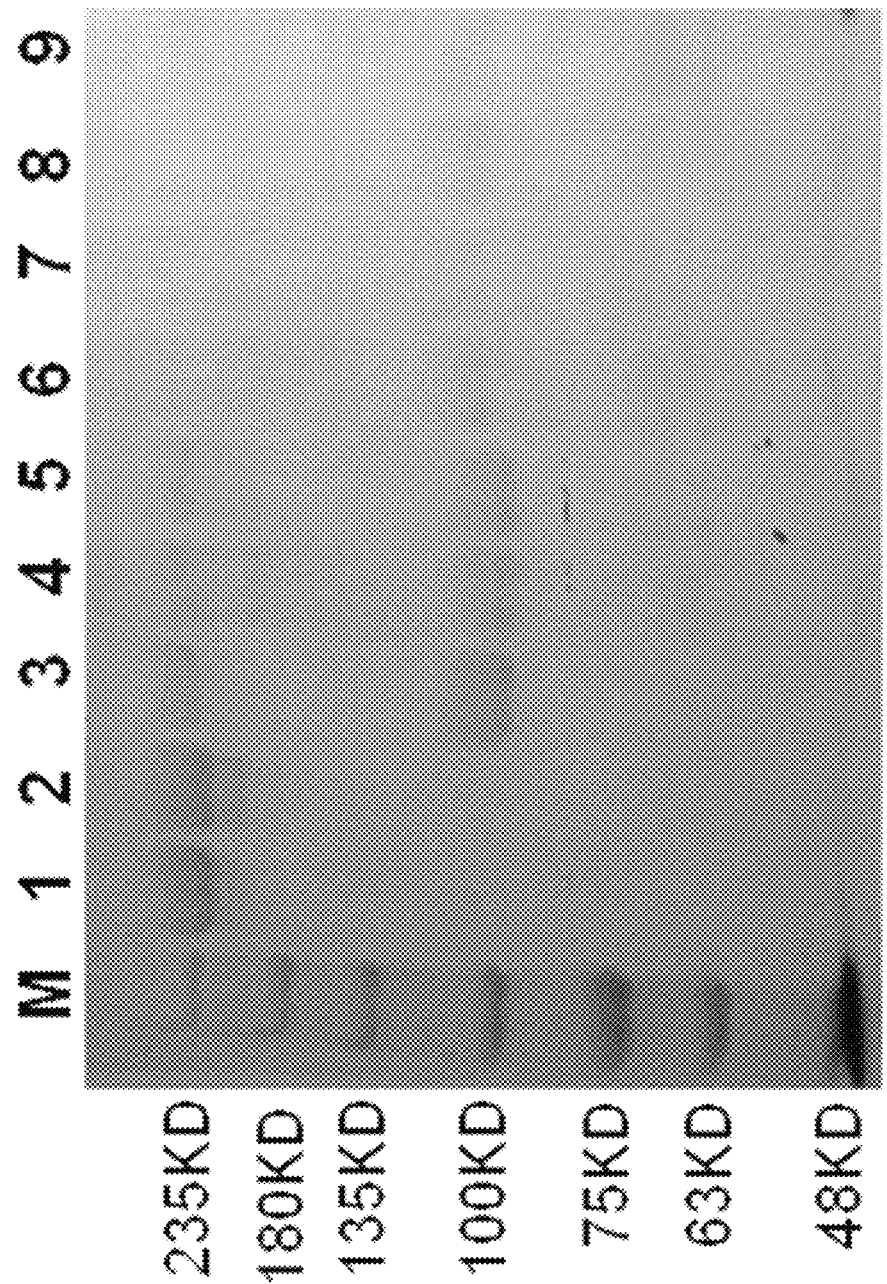
FIG. 23 is a gel image showing purified PDL1-TGFbR2-3A (lane 1), PDL1-TGFbR2-3A-IgG4 (lane 2), PDL1-TGFbR2-3AF1 (lane 3), PDL1-TGFbR2-3AF2 (lane 4), PDL1-TGFbR2-3AF3 (lane 5), PDL1-TGFbR2-3AR1 (lane 6), PDL1-TGFbR2-3AR2 (lane 7), PDL1-TGFbR2-3AR3 (lane 8), and PDL1-TGFbR2-3AR4 (lane 9). M is protein marker.
Figure 24:
FIG. 24 is a gel image showing purified PDL1-hIL21-3A-IgG4 (lane 1), PDL1-hIL21-3AF1 (lane 2), PDL1-hIL21-3AF2 (lane 3), PDL1-hIL21-3AF3 (lane 4), PDL1-hIL21-3AR1 (lane 5), PDL1-hIL21-3AR2 (lane 6), PDL1-hIL21-3AR3 (lane 7), and PDL1-hIL21-3AR4 (lane 8). M is protein marker.

Sequence alignment of the CH3 domains show that the 3A site is relatively conserved between species and between different immunoglobulins, as shown in FIG. 21. Thus, similar modifications can be made to antibodies from different animals, including human and non-human animals. The non-human animals include e.g., mice, rats, hamsters, guinea-pigs, rabbits, ferrets, cats, dogs, and primates. In some embodiments, the antibodies are from non-human primates (e.g., monkey, chimpanzee, gorilla, and the like), rodents (e.g., rats, mice, gerbils, hamsters, ferrets, rabbits), lagomorphs, swine (e.g., pig, miniature pig), equine, canine, feline, bovine, and other domestic, farm, and zoo animals. In some embodiments, the modification is made to antibodies from human, rodent (e.g., rat, mouse), camelid, dog, horn shark, *Xenopus laevis*, monkey (e.g., rhesus monkey), cat, or rabbit. In some embodiments, the modification is made to IgG, IgM, IgD, IgE, or IgA. Thus, in one aspect, the disclosure provides a modified Fc region or a polypeptide complex comprising a first polypeptide comprising a first CH3 domain, a second polypeptide comprising a second CH3 domain. In some embodiments, the CH3 domain is a heavy chain CH3 domain. The two polypeptides interact with each other and can form a homodimer or a heterodimer. One or two non-native polypeptides can be fused to the heavy chain CH3 domains of the one or two polypeptides at the 3A site. The 3A site starts from position 344 to position 382 (EU numbering). In some embodiments, the non-native polypeptide replaces 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, or 39 amino acids at the fusion site or is inserted between any of the two amino acids at this fusion site. In some embodiments, when a non-native polypeptide is inserted between two non-consecutive amino acids at the fusion site, it also replaces all amino acids between the two non-consecutive amino acids. In some embodiments, the non-native polypeptide is linked to two amino acid residues of the heavy chain CH3 domain of the modified immunoglobulin. The two amino acid residues can be consecutive or non-consecutive.

In some embodiments, the polypeptide complex comprises a first polypeptide comprising a first heavy chain CH3 domain, a second polypeptide comprising a second heavy chain CH3 domain, wherein a third polypeptide is fused to the first heavy chain CH3 domain at a region from position 344 to position 382 of the first heavy chain CH3 domain according to EU numbering. In some embodiments, the polypeptide complex comprises a first heavy chain polypeptide comprising a first heavy chain CH3 domain, a second heavy chain polypeptide comprising a second heavy chain CH3 domain, wherein a third polypeptide is fused to the first heavy chain CH3 domain at a region from position 344 to position 382 of the first heavy chain CH3 domain according to EU numbering.

In some embodiments, the non-native polypeptide is linked to two amino acid residues of the heavy chain CH3 domain of the modified immunoglobulin. In some embodiments, the two residues are selected from any two of positions 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, and 383 of the heavy chain CH3 domain according to EU numbering. The non-native polypeptide is linked to a starting amino acid and an ending amino acid in the heavy chain CH3 domain. The present disclosure also provides all different combinations of the starting amino acid and the ending amino acid at the 3A site. For example, if the non-native polypeptide is linked to the amino acid residues located at position 343 and 383, the entire 3A site (positions 344-382) is replaced by the non-native polypeptide. If the non-native polypeptide is linked to two consecutive amino acid residues, e.g., located at position 357 and 358, the non-native polypeptide is inserted between the two consecutive amino acid residues. The specific combinations of any two amino residues at positions 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, and 383 of the heavy chain CH3 domain (EU numbering) are provided.

In some embodiments, the starting amino acid is selected from 343, 344, 345, 346, 347, 348, 349, 350, 351, 352, 353, 354, 355, or 356. In some embodiments, the starting amino acid is selected from 357, 358, 359, 360, 361, or 362. In some embodiments, the ending amino acid is selected from 358, 359, 360, 361, 362, 363, 364, 365, 366, 367, 368, 369, 370, 371, 372, 373, 374, 375, 376, 377, 378, 379, 380, 381, 382, or 383. In some embodiments, the ending amino acid is selected from 358, 359, 360, 361, 362, or 363.

In some embodiments, the fusion site is located at a region from position 351 to 362 (EU numbering). In some embodiments, the non-native polypeptide replaces 1, 2, 3, 4, 5, 6, 7, 8, 9, 10, 11, 12, or all amino acids (e.g., 351-362) at the fusion site, or is inserted between any of the two amino acids at this fusion site, e.g., inserted at the position 351-352, 352-353, 353-354, 354-355, 355-356, 356-357, 357-358, 358-359, 359-360, 360-361, or 361-362.

In some embodiments, the two residues are selected from any two of positions 350, 351, 352, 353, 354, 355, 356, 357, 358, 359, 360, 361, 362, and 363 of the heavy chain CH3 domain according to EU numbering. The combinations of these starting amino acids and the ending amino acids are provided in the table below. For example, if the non-native polypeptide is linked to the amino acid residues located at position 350 and 363, the amino acids in this fusion site (positions 351-362) are replaced by the non-native polypeptide. If the non-native polypeptide is linked to two consecutive amino acid residues, e.g., located at position 350 and 351, the non-native polypeptide is inserted between the two consecutive amino acid residues.

TABLE 1

| Start | End | Comment |
|---|---|---|
| 350 | 351 | Insert |
| 350 | 352 | insert/delete |
| 350 | 353 | insert/delete |
| 350 | 354 | Insert/delete |
| 350 | 355 | Insert/delete |
| 350 | 356 | Insert/delete |
| 350 | 357 | Insert/delete |
| 350 | 358 | Insert/delete |
| 350 | 359 | Insert/delete |
| 350 | 360 | Insert/delete |
| 350 | 361 | Insert/delete |
| 350 | 362 | Insert/delete |
| 350 | 363 | Insert/delete |
| 351 | 352 | Insertion |
| 351 | 353 | Insert/delete |
| 351 | 354 | Insert/delete |
| 351 | 355 | Insert/delete |
| 351 | 356 | Insert/delete |
| 351 | 357 | Insert/delete |
| 351 | 358 | Insert/delete |
| 351 | 359 | Insert/delete |
| 351 | 360 | Insert/delete |
| 351 | 361 | Insert/delete |
| 351 | 362 | Insert/delete |
| 351 | 363 | Insert/delete |
| 352 | 353 | Insertion |
| 352 | 354 | Insert/delete |
| 352 | 355 | Insert/delete |
| 352 | 356 | Insert/delete |
| 352 | 357 | Insert/delete |
| 352 | 358 | Insert/delete |
| 352 | 359 | Insert/delete |
| 352 | 360 | Insert/delete |
| 352 | 361 | Insert/delete |
| 352 | 362 | Insert/delete |
| 352 | 363 | Insert/delete |
| 353 | 354 | Insertion |
| 353 | 355 | Insert/delete |
| 353 | 356 | Insert/delete |
| 353 | 357 | Insert/delete |
| 353 | 358 | Insert/delete |
| 353 | 359 | Insert/delete |
| 353 | 360 | Insert/delete |
| 353 | 361 | Insert/delete |
| 353 | 362 | Insert/delete |
| 353 | 363 | Insert/delete |
| 354 | 355 | Insertion |
| 354 | 356 | Insert/delete |
| 354 | 357 | Insert/delete |
| 354 | 358 | Insert/delete |
| 354 | 359 | Insert/delete |
| 354 | 360 | Insert/delete |
| 354 | 361 | Insert/delete |
| 354 | 362 | Insert/delete |
| 354 | 363 | Insert/delete |
| 355 | 356 | Insertion |
| 355 | 357 | Insert/delete |
| 355 | 358 | Insert/delete |
| 355 | 359 | Insert/delete |
| 355 | 360 | Insert/delete |
| 355 | 361 | Insert/delete |
| 355 | 362 | Insert/delete |
| 355 | 363 | Insert/delete |
| 356 | 357 | Insertion |

TABLE 1-continued

| Start | End | Comment |
|---|---|---|
| 356 | 358 | Insert/delete |
| 356 | 359 | Insert/delete |
| 356 | 360 | Insert/delete |
| 356 | 361 | Insert/delete |
| 356 | 362 | Insert/delete |
| 356 | 363 | Insert/delete |
| 357 | 358 | Insertion |
| 357 | 359 | Insert/delete |
| 357 | 360 | Insert/delete |
| 357 | 361 | Insert/delete |
| 357 | 362 | Insert/delete |
| 357 | 363 | Insert/delete |
| 358 | 359 | Insertion |
| 358 | 360 | Insert/delete |
| 358 | 361 | Insert/delete |
| 358 | 362 | Insert/delete |
| 358 | 363 | Insert/delete |
| 359 | 360 | Insertion |
| 359 | 361 | Insert/delete |
| 359 | 362 | Insert/delete |
| 359 | 363 | Insert/delete |
| 360 | 361 | Insertion |
| 360 | 362 | Insert/delete |
| 360 | 363 | Insert/delete |
| 361 | 362 | Insertion |
| 361 | 363 | Insert/delete |
| 362 | 363 | Insert |

In some embodiments, the fusion site is located at a region from 358 to 362 (EU numbering). In some embodiments, the non-native polypeptide replaces 1, 2, 3, 4, 5 or all amino acids at the fusion site or is inserted between any of the two amino acids at this fusion site, e.g., inserted at the position 358-359, 359-360, 360-361, or 361-362.

In some embodiments, the two residues are selected from any two of positions 357, 358, 359, 360, 361, 362, and 363 of the heavy chain CH3 domain according to EU numbering. The combinations of these starting amino acids and the ending amino acids are provided in the table below.

TABLE 2

| Starting | Ending | Comment |
|---|---|---|
| 357 | 358 | Insert |
| 357 | 359 | Insert/delete |
| 357 | 360 | Insert/delete |
| 357 | 361 | Insert/delete |
| 357 | 362 | Insert/delete |
| 357 | 363 | Insert/delete |
| 358 | 359 | Insert |
| 358 | 360 | Insert/delete |
| 358 | 361 | Insert/delete |
| 358 | 362 | Insert/delete |
| 358 | 363 | Insert/delete |
| 359 | 360 | Insert |
| 359 | 361 | Insert/delete |
| 359 | 362 | Insert/delete |
| 359 | 363 | Insert/delete |
| 360 | 361 | Insert |
| 360 | 362 | Insert/delete |
| 360 | 363 | Insert/delete |
| 361 | 362 | Insert |
| 361 | 363 | Insert/delete |
| 362 | 363 | Insert |

Thus, in some embodiments, the two residues are positions 357 and 358 of the heavy chain CH3 domain according to EU numbering. In some embodiments, the two residues are positions 357 and 359 of the heavy chain CH3 domain according to EU numbering. In some embodiments, the two residues are positions 357 and 360 of the heavy chain CH3 domain according to EU numbering. In some embodiments, the two residues are positions 357 and 361 of the heavy chain CH3 domain according to EU numbering. In some embodiments, the two residues are positions 357 and 362 of the heavy chain CH3 domain according to EU numbering. In some embodiments, the two residues are positions 357 and 363 of the heavy chain CH3 domain according to EU numbering. In some embodiments, the two residues are positions 358 and 359 of the heavy chain CH3 domain according to EU numbering. In some embodiments, the two residues are positions 358 and 360 of the heavy chain CH3 domain according to EU numbering. In some embodiments, the two residues are positions 358 and 361 of the heavy chain CH3 domain according to EU numbering. In some embodiments, the two residues are positions 358 and 362 of the heavy chain CH3 domain according to EU numbering. In some embodiments, the two residues are positions 358 and 363 of the heavy chain CH3 domain according to EU numbering. In some embodiments, the two residues are positions 359 and 360 of the heavy chain CH3 domain according to EU numbering. In some embodiments, the two residues are positions 359 and 361 of the heavy chain CH3 domain according to EU numbering. In some embodiments, the two residues are positions 359 and 362 of the heavy chain CH3 domain according to EU numbering. In some embodiments, the two residues are positions 359 and 363 of the heavy chain CH3 domain according to EU numbering. In some embodiments, the two residues are positions 360 and 361 of the heavy chain CH3 domain according to EU numbering. In some embodiments, the two residues are positions 360 and 362 of the heavy chain CH3 domain according to EU numbering. In some embodiments, the two residues are positions 360 and 363 of the heavy chain CH3 domain according to EU numbering. In some embodiments, the two residues are positions 361 and 362 of the heavy chain CH3 domain according to EU numbering. In some embodiments, the two residues are positions 361 and 363 of the heavy chain CH3 domain according to EU numbering. In some embodiments, the two residues are positions 362 and 363 of the heavy chain CH3 domain according to EU numbering.

The fusion of the non-native polypeptide at the 3A site does not interfere with the antigen-binding site of the immunoglobulins. In addition, the fused non-native polypeptide can maintain its bioactivity. Moreover, the modification at the 3A site does not significantly affect the binding affinity of Fc to FcγRIIA, FcγRIIIA, FcγRIIIB, or FcRn receptors. In some embodiments, the binding affinities of the modified Fc to FcγRIIA, FcγRIIIA, FcγRIIIB, or FcRn receptors are about the same as compared to the same immunoglobulins before any modifications. In some embodiments, the binding affinities of the modified Fc to FcγRIIA, FcγRIIIA, FcγRIIIB, or FcRn receptors are higher (e.g., at least 10%, 20%, 30%, 40%, or 50%) as compared to the same immunoglobulins before any modifications. In some embodiments, the binding affinities of the modified Fc to FcγRIIA, FcγRIIIA, FcγRIIIB, or FcRn receptors are lower (e.g., no more than 10%, 20%, 30%, 40%, or 50% lower) as compared to the same immunoglobulins before any modifications.

In some embodiments, the modified immunoglobulin has at least one of antibody-dependent cell cytotoxicity (ADCC), antibody-dependent cellular phagocytosis (ADCP), complement dependent cytotoxicity (CDC) or apoptotic activity. In some embodiments, when the fused polypeptide at the 3A site interacts with a target protein, the Fc will not bind FcγRIIA, FcγRIIIA, or FcγRIIIB receptors because of steric effects. Thus, when the fused polypeptide at the 3A site interacts with a target protein, the ADCC, ADCP, and CDC effects are reduced. This can provide several advantages. For example, for a bispecific antibody, it can be designed to target a tumor associated antigen and an immune cell antigen. If the bispecific antibody just binds to an immune cell antigen, the ADCC, ADCP, and CDC effects would be undesirable as the effects will kill the immune cells. However, this problem can be easily solved by the modified immunoglobulin format. In some embodiments, the antigen binding site can bind to the tumor antigen, and a scFv can be introduced to the fusion site to target an immune cell antigen. Once the modified immunoglobulin binds to the tumor cell, and in the same time the scFv at the 3A site does not bind to an immune cell, it can trigger ADCC, ADCP, and CDC effects. But when the scFv at the 3A site binds to the immune cell, the undesirable ADCC, ADCP, and CDC effects can be reduced or eliminated.

Moreover, the fusion of the non-native polypeptide at the 3A site does not interfere with the function of the non-native polypeptide. Particularly, the non-native polypeptide in the modified immunoglobulins can have about the same or even a higher level of biological activity as compared to an isolated non-native polypeptide. In some embodiments, the biological activity of the non-native polypeptide in the modified immunoglobulins can be at least or about 85%, 90%, 95%, or 100% of the isolated non-native polypeptide.

The fusion of the non-native polypeptide at the 3A site does not interfere with the binding affinity of the modified immunoglobulins. Particularly, the modified immunoglobulins can have about the same or even a higher level of binding affinity as compared to the parent immunoglobulins. As used herein, the term "parent" molecule refers to a molecule before any non-native polypeptide as described herein is fused to the molecule or any other modifications are made to the molecule. In some embodiments, the binding affinity can be at least or about 85%, 90%, 95%, or 100% of the parent immunoglobulins.

The fusion of the non-native polypeptide at the 3A site does not interfere with the expression level and does not reduce expression yield. Particularly, the modified immunoglobulins have a very high expression level. In some embodiments, the expression level can be at least or about 50%, 60%, 70%, 80%, 90%, or 100% higher than the expression level of a similar bispecific antibody (e.g., an antibody that binds to the same targets) or an immunocytokine (e.g., an antibody with a cytokine that is linked at the C-terminal of the Fc). In some embodiments, the modified immunoglobulins do not form aggregates easily. In some embodiments, the percentage of aggregates in the purified form (e.g., after purified by protein A chromatography) is less than 10%, 9%, 8%, 7%, 6%, 5%, 4%, 3%, 2% or 1%.

In addition, the modified immunoglobulins do not have mispairing problems as in the case of bispecific antibodies. Thus, it is easier to make and purify the modified immunoglobulins, and the yield can be much higher than a typical bispecific antibody.

Moreover, the modified immunoglobulins are stable and do not form aggregates or degrade easily. In some embodiments, the modified immunoglobulins are stable for at least 1, 2, 3, 4, 5, 6, 7, 8, 9, 10, 11, or 12 weeks, or at least 1, 2, 3, 4, 5, 6, 7, 8, 9, 10, 11, or 12 months at room temperature.

The present disclosure also provides modifications at some other sites of the Fc region. These sites include "3B" site, "3C" site, and "3D" site. One or two non-native polypeptides can be fused to the heavy chain CH3 domains of the one or two polypeptides at the 3B site. The 3B site starts from position 383 to position 391 (EU numbering). In some embodiments, the non-native polypeptide replaces 1, 2, 3, 4, 5, 6, 7, 8, 9, or 10 amino acids at the fusion site. In some embodiments, the non-native polypeptide replaces the entire amino acid sequences at the 3B site.

In some embodiments, the non-native polypeptide is inserted between any of the two amino acids at this fusion site. In some embodiments, the non-native polypeptide is linked to two amino acid residues of the heavy chain CH3 domain of the modified immunoglobulin. In some embodiments, the two residues are selected from positions 382, 383, 384, 385, 386, 387, 388, 389, 390, 391, and 392 of the heavy chain CH3 domain according to EU numbering, and all possible combinations of these two amino acid residues are also provided.

In some embodiments, one or two non-native polypeptides can be fused to the heavy chain CH3 domains of the one or two polypeptides at the 3C site. The 3C site starts from position 383 to position 385 (EU numbering). In some embodiments, the non-native polypeptide replaces 1, 2, 3, or 4 amino acids at the fusion site. In some embodiments, the non-native polypeptide replaces the entire amino acid sequences at the 3C site. In some embodiments, the non-native polypeptide is inserted between any of the two amino acids at this fusion site. In some embodiments, the non-native polypeptide is linked to two amino acid residues of the heavy chain CH3 domain of the modified immunoglobulin. In some embodiments, the two residues are selected from positions 382, 383, 384, 385, and 386 of the heavy chain CH3 domain according to EU numbering, and all possible combinations of these two amino acid residues are also provided. In some embodiments, the two residues are position 384 and 385 of the heavy chain CH3 domain according to EU numbering.

In some embodiments, one or two non-native polypeptides can be fused to the heavy chain CH3 domains of the one or two polypeptides at the 3D site. The 3D site starts from position 413 to position 422 (EU numbering). In some embodiments, the non-native polypeptide replaces 1, 2, 3, 4, 5, 6, 7, 8, 9, or 10 amino acids at the fusion site. In some embodiments, the non-native polypeptide replaces the entire amino acid sequences at the 3D site. In some embodiments, the non-native polypeptide is inserted between any of the two amino acids at this fusion site. In some embodiments, the non-native polypeptide is linked to two amino acid residues of the heavy chain CH3 domain of the modified immunoglobulin. In some embodiments, the two residues are selected from positions 412, 413, 414, 415, 416, 417, 418, 419, 420, 421, 422, and 423 of the heavy chain CH3 domain according to EU numbering, and all possible combinations of these two amino acid residues are also provided.

In some embodiments, the immunoglobulin described herein has one or two heavy chains (e.g., intact, a portion of, or modified heavy chains described herein), and one or two non-native polypeptides can be fused to the N-terminus or C-terminus of the one or two heavy chains. In some embodiments, the immunoglobulin described herein has an Fc region (e.g., any of the wildtype or modified Fc regions described herein), and one or two non-native polypeptides can be fused to the N-terminus or C-terminus of the FC region.

In some embodiments, the immunoglobulin described herein has one or two light chains (e.g., intact, a portion of, or modified light chains described herein), and one or two non-native polypeptides can be fused to the N-terminus or C-terminus of the one or two light chains.

Figure 33:
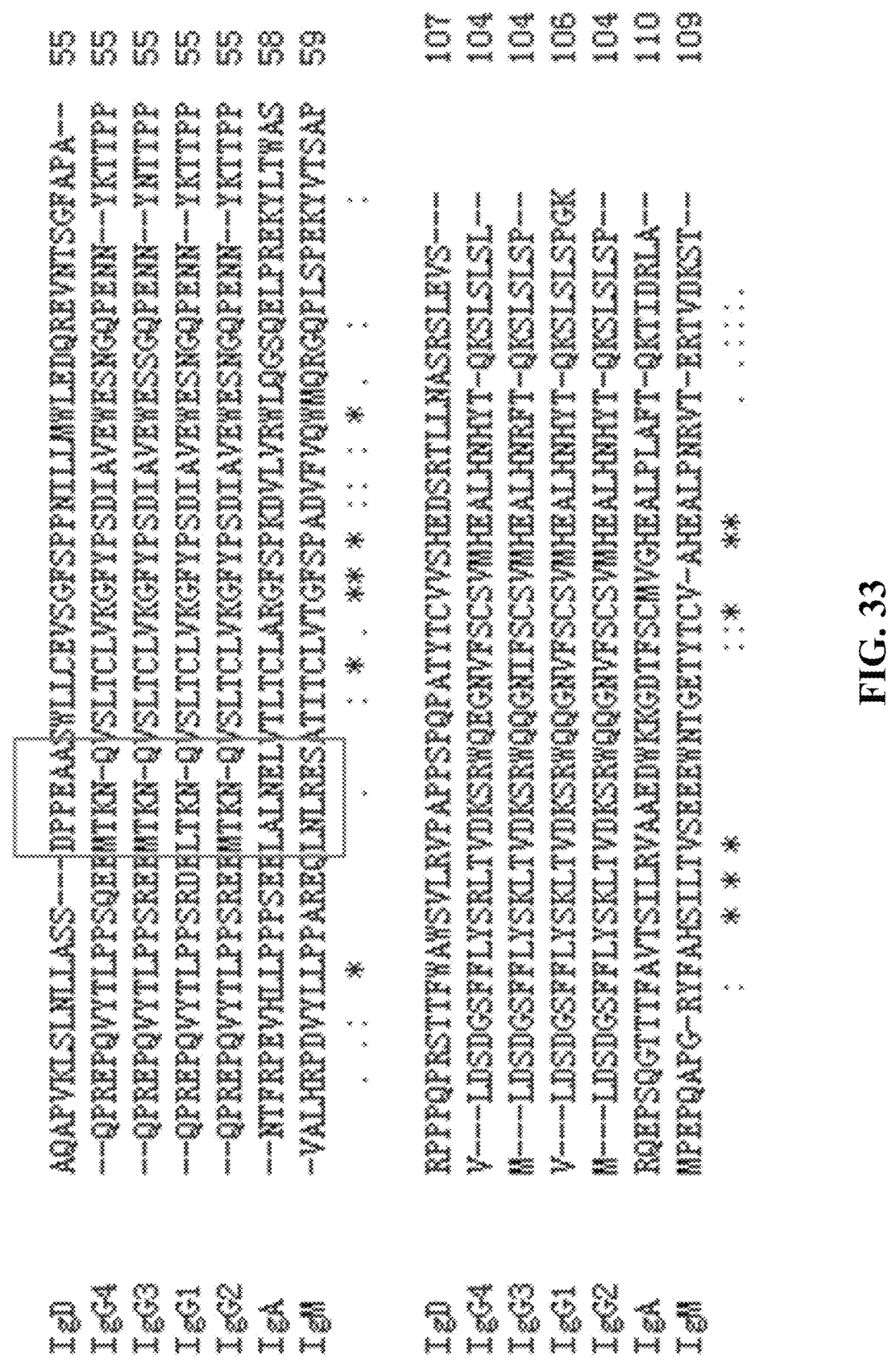

In some embodiments, the immunoglobulin described herein is a human immunoglobulin. In some embodiments, the human immunoglobulin is IgA, IgD, IgM, IgE, or IgG. In some embodiments, the human IgG is IgG1, IgG2, IgG3, or IgG4. A sequence alignment between amino acids 269-375 of human IgD (SEQ ID NO: 102), the CH3-CHS region of human IgG4 (SEQ ID NO: 107), the CH3-CHS region of human IgG3 (SEQ ID NO: 106), the CH3-CHS region of human IgG1 (SEQ ID NO: 104), the CH3-CHS region of human IgG2 (SEQ ID NO: 105), amino acids 224-333 of human IgA (SEQ ID NO: 101), and amino acids 324-433 of human IgM (SEQ ID NO: 103) is shown in FIG. 33. Positions 358-362 of the heavy chain CH3 domain of human IgG1, IgG2, IgG3, IgG4 (according to EU numbering); and the corresponding residues in human IgA, IgD, IgM are labelled in a box. Non-native polypeptides can be similarly fused to this site. Specifically, the fusion site at the heavy chain CH3 domain has the following amino acid sequences: LTKNQ (human IgG1; SEQ ID NO: 130); MTKNQ (human IgG2; SEQ ID NO: 131); MTKNQ (human IgG3; SEQ ID NO: 132); and MTKNQ (human IgG4; SEQ ID NO: 133). The amino residues for the fusion site in human IgA, IgD, and IgM are LALNEL (SEQ ID NO: 134), DPPEAA (SEQ ID NO: 135), and LNLRES (SEQ ID NO: 136), respectively. The above alignment result shows that positions 358-362 of the heavy chain CH3 domain (according to EU numbering) are not highly conserved across human immunoglobulins. Therefore, the modifications described herein (e.g., fusion of non-native polypeptide) within the regions described herein can be performed without affecting protein expression, stability, and/or function. In some embodiments, the CH3 region is a constant domain corresponding to the CH3 exon coding region, without CHS region (if there is one), from an immunoglobulin heavy chain. In some embodiments, the CHS region is at the end of the CH3. The CHS region is a coding region at the C-terminal end of a secreted immunoglobulin heavy chain. Details can be found at the international ImMunoGeneTics information system (IMGT), which is incorporated herein by reference in its entirety. Similarly, a sequence alignment between the CH3-CHS region of human IgG4 (SEQ ID NO: 107), the CH3-CHS region of human IgG3 (SEQ ID NO: 106), the CH3-CHS region of human IgG1 (SEQ ID NO: 104), and the CH3-CHS region of human IgG2 (SEQ ID NO: 105) is shown in FIG. 34. Positions 358-362 of the heavy chain CH3 domain of human IgG1, IgG2, IgG3, IgG4 (according to EU numbering) are labelled. In some embodiments, one or two non-native polypeptides can be fused to the heavy chain CH3 domains of IgG (e.g., IgG1, IgG2, IgG3, or IgG4), IgA, IgD, and IgM at the fusion site. In some embodiments, the non-native polypeptide replaces 1, 2, 3, 4, 5, 6, 7, 8, 9, or 10 amino acids at the fusion site. In some embodiments, the non-native polypeptide replaces the entire amino acid sequences at the fusion site. In some embodiments, the non-native polypeptide is inserted between any of the two amino acids at this fusion site. In some embodiments, the non-native polypeptide is linked to two amino acid residues of the heavy chain CH3 domain of the modified immunoglobulin.

In some embodiments, the immunoglobulin described herein is a rodent immunoglobulin (e.g., mouse IgG, rat IgG). In some embodiments, the rat immunoglobulin is rat IgG1, rat IgG2A, rat IgG2B, or rat IgG2C. In some embodiments, the immunoglobulin described herein is a mouse immunoglobulin. In some embodiments, the mouse immunoglobulin is mouse IgG1, mouse IgG2A, mouse IgG2B, mouse IgG2C, or mouse IgG3. A sequence alignment between the CH3-CHS region of rat IgG2C (SEQ ID NO: 111), the CH3-CHS region of mouse IgG3 (SEQ ID NO: 116), the CH3-CHS region of human IgG1 (SEQ ID NO:

104), the CH3-CHS region of rat IgG1 (SEQ ID NO: 108), the CH3-CHS region of rat IgG2A (SEQ ID NO: 109), the CH3-CHS region of mouse IgG1 (SEQ ID NO: 112), the CH3-CHS region of mouse IgG2B (SEQ ID NO: 114), the CH3-CHS region of rat IgG2B (SEQ ID NO: 110), the CH3-CHS region of mouse IgG2A (SEQ ID NO: 113), and the CH3-CHS region of mouse IgG2C (SEQ ID NO: 115) is shown in FIG. 35. Positions 358-362 of the heavy chain CH3 domain of human IgG1 (according to EU numbering), and the corresponding residues in mouse IgG (e.g., IgG1, IgG2A, IgG2B, IgG2C, or IgG3) and rat IgG (e.g., IgG1, IgG2A, IgG2B, or IgG2C) are labelled by a bracket. Specifically, the amino acid residues corresponding to positions 358-362 of the heavy chain CH3 domain (according to EU numbering) are MSKNK (rat IgG2C; SEQ ID NO: 137), MSKKK (mouse IgG3; SEQ ID NO: 138), MTQNE (rat IgG1; SEQ ID NO: 139), MTQSQ (rat IgG2A; SEQ ID NO: 140), MAKDK (mouse IgG1; SEQ ID NO: 141), LSRKD (mouse IgG2B; SEQ ID NO: 142), LTEQT (rat IgG2B; SEQ ID NO: 143), MTKKQ (mouse IgG2A; SEQ ID NO: 144), and MTKKE (mouse IgG2C; SEQ ID NO: 145). In some embodiments, the immunoglobulin described herein is a monkey immunoglobulin (e.g., monkey IgG). In some embodiments, the monkey immunoglobulin is monkey IgG1, monkey IgG2, or monkey IgG3. A sequence alignment between the CH3-CHS region of human IgG1 (SEQ ID NO: 104), the CH3 region of monkey IgG3 (SEQ ID NO: 119), the CH3-CHS region of monkey IgG1 (SEQ ID NO: 117), and the CH3-CHS region of monkey IgG2 (SEQ ID NO: 118) is shown in FIG. 36. Positions 358-362 of the heavy chain CH3 domain of human IgG1 (according to EU numbering), and the corresponding residues in monkey IgG (e.g., IgG1, IgG2, or IgG3) are labelled by a bracket. Specifically, the amino acid residues corresponding to positions 358-362 of the heavy chain CH3 domain (according to EU numbering) are LTKNQ (monkey IgG3; SEQ ID NO: 146), LTKNQ (monkey IgG1; SEQ ID NO: 147), and LTKNQ (monkey IgG2; SEQ ID NO: 148). In some embodiments, the immunoglobulin described herein is a *Canis* (e.g., dog) immunoglobulin (e.g., dog IgG). In some embodiments, the immunoglobulin is Canine IgG1, Canine IgG2, Canine IgG3, or Canine IgG4. A sequence alignment between the CH3-CHS region of human IgG1 (SEQ ID NO: 104), the CH3-CHS region of Canine IgG2 (SEQ ID NO: 121), the CH3-CHS region of Canine IgG3 (SEQ ID NO: 122), the CH3-CHS region of Canine IgG1 (SEQ ID NO: 120), and the CH3-CHS region of Canine IgG4 (SEQ ID NO: 121) is shown in FIG. 37. Positions 358-362 of the heavy chain CH3 domain of human IgG1 (according to EU numbering), and the corresponding residues in Canine IgG (e.g., IgG1, IgG2, IgG3, or IgG4) are labelled by a bracket. Specifically, the amino acid residues corresponding to positions 358-362 of the heavy chain CH3 domain (according to EU numbering) are LSKNT (Canine IgG2; SEQ ID NO: 149), MSKNT (Canine IgG3; SEQ ID NO: 150), LSSSDT (Canine IgG1; SEQ ID NO: 151), and LSSSDT (Canine IgG4; SEQ ID NO: 152). The site that corresponds to positions 358-362 of the heavy chain CH3 domain of human IgG1 (according to EU numbering) can be used as fusion sites for non-native peptides. In some embodiments, one or two non-native polypeptides can be fused to these fusion site. In some embodiments, the non-native polypeptide replaces 1, 2, 3, 4, 5, 6, 7, 8, 9, or 10 amino acids at the fusion site. In some embodiments, the non-native polypeptide replaces the entire amino acid sequences at the fusion site. In some embodiments, the non-native polypeptide is inserted between any of the two amino acids at this fusion site. In some embodiments, the non-native polypeptide is linked to two amino acid residues of the heavy chain CH3 domain of the modified immunoglobulin.

Antibody Formats

The modified immunoglobulins can have various forms or formats. In some embodiments, the parent antibody before any modification can be an intact immunoglobulin molecule (e.g., IgG1, IgG2a, IgG2b, IgG3, IgM, IgD, IgE, IgA). The IgG subclasses (IgG1, IgG2, IgG3, and IgG4) are highly conserved, differ in their constant region, particularly in their hinges and upper CH2 domains. The EU numbering of these immunoglobulins, the sequences and differences of the IgG subclasses are known in the art, and are described, e.g., in Vidarsson, et al, "IgG subclasses and allotypes: from structure to effector functions." Frontiers in immunology 5 (2014); Irani, et al. "Molecular properties of human IgG subclasses and their implications for designing therapeutic monoclonal antibodies against infectious diseases." Molecular immunology 67.2 (2015): 171-182; Shakib, Farouk, ed. The human IgG subclasses: molecular analysis of structure, function and regulation. Elsevier, 2016; Lefranc et al., "IMGT® and 30 years of Immunoinformatics Insight in antibody V and C domain structure and function." Antibodies 8.2 (2019): 29; each of which is incorporated herein by reference in its entirety.

The antibody can also be an immunoglobulin molecule that is derived from any species (e.g., human, rodent, rat, mouse, camelid, dog, horn shark, *Xenopus laevis*, rhesus monkey, cat, rabbit). Antibodies disclosed herein also include, but are not limited to, polyclonal, monoclonal, monospecific, polyspecific antibodies, and chimeric antibodies that include an immunoglobulin binding domain fused to another polypeptide. The term "antigen binding domain" or "antigen binding fragment" is a portion of an antibody that retains specific binding activity of the intact antibody, i.e., any portion of an antibody that is capable of specific binding to an epitope on the intact antibody's target molecule. It includes, e.g., Fab, Fab', F(ab')2, and variants of these fragments. Thus, in some embodiments, an antibody or an antigen binding fragment thereof can be, e.g., a scFv, a Fv, a Fd, a dAb, a bispecific antibody, a bispecific scFv, a diabody, a linear antibody, a single-chain antibody molecule, a multi-specific antibody formed from antibody fragments, and any polypeptide that includes a binding domain which is, or is homologous to, an antibody binding domain. Non-limiting examples of antigen binding domains include, e.g., the heavy chain and/or light chain CDRs of an intact antibody, the heavy and/or light chain variable regions of an intact antibody, full length heavy or light chains of an intact antibody, or an individual CDR from either the heavy chain or the light chain of an intact antibody.

Fragments of antibodies are suitable for use in the methods described herein are also provided. The Fab fragment contains a variable and constant domain of the light chain and a variable domain and the first constant domain (CH1) of the heavy chain. F(ab')2 antibody fragments comprise a pair of Fab fragments which are generally covalently linked near their carboxy termini by hinge cysteines between them. Other chemical couplings of antibody fragments are also known in the art.

In some embodiments, the heavy chain of the antibody can be of any isotype including IgM, IgG, IgE, IgA, or IgD or sub-isotype including IgG1, IgG2, IgG2a, IgG2b, IgG3, IgG4, IgE1, IgE2, etc. The light chain can be a kappa light chain or a lambda light chain. An antibody can comprise two identical copies of a light chain and two identical copies of a heavy chain.

The modified immunoglobulins can specifically bind to various antigens. In some embodiments, the antigen is a fusion protein, an enzyme, a soluble protein, a structural protein, a transcriptional regulatory protein, a receptor, a translational regulatory protein, a chromatin protein, a hormone, a cell cycle regulatory protein, a G protein, a neuroactive peptide, an immunomodulatory protein, a blood component protein, a heat shock protein, dihydrofolate reductase, an antibiotic resistance protein, a functional fragment of any one of the proteins, an epitope fragment of any one of the proteins, and any combination thereof.

In some embodiments, the modified immunoglobulin binds to an antigen, and the modified immunoglobulin has about the same or a higher expression level as compared to that of a monoclonal antibody that specifically binds to the same antigen. In some embodiments, the modified immunoglobulin binds to two antigens, and the modified immunoglobulin has about the same or a higher expression level as compared to that of a bispecific antibody that specifically binds to the same two antigens. In some embodiments, the modified immunoglobulin binds to three antigens, and the modified immunoglobulin has about the same or a higher expression level as compared to that of a tri-specific antibody that specifically binds to the same three antigens. In some embodiments, the modified immunoglobulin binds to four antigens, and the modified immunoglobulin has about the same or a higher expression level as compared to that of a tetra-specific antibody that specifically binds to the same four antigens.

In some embodiments, the antigen is a tumor-associated antigen. As used herein, the term "tumor associated antigen" refers to an antigen that is or can be presented on a tumor cell surface and that is located on or within tumor cells. In some other embodiments, the tumor associated antigens can be exclusively expressed on tumor cells or may represent a tumor specific mutation compared to non-tumor cells. In some other embodiments, the tumor associated antigens can be found in both tumor cells and non-tumor cells, but is overexpressed on tumor cells when compared to non-tumor cells or are accessible for antibody binding in tumor cells due to the less compact structure of the tumor tissue compared to non-tumor tissue. In some embodiments the tumor associated antigen is located on the vasculature of a tumor. Illustrative examples of a tumor associated surface antigen are CD10, CD19, CD20, CD22, CD21, CD22, CD25, CD30, CD33, CD34, CD37, CD44v6, CD45, CD133, Fms-like tyrosine kinase 3 (FLT-3, CD135), chondroitin sulfate proteoglycan 4 (CSPG4, melanoma-associated chondroitin sulfate proteoglycan), Epidermal growth factor receptor (EGFR), Her2neu, Her3, IGFR, IL3R, fibroblast activating protein (FAP), CDCP1, Derlinl, Tenascin, frizzled 1-10, the vascular antigens VEGFR2 (KDR/FLK1), VEGFR3 (FLT4, CD309), PDGFR-alpha (CD140a), PDGFR-beta (CD140b) Endoglin, CLEC14, Tem1-8, and Tie2. Further examples may include A33, CAMPATH-1 (CDw52), Carcinoembryonic antigen (CEA), Carboanhydrase IX (MN/CA IX), de2-7 EGFR, EGFRvIII, EpCAM, Ep-CAM, Folate-binding protein, G250, Fms-like tyrosine kinase 3 (FLT-3, CD135), c-Kit (CD117), CSF1R (CD115), HLA-DR, IGFR, IL-2 receptor, IL3R, MCSP (Melanoma-associated cell surface chondroitin sulfate proteoglycane), Muc-1, Prostate-specific membrane antigen (PSMA), Prostate stem cell antigen (PSCA), Prostate specific antigen (PSA), and TAG-72.

In some embodiments, the antigen is an antigen for an effector cell. As used herein, the term "effector cell" refers to a cell that actively responds to a stimulus and effects some changes. In some embodiments, the effector cell is an immune cell, e.g., a NK cell, a T cell, a B cell, a monocyte, a microphage, a dendritic cell, or a neutrophil. Thus, the antigen can be an immune cell antigen. As used herein, the term "immune cell antigen" refers to an antigen that is primarily presented on an immune cell (e.g., T cells, B cells, NK cells). In certain embodiments, the antigen is CD3, 4-1BB (CD137), OX40 (CD134), CD16, CD47, CD19, CD20, CD22, CD33, CD38, CD123, CD133, CEA, cdH3, EpCAM, epidermal growth factor receptor (EGFR), EGFRvIII (a mutant form of EGFR), HER2, HER3, dLL3, BCMA, Sialyl-Lea, 5T4, ROR1, melanoma-associated chondroitin sulfate proteoglycan, mesothelin, folate receptor 1, VEGF receptor, EpCAM, HER2/neu, HER3/neu, G250, CEA, MAGE, proteoglycans, VEGF, FGFR, alphaVbeta3-integrin, HLA, HLA-DR, ASC, CD1, CD2, CD4, CD5, CD6, CD7, CD8, CD11, CD13, CD14, CD21, CD23, CD24, CD28, CD30, CD37, CD40, CD41, CD44, CD52, CD64, c-erb-2, CALLA, MHCII, CD44v3, CD44v6, p9'7, ganglioside GM1, GM2, GM3, GD1a, GD1b, GD2, GD3, GT1b, GT3, GQ1, NY-ESO-1, NFX2, SSX2, SSX4 Trp2, gp100, tyrosinase, Muc-1, telomerase, survivin, G250, p53, CA125 MUC, Wue antigen, Lewis Y antigen, HSP-27, HSP-70, HSP-72, HSP-90, Pgp, MCSP, EpHA2 and cell surface targets GC182, GT468 or GT512.

In some embodiments, the antigen is an immune checkpoint molecule. Immune checkpoints are regulators of the immune system. In some embodiments, the immune checkpoint molecule is PD-1, PD-L1, PD-L2, CTLA-4, B7-H3, TIM-3, LAG-3, VISTA, ICOS, 4-1BB, OX40, GITR, or CD40. In some embodiments, the antigen is programmed cell death protein 1 (PD-1), cytotoxic T-lymphocyte-associated protein 4 (CTLA-4), Lymphocyte Activating 3 (LAG-3), B And T Lymphocyte Associated (BTLA), Programmed Cell Death 1 Ligand 1 (PD-L1), CD27, CD28, CD40, CD47, CD137, CD154, T-Cell Immunoreceptor With Ig And ITIM Domains (TIGIT), Glucocorticoid-Induced TNFR-Related Protein (GITR), T-cell immunoglobulin and mucin-domain containing-3 (TIM-3), or TNF Receptor Superfamily Member 4 (TNFRSF4 or OX40).

Examples of therapeutic antibodies that can be used in the modifications include, but are not limited to, rituximab (Rituxan, IDEC/Genentech/Roche) (see for example U.S. Pat. No. 5,736,137), a chimeric anti-CD20 antibody approved to treat Non-Hodgkin's lymphoma; HuMax-CD20, an anti-CD20 currently being developed by Genmab, an anti-CD20 antibody described in U.S. Pat. No. 5,500,362, AME-133 (Applied Molecular Evolution), hA20 (Immunomedics, Inc.), HumaLYM (Intracel), and PRO70769 (PCT Application No. PCT/US2003/040426), trastuzumab (Herceptin, Genentech) (see for example U.S. Pat. No. 5,677,171), a humanized anti-Her2/neu antibody approved to treat breast cancer; pertuzumab (rhuMab-2C4, Omnitarg), currently being developed by Genentech; an anti-Her2 antibody described in U.S. Pat. No. 4,753,894; cetuximab (Erbitux, Imclone) (U.S. Pat. No. 4,943,533; PCT Publication No. WO 96/40210), a chimeric anti-EGFR antibody in clinical trials for a variety of cancers; ABX-EGF (U.S. Pat. No. 6,235,883), currently being developed by Abgenix-Immunex-Amgen; HuMax-EGFr (U.S. Pat. No. 7,247,301), currently being developed by Genmab; 425, EMD55900, EMD62000, and EMD72000 (Merck KGaA) (U.S. Pat. No. 5,558,864; Murthy et al., (1987) Arch. Biochem. Biophys. 252 (2): 549-60; Rodeck et al., (1987) J. Cell. Biochem. 35 (4): 315-20; Kettleborough et al., (1991) Protein Eng. 4 (7): 773-83); ICR62 (Institute of Cancer Research) (PCT Publication No. WO 95/20045; Modjtahedi et al., (1993) J. Cell Biophys. 22 (1-3): 129-46; Modjtahedi et al., (1993) Br. J.

Cancer 67 (2): 247-53; Modjtahedi et al., (1996) Br. J. Cancer 73 (2): 228-35; Modjtahedi et al., (2003) Int. J. Cancer 105 (2): 273-80); TheraCIM hR3 (YM Biosciences, Canada and Centro de Immunologia Molecular, Cuba (U.S. Pat. Nos. 5,891,996; 6,506,883; Mateo et al., (1997) Immunotechnol. 3 (1): 71-81); mAb-806 (Ludwig Institute for Cancer Research, Memorial Sloan-Kettering) (Jungbluth et al., (2003) Proc. Natl. Acad. Sci. USA 100 (2): 639-44); KSB-102 (KS Biomedix); MR1-1 (IVAX, National Cancer Institute) (PCT Publication No. WO 0162931); and SC100 (Scancell) (PCT WO 01/88138); alemtuzumab (Campath, Millenium), a humanized mAb currently approved for treatment of B-cell chronic lymphocytic leukemia; muromonab-CD3 (Orthoclone OKT3), an anti-CD3 antibody developed by Ortho Biotech/Johnson & Johnson, ibritumomab tiuxetan (Zevalin), an anti-CD20 antibody developed by IDEC/Schering AG, gemtuzumab ozogamicin (Mylotarg), an anti-CD33 (p67 protein) antibody developed by Celltech/Wyeth, alefacept (Amevive), an anti-LFA-3 Fc fusion developed by Biogen), abciximab (ReoPro), developed by Centocor/Lilly, basiliximab (Simulect), developed by Novartis, palivizumab (Synagis), developed by Medimmune, infliximab (Remicade), an anti-TNFalpha antibody developed by Centocor, adalimumab (Humira), an anti-TNFalpha antibody developed by Abbott, Humicade, an anti-TNFalpha antibody developed by Celltech, golimumab (CNTO-148), a fully human TNF antibody developed by Centocor, etanercept (Enbrel), an p75 TNF receptor Fc fusion developed by Immunex/Amgen, lenercept, an p55TNF receptor Fc fusion previously developed by Roche, ABX-CBL, an anti-CD147 antibody being developed by Abgenix, ABX-IL8, an anti-IL8 antibody being developed by Abgenix, ABX-MA1, an anti-MUC18 antibody being developed by Abgenix, Pemtumomab (R1549, 90Y-muHMFG1), an anti-MUC1 in development by Antisoma, Therex (R1550), an anti-MUC1 antibody being developed by Antisoma, AngioMab (AS1405), being developed by Antisoma, HuBC-1, being developed by Antisoma, Thioplatin (AS1407) being developed by Antisoma, Antegren (natalizumab), an anti-alpha-4-beta-1 (VLA-4) and alpha-4-beta-7 antibody being developed by Biogen, VLA-1 mAb, an anti-VLA-1 integrin antibody being developed by Biogen, LTBR mAb, an anti-lymphotoxin beta receptor (LTBR) antibody being developed by Biogen, CAT-152, an anti-TGF-.beta. 2 antibody being developed by Cambridge Antibody Technology, ABT 874 (J695), an anti-IL-12 p40 antibody being developed by Abbott, CAT-192, an anti-TGF.beta. 1 antibody being developed by Cambridge Antibody Technology and Genzyme, CAT-213, an anti-EotaxinI antibody being developed by Cambridge Antibody Technology, LymphoStat-B an anti-Blys antibody being developed by Cambridge Antibody Technology and Human Genome Sciences Inc., TRAIL-R1mAb, an anti-TRAIL-R1 antibody being developed by Cambridge Antibody Technology and Human Genome Sciences, Inc., Avastin bevacizumab, rhuMAb-VEGF), an anti-VEGF antibody being developed by Genentech, an anti-HER receptor family antibody being developed by Genentech, Anti-Tissue Factor (ATF), an anti-Tissue Factor antibody being developed by Genentech, Xolair (Omalizumab), an anti-IgE antibody being developed by Genentech, Raptiva (Efalizumab), an anti-CD11a antibody being developed by Genentech and Xoma, MLN-02 Antibody (formerly LDP-02), being developed by Genentech and Millenium Pharmaceuticals, HuMax CD4, an anti-CD4 antibody being developed by Genmab, HuMax-IL15, an anti-IL15 antibody being developed by Genmab and Amgen, HuMax-Inflam, being developed by Genmab and Medarex, HuMax-Cancer, an anti-Heparanase I antibody being developed by Genmab and Medarex and Oxford GeoSciences, HuMax-Lymphoma, being developed by Genmab and Amgen, HuMax-TAC, being developed by Genmab, IDEC-131, and anti-CD40L antibody being developed by DEC Pharmaceuticals, IDEC-151 (Clenoliximab), an anti-CD4 antibody being developed by DEC Pharmaceuticals, IDEC-114, an anti-CD80 antibody being developed by DEC Pharmaceuticals, IDEC-152, an anti-CD23 being developed by DEC Pharmaceuticals, anti-macrophage migration factor (MIF) antibodies being developed by DEC Pharmaceuticals, BEC2, an anti-idiotypic antibody being developed by Imclone, IMC-1C11, an anti-KDR antibody being developed by Imclone, DC101, an anti-flk-1 antibody being developed by Imclone, anti-VE cadherin antibodies being developed by Imclone, CEA-Cide (labetuzumab), an anti-carcinoembryonic antigen (CEA) antibody being developed by Immunomedics, LymphoCide (Epratuzumab), an anti-CD22 antibody being developed by Immunomedics, AFP-Cide, being developed by Immunomedics, MyelomaCide, being developed by Immunomedics, LkoCide, being developed by Immunomedics, ProstaCide, being developed by Immunomedics, MDX-010, an anti-CTLA4 antibody being developed by Medarex, MDX-060, an anti-CD30 antibody being developed by Medarex, MDX-070 being developed by Medarex, MDX-018 being developed by Medarex, Osidem (DM-1), and anti-Her2 antibody being developed by Medarex and Immuno-Designed Molecules, HuMax-CD4, an anti-CD4 antibody being developed by Medarex and Genmab, HuMax-IL15, an anti-IL15 antibody being developed by Medarex and Genmab, CNTO 148, an anti-TNF.alpha. antibody being developed by Medarex and Centocor/J&J, CNTO 1275, an anti-cytokine antibody being developed by Centocor/J&J, MOR101 and MOR102, anti-intercellular adhesion molecule-1 (ICAM-1) (CD54) antibodies being developed by MorphoSys, MOR201, an anti-fibroblast growth factor receptor 3 (FGFR-3) antibody being developed by MorphoSys, Nuvion (visilizumab), an anti-CD3 antibody being developed by Protein Design Labs, HuZAF, an anti-gamma interferon antibody being developed by Protein Design Labs, Anti-α5β1 Integrin, being developed by Protein Design Labs, anti-IL-12, being developed by Protein Design Labs, ING-1, an anti-Ep-CAM antibody being developed by Xoma, Xolair (Omalizumab) a humanized anti-IgE antibody developed by Genentech and Novartis, and MLN01, an anti-Beta2 integrin antibody being developed by Xoma. In another embodiment, the therapeutics include KRN330 (Kirin); huA33 antibody (A33, Ludwig Institute for Cancer Research); CNTO 95 (alpha V integrins, Centocor); MEDI-522 (alpha V. beta. 3 integrin, Medimmune); volociximab (alpha V.beta. 1 integrin, Biogen/PDL); Human mAb 216 (B cell glycosolated epitope, NCI); BiTE MT103 (bispecific CD19 CD3, Medimmune); 4G7 H22 (Bispecific Bcell. times. FcgammaRl, Medarex/Merck KGa); rM28 (Bispecific CD28. times. MAPG, EP Patent No. EP1444268); MDX447 (EMD 82633) (Bispecific CD64 EGFR, Medarex); Catumaxomab (removab) (Bispecific EpCAM anti-CD3, Trion/Fres); Ertumaxomab (bispecific HER2/CD3, Fresenius Biotech); oregovomab (OvaRex) (CA-125, ViRexx); Rencarex (WX G250) (carbonic anhydrase IX, Wilex); CNTO 888 (CCL2, Centocor); TRC105 (CD105 (endoglin), Tracon); BMS-663513 (CD137 agonist, Brystol Myers Squibb); MDX-1342 (CD19, Medarex); Siplizumab (MEDI-507) (CD2, Medimmune); Ofatumumab (Humax-CD20) (CD20, Genmab); Rituximab (Rituxan) (CD20, Genentech); veltuzumab (hA20) (CD20, Immunomedics); Epratuzumab (CD22, Amgen);

lumiliximab (IDEC 152) (CD23, Biogen); muromonab-CD3 (CD3, Ortho); HuM291 (CD3 fc receptor, PDL Biopharma); HeFi-1, CD30, NCI); MDX-060 (CD30, Medarex); MDX-1401 (CD30, Medarex); SGN-30 (CD30, Seattle Genentics); SGN-33 (Lintuzumab) (CD33, Seattle Genentics); Zanolimumab (HuMax-CD4) (CD4, Genmab); HCD122 (CD40, Novartis); SGN-40 (CD40, Seattle Genentics); Campathlh (Alemtuzumab) (CD52, Genzyme); MDX-1411 (CD70, Medarex); hLL1 (EPB-1) (CD74.38, Immunomedics); Galiximab (IDEC-144) (CD80, Biogen); MT293 (TRC093/D93) (cleaved collagen, Tracon); HuLuc63 (CS1, PDL Pharma); ipilimumab (MDX-010) (CTLA4, Brystol Myers Squibb); Tremelimumab (Ticilimumab, CP-675, 2) (CTLA4, Pfizer); HGS-ETR1 (Mapatumumab) (DR4 TRAIL-R1 agonist, Human Genome Science/Glaxo Smith Kline); AMG-655 (DR5, Amgen); Apomab (DR5, Genentech); CS-1008 (DR5, Daiichi Sankyo); HGS-ETR2 (lexatumumab) (DR5 TRAIL-R2 agonist, HGS); Cetuximab (Erbitux) (EGFR, Imclone); IMC-11F8, (EGFR, Imclone); Nimotuzumab (EGFR, YM Bio); Panitumumab (Vectabix) (EGFR, Amgen); Zalutumumab (HuMaxEGFr) (EGFR, Genmab); CDX-110 (EGFRvIII, AVANT Immunotherapeutics); adecatumumab (MT201) (Epcam, Merck); edrecolomab (Panorex, 17-1A) (Epcam, Glaxo/Centocor); MORAb-003 (folate receptor a, Morphotech); KW-2871 (ganglioside GD3, Kyowa); MORAb-009 (GP-9, Morphotech); CDX-1307 (MDX-1307) (hCGb, Celldex); Trastuzumab (Herceptin) (HER2, Celldex); Pertuzumab (rhuMAb 2C4) (HER2 (DI), Genentech); apolizumab (HLA-DR beta chain, PDL Pharma); AMG-479 (IGF-1R, Amgen); anti-IGF-1R R1507 (IGF1-R, Roche); CP 751871 (IGF-R, Pfizer); IMC-A12 (IGF1-R, Imclone); BIIB022 (IGF-1R, Biogen); Mik-beta-1 (IL-2Rb (CD122), Hoffman LaRoche); CNTO 328 (IL6, Centocor); Anti-KIR (1-7F9) (Killer cell Ig-like Receptor (KIR), Novo); Hu3S193 (Lewis (y), Wyeth, Ludwig Institute of Cancer Research); hCBE-11 (LTBR, Biogen); HuHMFG1 (MUC1, Antisoma/NCI); RAV12 (N-linked carbohydrate epitope, Raven); CAL (parathyroid hormone-related protein (PTH-rP), University of California); CT-011 (PD1, CureTech); MDX-1106 (ono-4538) (PD1, Medarex/Ono); MAb CT-011 (PD1, Curetech); IMC-3G3 (PDGFRa, Imclone); bavituximab (phosphatidylserine, Peregrine); huJ591 (PSMA, Cornell Research Foundation); muJ591 (PSMA, Cornell Research Foundation); GC1008 (TGFb (pan) inhibitor (IgG4), Genzyme); Infliximab (Remicade) (TNF.alpha., Centocor); A27.15 (transferrin receptor, Salk Institute, INSERN WO 2005/111082); E2.3 (transferrin receptor, Salk Institute); Bevacizumab (Avastin) (VEGF, Genentech); HuMV833 (VEGF, Tsukuba Research Lab) PCT Publication No. WO/2000/034337, University of Texas); IMC-18F1 (VEGFR1, Imclone); IMC-IL21 (VEGFR2, Imclone). Many of these antibodies are described in e.g., in WO2019057122A1. These references are incorporated herein by reference in the entirety.

In some embodiments, the parent immunoglobulins or the modified immunoglobulins can have a format as shown in Table 3 below. Detailed descriptions of these antibody formats can be found, e.g., in Brinkmann, et al., "The making of bispecific antibodies." MAbs. Vol. 9. No. 2. Taylor & Francis, 2017, which is incorporated herein by reference in the entirety. In some embodiments, the parent immunoglobulins or the modified immunoglobulins can have a format as shown in FIGS. 20A-20D.

TABLE 3

| | | | |
|---|---|---|---|
| Bispecific antibody conjugates | IgG2 | Appended & Fc-modified IgGs | IgG(kih)-Fv |
| | CovX-Body | | IgG(HA-TF-Fv |
| Hybrid bispecific IgGs | IgG | | IgG(kih)-scFab |
| | Mouse/rat chimeric IgG | | scFab-Fc(kih)-scFv2 |
| | κ/λ-body common HC | | scFab-Fc(kih)-scFv |
| Non-immunoglobulin fusion proteins | DNL-Fab$_2$-IgG-Cytokine$_2$ | | Half DVD-Ig |
| Fc-modified IgGs | IgG(kih) | | DVD-Ig(four-in-one) |
| | IgG(kih) common LC | | CrossMab-Fab |
| | ZW1 IgG common LC | Modified Fc and CH3 fusion proteins | scFv-Fc(kih) |
| | Biclonics common LC | | scFv-Fc(CH3 charge pairs) |
| | CrossMab (IgG-kih) | | scFv-Fc(EW-RVT) |
| | scFab-IgG(kih) | | scFv-Fc(HA-TF) |
| | orthogonal Fab IgG(kih) | | scFv-Fc(SEEDbody) |
| | DuetMab | | taFV-Fc(kih) |
| | CH3 charge pairs + CH1/CL charge pairs | | scFv-Fc(kih)-scFv |
| | hinge/CH3 charge pairs | | Fab-Fc(kih)-scFV |
| | Duobody | | Fab-scFV-Fc(BEAT) |
| | four-in-one CrossMab (kih) | | Fab-scFV-Fc(SEEDbody) |
| | LUZ-Y common LC | | DART-Fc |
| | LUZ-Y scFab-IgG | | scFV-CH3(kih) |
| | FcFc | | TriFabs |
| Appended IgGs-LC fusions | IgG-scFv(LC) | Appended IgGs-HC fusions | IgG-HC-scFv |
| | ScFv(LC)-IgG | | IgG-dAb |
| | dAb-IgG | | IgG-taFv |
| Appended IgGs-HC&LC fusions | DVD-Ig | | IgG-CrossFab |
| | TVD-Ig | | IgG-orthogonal Fab |
| | CODV-Ig | | IgG-(CαCβ)Fab |
| | scFv4-IgG | | scFv-HC-IgG |
| | Zybody | | tandem Fab-IgG(orthogonal Fab) |

TABLE 3-continued

| | | | |
|---|---|---|---|
| Fc fusions | DL-diabody | | Fab-IgG(CαCβFab) |
| | scDb-Fc | | Fab-IgG(CR3) |
| | taFv-Fc | | Fab-hinge-IgG(CR3) |
| | scFv-Fc-scFv | Modified | DAF(two-in-one-IgG) |
| | HCAb-VHH | IgGs | DutaMab |
| | Fab-scFv-Fc | CH3 | Di-diabody |
| | scFv4-Ig | fusinos | scDb-C$_H$3 |
| Non-immunoglobulin fusions | DNL-Fab$_4$-IgG | — | — |

The binding affinity of an antibody to the antigen is determined by CDRs. They are part of the variable chains in immunoglobulins (antibodies) and T cell receptors. Methods for identifying the CDR regions of an antibody by analyzing the amino acid sequence of the antibody are well known, and a number of definitions of the CDRs are commonly used. The Kabat definition is based on sequence variability, and the Chothia definition is based on the location of the structural loop regions. These methods and definitions are described in, e.g., Martin, "Protein sequence and structure analysis of antibody variable domains," Antibody engineering, Springer Berlin Heidelberg, 2001. 422-439; Abhinandan, et al. "Analysis and improvements to Kabat and structurally correct numbering of antibody variable domains," Molecular immunology 45.14 (2008): 3832-3839; Wu, T. T. and Kabat, E. A. (1970) J. Exp. Med. 132: 211-250; Martin et al., Methods Enzymol. 203:121-53 (1991); Morea et al., Biophys Chem. 68(1-3):9-16 (October 1997); Morea et al., J Mol Biol. 275(2):269-94 (January 0.1998); Chothia et al., Nature 342(6252):877-83 (December 1989); Ponomarenko and Bourne, BMC Structural Biology 7:64 (2007); each of which is incorporated herein by reference in its entirety.

The CDRs are important for recognizing an epitope of an antigen. As used herein, an "epitope" is the smallest portion of a target molecule capable of being specifically bound by the antigen binding domain of an antibody. The minimal size of an epitope may be about three, four, five, six, or seven amino acids, but these amino acids need not be in a consecutive linear sequence of the antigen's primary structure, as the epitope may depend on an antigen's three-dimensional configuration based on the antigen's secondary and tertiary structure.

The non-native polypeptides can be fused to various modified immunoglobulins, antibodies, antibody-like, or IgG-like molecules, as long as these molecules have a heavy chain CH3 domain.

In some embodiments, the antibody is a multi-specific antibody. Multimerization of antibodies may be accomplished through natural aggregation of antibodies or through chemical or recombinant linking techniques known in the art. For example, some percentage of purified antibody preparations (e.g., purified IgG1 molecules) spontaneously form protein aggregates containing antibody homodimers and other higher-order antibody multimers.

In some embodiments, the multi-specific antibody is a bi-specific antibody. Bi-specific antibodies can be made by engineering the interface between a pair of antibody molecules to maximize the percentage of heterodimers that are recovered from recombinant cell culture. For example, the interface can contain at least a part of the CH3 domain of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers. This method is described, e.g., in WO 96/27011, which is incorporated by reference in its entirety. While the modification is made to Fc region, the present disclosure also shows that the modification is compatible with knobs-in-holes. The "knobs into holes" approach introduces a mutation for an amino acid with a large sidechain in one heavy chain, and a mutation for an amino acid with a small sidechain in the other heavy chain. Thus, the same heavy chains are less likely to associate with each other and the two different heavy chains have a higher chance to associate with each other. The "knobs into holes" approaches are described, e.g., in Ridgway, John B B, Leonard G. Presta, and Paul Carter. "'Knobs-into-holes' engineering of antibody CH3 domains for heavy chain heterodimerization." *Protein Engineering, Design and Selection* 9.7 (1996), which is incorporated herein by reference in its entirety. In some embodiments, one or more amino acid residues in the CH3 domain of the IgG are substituted. In some embodiments, one heavy chain has one or more of the following substitutions Y349C and T366W. The other heavy chain can have one or more the following substitutions E356C, T366S, L368A, and Y407V. In some embodiments, one heavy chain has a T366Y (knob) substitution, and the other heavy chain has a Y407T (hole) substitution. In some embodiments, one heavy chain has a T366Y (knob) substitution, and the other heavy chain has one, two, or three of these substitutions T366S, L368A, Y407V (hole).

In some embodiments, the antibody has a format, such as DVD-Ig, CrossMab, BiTE etc. These formats are described in e.g., Spiess et al., "Alternative molecular formats and therapeutic applications for bispecific antibodies." Molecular immunology 67.2 (2015): 95-106, which is incorporated herein by reference in its entirety. In certain embodiments, the bispecific polypeptide complex as provided herein is based on a bispecific format selected from Triomabs; hybrid hybridoma (quadroma); Multispecific anticalin platform (Pieris); Diabodies; Single chain diabodies; Tandem single chain Fv fragments; TandAbs, Trispecific Abs; Darts (dual affinity retargeting; Macrogenics); Bispecific Xmabs (Xencor); Bispecific T cell engagers (Bites; Amgen; 55 kDa); Triplebodies; Tribody (Fab-scFv) Fusion Protein (CreativeBiolabs) multifunctional recombinant antibody derivates; Duobody platform (Genmab); Dock and lock platform; Humanized bispecific IgG antibody (REGN1979) (Regeneron); Mab2 bispecific antibodies (F-Star); DVD-Ig (dual variable domain immunoglobulin) (Abbvie); kappa-lambda bodies; TBTI (tetravalent bispecific tandem Ig); and CrossMab. In certain embodiments, the bispecific polypeptide complex as provided herein is based on the format of a "whole" antibody, such as whole IgG or IgG-like molecules, and small recombinant formats, such as tandem single chain variable fragment molecules (taFvs), diabodies (Dbs), single chain diabodies (scDbs) and various other derivatives of these, and BiTE (bispecific T cell engager).

"MAb-Fv" or "IgG-Fv" refers to a fusion protein formed by fusion of VH to the C-terminus of one Fc chain and the VL domain either expressed separately or fused to the C-terminus of the other resulted in a bispecific, trivalent IgG-Fv (mAb-Fv) fusion protein, with the Fv stabilized by an interdomain disulphide bond.

"ScFab-Fc-scFv2" and "ScFab-Fc-scFv" refer to a fusion protein formed by fusion of a single-chain Fab with Fc and disulphide-stabilized Fv domains.

"Appended IgG" refers to a fusion protein with a Fab arm fused to an IgG to form the format of bispecific (Fab) 2-Fc. It can form a "IgG-Fab" or a "Fab-IgG", with a Fab fused to the C-terminus or N-terminus of an IgG molecule with or without a connector.

"DVD-Ig" refers to a dual-variable-domain antibody that is formed by fusion of an additional VH domain and VL domain of a second specificity to an IgG heavy chain and light chain. "CODV-Ig" refers to a related format where the two VH and two VL domains are linked in a way that allows crossover pairing of the variable VH-VL domains, which are arranged either (from N- to C-terminus) in the order VH A-VH B and VL B-VL A, or in the order HV B-HV A and VL A-VL B.

A "CrossMab" refers to a technology of pairing of unmodified light chain with the corresponding unmodified heavy chain and pairing of the modified light chain with the corresponding modified heavy chain, thus resulting an antibody with reduced mispairing in the light chain.

A "BITE" is a bispecific T-cell engager molecule, comprising a first scFv with a first antigen specificity in the VL-VL orientation linked to a second scFv with a second specificity in the VH-VL orientation.

Modified immunoglobulins of the present disclosure can also be modified in the Fc region to provide desired effector functions or serum half-life.

Any of the antibodies or antigen-binding fragments described herein can be conjugated to a stabilizing molecule (e.g., a molecule that increases the half-life of the modified immunoglobulin in a subject or in solution). Non-limiting examples of stabilizing molecules include: a polymer (e.g., a polyethylene glycol) or a protein (e.g., serum albumin, such as human serum albumin). The conjugation of a stabilizing molecule can increase the half-life or extend the biological activity of an antibody or an antigen-binding fragment in vitro (e.g., in tissue culture or when stored as a pharmaceutical composition) or in vivo (e.g., in a human).

In some embodiments, the antibodies or antigen-binding fragments described herein can be conjugated to a therapeutic agent. The antibody-drug conjugate comprising the modified immunoglobulin can covalently or non-covalently bind to a therapeutic agent. In some embodiments, the therapeutic agent is a cytotoxic or cytostatic agent (e.g., cytochalasin B, gramicidin D, ethidium bromide, emetine, mitomycin, etoposide, tenoposide, vincristine, vinblastine, colchicin, doxorubicin, daunorubicin, dihydroxy anthracin, maytansinoids such as DM-1 and DM-4, mitoxantrone, mithramycin, actinomycin D, 1-dehydrotestosterone, glucocorticoids, procaine, tetracaine, lidocaine, propranolol, puromycin, epirubicin, and cyclophosphamide and analogs).

In some embodiments, the therapeutic agent can be linked to the non-native polypeptides as described herein. For example, one or more therapeutic agents can be covalently linked to one or more amino acids (e.g., side chains) of the non-native polypeptides (e.g., fused to different fusion sites as described herein).

In one aspect, at least 1, 2, 3, 4, 5, or 6 polypeptides are fused to a modified immunoglobulin. In some embodiments, a polypeptide is fused to a heavy chain CH3 domain of a modified immunoglobulin from one or more amino acid residues. In some embodiments, the polypeptide is fused to one amino acid residue of the heavy chain CH3 domain. In some embodiments, the polypeptide is fused to the C-terminal amino acid residue of the heavy chain CH3 domain.

In some embodiments, the fusion polypeptide can be added to multispecific antigen binding proteins. In some embodiments, a multispecific antigen binding protein (MABP) comprising: (a) a first antigen binding portion comprising a heavy chain variable domain (VH) and a light chain variable domain (VL), wherein the VH and VL together form an antigen-binding site that specifically binds a first epitope, and (b) a second antigen binding portion comprising a single domain antibody (sdAb) that specifically binds a second epitope, wherein the first antigen binding portion and the second antigen binding portion are fused to each other. In some embodiments, the MABP comprises any one of 1, 2, 3, 4, 5, 6, 7, 8, or more different antigen binding portions that each comprises an sdAb. In some embodiments, two identical sdAbs are fused to each other, which is further fused to the first antigen binding portion. In some embodiments, two different sdAbs are fused to each other, which is further fused to the first antigen binding portion. In some embodiments, provided is a multispecific (such as bispecific) antigen binding protein comprising: (a) two copies of a first antigen binding portion each comprising a heavy chain variable domain (VH) and a light chain variable domain (VL), wherein the VH and VL together form an antigen-binding site that specifically binds a first epitope, and (b) a single copy of a second antigen binding portion comprising an sdAb that specifically binds a second epitope, wherein the second antigen binding portion is fused to one of the two copies of the first antigen binding portion. In some embodiments, there is provided a multispecific (such as bispecific) antigen binding protein comprising: (a) two copies of a first antigen binding portion each comprising a heavy chain variable domain (VH) and a light chain variable domain (VL), wherein the VH and VL together form an antigen-binding site that specifically binds a first epitope, and (b) a plurality (such as 2, 3, or 4) of identical or different sdAbs that each specifically binds an epitope that is different from the first epitope, wherein the sdAbs are fused to each other, and/or to the first antigen binding portion. Various multispecific antigen binding proteins are described in WO2018014855A1, which is incorporated herein by reference in its entirety.

Figure 20A:
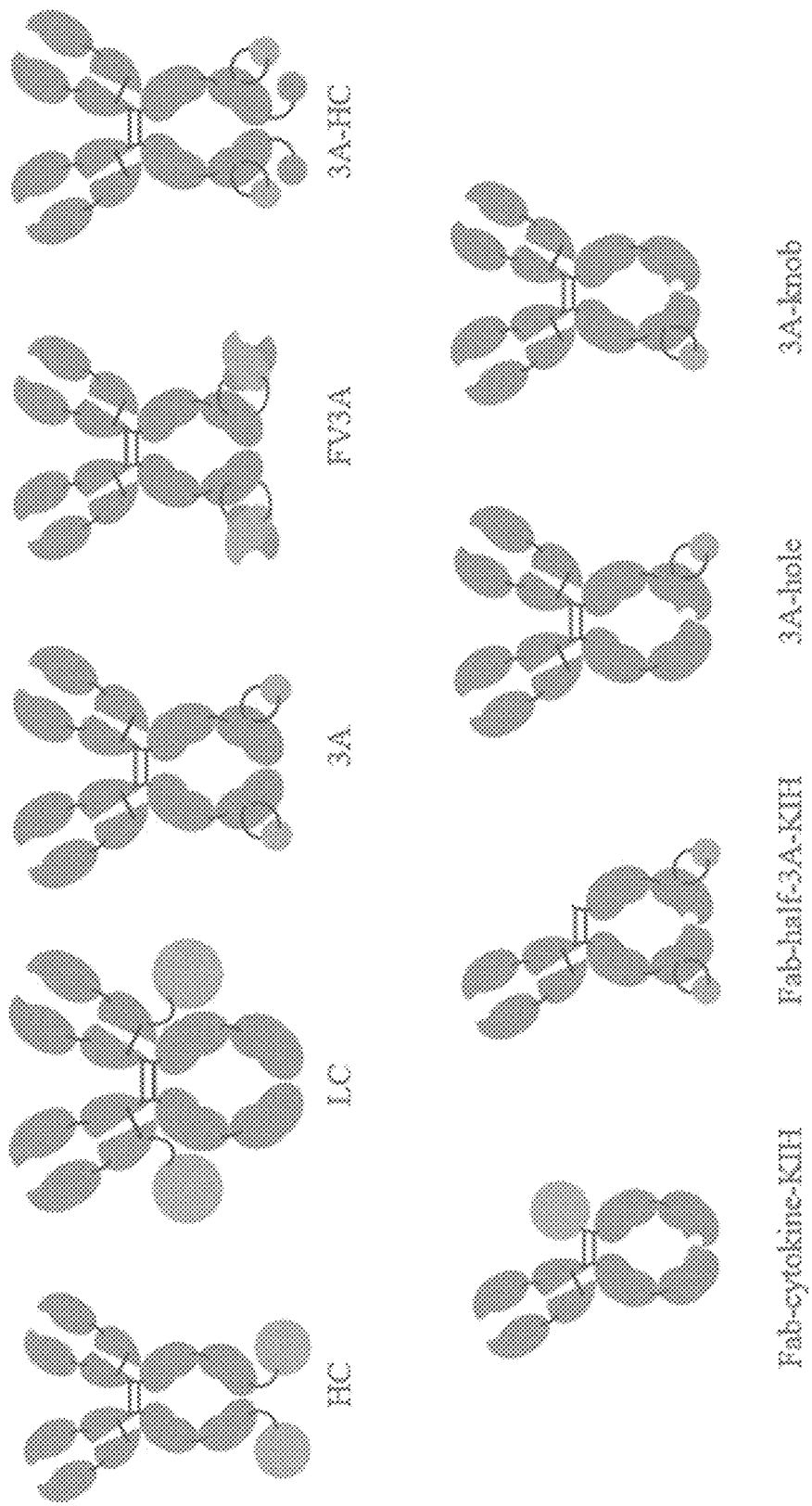

FIGS. 20A-20D further provide several exemplary immunoglobulin formats. As shown in FIG. 20A, in the HC format, a non-native polypeptide is linked to the C-terminal of the heavy chain of an antibody. In contrast, in the LC format, a non-native polypeptide is linked to C-terminal of the light chain of an antibody. Examples of modified immunoglobulins having the HC format include PDL1-mIL7-HC in Example 2, PDL1-hIL21-HC in Example 6, M7824 in Examples 7 and 9; and 1A7-selicrelumab-FVHC-IgG4 in Example 23. Examples of modified immunoglobulins having the LC format include PDL1-mIL7-LC in Example 2.

3A shows that a non-native polypeptide is fused to the 3A site of an antibody. FV3A indicates that the fused non-native polypeptide is a scFv. In the 3A-HC format, a functional polypeptide is further linked to the C-terminal of the heavy chain of the 3A format. Examples of modified immunoglobulins having the 3A format include PDL1-mIL7-3A in Example 3; 3F2-hIL7-3A in Example 5; 3F2-hIL21-3A in Example 6; PDL1-TGFbR2-3A in Examples 7, 9, and 11; PDL1-TGFbR2-3A-IgG4 in Examples 9 and 11; PDL1-TGFbR2-3AF1 in Example 9; PDL1-CD86-3A in Examples 12 and 13; PDL1-CD86-3A-IgG4 in Examples 12 and 13; PD1-KN035-3A-IgG1 in Example 12; PD1-KN035-3A in Example 12; and 3F2-mIL12-3A in Example 16. Examples of modified immunoglobulins having the FV3A format include PDL1-C40-6A7-FV3A in Examples 8 and 10; PDL1-C40-6A7-FV3A-IgG4 in Examples 8 and 10; PD1-PL1-3F2-FV3A-IgG1 in Examples 8 and 12; and 1A7-selicrelumab-FV3A-IgG4 in Example 23. Examples of modified immunoglobulins having the 3A-HC format include PDL1-mIL7-3A-mIFNa4 in Example 3; 3F2-hIL7-3A-mIFNa4 in Example 5; 3F2-hIL21-3A-mIFNa4 in Example 6; PDL1-CD86-3A-TGFbR2 in Example 13; and 3F2-mIL12-3A-mIFNa4 in Example 17.

In Fab-cytokine-KIH format, the VH and CH1 domains of a heavy chain are replaced by a cytokine. KIH indicates that knobs-in-holes modifications are added to the two heavy chains. Examples of modified immunoglobulins having the Fab-cytokine-KIH format include PDL1-hIL21-KIH in Example 2.

Similarly, in Fab-half-3A-KIH format, the VH and CH1 domains of a heavy chain are removed. A non-native polypeptide is fused to the 3A site of the antibody. Examples of modified immunoglobulins having the Fab-half-3A-KIH format include PDL1-mIL7-Fab-half-3A-KIH in Example 4.

In 3A-hole format, the non-native polypeptide is fused to the 3A site of the heavy chain with hole modifications. In contrast, in 3A-knob format, the non-native polypeptide is fused to the 3A site of the heavy chain with knob modifications. Examples of modified immunoglobulins having the 3A-hole format include PDL1-mIL7-3A-hole in Example 4; and CT4-KN035-3A-hole in Example 12. Examples of modified immunoglobulins having the 3A-knob format include PDL1-mIL7-3A-knob in Example 4; and CT4-KN035-3A-knob in Example 12. These formats can be combined with each other, and with various modifications as described herein.

The 3A-HC format can have 1, 2, 3, 4, 5, or 6 antigen-binding sites (i.e., the first, second, third, fourth, fifth, and sixth antigen-binding sites). In some embodiments, the antigen-binding site comprises a VH and a VL. In some embodiments, the antigen-binding site comprises a VHH.

In some embodiments, the antigen-binding site comprises an antibody or antigen-binding fragment thereof described herein (e.g., a scFv). In some embodiments, the first and the second antigen-binding sites target to the same antigen. In some embodiments, the first and the second antigen-binding sites target to different antigens. In some embodiments, the third and the fourth antigen-biding sites target to the same antigen. In some embodiments, the third and the fourth antigen-binding sites target to different antigens. In some embodiments, the fifth and the sixth antigen-binding sites target to the same antigen. In some embodiments, the fifth and the sixth antigen-binding sites target to different antigens. In some embodiments, the format is shown in FIG. 20C.

In some embodiments, the 3A-HC format can have two non-native polypeptides (e.g., targeting E and F, respectively) fused at the 3A sites of two heavy chains; and two non-native polypeptides (e.g., targeting G and H, respectively) fused to the C-terminus of the two heavy chains. The 3A-HC format also can have a first antigen-binding site targeting A and a second antigen-binding site targeting B. In addition, the 3A-HC format can have two non-native polypeptides (e.g., targeting C and D, respectively) fused to the C-terminus of the two light chains. A Fab domain targeting K can also be fused to one of the antigen-binding sites in 3A-HC. FIG. 20B provides an exemplary immunoglobulin format.

Figure 20D:
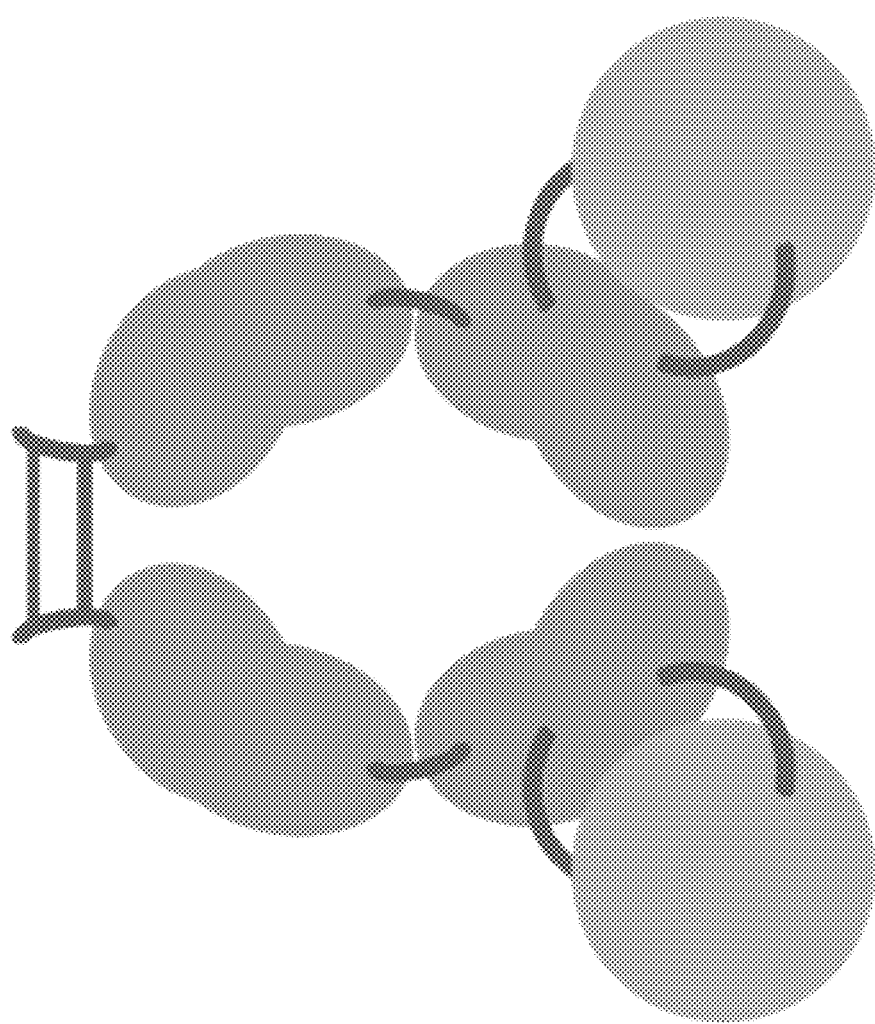

In some embodiments, one or two non-native polypeptides can be fused to the 3A sites of the variant Fc. FIG. 20D provides an exemplary format of a protein comprising a variant Fc as described herein.

In some embodiments, the modified immunoglobulin as described herein is a bispecific antibody, e.g., a bispecific antibody targeting PD-1 and CD40. In some embodiments, toxicity of the bispecific antibody having a 3A format (e.g., 1A7-selicrelumab-FV3A-IgG4) is less than 80%, less than 70%, less than 60%, less than 50%, less than 40%, less than 30%, less than 20%, or less than 10% as compared to that of a corresponding bispecific antibody having a HC format (e.g., 1A7-selicrelumab-FVHC-IgG4). In some embodiments, the toxicity is evaluated by blood biochemical tests (e.g., by measuring ALT and/or AST levels), or histopathological examination of liver.

Fused Polypeptides

Various polypeptides can be fused to modified immunoglobulins. The polypeptides can be fused to any sites described herein (e.g., the 3A site and/or the C-terminal of the heavy chain). As shown in the present disclosure, after the polypeptide is fused to the Fc region, the fused polypeptide can adopt a proper conformation and maintain its bioactivity.

As used herein, the term "fusion protein" in the present disclosure refers to a molecule comprising two or more proteins or the fragments thereof which are linked by the covalent bond via their respective main chains of the peptides, and more preferably, the fusion protein is generated by the genetic expression of the polynucleotide molecules encoding these proteins. In some embodiments, the fusion protein comprises an immunoglobulin domain. In some embodiments, the fusion protein is an Fc-fusion protein.

In some embodiments, the fused polypeptide is a fusion protein, an enzyme, a soluble protein, a structural protein, a transcriptional regulatory protein, a receptor, a translational regulatory protein, a chromatin protein, a hormone, a cell cycle regulatory protein, a G protein, a neuroactive peptide, an immunomodulatory protein, a blood component protein, a heat shock protein, dihydrofolate reductase, an antibiotic resistance protein, a functional fragment of any one of the proteins, an epitope fragment of any one of the proteins, and any combination thereof.

In some embodiments, the fused polypeptide is an antibody or antigen binding fragment thereof (e.g., scFv). In some embodiments, the fused polypeptide is a single-chain variable fragment (scFv). The scFv usually has one heavy chain variable domain, and one light chain variable domain. In some embodiments, the scFv has two heavy chain variable domains, and two light chain variable domains.

In some embodiments, the fused polypeptide is a single domain antibody. A single-domain antibody (sdAb), also known as a nanobody, is an antibody fragment consisting of a single monomeric variable antibody domain. Like a whole antibody, it can bind selectively to a specific antigen. In some embodiments, the single-domain antibodies are engineered from heavy-chain antibodies found in camelids and are called VEER fragments. As used herein, the "VEER" refers to the antigen-binding fragment of heavy chain only antibodies.

In some embodiments, the fused polypeptide is a cytokine. As used herein, the term "cytokine" refers to any protein or peptide, analog or functional fragment thereof, which is capable of stimulating or inducing a cytocidal immune response against a preselected cell-type, for example, a cancer cell or a virally-infected cell, in a mammal. Accordingly, it is contemplated that a variety of cytokines can be fused to the Fc at the sites described herein. Useful cytokines include, for example, tumor necrosis factors (TNFs), interleukins (ILs), lymphokines (Ls), colony stimulating factors (CSFs), interferons (IFNs) including species variants, truncated analogs thereof which are capable of stimulating or inducing such cytocidal immune responses. Useful tumor necrosis factors include, for example, TNF. Useful lymphokines include, for example, LT. Useful colony stimulating factors include, for example, GM-CSF and M-CSF. Useful interleukins include, for example, IL-2, IL-4, IL-5, IL-7, IL-15 and IL-18. Useful interferons, include, for example, IFN-α, IFN-β and IFN-γ. In some embodiments, the interferon is an IFN-α, IFN-β, IFN-ε, IFN-κ, IFN-τ, IFN-δ, IFN-ζ, IFN-ω, or IFN-γ. In some embodiments, the interferon is IFNa1, IFNa2, IFNa4, IFNa5, IFNa6, IFNa7, IFNa8, IFNa10, IFNa13, IFNa14, IFNa16, IFNa17, or IFNa21. In some embodiments, the interferon is mouse IFNa4 (mIFNa4). In some embodiments, the mIFNa4 comprises a sequence that is at least 80%, at least 85%, at least 90%, at least 95%, or 100% identical to SEQ ID NO: 10 or NCBI reference NP_034634.1. In some embodiments, the interferon is human IFNa4 (hIFNa4). In some embodiments, the hIFNa4 comprises a sequence that is at least 80%, at least 85%, at least 90%, at least 95%, or 100% identical to SEQ ID NO: 129 or NCBI reference NP_066546.1.

In some embodiments, the cytokine is IL-1, IL-2, IL-3, IL-4, IL-5, IL-6, IL-7, IL-8, IL-9, IL-10, IL-11, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-35, or IL-36.

In some embodiments, the cytokine is IL4, IL6, or IL10. Some preferred cytokines are listed in the table below.

TABLE 4

| Cytokine | NCBI REF |
|---|---|
| IL7 | NP_000871.1 |
| IL21 | NP_068575.1 |
| TGFbR2 | NP_003233.4 |
| IL4 | NP_000580.1 |
| IL6 | NP_000591.1 |
| IL10 | NP_000563.1 |
| TGFB1 | NP_000651.3 |
| APRIL | NP_003799.1 |
| CD161 | NP_002249.1 |
| SOST | NP_079513.1 |
| B7H4 | NP_078902.2 |
| SIGLEC15 | NP_998767.1 |
| DLL3 | NP_982353.1 |
| MCSFR (CSF1R) | NP_003799.1 |

In some embodiments, the cytokine is IL3 (e.g., human IL3), e.g., with a sequence set forth in SEQ ID NO: 93. In some embodiments, the cytokine is IL4 (e.g., human IL4) with sequence set forth in SEQ ID NO: 94. In some embodiments, the cytokine is IL5 (e.g., human IL5) with sequence set forth in SEQ ID NO: 95. In some embodiments, the cytokine is IL6 (e.g., human IL6) with sequence set forth in SEQ ID NO: 96. In some embodiments, the cytokine is IL8 (e.g., human IL8) with sequence set forth in SEQ ID NO: 97. In some embodiments, the cytokine is IL9 (e.g., human IL9) with sequence set forth in SEQ ID NO: 98. In some embodiments, the cytokine is IL13 (e.g., human IL13) with sequence set forth in SEQ ID NO: 99. In some embodiments, the cytokine is IL15 (e.g., human IL15) with sequence set forth in SEQ ID NO: 100.

Thus, in some embodiments, the modified immunoglobulin is an immunocytokine. As used herein, the term "immunocytokine" refers to a fusion of (i) an antibody binding site having binding specificity for, and capable of binding a pre-selected antigen, for example, a cell-type specific antigen, and (ii) a cytokine that is capable of inducing or stimulating a cytocidal immune response typically against a cancer or virally-infected cell. Examples of pre-selected antigens include cell surface antigens such as on cancer cells or virally-infected cells, and insoluble intracellular antigens, for example, of necrotic cells, which can remain attached to the cell membrane. Preferred antigens are target antigens that are characteristic of tumor cells, such as tumor specific antigens. Accordingly, the immunocytokine is capable of selectively delivering the cytokine to a target (which typically is a cell) in vivo so that the cytokine can mediate a localized immune response against a target cell.

In some embodiments, the fused polypeptide comprises all or a portion (e.g., a soluble portion) of IL7 (NCBI Ref: NP_000871.1), IL21 (NCBI Ref: NP_068575.1), IL4 (NCBI Ref: NP_000580.1), IL6 (NCBI Ref: NP_000591.1), or IL10 (NCBI Ref: NP_000563.1). In some embodiments, the fused polypeptide comprises a soluble region of TGFbR2 (NCBI Ref: NP_003233.4). In some embodiments, the fused polypeptide comprises a soluble portion of TGFB1 (NCBI Ref: NP_000651.3, e.g., amino acids 292-390 of NP_000651.3), APRIL (NCBI Ref: NP_003799.1, e.g., amino acids 115-250 of NP_003799.1), CD161 (NCBI Ref: NP_002249.1, e.g., amino acids 68-225 of NP_002249.1), SOST (NCBI Ref: NP_079513.1, e.g., 82-162 of NP_079513.1), B7H4 (NCBI Ref: NP_078902.2, e.g., amino acids 29-258 of NP_078902.2), SIGLEC15 (NCBI Ref: NP_998767.1, e.g., amino acids 20-263 of NP_998767.1), DLL3 (NCBI Ref: NP_982353.1, e.g., amino acids 27-492 of NP_982353.1), and/or MCSFR (CSF1R; NCBI Ref: NP_003799.1, e.g., amino acids 20-512 of NP_003799.1). In some embodiments, the fused polypeptide comprises all or a portion of TGFB1 (NCBI Ref: NP_000651.3), APRIL (NCBI Ref: NP_003799.1), CD161 (NCBI Ref: NP_002249.1), SOST (NCBI Ref: NP_079513.1), B7H4 (NCBI Ref: NP_078902.2), SIGLEC15 (NCBI Ref: NP_998767.1), DLL3 (NCBI Ref: NP_982353.1), and/or MCSFR (CSF1R; NCBI Ref: NP_003799.1). In some embodiments, the fused polypeptide is at least or about 70%, 80%, 90%, 95%, or 100% identical to these sequences.

In some embodiments, the fused polypeptide comprises all or a portion of SEQ ID NO: 14. In some embodiments, the fused polypeptide comprises all or a portion of SEQ ID NO: 15.

In some embodiments, the fused polypeptide is an agonist. In some embodiments, the fused polypeptide is an antagonist.

In some embodiments, the fused polypeptide is a single chain fragment variable (scFv).

In some embodiments, the scFv can specially bind to any antigens as described herein. In some embodiments, the scFv can specifically bind to CD40, and comprises all or a portion of SEQ ID NO: 16. In some embodiments, the scFv can specifically bind to CD40, and comprises all or a portion of SEQ ID NO: 132.

In some embodiments, the scFv can specifically bind to PD-L1. In some embodiments, the scFv can specifically bind to CD40. In some embodiments, the fused polypeptide comprises all or a portion of SEQ ID NO: 17 or SEQ ID NO: 16. In some embodiments, the fused polypeptide comprises all or a portion of SEQ ID NO: 132.

In some embodiments, the scFv specifically binds to CD86.

In some embodiments, the fused polypeptide is an antigen that is designed to induce an immune response in a subject. Thus, the disclosure also provides methods of inducing antibodies in a subject. The methods involve administering the modified immunoglobulins to the subject, optionally with adjuvants. The modified immunoglobulins can specifically target antigen presenting cells (e.g., by targeting markers on antigen presenting cells), and effectively deliver the antigens to the antigen presenting cells, thereby increasing efficiency of producing antibodies for this antigen.

In some embodiments, the fused polypeptide has a molecular weight at least or about 5 kD, 6 kD, 7 kD, 8 kD, 9 kD, 10 kD, 20 kD, 30 kD, 40 kD, 50 kD, 60 kD, 70 kD, 80 kD, 90 kD, or 100 kD. In some embodiments, the fused polypeptide has a molecular weight no more than 5 kD, 6 kD, 7 kD, 8 kD, 9 kD, 10 kD, 20 kD, 30 kD, 40 kD, 50 kD, 60 kD, 70 kD, 80 kD, 90 kD, or 100 kD. In some embodiments, the fused polypeptide is a functional protein and is less than 50 kD.

In some embodiments, the fused polypeptide has at least or about 50, 60, 70, 80, 90, 100, 110, 120, 130, 140, 150, 160, 170, 180, 190, 200, 250, 300, 350, 400, 450, 500, 550, 600, 650, 700, 750, 800, 850, 900, 950, or 1000 amino acid residues. In some embodiments, the fused polypeptide has no more than 50, 60, 70, 80, 90, 100, 110, 120, 130, 140, 150, 160, 170, 180, 190, 200, 250, 300, 350, 400, 450, 500, 550, 600, 650, 700, 750, 800, 850, 900, 950, or 1000 amino acid residues. In some embodiments, the fused polypeptide has about 50~400 amino acid resides, about 50~300 amino acid resides, about 50~200 amino acid resides, about 100~300 amino acid resides, or about 100~200 amino acid resides. In some embodiments, the fused polypeptide is a functional protein and has less than 500 amino acid residues.

Linker Sequence

The polypeptides can be fused to any sites described herein (e.g., the 3A site and/or the C-terminus) of any polypeptides described herein (e.g., a polypeptide having a heavy chain with CH3 domain), optionally through a linker sequence.

In some embodiments, the linker sequence comprises at least or about 5, 6, 7, 8, 9, 10, 11, 12, 13, 14, 15, 16, 17, 18, 19, 20, 30, 40, or 50 amino acid residues. In some embodiments, the linker sequence comprises at least or about 4, 5, 6, 7, 8, 9, 10, 11, 12, 13, 14, 15, 16, 20, 25, 30, or 40 glycine residues. In some embodiments, the linker sequence comprises at least or about 1, 2, 3, 4, 5, 6, 7, or 8 serine residues. In some embodiments, the linker sequence comprises or consists of both glycine and serine residues. In some embodiments, the linker sequence comprises or consists of a sequence that is at least or about 70%, at least or about 75%, at least or about 80%, at least or about 85%, at least or about 90%, at least or about 95%, at least or about 99%, or 100% identical to GGGGS (SEQ ID NO: 30) or GGGGSGGGGSGGGGS (SEQ ID NO: 124). In some embodiments, the linker sequence comprises or consists of a sequence that is at least or about 70%, at least or about 75%, at least or about 80%, at least or about 85%, at least or about 90%, at least or about 95%, at least or about 99%, or 100% identical to GGGGSGGGGSGGGGSGGGGS (SEQ ID NO: 9) or GGGGSGGGGSGGGGSGGGGSG (SEQ ID NO: 90). In some embodiments, the linker sequence comprises at least 1, 2, 3, 4, 5, 6, 7, or 8 repeats of GGGGS (SEQ ID NO: 31). In some embodiments, the linker sequence has no more than 10, 11, 12, 13, 14, 15, 16, 17, 18, 19, 20, 30, 40, or 50 amino acid residues.

In one aspect, a polypeptide is fused to a heavy chain CH3 domain of a modified immunoglobulin. In some embodiments, the inserted polypeptide includes an N-terminal linker sequence and a C-terminal linker sequence. As used herein, the term "N-terminal linker sequence" refers to a linker sequence that is located at the N-terminal of the inserted or fused polypeptide. As used herein, the term "C-terminal linker sequence" refers to a linker sequence that is located at the C-terminal of the inserted or fused polypeptide. The N-terminal linker sequence and the C-terminal linker sequence can be the same or different, and can comprise or consist of any linker sequences as described herein.

Antibodies and Antigen-Binding Fragments

The disclosure provides antibodies and antigen-binding fragments thereof that specifically bind to various antigens as described herein. In some embodiments, the antigen is a tumor-associated antigen. In some embodiments, the antigen is an immune cell antigen. In some embodiments, the antigen is an immune checkpoint molecule.

In some embodiments, the antibody or antigen-binding fragment thereof that comprises at least a CH3 domain. In some embodiments, the antibody or antigen-binding fragment thereof specifically binds to an immune checkpoint molecule. In some embodiments, the antibody or antigen-binding fragment thereof is an agonist. In some embodiments, the antibody or antigen-binding fragment thereof is an antagonist.

The disclosure provides antibodies and antigen-binding fragments thereof that specifically bind to CTLA4. In some embodiments, the antibodies and antigen-binding fragments described herein are capable of binding to CTLA4 and can inhibit CTLA4 inhibitory pathway thus increase immune response. The disclosure provides mouse anti-CTLA4 antibody 4G12 and the humanized antibodies thereof.

The CDR sequences for 4G12, and 4G12 derived antibodies include CDRs of the heavy chain variable domain, SEQ ID NOs: 54-56, and CDRs of the light chain variable domain, SEQ ID NOs: 57-59, as defined by Kabat numbering (See FIG. 49). Under Chothia numbering, the CDR sequences of the heavy chain variable domain are set forth in SEQ ID NOs: 66-68, and CDRs of the light chain variable domain are set forth in SEQ ID NOs: 69-71 (See FIG. 50).

The amino acid sequence for heavy chain variable region (VH) and light chain variable region (VL) of 4G12, and 4G12 derived antibodies are also provided. The amino acid sequence for the heavy chain variable region of humanized 4G12 antibody (e.g., CT4-4G12-IgG1) is set forth in SEQ ID NO: 44. The amino acid sequence for the light chain variable region of humanized CT4-4G12 antibody (e.g., CT4-4G12-IgG1) is set forth in SEQ ID NO: 45. The amino acid sequence for the heavy chain variable region of mouse 4G12 antibody is set forth in SEQ ID NO: 50. The amino acid sequence for the light chain variable region of mouse 4G12 antibody is set forth in SEQ ID NO: 51.

In some embodiments, amino acid sequences of the heavy chain and light chain of CT4-4G12-IgG1 are set forth in SEQ ID NO: 42 and SEQ ID NO: 43, respectively. In some embodiments, the 4G12, or 4G12 derived antibodies (e.g., humanized antibodies) have an IgG1 or IgG4 subtype.

Details of the CTLA4 antibody 4G12 can be found, e.g., in PCT/CN2017/102816, which is incorporated herein by reference in its entirety.

The disclosure provides antibodies and antigen-binding fragments thereof that specifically bind to OX40. In some embodiments, the antibodies and antigen-binding fragments described herein are capable of binding to OX40 and can promote OX40 signaling pathway thus increase immune response. The disclosure provides mouse anti-OX40 antibody 9H3 and the humanized antibodies thereof.

The CDR sequences for 9H3, and 9H3 derived antibodies include CDRs of the heavy chain variable domain, SEQ ID NOs: 60-62, and CDRs of the light chain variable domain, SEQ ID NOs: 63-65, as defined by Kabat numbering (See FIG. 49). Under Chothia numbering, the CDR sequences of the heavy chain variable domain are set forth in SEQ ID NOs: 72-74, and CDRs of the light chain variable domain are set forth in SEQ ID NOs: 75-77 (See FIG. 50).

The amino acid sequence for heavy chain variable region (VH) and light chain variable region (VL) of 9H3, and 9H3 derived antibodies are also provided. The amino acid sequence for the heavy chain variable region of humanized 9H3 antibody (e.g., O40-9H3-IgG1) is set forth in SEQ ID NO: 48. The amino acid sequence for the light chain variable region of humanized 9H3 antibody (e.g., 9H3-IgG1) is set forth in SEQ ID NO: 49. The amino acid sequence for the heavy chain variable region of mouse 9H3 antibody is set forth in SEQ ID NO: 52. The amino acid sequence for the light chain variable region of mouse 9H3 antibody is set forth in SEQ ID NO: 53.

In some embodiments, the scFv described herein is derived from 9H3, and 9H3 derived antibodies. In some embodiments, the 9H3, or 9H3 derived antibodies (e.g., humanized antibodies) have an IgG1 subtype.

Details of the anti-OX40 antibody 9H3 can be found, e.g., in PCT/CN2017/112832, which is incorporated herein by reference in its entirety.

The disclosure provides antibodies and antigen-binding fragments thereof that specifically bind to PD-L1. In some embodiments, the antibodies and antigen-binding fragments described herein are capable of binding to PD-L1 and can block PD1/PD-L1 signaling pathway thus increase immune response. The disclosure provides mouse anti-PD-L1 antibody 3F2 and the humanized antibodies thereof.

The CDR sequences for 3F2, and 3F2 derived antibodies include CDRs of the heavy chain variable domain, SEQ ID NOs: 18-20, and CDRs of the light chain variable domain, SEQ ID NOs: 21-23, as defined by Kabat numbering (See FIG. 49). Under Chothia numbering, the CDR sequences of the heavy chain variable domain are set forth in SEQ ID NOs: 78-80, and CDRs of the light chain variable domain are set forth in SEQ ID NOs: 81-83 (See FIG. 50).

In some embodiments, amino acid sequences of the heavy chain and light chain of PDL1-3F2-IgG1 are set forth in SEQ ID NO: 36 and SEQ ID NO: 37, respectively.

In some embodiments, the 3F2, or 3F2 derived antibodies (e.g., humanized antibodies) have an IgG1 or IgG4 subtype. In some embodiments, the scFv described herein is derived from 3F2, and 3F2 derived antibodies. In some embodiments, the amino acid sequence of the scFv derived from 3F2 is set forth in SEQ ID NO: 17.

Details of the anti-PD-L1 antibody 3F2 can be found, e.g., PCT/CN2020/075983, which is incorporated herein by reference in its entirety.

The disclosure provides antibodies and antigen-binding fragments thereof that specifically bind to PD-1. In some embodiments, the antibodies and antigen-binding fragments described herein are capable of binding to PD-1 and can inhibit PD1 signaling pathway thus increase immune response. The disclosure provides mouse anti-PD-1 antibody 1A7 and the humanized antibodies thereof.

The CDR sequences for 1A7, and 1A7 derived antibodies include CDRs of the heavy chain variable domain, SEQ ID NOs: 24-26, and CDRs of the light chain variable domain, SEQ ID NOs: 27-29, as defined by Kabat numbering (See FIG. 49). Under Chothia numbering, the CDR sequences of the heavy chain variable domain are set forth in SEQ ID NOs: 84-86, and CDRs of the light chain variable domain are set forth in SEQ ID NOs: 87-89 (See FIG. 50).

The amino acid sequence for heavy chain variable region (VH) and light chain variable region (VL) of 1A7, and 1A7 derived antibodies are also provided. The amino acid sequence for the heavy chain variable region of humanized 1A7 antibody (e.g., PD1-1A7-IgG4) is set forth in SEQ ID NO: 40. The amino acid sequence for the light chain variable region of humanized 1A7 antibody (e.g., PD1-1A7-IgG4) is set forth in SEQ ID NO: 41.

In some embodiments, the scFv described herein is derived from 1A7, and 1A7 derived antibodies. In some embodiments, the 1A7, or 1A7 derived antibodies (e.g., humanized antibodies) have an IgG1 or IgG4 subtype.

Details of the anti-PD-1 antibody 1A7 can be found, e.g., PCT/CN2018/077016, which is incorporated herein by reference in its entirety.

The disclosure provides antibodies and antigen-binding fragments thereof that specifically bind to CD40. In some embodiments, the antibodies and antigen-binding fragments described herein are capable of binding to CD40 and can promote CD40 signaling pathway thus increase immune response. The disclosure provides mouse anti-CD40 antibody 6A7 and the humanized antibodies thereof.

The amino acid sequence for heavy chain variable region (VH) and light chain variable region (VL) of 6A7, and 6A7 derived antibodies are also provided. The amino acid sequence for the heavy chain variable region of humanized 6A7 antibody (e.g., C40-6A7-IgG2) is set forth in SEQ ID NO: 91. The amino acid sequence for the light chain variable region of humanized 6A7 antibody (e.g., C40-6A7-IgG2) is set forth in SEQ ID NO: 92.

In some embodiments, the 6A7, or 6A7 derived antibodies (e.g., humanized antibodies) have an IgG1, IgG2, or IgG4 subtype. In some embodiments, the scFv described herein is derived from 6A7, and 6A7 derived antibodies. In some embodiments, the amino acid sequence of the scFv derived from 6A7 is set forth in SEQ ID NO: 16. In some embodiments, the scFv derived from 6A7 comprises at least 1, at least 2, at least 3, at least 4, at least 5, at least 6, at least 7, at least 8, at least 9, or at least 10 mutations to increase scFv stability.

Details of the anti-CD40 antibody 6A7 can be found, e.g., PCT/CN2018/096494, which is incorporated herein by reference in its entirety.

In some embodiments, the amino acid sequence for the heavy chain variable region of the anti-CD40 antibody (e.g., selicrelumab) is set forth in SEQ ID NO: 130. In some embodiments, the amino acid sequence for the light chain variable region of the anti-CD40 antibody (e.g., selicrelumab) is set forth in SEQ ID NO: 131.

Protein Complexes Targeting IL12 Pathway

The present disclosure provides a protein complex that targets IL12 pathway. In some embodiments, the protein complex is an modified immunoglobulin. In some embodiments, the modified immunoglobulin comprises a cytokine. In some embodiments, the cytokine is IL12 (e.g., human IL12). In some embodiments, the IL12 is IL12a. In some embodiments, the IL12a is a mouse IL12a (mIL12a). In some embodiments, the mIL12a comprises a sequence that is at least 80%, at least 85%, at least 90%, at least 95%, or 100% identical to SEQ ID NO: 125. In some embodiments, the mIL12a comprises a sequence that is at least 80%, at least 85%, at least 90%, at least 95%, or 100% identical to NCBI reference NP_001152896.1 or NP_032377.1. In some embodiments, the IL12a is a human IL12a (hIL12a). In some embodiments, the hIL12a comprises a sequence that is at least 80%, at least 85%, at least 90%, at least 95%, or 100% identical to SEQ ID NO: 127. In some embodiments, the hIL12a comprises a sequence that is at least 80%, at least 85%, at least 90%, at least 95%, or 100% identical to NCBI reference NP_000873.2. In some embodiments, the interleukin 12 is IL12b. In some embodiments, the IL12b is a mouse IL12b (mIL12b). In some embodiments, the mIL12b comprises a sequence that is at least 80%, at least 85%, at least 90%, at least 95%, or 100% identical to SEQ ID NO: 126. In some embodiments, the mIL12b comprises a sequence that is at least 80%, at least 85%, at least 90%, at least 95%, or 100% identical to NCBI reference NP_001290173.1. In some embodiments, the IL12b is a human IL12b (hIL12b). In some embodiments, the hIL12b comprises a sequence that is at least 80%, at least 85%, at least 90%, at least 95%, or 100% identical to SEQ ID NO: 128. In some embodiments, the hIL12b comprises a sequence that is at least 80%, at least 85%, at least 90%, at least 95%, or 100% identical to NCBI reference NP_002178.2. In some embodiments, the interleukin 12 polypeptide is an IL12a and IL12b fusion protein, optionally linked with a linker sequence described herein. In some embodiments, IL12a and IL12b associate with each other by non-covalent interaction, forming a functional IL12 unit.

In one aspect, the disclosure is related to a protein complex comprising a targeting moiety fused with an immunomodulatory moiety. In some embodiments, (a) the targeting moiety specifically binds to a PD-1 ligand; and (b) the immunomodulatory moiety specifically binds to interleukin-12 receptor (IL12R). As used herein, a "targeting moiety" refers to a molecule that has the ability to localize and bind to a specific molecule or cellular component. The targeting moiety can be an antibody, antibody fragment, scFv, Fc-containing polypeptide, fusion antibody, polypeptide, peptide, aptamer, ligand, nucleic acid, or any combination thereof. In some embodiments, a targeting moiety can bind to a molecule present in a cell or tissue. In some embodiments, the targeting moiety can bind to a molecule in a diseased cell or tissue, e.g., a cancer cell or tumor. In some embodiments, the targeting molecule can bind to a normal cell or tissue, e.g., an immune cell such as T cell. In some embodiments, the targeting moiety can bind to a cellular or extracellular molecule that modulates the immune response. In some embodiments, the targeting moiety binds to a PD-1 ligand (e.g., PD-L1). As used herein, an "immunomodulatory moiety" refers to a ligand, peptide, polypeptide, or Fc-containing polypeptide that binds a specific component of an immune cell (e.g., T cell, regulatory T cell, myeloid suppressor cell, or dendritic cell) and modulates the number or function of immune cells. In some embodiments, the "immunomodulatory moiety" specifically binds a cytokine, cytokine receptor, co-stimulatory molecule, or co-inhibitory molecule that modulates the immune system. In some embodiments, the immunomodulatory moiety specifically binds to IL-12R. In some embodiments, the immunomodulatory moiety is an agonist that increases the function of the bound molecule.

In some embodiments, the immunomodulatory moiety comprises an antibody or antigen-binding fragment, a single chain variable fragment (scFv), a Fc-containing polypeptide, or a fusion protein that specifically binds IL12R.

In some embodiments, the immunomodulatory moiety is an IL12R agonist.

In some embodiments, the immunomodulatory moiety comprises IL12. In some embodiments, the IL12 comprises a IL12a (e.g., a human IL12a), a IL12b (e.g., a human IL12b), and/or a variant thereof.

In some embodiments, the targeting moiety comprises an antibody or antigen-binding fragment, a single chain variable fragment (scFv), a Fc-containing polypeptide, or a fusion protein that specifically binds to the PD-1 ligand.

In some embodiments, the targeting moiety comprises a full-length antibody.

In some embodiments, the targeting moiety comprises an extracellular domain of PD-1.

In some embodiments, the PD-1 ligand is PD-L1 or PD-L2.

In some embodiments, the targeting moiety blocks the interaction between PD-1 and the PD-1 ligand.

In some embodiments, targeting moiety has a KD of less than $1 \times 10^{-8}$M or less than $1 \times 10^{-9}$M with the PD-1 ligand.

In some embodiments, the targeting moiety comprises a polypeptide. In some embodiments, the immunomodulatory moiety is fused to the N-terminus or the C-terminus of the polypeptide.

In some embodiments, the immunomodulatory moiety comprises a polypeptide. In some embodiments, the targeting moiety is fused to the N-terminus or the C-terminus of the polypeptide.

In some embodiments, the targeting moiety comprises a polypeptide comprising a CH3 domain. In some embodiments, the immunomodulatory moiety is fused to the CH3 domain.

In some embodiments, the targeting moiety and the immunomodulatory moiety are fused to a scaffold protein (e.g., an albumin).

In some embodiments, the protein complex comprises a bispecific antibody. In some embodiments, the bispecific antibody binds to the PD-1 ligand and the IL12R.

In some embodiments, the protein complex comprises two or more immunomodulatory moieties that specifically bind to IL12R.

In some embodiments, the protein complex comprises two or more targeting moieties that specifically bind to a PD-1 ligand.

In some embodiments, the protein complex comprises an Fc comprising two CH3 domains.

In some embodiments, the immunomodulatory moiety is linked to a CH3 domain of the two CH3 domains in the Fc.

In some embodiments, the immunomodulatory moiety is linked to the C-terminus of a CH3 domain of the two CH3 domains.

In some embodiments, the immunomodulatory moiety is fused to a CH3 domain of the two CH3 domains in the Fc at a region from position 344 to position 382 of the CH3 domain according to EU numbering.

In some embodiments, the immunomodulatory moiety comprises IL12a and IL12b. In some embodiments, IL12a is linked to the Fc.

In some embodiments, the immunomodulatory moiety comprises IL12a and IL12b. In some embodiments, IL12b is linked to the Fc.

In some embodiments, the targeting moiety is linked to a CH3 domain of the two CH3 domains in the Fc.

In some embodiments, the targeting moiety is linked to the C-terminus of a CH3 domain of the two CH3 domains in the Fc.

In some embodiments, the targeting moiety is fused to a CH3 domain of the two CH3 domains in the Fc at a region from position 344 to position 382 of the CH3 domain according to EU numbering.

In some embodiments, the targeting moiety comprises a scFv (e.g., a scFv targeting the PD-1 ligand).

In some embodiments, the protein complex comprises two light chains.

In some embodiments, the immunomodulatory moiety is linked to one of the two light chains.

In some embodiments, the targeting moiety is linked to one of the two light chains.

In some embodiments, the protein complex further comprises an interferon (e.g., IFNa1, IFNa4, and/or IFNγ).

In some embodiments, the protein complex further comprises a cytokine (e.g., IL2, IL7, IL15, IL18, and/or IL21).

In some embodiments, the interferon or the cytokine is linked to the protein complex by a linker sequence.

In some embodiments, the protein complex comprises a linker sequence (GGGGS)n. In some embodiments, n can be 1, 2, 3, 4, 5, 6, 7 or 8.

In some embodiments, the targeting moiety comprises an anti-PD-L1 antibody or antigen-binding fragment thereof.

In some embodiments, the anti-PD-L1 antibody or antigen-binding fragment thereof is an IgG (e.g., IgG1, IgG2 or IgG4).

In some embodiments, the targeting moiety comprises a heavy chain variable region (VH) comprising complementarity determining regions (CDRs) 1, 2, and 3, and a light chain variable region (VL) comprising CDRs 1, 2, and 3.

In some embodiments, the VH CDR1 region comprises an amino acid sequence that is at least 80% identical to a selected VH CDR1 amino acid sequence, the VH CDR2 region comprises an amino acid sequence that is at least 80% identical to a selected VH CDR2 amino acid sequence, and the VH CDR3 region comprises an amino acid sequence that is at least 80% identical to a selected VH CDR3 amino acid sequence. In some embodiments, the VL CDR1 region comprises an amino acid sequence that is at least 80% identical to a selected VL CDR1 amino acid sequence, the VL CDR2 region comprises an amino acid sequence that is at least 80% identical to a selected VL CDR2 amino acid sequence, and the VL CDR3 region comprises an amino acid sequence that is at least 80% identical to a selected VL CDR3 amino acid sequence. In some embodiments, the selected VH CDRs 1, 2, and 3 amino acid sequences and the selected VL CDRs, 1, 2, and 3 amino acid sequences are one of the following:

(1) the selected VH CDRs 1, 2, 3 amino acid sequences are set forth in SEQ ID NOs: 1, 2, 3, respectively, and the selected VL CDRs 1, 2, 3 amino acid sequences are set forth in SEQ ID NOs: 4, 5, 6, respectively; and (2) the selected VH CDRs 1, 2, 3 amino acid sequences are set forth in SEQ ID NOs: 7, 8, 9, respectively, and the selected VL CDRs 1, 2, 3 amino acid sequences are set forth in SEQ ID NOs: 10, 11, 12, respectively.

In some embodiments, the targeting moiety comprises a heavy chain variable region (VH) comprising an amino acid sequence that is at least 90% identical to SEQ ID NO: 13, 14, 15, or 16, and a light chain variable region (VL) comprising an amino acid sequence that is at least 90% identical to SEQ ID NO: 17, 18, or 19.

In some embodiments, the immunomodulatory moiety comprises a sequence that is at least 80% identical to SEQ ID NO: 28 and a sequence that is at least 80% identical to SEQ ID NO: 29.

In one aspect, the disclosure is related to a method of treating a subject having cancer, the method comprising administering a therapeutically effective amount of a composition comprising the protein complex as described herein, to the subject.

In some embodiments, the subject has a PD-L1-expressing cancer.

In some embodiments, the cancer is resistant to anti-PD-1 antibody or anti-PD-L1 antibody treatment.

In some embodiments, the method described herein further comprises administering an effective amount of an anti-PD-1 antibody or an anti-PD-L1 antibody to the subject.

In one aspect, the disclosure is related to a method of increasing immune response in tumor microenvironment in a subject, the method comprising administering a therapeutically effective amount of a composition comprising the protein complex as described herein to the subject.

In one aspect, the disclosure is related to a method of activating T cells in tumor microenvironment of a subject, the method comprising administering a therapeutically effective amount of a composition comprising the protein complex as described herein to the subject.

In one aspect, the disclosure is related to a method of reducing IL12 toxicity when delivering IL12 into a subject, the method comprising administering a therapeutically effective amount of a composition comprising the protein complex as described herein, to the subject.

In one aspect, the disclosure is related to an isolated molecule comprising the protein complex as described herein; covalently bound to a therapeutic agent.

In some embodiments, the therapeutic agent is a cytotoxic or cytostatic agent.

In one aspect, the disclosure is related to a pharmaceutical composition comprising the protein complex as described herein; and a pharmaceutically acceptor carrier.

In one aspect, the disclosure is related to a nucleic acid encoding the protein complex as described herein.

In one aspect, the disclosure is related to a vector comprising the nucleic acid as described herein.

In one aspect, the disclosure is related to a host cell comprising the nucleic acid as described herein.

In one aspect, the disclosure is related to a method for producing a protein complex, the method comprising culturing the host cell as described herein under conditions suitable to produce the protein complex.

In some embodiments, the disclosure is related to a fused polypeptide. In some embodiments, the fused polypeptide comprises all or a portion of IL12a (NCBI Ref: NP_000873.2).

In some embodiments, the cytokine described herein is IL12. In some embodiments, the IL12 comprises IL12b (e.g., human IL12b). In some embodiments, the IL12 comprises a variant (e.g., a fusion protein or a truncated protein thereof) of IL12a and/or IL12b. In some embodiments, the IL12 does not comprise a signal peptide (e.g., a signal peptide of IL12a or IL12b).

Methods of Making Modified Immunoglobulins

The present disclosure also provides recombinant vectors (e.g., an expression vectors) that include an isolated polynucleotide disclosed herein (e.g., a polynucleotide that encodes a polypeptide disclosed herein), host cells into which are introduced the recombinant vectors (i.e., such that the host cells contain the polynucleotide and/or a vector comprising the polynucleotide), and the production of modified immunoglobulins by recombinant techniques.

As used herein, a "vector" is any construct capable of delivering one or more polynucleotide(s) of interest to a host cell when the vector is introduced to the host cell. An "expression vector" is capable of delivering and expressing the one or more polynucleotide(s) of interest as an encoded polypeptide in a host cell into which the expression vector has been introduced. Thus, in an expression vector, the polynucleotide of interest is positioned for expression in the vector by being operably linked with regulatory elements such as a promoter, enhancer, and/or a poly-A tail, either within the vector or in the genome of the host cell at or near or flanking the integration site of the polynucleotide of interest such that the polynucleotide of interest will be translated in the host cell introduced with the expression vector.

A vector can be introduced into the host cell by methods known in the art, e.g., electroporation, chemical transfection (e.g., DEAE-dextran), transformation, transfection, and infection and/or transduction (e.g., with recombinant virus). Thus, non-limiting examples of vectors include viral vectors (which can be used to generate recombinant virus), naked DNA or RNA, plasmids, cosmids, phage vectors, and DNA or RNA expression vectors associated with cationic condensing agents.

The expression vectors can include at least one selectable marker. Such markers include e.g., dihydrofolate reductase or neomycin resistance for eukaryotic cell culture and tetracycline or ampicillin resistance genes for culturing in *E. coli* and other bacteria. Representative examples of appropriate hosts include, but are not limited to, bacterial cells, such as *E. coli*, *Streptomyces*, and *Salmonella typhimurium* cells; fungal cells, such as yeast cells; insect cells such as *Drosophila* S2 and *Spodoptera* Sf9 cells; animal cells such as CHO, COS, Bowes melanoma, and HK 293 cells; and plant cells. Appropriate culture mediums and conditions for the host cells described herein are known in the art.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

Additional modifications to the antibodies or antigen-binding fragments can be made. For example, a cysteine residue(s) can be introduced into the Fc region, thereby allowing interchain disulfide bond formation in this region. The homodimeric antibody thus generated may have any increased half-life in vitro and/or in vivo. Homodimeric antibodies with increased half-life in vitro and/or in vivo can also be prepared using heterobifunctional cross-linkers as described, for example, in Wolff et al., "Monoclonal antibody homodimers: enhanced antitumor activity in nude mice." Cancer research 53.11 (1993): 2560-2565. Alternatively, an antibody can be engineered which has dual Fc regions.

In some embodiments, a covalent modification can be made to the modified immunoglobulin. These covalent modifications can be made by chemical or enzymatic synthesis, or by enzymatic or chemical cleavage. Other types of covalent modifications of the antibody or antibody fragment are introduced into the molecule by reacting targeted amino acid residues of the antibody or fragment with an organic derivatization agent that is capable of reacting with selected side chains or the N- or C-terminal residues.

In some embodiments, antibody variants are provided having a carbohydrate structure that lacks fucose attached (directly or indirectly) to an Fc region. For example, the amount of fucose in such antibody composition may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues; or position 314 in Kabat numbering); however, Asn297 may also be located about ±3 amino acids upstream or downstream of position 297, i.e., between positions 294 and 300, due to minor sequence variations in antibodies. Such fucosylation variants may have improved ADCC function. In some embodiments, to reduce glycan heterogeneity, the Fc region of the antibody can be further engineered to replace the Asparagine at position 297 with Alanine (N297A).

In some embodiments, to facilitate production efficiency by avoiding Fab-arm exchange, the Fc region of the antibodies was further engineered to replace the serine at position 228 (EU numbering) of IgG4 with proline (S228P). A detailed description regarding S228 mutation is described, e.g., in Silva et al. "The S228P mutation prevents in vivo and in vitro IgG4 Fab-arm exchange as demonstrated using a combination of novel quantitative immunoassays and physiological matrix preparation." Journal of Biological Chemistry 290.9 (2015): 5462-5469, which is incorporated by reference in its entirety.

The disclosure also provides a nucleic acid sequence that is at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% identical to any nucleotide sequence as described herein, and an amino acid sequence that is at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% identical to any amino acid sequence as described herein.

In some embodiments, the disclosure relates to nucleotide sequences encoding any peptides that are described herein, or any amino acid sequences that are encoded by any nucleotide sequences as described herein. In some embodiments, the nucleic acid sequence is less than 10, 20, 30, 40, 50, 60, 70, 80, 90, 100, 110, 120, 130, 150, 200, 250, 300, 350, 400, 500, or 600 nucleotides. In some embodiments, the amino acid sequence is less than 5, 6, 7, 8, 9, 10, 20, 30, 40, 50, 60, 70, 80, 90, 100, 110, 120, 130, 140, 150, 160, 170, 180, 190, 200, 250, 300, 350, 400 or 500 amino acid residues.

In some embodiments, the amino acid sequence (i) comprises an amino acid sequence; or (ii) consists of an amino acid sequence, wherein the amino acid sequence is any one of the sequences as described herein.

In some embodiments, the nucleic acid sequence (i) comprises a nucleic acid sequence; or (ii) consists of a nucleic acid sequence, wherein the nucleic acid sequence is any one of the sequences as described herein.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences. For example, the comparison of sequences and determination of percent identity between two sequences can be accomplished using a Blossum 62 scoring matrix with a gap penalty of 12, a gap extend penalty of 4, and a frameshift gap penalty of 5.

Methods of Treatment

The modified immunoglobulins as described herein can be used for various therapeutic purposes.

In one aspect, the disclosure provides methods for treating a cancer in a subject, methods of reducing the rate of the increase of volume of a tumor in a subject over time, methods of reducing the risk of developing a metastasis, or methods of reducing the risk of developing an additional metastasis in a subject. In some embodiments, the treatment can halt, slow, retard, or inhibit progression of a cancer. In some embodiments, the treatment can result in the reduction of in the number, severity, and/or duration of one or more symptoms of the cancer in a subject.

In one aspect, the disclosure features methods that include administering a therapeutically effective amount of a modified immunoglobulin disclosed herein to a subject in need thereof (e.g., a subject having, or identified or diagnosed as having, a cancer), e.g., breast cancer (e.g., triple-negative breast cancer), carcinoid cancer, cervical cancer, endometrial cancer, glioma, head and neck cancer, liver cancer, lung cancer, small cell lung cancer, lymphoma, melanoma, ovarian cancer, pancreatic cancer, prostate cancer, renal cancer, colorectal cancer, gastric cancer, testicular cancer, thyroid cancer, bladder cancer, urethral cancer, or hematologic malignancy. In some embodiments, the cancer is unresectable melanoma or metastatic melanoma, non-small cell lung carcinoma (NSCLC), small cell lung cancer (SCLC), bladder cancer, or metastatic hormone-refractory prostate cancer. In some embodiments, the subject has a solid tumor. In some embodiments, the cancer is squamous cell carcinoma of the head and neck (SCCHN), renal cell carcinoma (RCC), triple-negative breast cancer (TNBC), or colorectal carcinoma. In some embodiments, the subject has Hodgkin's lymphoma. In some embodiments, the subject has triple-negative breast cancer (TNBC), gastric cancer, urothelial cancer, Merkel-cell carcinoma, or head and neck cancer. In some embodiments, the cancer is melanoma, pancreatic carcinoma, mesothelioma, hematological malignancies, especially Non-Hodgkin's lymphoma, lymphoma, chronic lymphocytic leukemia, or advanced solid tumors.

In some embodiments, the compositions and methods disclosed herein can be used for treatment of patients at risk for a cancer. Patients with cancer can be identified with various methods known in the art.

In one aspect, the disclosure provides methods for treating, preventing, or reducing the risk of developing disorders associated with an abnormal or unwanted immune response, e.g., an autoimmune disorder. In some embodiments, the methods described herein can be used to treat inflammation. In some embodiments, the inflammatory or autoimmune disease is arthritis, colitis, psoriasis, asthma, Crohn's disease, or multiple sclerosis.

As used herein, by an "effective amount" is meant an amount or dosage sufficient to effect beneficial or desired results including halting, slowing, retarding, or inhibiting progression of a disease, e.g., a cancer or an autoimmune disease. An effective amount will vary depending upon, e.g., an age and a body weight of a subject to which the therapeutic agent is to be administered, a severity of symptoms and a route of administration, and thus administration can be determined on an individual basis.

An effective amount can be administered in one or more administrations. By way of example, an effective amount of a modified immunoglobulin is an amount sufficient to ameliorate, stop, stabilize, reverse, inhibit, slow and/or delay progression of an autoimmune disease or a cancer in a patient or is an amount sufficient to ameliorate, stop, stabilize, reverse, slow and/or delay proliferation of a cell (e.g., a biopsied cell, any of the cancer cells described herein, or cell line (e.g., a cancer cell line)) in vitro. As is understood in the art, an effective amount of modified immunoglobulin may vary, depending on, inter alia, patient history as well as other factors such as the type (and/or dosage) of the therapeutic agent used.

Effective amounts and schedules for administering the modified immunoglobulins, and/or compositions disclosed herein may be determined empirically, and making such determinations is within the skill in the art. Those skilled in the art will understand that the dosage that must be administered will vary depending on, for example, the mammal that will receive the modified immunoglobulins, and/or compositions disclosed herein, the route of administration, the particular type of modified immunoglobulins, and/or compositions disclosed herein used and other drugs being administered to the mammal.

A typical daily dosage of an effective amount of the modified immunoglobulin is 0.01 mg/kg to 100 mg/kg (mg per kg of patient weight). In some embodiments, the dosage can be less than 100 mg/kg, 10 mg/kg, 9 mg/kg, 8 mg/kg, 7 mg/kg, 6 mg/kg, 5 mg/kg, 4 mg/kg, 3 mg/kg, 2 mg/kg, 1 mg/kg, 0.5 mg/kg, or 0.1 mg/kg. In some embodiments, the dosage can be greater than 10 mg/kg, 9 mg/kg, 8 mg/kg, 7 mg/kg, 6 mg/kg, 5 mg/kg, 4 mg/kg, 3 mg/kg, 2 mg/kg, 1 mg/kg, 0.5 mg/kg, 0.1 mg/kg, 0.05 mg/kg, or 0.01 mg/kg. In some embodiments, the dosage is about 10 mg/kg, 9 mg/kg, 8 mg/kg, 7 mg/kg, 6 mg/kg, 5 mg/kg, 4 mg/kg, 3 mg/kg, 2 mg/kg, 1 mg/kg, 0.9 mg/kg, 0.8 mg/kg, 0.7 mg/kg, 0.6 mg/kg, 0.5 mg/kg, 0.4 mg/kg, 0.3 mg/kg, 0.2 mg/kg, or 0.1 mg/kg.

In any of the methods described herein, the modified immunoglobulin, or pharmaceutical composition (e.g., any of the modified immunoglobulins, or pharmaceutical compositions described herein) and, optionally, at least one additional therapeutic agent can be administered to the subject at least once a week (e.g., once a week, twice a week, three times a week, four times a week, once a day, twice a day, or three times a day). In some embodiments, at least one modified immunoglobulin and at least one additional therapeutic agent are administered in the same composition (e.g., a liquid composition). In some embodiments, the at least one modified immunoglobulin and the at least one additional therapeutic agent are administered in two different compositions (e.g., a liquid composition containing at least one modified immunoglobulin and a solid oral composition containing at least one additional therapeutic agent). In some embodiments, the at least one additional therapeutic agent is administered as a pill, tablet, or capsule. In some embodiments, the at least one additional therapeutic agent is administered in a sustained-release oral formulation.

In some embodiments, the one or more additional therapeutic agents can be administered to the subject prior to, or after administering the modified immunoglobulin. In some embodiments, the one or more additional therapeutic agents and the at least one modified immunoglobulin are administered to the subject such that there is an overlap in the bioactive period of the one or more additional therapeutic agents and the at least one modified immunoglobulin in the subject.

In some embodiments, the subject can be administered the at least one modified immunoglobulin over an extended period of time (e.g., over a period of at least 1 week, 2 weeks, 3 weeks, 1 month, 2 months, 3 months, 4 months, 5 months, 6 months, 7 months, 8 months, 9 months, 10 months, 11 months, 12 months, 1 year, 2 years, 3 years, 4 years, or 5 years). A skilled medical professional may determine the length of the treatment period using any of the methods described herein for diagnosing or following the effectiveness of treatment (e.g., the observation of at least one symptom of cancer).

In some embodiments, one or more additional therapeutic agents can be administered to the subject. The additional therapeutic agent can comprise one or more inhibitors selected from the group consisting of an inhibitor of B-Raf, an EGFR inhibitor, an inhibitor of a MEK, an inhibitor of ERK, an inhibitor of K-Ras, an inhibitor of c-Met, an inhibitor of anaplastic lymphoma kinase (ALK), an inhibitor of a phosphatidylinositol 3-kinase (PI3K), an inhibitor of an Akt, an inhibitor of mTOR, a dual PI3K/mTOR inhibitor, an inhibitor of Bruton's tyrosine kinase (BTK), and an inhibitor of Isocitrate dehydrogenase 1 (IDH1) and/or Isocitrate dehydrogenase 2 (IDH2). In some embodiments, the additional therapeutic agent is an inhibitor of indoleamine 2,3-dioxygenase-1) (IDO1) (e.g., epacadostat). In some embodiments, the additional therapeutic agent can comprise one or more inhibitors selected from the group consisting of an inhibitor of HER3, an inhibitor of LSD1, an inhibitor of MDM2, an inhibitor of BCL2, an inhibitor of CHK1, an inhibitor of activated hedgehog signaling pathway, and an agent that selectively degrades the estrogen receptor.

In some embodiments, the additional therapeutic agent can comprise one or more therapeutic agents selected from the group consisting of Trabectedin, nab-paclitaxel, Trebananib, Pazopanib, Cediranib, Palbociclib, everolimus, fluoropyrimidine, IFL, regorafenib, Reolysin, Alimta, Zykadia, Sutent, temsirolimus, axitinib, everolimus, sorafenib, Votrient, Pazopanib, IMA-901, AGS-003, cabozantinib, Vinflunine, an Hsp90 inhibitor, Ad-GM-CSF, Temazolomide, IL-2, IFNa, vinblastine, Thalomid, dacarbazine, cyclophosphamide, lenalidomide, azacytidine, lenalidomide, bortezomid, amrubicine, carfilzomib, pralatrexate, and enzastaurin.

In some embodiments, the additional therapeutic agent can comprise one or more therapeutic agents selected from the group consisting of an adjuvant, a TLR agonist, tumor necrosis factor (TNF) alpha, IL-1, HMGB1, an IL-10 antagonist, an IL-4 antagonist, an IL-13 antagonist, an IL-17 antagonist, an HVEM antagonist, an ICOS agonist, a treatment targeting CX3CL1, a treatment targeting CXCL9, a treatment targeting CXCL10, a treatment targeting CCLS, an LFA-1 agonist, an ICAM1 agonist, and a Selectin agonist. In some embodiments, carboplatin, nab-paclitaxel, pacli- taxel, cisplatin, pemetrexed, gemcitabine, FOLFOX, or FOLFIRI are administered to the subject.

In some embodiments, the additional therapeutic agent is an anti-OX40 antibody, an anti-PD-1 antibody, an anti-PD-L1 antibody, an anti-PD-L2 antibody, an anti-LAG-3 antibody, an anti-TIGIT antibody, an anti-BTLA antibody, an anti-CTLA-4 antibody, or an anti-GITR antibody.

Pharmaceutical Compositions and Routes of Administration

Also provided herein are pharmaceutical compositions that contain at least one (e.g., one, two, three, or four) of the modified immunoglobulins described herein. Two or more (e.g., two, three, or four) of any of the modified immunoglobulins described herein can be present in a pharmaceutical composition in any combination. The pharmaceutical compositions may be formulated in any manner known in the art.

A "pharmaceutically acceptable carrier" refers to an ingredient in a pharmaceutical formulation, other than an active ingredient, which is bioactivity acceptable and nontoxic to a subject. Pharmaceutical acceptable carriers for use in the pharmaceutical compositions disclosed herein may include, for example, pharmaceutically acceptable liquid, gel, or solid carriers, aqueous vehicles, nonaqueous vehicles, antimicrobial agents, isotonic agents, buffers, antioxidants, anesthetics, suspending/dispending agents, sequestering or chelating agents, diluents, adjuvants, excipients, or nontoxic auxiliary substances, other components known in the art, or various combinations thereof. Some suitable components may include, for example, antioxidants, fillers, binders, disintegrants, buffers, preservatives, lubricants, flavorings, thickeners, coloring agents, emulsifiers or stabilizers such as sugars and cyclodextrins. Suitable antioxidants may include, for example, methionine, ascorbic acid, EDTA, sodium thiosulfate, platinum, catalase, citric acid, cysteine, thioglycerol, thioglycolic acid, thiosorbitol, butylated hydroxanisol, butylated hydroxytoluene, and/or propyl gallate. As disclosed herein, inclusion of one or more antioxidants such as methionine in a pharmaceutical composition provided herein decreases oxidation of the polypeptide complex or the bispecific polypeptide complex. This reduction in oxidation prevents or reduces loss of binding affinity, thereby improving protein stability and maximizing shelf-life. Therefore, in certain embodiments, compositions are provided that comprise the polypeptide complex or the bispecific polypeptide complex disclosed herein and one or more antioxidants such as methionine.

Pharmaceutical compositions are also formulated to be compatible with their intended route of administration (e.g., intravenous, intraarterial, intramuscular, intradermal, subcutaneous, or intraperitoneal). Preparations of the compositions can be formulated and enclosed in ampules, disposable syringes, or multiple dose vials. Where required (as in, for example, injectable formulations), proper fluidity can be maintained by, for example, the use of a coating, such as lecithin, or a surfactant. Absorption of the modified immunoglobulin can be prolonged by including an agent that delays absorption (e.g., aluminum monostearate and gelatin). Alternatively, controlled release can be achieved by implants and microencapsulated delivery systems, which can include biodegradable, biocompatible polymers (e.g., ethylene vinyl acetate, polyanhydrides, polyglycolic acid, collagen, polyorthoesters, and polylactic acid).

Compositions containing one or more of any of the modified immunoglobulins described herein can be formulated for parenteral (e.g., intravenous, intraarterial, intramuscular, intradermal, subcutaneous, or intraperitoneal) administration in dosage unit form (i.e., physically discrete units containing a predetermined quantity of active compound for ease of administration and uniformity of dosage).

Pharmaceutical compositions for parenteral administration are preferably sterile and substantially isotonic and manufactured under Good Manufacturing Practice (GMP) conditions. Pharmaceutical compositions can be provided in unit dosage form (i.e., the dosage for a single administration). For injection, modified immunoglobulins can be formulated in aqueous solutions, preferably in physiologically-compatible buffers to reduce discomfort at the site of injection.

Exemplary doses include milligram or microgram amounts of any of the modified immunoglobulins described herein per kilogram of the subject's weight (e.g., about 1 µg/kg to about 500 mg/kg; about 100 µg/kg to about 500 mg/kg; about 100 µg/kg to about 50~mg/kg; about 10 µg/kg to about 5 mg/kg; about 10 µg/kg to about 0.5 mg/kg; about 1 µg/kg to about 50~µg/kg; about 1 mg/kg to about 10 mg/kg; or about 1 mg/kg to about 5 mg/kg). While these doses cover a broad range, one of ordinary skill in the art will understand that therapeutic agents, including modified immunoglobulins, vary in their potency, and effective amounts can be determined by methods known in the art. Typically, relatively low doses are administered at first, and the attending health care professional or veterinary professional (in the case of therapeutic application) or a researcher (when still working at the development stage) can subsequently and gradually increase the dose until an appropriate response is obtained. In addition, it is understood that the specific dose level for any particular subject will depend upon a variety of factors including the activity of the specific compound employed, the age, body weight, general health, gender, and diet of the subject, the time of administration, the route of administration, the rate of excretion, and the half-life of the modified immunoglobulins in vivo.

The pharmaceutical compositions can be included in a container, pack, or dispenser together with instructions for administration. The disclosure also provides methods of manufacturing the modified immunoglobulins for various uses as described herein.

EXAMPLES

The invention is further described in the following examples, which do not limit the scope of the invention described in the claims.

Example 1. Methods of Making and Purifying Antibodies

ExpiCHO-S cells (Thermo-Fisher, GIBCO, Catalog #A29133) were co-transfected with plasmids (at a molar ratio of 1:1) encoding the antibody heavy chain and the light chain. The transfected cells were cultured in a shaking incubator at 35° C. and with 8% CO2. Supernatant was collected from the cell culture after 12 days. The antibodies were then purified by chromatography columns filled with protein A beads, connected with an AKTA™ AVANT150 system.

Example 2. PD-L1 Antibody Modification at C-Terminus or Fab Region

Many bispecific antibody formats and immunocytokine formats are proposed for various treatment purposes (See e.g., FIGS. 20A-20D). Despite their conceptual advantages, it is difficult to make and manufacture these antibodies. Many existing manufacturing approaches for these antibody formats suffer from low efficiency and are limited by the complicated purification processes. Even for bispecific antibodies with knobs-in-holes modifications, they still had mispairing and low yield problems.

Experiments were performed to evaluate the expression efficiency and stability of these bispecific antibodies and immunocytokines. Plasmids were constructed to express a fusion protein that comprises a mouse interleukin 7 (mIL7, molecular weight: 17.5 kDa), linked at the heavy chain C-terminus of an anti-PD-L1 IgG1 antibody (PDL1-avelumab; heavy chain SEQ ID NO: 35 and light chain SEQ ID NO: 4). The fusion protein was named PDL1-mIL7-HC and its structure is illustrated in FIG. 20A as HC. A cytokine (e.g., mIL7) is attached to the C-terminus of the heavy chains.

Plasmids were also constructed to link the mIL7 to the C-terminus of the anti-PD-L1 antibody light chain (PDL1-mIL7-LC). Schematic structures of the PDL1-mIL7-LC fusion proteins are shown in FIG. 20A as LC. A cytokine (e.g., mIL7) is attached to C-terminal of the light chains.

The expression level of the two fusion proteins were evaluated. Specifically, ExpiCHO-S cells were transfected by the plasmids and the expressed fusion proteins were purified and analyzed by gel electrophoresis. As shown in FIG. 1, the PDL1-mIL7-HC fusion protein in Lane 6 presented multiple non-target bands in the native gel. The PDL1-mIL7-LC fusion protein in Lane 11 did not have any visible bands in the native gel, indicating a low expression level.

Figure 2:
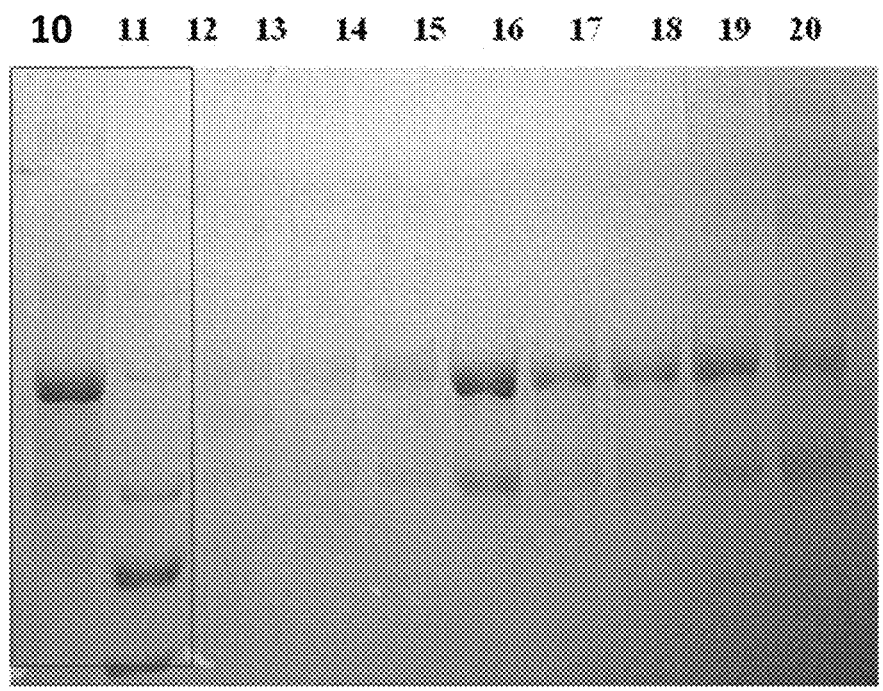
FIG. 2 is an image of electrophoresis showing PDL1-hIL21-KIH in Lane 10. Lane 11 is protein marker.

An asymmetric antibody was also expressed to replace one Fab arm of a PD-L1 antibody with human interleukin 21 (hIL21) with sequence set forth in SEQ ID NO: 12 (amino acids 25-162 of NP_068575.1). Knobs-in-holes (KIH) modification was also introduced at the Fc region. The fusion protein PDL1-hIL21-KIH structure is shown in FIG. 20A as Fab-cytokine-KIH, wherein the circle represents 11E21. It is linked to hinge region of a heavy chain was purified and analyzed by gel electrophoresis. Results in FIG. 2 showed that PDL1-hIL21-KIH in Lane 10 presented multiple non-target bands in the native gel.

In summary, expression levels for the modified antibodies with a symmetric structure (e.g., PDL1-mIL7-HC, or PDL1-mIL7-LC) varied greatly between different projects. The expression level can be low and the expressed sample had non-target proteins. Similarly, the modified antibody with an asymmetric structure (e.g., PDL1-hIL21-KIH) was difficult to purify because of the large amount of the non-target protein in the samples.

Example 3. PD-L1 Antibody Fused at the 3A Site

Figure 3:
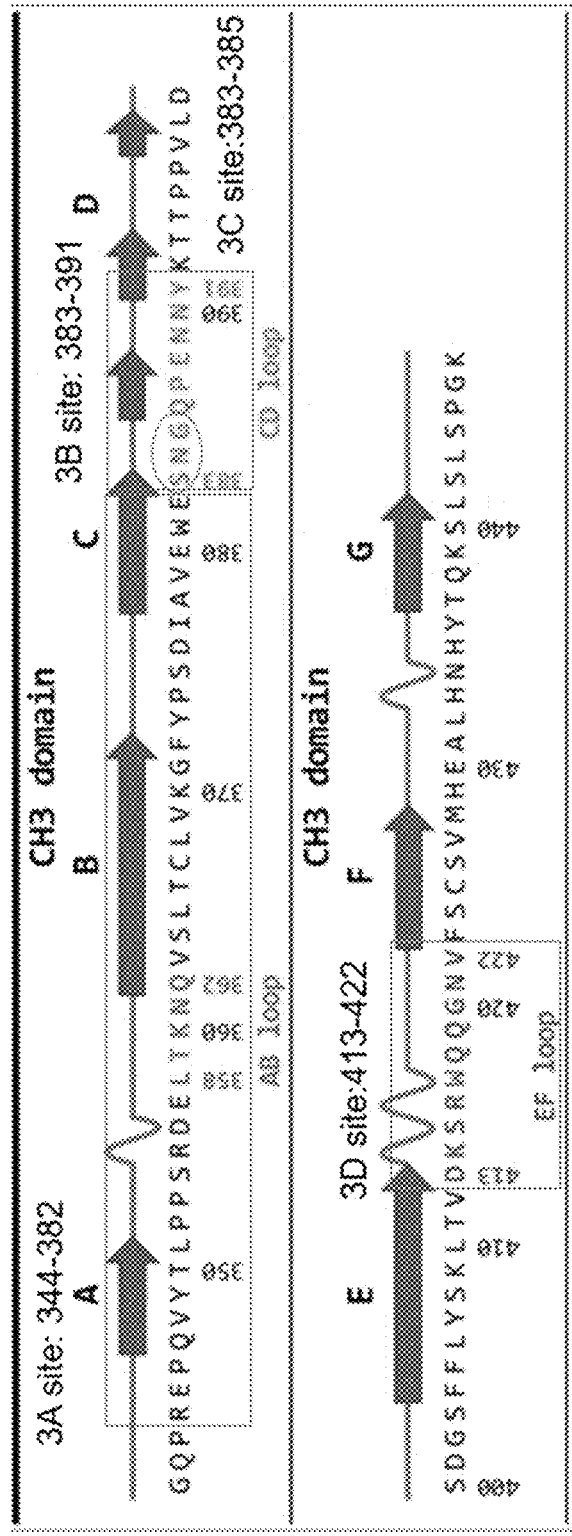
FIG. 3 is a schematic diagram showing the heavy chain CH3 domain of an antibody according to EU numbering. Four fusion sites are highlighted by rectangles or circles.

Plasmids were constructed to express a fusion protein that comprises a mouse interleukin 7 domain, fused to the 3A site of an anti-PD-L1 IgG1 antibody (PDL1-avelumab), as shown in FIG. 3. As the fusion site was located within the 3A site of the heavy chain CH3 domain of the PD-L1 antibody, the fusion protein was named PDL1-mIL7-3A (structure shown in FIG. 20A as 3A, the heavy chain is SEQ ID NO: 5).

Other fusion sites of the heavy chain CH3 domain of the antibody were also tested (FIG. 3). For example, the IL7 was fused at the 3B site (SEQ ID NO: 6); 3C site (SEQ ID NO: 7); and 3D site (SEQ ID NO: 8). Sequence alignment between human IgG1, IgG2 and IgG4 (SEQ ID NOs: 1-3) heavy chain constant regions are shown in FIG. 4, wherein the amino acid sequences are shown as follows (sequences and EU numbering can be found at the international ImMunoGeneTics information system (IMGT), which is incorporated herein by reference in the entirety). The isoforms of IgG1, IgG2 and IgG4 (SEQ ID NOs: 32-34) are shown in FIG. 48.

IgG1-CH:
(SEQ ID NO: 1)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK

IgG2-CH:
(SEQ ID NO: 2)
STKGPSVFPLAPCSRSTSESTAALGCLVKDYFPEPVTVSWNSGALTSGVH

TFPAVLQSSGLYSLSSVVTVPSSNFGTQTYTCNVDHKPSNTKVDKTVERK

CCVECPPCPAPPVAGPSVFLFPPKPKDTLMISRTPEVTCVVVDVSHEDPE

VQFNWYVDGVEVHNAKTKPREEQFNSTFRVVSVLTVVHQDWLNGKEYKCK

VSNKGLPAPIEKTISKTKGQPREPQVYTLPPSREEMTKNQVSLTCLVKGF

YPSDIAVEWESNGQPENNYKTTPPMLDSDGSFFLYSKLTVDKSRWQQGNV

FSCSVMHEALHNHYTQKSLSLSPGK

IgG4-CH:
(SEQ ID NO: 3)
STKGPSVFPLAPCSRSTSESTAALGCLVKDYFPEPVTVSWNSGALTSGVH

TFPAVLQSSGLYSLSSVVTVPSSSLGTKTYTCNVDHKPSNTKVDKRVESK

YGPPCPPCPAPEFLGGPSVFLFPPKPKDTLMISRTPEVTCVVVDVSQEDP

EVQFNWYVDGVEVHNAKTKPREEQFNSTYRVVSVLTVLHQDWLNGKEYKC

KVSNKGLPSSIEKTISKAKGQPREPQVYTLPPSQEEMTKNQVSLTCLVKG

FYPSDIAVEWESNGQPENNYKTTPPVLDSDGSFFLYSRLTVDKSRWQEGN

VFSCSVMHEALHNHYTQKSLSLSLGK

Further, mouse interferon alpha 4 (mIFNa4) (SEQ ID NO: 10) was connected to the C-terminus of the mIL7-fused anti-PD-L1 antibody heavy chain through a linker sequence (SEQ ID NO: 9) (structure shown in FIG. 20A as 3A-HC). The constructs were used to transfect CHO cells and the expression levels were evaluated. As shown in the table below, the 3A fusion site exhibited the highest expression levels as compared to antibodies with fusions at 3B, 3C or 3D sites.

TABLE 5

| Lane | Name | Total (mg) | Concentration (μg/mL) |
|---|---|---|---|
| 1 | PDL1-mIL7-3A | 4.32 | 144 |
| 2 | PDL1-mIL7-3B | 0.8184 | 27.28 |
| 3 | PDL1-mIL7-3C | 0.267 | 8.9 |
| 4 | PDL1-mIL7-3D | 2.28 | 0* |
| 5 | PDL1-mIL7-3A-mIFNa4 | 4.86 | 162 |
| 6 | PDL1-mIL7-3B-mIFNa4 | 1.68 | 56 |
| 7 | PDL1-mIL7-3C-mIFNa4 | 1.116 | 37.2 |
| 8 | PDL1-mIL7-3D-mIFNa4 | 0.756 | 25.2 |

*Note: actually concentration is 0 due to aggregation.

Figure 5A:
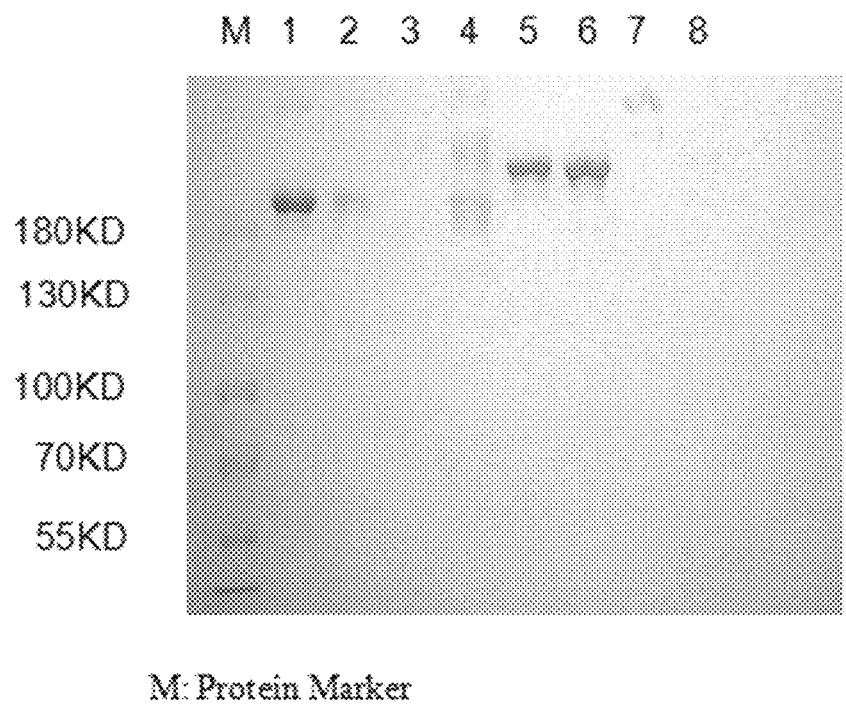
FIG. 5A is an image of electrophoresis showing purified proteins as shown in Table 5.

The fusion proteins were purified by protein A chromatography and analyzed by a native gel. As shown in FIG. 5A, PDL1-mIL7-3A (Lane 1), PDL1-mIL7-3A-mIFNa4 (Lane 5) and PDL1-mIL7-3B-mIFNa4 (Lane 6) each presented a clear band, confirming the expression levels as determined in the table. PDL1-mIL7-3D (Lane 4) was determined to have an expression level comparable to PDL1-mIL7-3B-mIFNa4 (Lane 6), but did not exhibit one clear band in FIG. 5A, indicating that PDL1-mIL7-3D had aggregation. PDL1-mIL7-3A, PDL1-mIL7-3B, PDL1-mIL7-3A-mIFNa4 and PDL1-mIL7-3B-mIFNa4, all had one clear band, indicating that these modified antibodies had relatively high purity.

Figure 5B:
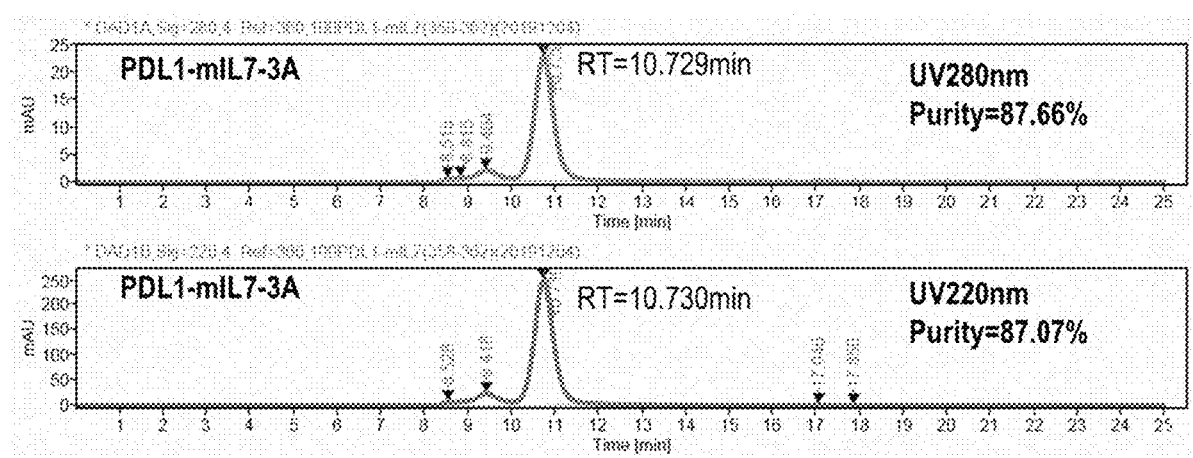
FIG. 5B is an image showing the SEC-HPLC (size exclusion chromatography) result of PDL1-mIL7-3A.
Figure 5C:
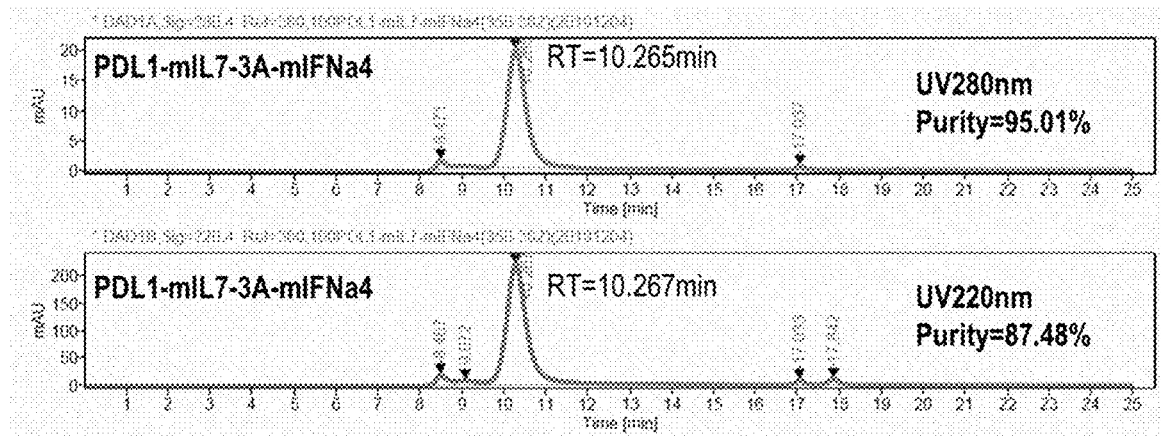
FIG. 5C is an image showing the SEC-HPLC result of PDL1-mIL7-3A-mIFNa4.

The results of PDL1-mIL7-3A and PDL1-mIL7-3A-mIFNa4 were further confirmed by size-exclusive chromatography HPLC (SEC-HPLC) in FIG. 5B-5C. As shown in FIGS. 5B-5C, the result from SEC-HPLC only had one major peak for PDL1-mIL7-3A and PDL1-mIL7-3A-mIFNa4, indicating that these modified antibodies had high expression levels with high purity, and the expression products were stable and did not form aggregates.

Determination of Binding Affinity to PD-L1 Protein

The binding affinity between purified 6×Histidine-tagged human PD-L1 (hPDL1-His) and PDL1-avelumab, PDL1-mIL7-3A, or PDL1-mIL7-3A-mIFNa4 were measured by surface plasmon resonance (SPR) using Biacore™ (Biacore, INC, Piscataway N.J.) T200 biosensor equipped with pre-immobilized protein A sensor chips. In PDL1-mIL7-3A, mIL7 was fused to the 3A site. In PDL1-mIL7-3A-mIFNa4, mIFNa4 was linked to the C-terminal of the antibody PDL1-mIL7-3A.

The fusion proteins (1 μg/mL) were injected into Biacore™ T200 biosensor at 10 μL/min for 20 seconds to achieve to a desired protein density. 6×Histidine-tagged human PD-L1 protein (hPDL1-His) were then injected at 30 μL/min for 180 seconds. Dissociation was monitored for 300 seconds. The chip was regenerated after the last injection of each titration with Glycine (pH 2.0, 30 μL/min for 5 seconds). As a person of ordinary skill in the art would understand, the same method with appropriate adjustments for parameters (e.g., antibody concentration) was performed for each tested antibody. The results for the tested antibodies are shown in the table below.

TABLE 6

| Capture Solution | analysis | kon (1/Ms) | koff (1/s) | KD (M) |
|---|---|---|---|---|
| PDL1-avelumab | hPDL1-His | 2.29E+04 | 8.40E−05 | 3.67E−09 |
| PDL1-mIL7-3A | hPDL1-His | 2.43E+04 | 7.54E−05 | 3.11E−09 |
| PDL1-mIL7-3A-mIFNa4 | hPDL1-His | 2.41E+04 | 7.86E−05 | 3.26E−09 |

Kinetic association rates (kon) and dissociation rates (koff) were obtained simultaneously by fitting the data globally to a 1:1 Langmuir binding model (Karlsson, R. Roos, H. Fagerstam, L. Petersson, B., 1994. Methods Enzymology 6. 99-110) using Biacore™ T200 Evaluation Software 3.0. Affinities were calculated from the quotient of the kinetic rate constants (KD=koff/kon). The results indicated that PDL1-mIL7-3A and PDL1-mIL7-3A-mIFNa4 had similar binding affinity to human PD-L1 protein, as compared to the unmodified parent anti-PD-L1 antibody (PDL1-avelumab).

Verification of Cytokine Activity

The following materials were used.

Red blood cell lysis buffer was purchased from Beyotime Biotechnology (Catalog number C3702).

Anti-CD16/32 (aCD16/32) antibody was purchased from Miltenyi Biotec.

Fetal Bovine Serum (FBS) was purchased from ExCell Biotech Co, Ltd.

Phospho-STAT5 (Tyr694) Monoclonal Antibody (SRBCZX) APC, eBioscience™ was purchased from ThermoFisher (Catalog number 17-9010-41).

Phospho-STAT1 (Ser727) Recombinant Rabbit Monoclonal Antibody (Stat1S727-C6), PE was purchased from ThermoFisher (Catalog number MA5-28056).

CD8a Monoclonal Antibody (53-6.7), FITC, eBioscience™ was purchased from ThermoFisher (Catalog number 11-0081-82).

The bioactivities of the inserted mIL7 and mIFNa4 were measured. Mouse spleen was collected from BALB/c background mice. The spleen was grinded and passed through a filter. The filter was washed with 3 ml PBS and the grinded spleen cells were centrifuged at 400 g/min for 3 minutes. After centrifugation, supernatant was discarded and 1 ml red blood cell lysis buffer was added to lyse red blood cells at 4° C. for 15 minutes. The remaining cells were resuspended by 5 ml PBS, then centrifuged at 400 g/min for 3 minutes, followed by removal of supernatant after centrifugation. The cell resuspension, centrifugation and removal of supernatant were repeated once. The remaining cells were resuspended by 200 μl PBS and the aCD16/32 (anti-mouse CD16/32) antibody was added to block the cells at 4° C. for 15 minutes. The blocked cells were further diluted in 10 ml PBS and cell number was counted. The cells were then centrifuged at 400 g/min for 3 minutes, followed by removal of supernatant. An appropriate volume of RPMI 1640 medium was added to adjust cell titer.

Cells were treated by a particular cytokine (e.g., mouse interleukin 7, or mIL7), or the fusion proteins that comprise a cytokine domain. Specifically, 200 μl of cell suspension was added to each well in a 96-well plate, such that each well had $10^5$ cells. Then, PBS (5 μl), mIL7 protein (100 ng), PDL1-mIL7-3A (550 ng) or PDL1-mIL7-3A-mIFNa4 (650 ng) were added to separate wells, respectively. The mIL7 in the mIL7 group, the PDL1-mIL7-3A group and the PDL1-mIL7-3A-mIFNa4 group are roughly equivalent. The cells were gently mixed and incubated at 37° C. for 30 minutes.

The treated cells were permeabilized by 4% formaldehyde (final concentration)-PBS solution at room temperature for 15 minutes. Then, the cells were washed by PBS once, resuspended in 100% ice-cold methanol and incubated in ice bath for 30 minutes. After the incubation, the cells were washed by PBS (supplemented with 0.5% BSA) three times.

Figure 6:
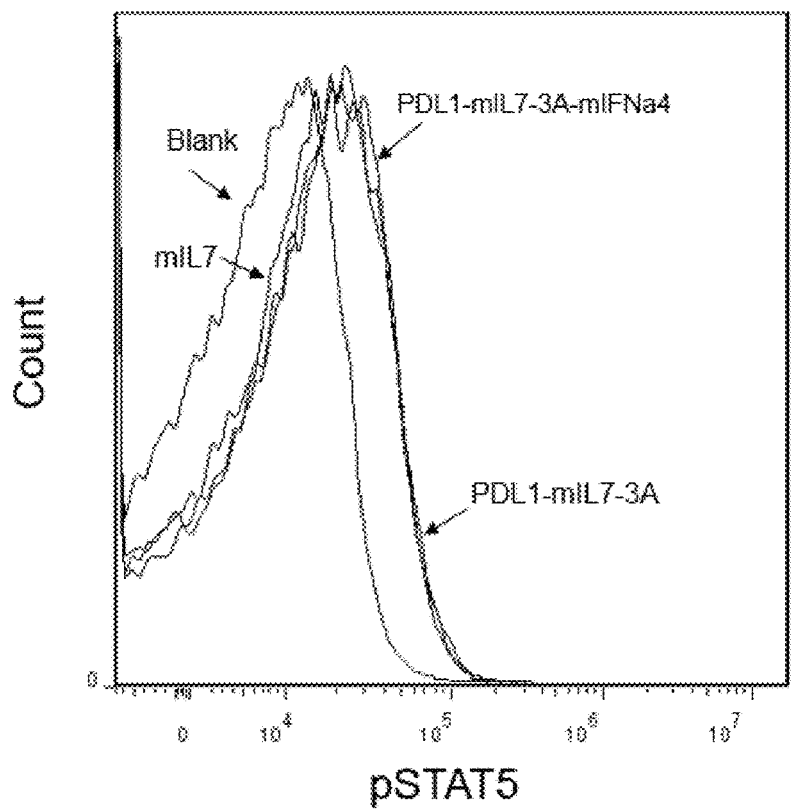
FIG. 6 shows pSTAT5 signals determined by flow cytometry in mouse spleen cells treated by PBS (blank), mIL7 protein, PDL1-mIL7-3A-mIFNa4, or PDL1-mIL7-3A.

In one experiment, the mIL7 activity was measured. APC-labeled phospho-STAT5 (Tyr694) Monoclonal Antibody (SRBCZX, eBioscience™) and FITC-labeled CD8a Monoclonal Antibody (53-6.7; eBioscience™) were added to stain the cells at 4° C. for 30 minutes. After the staining step, the stained cells were washed by PBS and analyzed by flow cytometry. Because mIL7 can phosphorylate mouse spleen STAT5 at Tyr694, the presence of mIL7 would be indicated by an increased fluorescence signal of APC (Allophycocyanin). As shown in FIG. 6, the mIL7 protein, PDL1-mIL7-3A and PDL1-mIL7-3A-mIFNa4 all exhibited an increased APC level, compared to PBS-treated spleen cells (blank).

Figure 7:
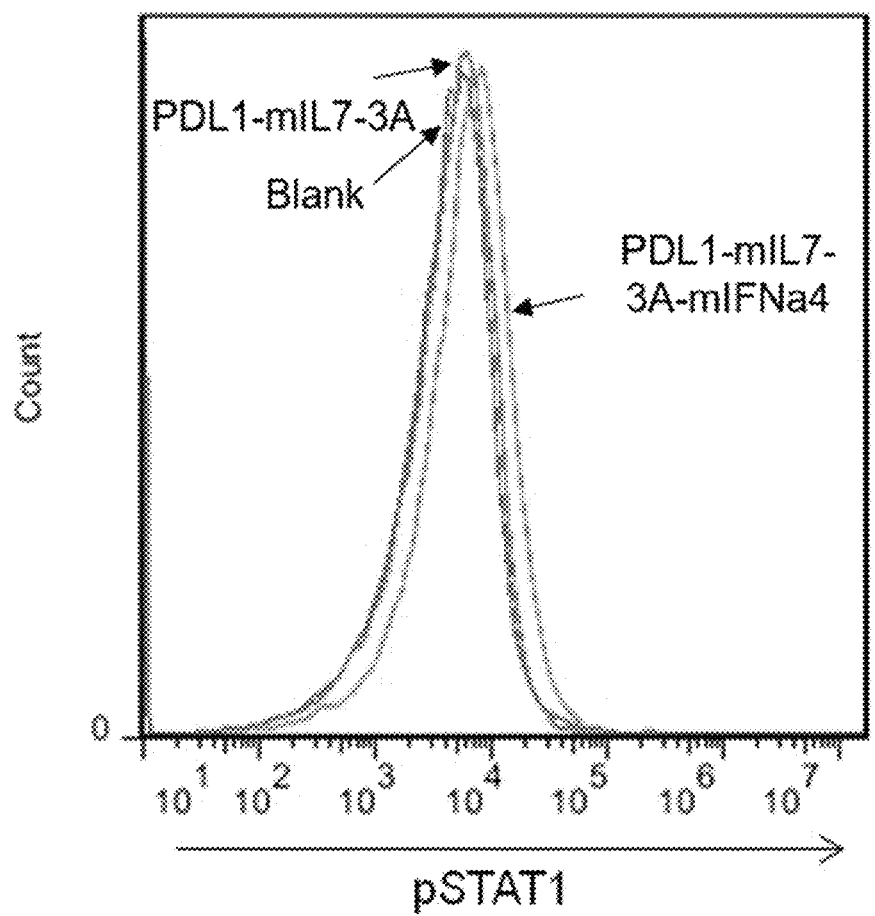
FIG. 7 shows pSTAT1 signals determined by flow cytometry in mouse spleen cells treated by PBS (blank), PDL1-mIL7-3A, or PDL1-mIL7-3A-mIFNa4.

In a separate experiment, mIFNa4 activity was measured by a similar method. Phospho-STAT1 (Ser727) Recombinant Rabbit Monoclonal Antibody (Stat1S727-C6) and FITC-labeled CD8a Monoclonal Antibody (53-6.7; eBioscience™) were added to stain the cells at 4° C. for 30 minutes. After the staining step, the stained cells were washed by PBS and analyzed by flow cytometry. Because mIFNa4 can phosphorylate mouse spleen STAT1 at Ser727, the presence of mIFNa4 would be indicated by an increased fluorescence signal. As shown in FIG. 7, only the PDL1-mIL7-3A-mIFNa4 exhibited an increased signal, while the PDL1-mIL7-3A presented an unchanged signal compared to PBS-treated spleen cells (blank).

The experiments above indicated that the inserted mIL7 and mIFNa4 in the modified antibodies preserved their bioactivity.

Determination of Binding Affinity to Fc Receptors

The binding affinity of PD-L1 antibody (PDL1-avelumab), PDL1-mIL7-3A-mIFNa4, and PDL1-mIL7-3A against various Fc receptors were measured by surface plasmon resonance (SPR) using Biacore™ (Biacore, INC, Piscataway N.J.) T200 biosensor equipped with pre-immobilized protein A sensor chips. The Fc receptors included FcγRIIB (FcγRIIB-Acro), FcγRIIA (FcγRIIA-H167-Acro), FcγRIIIA (FcγRIIIA-V176-Acro), FcγRIIIB (FcγRIIIB-NA1-Acro), FcγRI (FcγRI-Sino), and FcRn (FcRn-Acro).

In a different experiment, the binding affinity of PD1-PL1-3F2-FV3A-IgG1, AB-IgG1 (a control antibody with same IgG1 subtype as PD1-PL1-3F2-FV3A-IgG1), PDL1-C40-6A7-FV3A-IgG4, and AB-IgG4 (a control antibody with same IgG4 subtype as PDL1-C40-6A7-FV3A-IgG4) against various Fc receptors were measured using Biacore™ as described above. The Fc receptors included FcγRI (FcγRI-Sino), FcγRIIA (FcγRIIA-H167-Acro and FcγRIIA-R167), FcγRIIB, FcγRIIIA (FcγRIIIA-F176 and FcγRIIIA-V176-Acro), and FcγRIIIB (FcγRIIIB-NA1-Acro).

Specifically, PD1-PL1-3F2-FV3A-IgG1 was generated by fusing a scFv (SEQ ID NO: 17) having the VH and VL sequences of anti-PD-L1 antibody PDL1-3F2 (PDL1-3F2-IgG1, or 3F2) to the 3A site of anti-PD-1 antibody PD1-1A7-IgG4 (VH SEQ ID NO: 40; VL SEQ ID NO: 41), followed by a replacement of IgG4 with IgG1 subtype. PDL1-C40-6A7-FV3A-IgG4 was generated by fusing a scFv (SEQ ID NO: 16) having the VH and VL sequences of an anti-CD40 antibody C40-6A7 (6A7) to the 3A site of PDL1-avelumab, followed by a replacement of IgG1 with IgG4 subtype. The two fusion protein structures are shown in FIG. 20A as FV3A.

TABLE 7

| Product | Full name | Vendor | Catalog # |
| --- | --- | --- | --- |
| FcγRI-Sino | CD64 Protein, Human, Recombinant (His Tag) | Sino Biological Inc. | 10256-H08S |
| FcγRIIIA-V176-Acro | Human Fc gamma RIIIA/CD16a (V176) Protein, His Tag (SPR & BLI verified) | ACRO Biosystems | CD8-H52H4 |

TABLE 7-continued

| Product | Full name | Vendor | Catalog it |
|---|---|---|---|
| FcγRIIIB-NA1-Acro | Human Fc gamma RIIIB/CD16b (NA1) Protein, His Tag (SPR & BLI verified) | ACRO Biosystems | CDB-H5227 |
| FcγRIIB-Acro | Human Fc gamma RIIIB/CD16b (NA2) Protein, His Tag (SPR & BLI verified) | ACRO Biosystems | CDB-H5222 |
| FCRIIIB-Sino | CD16b Protein, Human, Recombinant (NA1 allotypes, His Tag) | Sino Biological Inc. | 11046-H08H1 |
| FcγRIIA-H167-Acro | Human Fc gamma RIIA/CD32a (H167) Protein, His Tag (SPR & BLI verified) | ACRO Biosystems | CD1-H5223 |
| FcRn | Human FcRn/FCGRT&B2M Heterodimer Protein, His Tag&Strep II Tag (SPR & BLI verified) | ACRO Biosystems | FCM-H5286 |
| FcγRIIA-R167 | Human Fc gamma RIIA/CD32a (R167) Protein, His Tag (BLI verified) | ACRO Biosystems | CDA-H5221 |
| FCRIIA-R167-Sino | CD32A Protein, Human, Recombinant (167 Arg, His Tag) | Sino Biological Inc. | 10374-H08C |
| FcγRIIIA-F176 | Human Fc gamma RIIIA/CD16a (F176) Protein, His Tag (SPR & BLI verified) | ACRO Biosystems | CDA-H5220 |
| FCRIIIA-F176-Sino | CD16a Protein, Human, Recombinant (176 Val, His Tag) | Sino Biological Inc. | 10389-H08C1 |

Figures 9A, 9B:
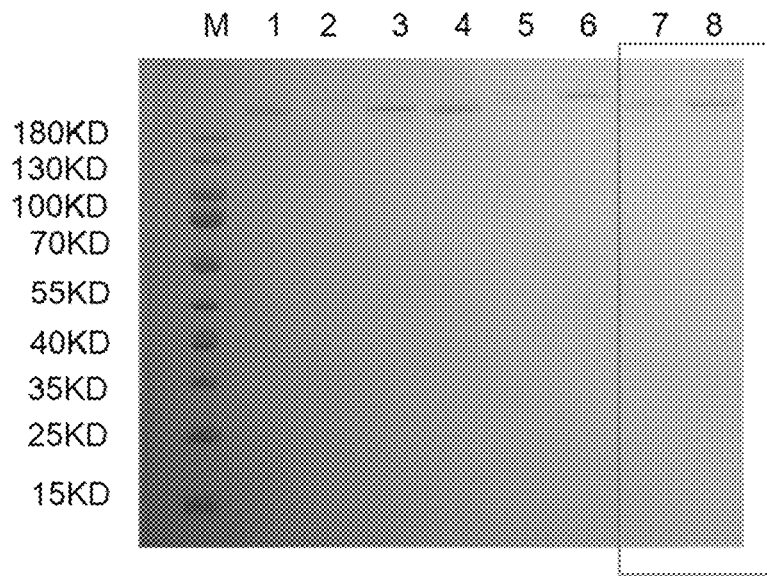
FIG. 9A is an image of electrophoresis showing purified proteins.
FIG. 9B is a table showing lane numbers, corresponding protein names (storage temperature), theoretical molecular weight (MW) and apparent molecular weight for the results in FIG. 9A.
Figure 9C:
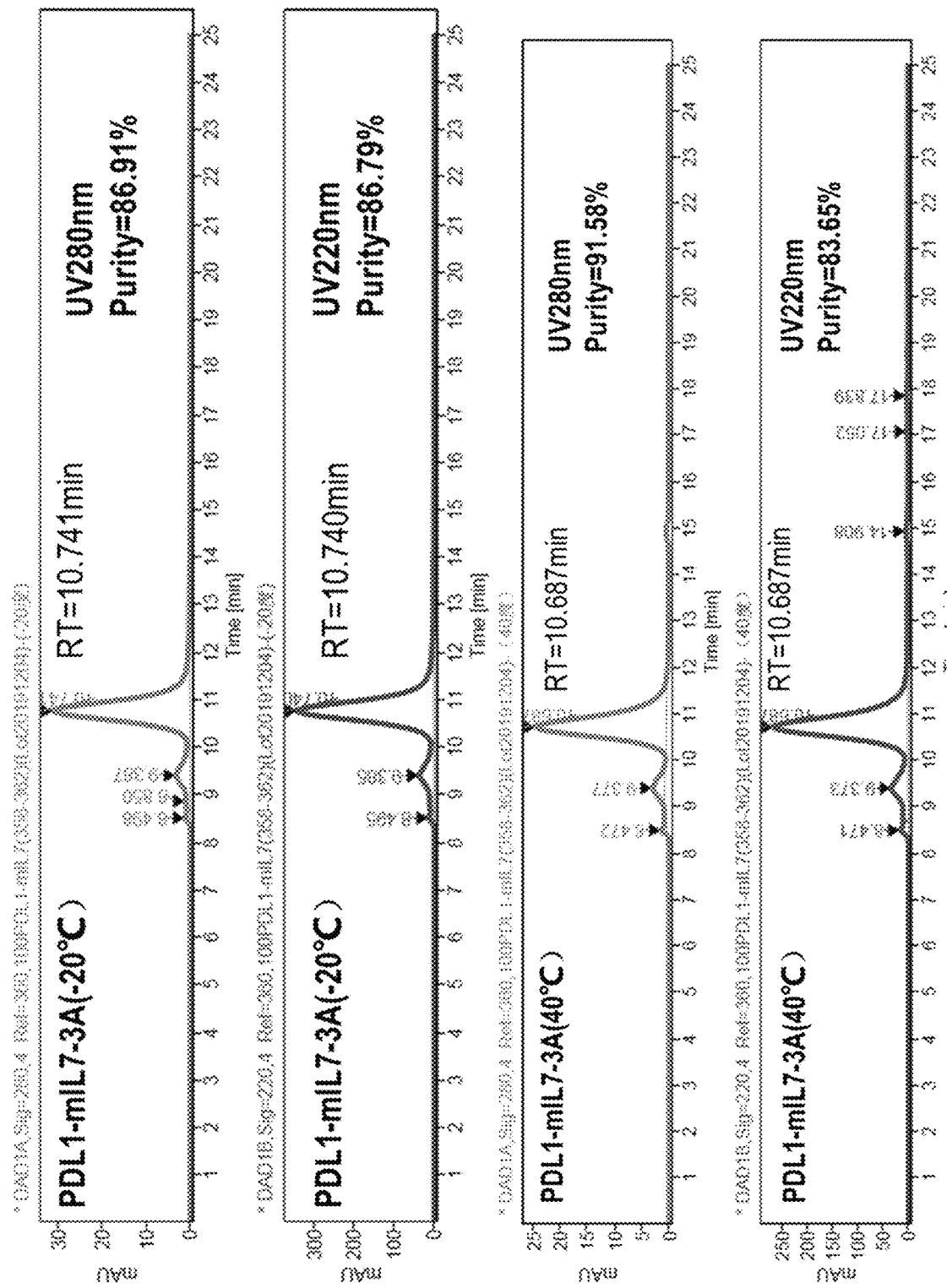
FIG. 9C are SEC-HPLC results of the proteins as shown in FIG. 9B.

The results are shown in FIGS. 8A-8B, the fusion of mIL7 and mIFNa4 at the anti-PD-L1 antibody did not substantially change the antibody's binding affinity to FcγRIIA, FcγRIIIA, FcγRIIIB or FcRn, as compared to that of the parent anti-PD-L1 antibody. In addition, fused scFv with IgG1 or IgG4 subtype did not substantially change the antibody's binding affinity to various Fc receptors including FcγRI, FcγRIIA, FcγRIIB, FcγRIIIA, and FcγRIIIB Protein Stability Test The fusion protein PDL1-mIL7-3A was stored at −20° C. or 40° C. for one month, and then analyzed by a native gel and size-exclusive chromatography (SEC). Results are shown in FIGS. 9A-9C. The apparent molecular weight (MW) of each treated protein as indicated by the native gel was also compared to the theoretical value (FIG. 9B).

The proteins stored at −20° C. presented one clear band. After being stored at 40° C. for 1 month, PDL1-mIL7-3A remained stable.

Example 4. Combination of 3A Insertion with Knob-In-Hole (KIH)

Figures 10A, 10B:
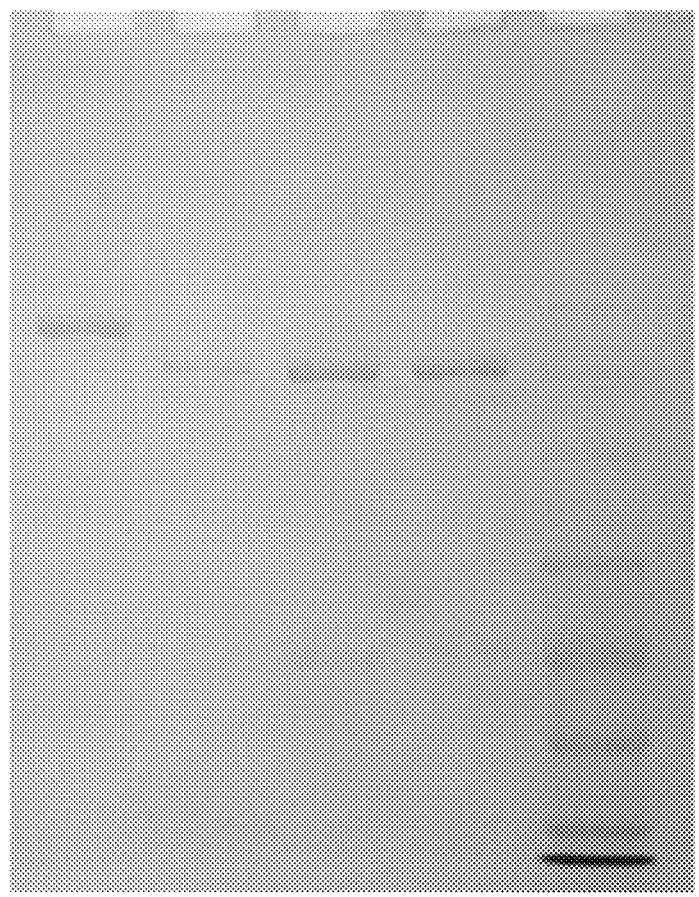
FIG. 10A is an image of electrophoresis showing several purified proteins.
FIG. 10B is a table showing lane numbers and corresponding protein names for the results in FIG. 10A.

The compatibility of 3A insertion and KIH modification were tested. Four fusion proteins were designed (FIG. 10B).

The expressed fusion proteins were purified and analyzed by gel electrophoresis. As shown in FIG. 10A, the fusion proteins with mIL7 fused at the knob chain (PDL1-mIL7-3A-knob, structure shown in FIG. 20A as 3A-knob, the hole chain (PDL1-mIL7-3A-hole, structure shown in FIG. 20A as 3A-hole), or both chains (PDL1-mIL7-Fab-half-3A-KIH, structure shown in FIG. 20A as Fab-half-3A-KIH) exhibited one clear major band. Thus, 3A insertion can be used in combination with the KIH-1 modification.

Example 5. PD-L1 Antibody Fused with hIL7

A PD-L1 IgG1 antibody PDL1-3F2 (PDL1-3F2-IgG1, or 3F2; heavy chain SEQ ID NO: 36; light chain SEQ ID NO: 37) was fused either with human interleukin 7 (hIL7) at the 3A site (3F2-hIL7-3A), or with hIL7 (SEQ ID NO: 11) at the 3A site and mIFNa4 (SEQ ID NO: 10) at the heavy chain C-terminus (3F2-hIL7-3A-mIFNa4), respectively.

The fusion proteins, 3F2-hIL7-3A and 3F2-hIL7-3A-mIFNa4, were purified and analyzed by SEC and gel electrophoresis. The results are shown in FIGS. 11A-11C, and 12A-12C. Both fusion proteins exhibited a clear major band in the native gel and one clear major peak in the SEC result.

The binding affinity between purified human PD-L1 and 3F2, 3F2-hIL7-3A or 3F2-hIL7-3A-mIFNa4 were measured by surface plasmon resonance (SPR) using Biacore™ (Biacore, INC, Piscataway N.J.) T200 biosensor equipped with pre-immobilized protein A sensor chips. The experiment was performed as described in Example 3 and the results for the tested proteins immunocytokines (ICKs) are shown in the table below.

TABLE 8

| Capture 1 Solution | kon (1/Ms) | koff (1/s) | KD (M) |
|---|---|---|---|
| 3F2-mHvKv-IgG1 | 1.75E+06 | 6.52E−04 | 3.72E−10 |
| 3F2-hIL7-3A | 1.78E+06 | 8.79E−04 | 4.93E−10 |
| 3F2-hIL7-3A-mIFNa4 | 1.17E+06 | 8.03E−04 | 6.85E−10 |

The results indicated that the modified antibodies had similar binding affinity to human PD-L1 protein as compared to that of the unmodified parent anti-PD-L1 antibody.

Figure 13:
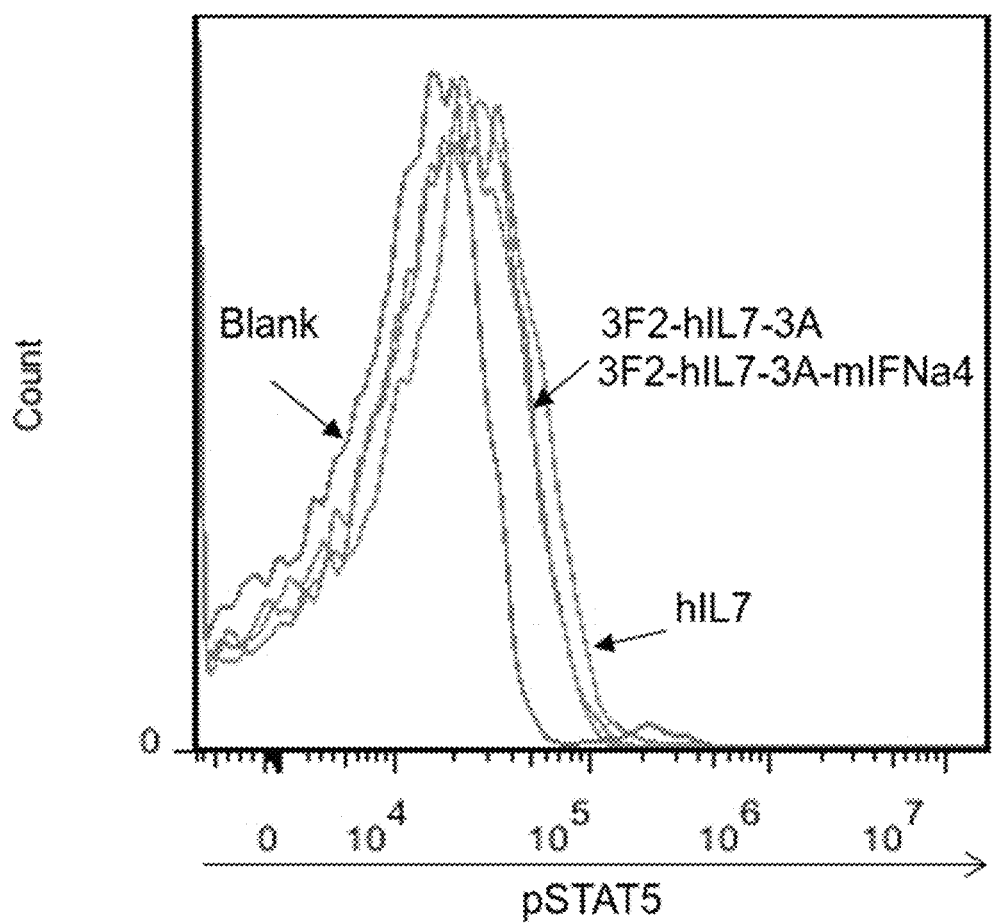
FIG. 13 shows pSTAT5 levels determined by flow cytometry in mouse spleen cells treated by PBS (blank), hIL7 protein, 3F2-hIL7-3A, or 3F2-hIL7-3A-mIFNa4.

Experiments were also performed to evaluate the hIL7 activity by using the mouse spleen cells. Specifically, the collected cells were first treated by PBS, hIL7 protein, 3F2-hIL7-3A or 3F2-hIL7-3A-mIFNa4, and then stained with phospho-STAT5 (Tyr694) Monoclonal Antibody (SRBCZX) and CD8a Monoclonal Antibody (53-6.7). After the staining step, the cells were washed by PBS and analyzed by flow cytometry. Because hIL7 can phosphorylate mouse spleen STAT5 at Tyr694, the hIL7 activity would be indicated by an increased APC (Allophycocyanin) signal. As shown in FIG. 13, the hIL7 protein, 3F2-hIL7-3A, and 3F2-hIL7-3A-mIFNa4 all exhibited an increased APC (Allophycocyanin) level, compared to that of PBS-treated spleen cells (blank). The experiments above indicated that the inserted hIL7 in the antibodies preserved its bioactivity.

Example 6. PD-L1 Antibody Fused with hIL21

Figures 14A, 14B:
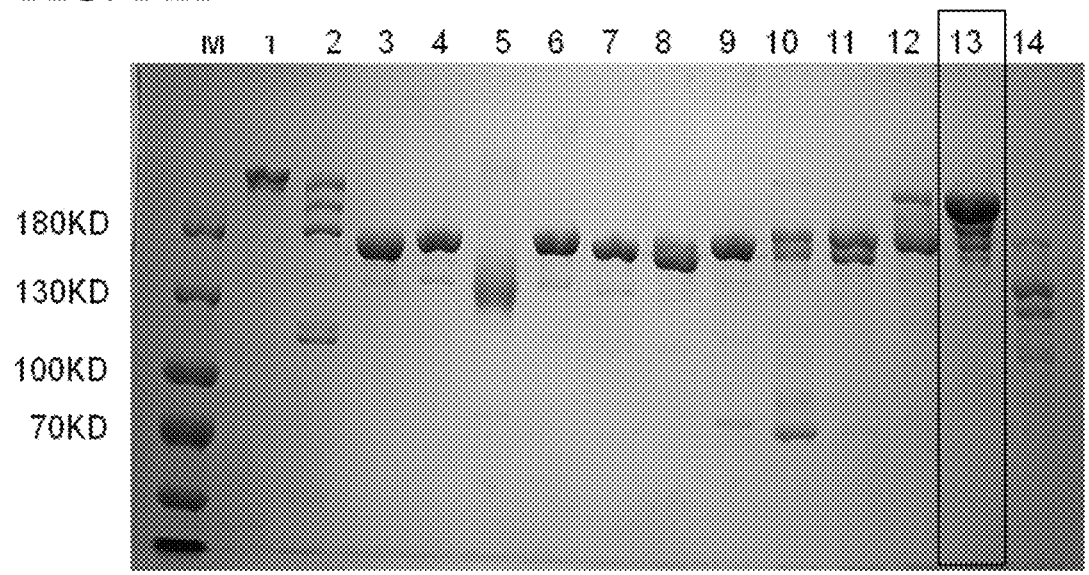
FIG. 14A is a gel image showing PDL1-hIL21-HC in Lane 13.
FIG. 14B is a table showing lane number and corresponding protein name.

Plasmids were designed to express a fusion protein with human interleukin 21 (hIL21) (SEQ ID NO: 12) that is linked to the C-terminus of PDL1-avelumab heavy chain, as shown in FIG. 20A (See the HC structure). The fusion protein PDL1-hIL21-HC, was purified and analyzed by gel electrophoresis. As shown in FIGS. 14A-14B, non-target bands were detected the target band on the native gel.

Human interleukin 21 (hIL21) was fused at the 3A site of PDL1-3F2 antibody (3F2-hIL21-3A). mIFNa4 was added to the C-terminal of the heavy chain of 3F2-hIL21-3A (3F2-hIL21-3A-mIFNa4). The fusion proteins, 3F2-hIL21-3A and 3F2-hIL21-3A-mIFNa4, were purified and analyzed by SEC-HPLC and gel electrophoresis. The results are shown in FIGS. 15A-15C, and 16A-16C. Both fusion proteins exhibited a clear major band in the native gel and a clear major peak in the SEC-HPLC result.

The binding affinity between purified human PD-L1 and the parent PD-L1 antibody (3F2), 3F2-hIL21-3A or 3F2-hIL21-3A-mIFNa4 were measured by SPR. The experiment was performed as described in the methods described above and the results are summarized in the table below.

TABLE 9

| Capture Solution | kon (1/Ms) | koff (1/s) | KD (M) |
| --- | --- | --- | --- |
| 3F2-mHvKv-IgG1 | 1.75E+06 | 6.52E-04 | 3.72E-10 |
| 3F2-hIL21-3A | 1.19E+06 | 6.13E-04 | 5.15E-10 |
| 3F2-hIL21-3A-mIFNa4 | 1.17E+06 | 7.20E-04 | 6.13E-10 |

The results indicated that 3F2-hIL21-3A and 3F2-hIL21-3A-mIFNa4 had similar binding affinity to human PD-L1 protein as compared to the parent PD-L1 antibody.

Figure 17:
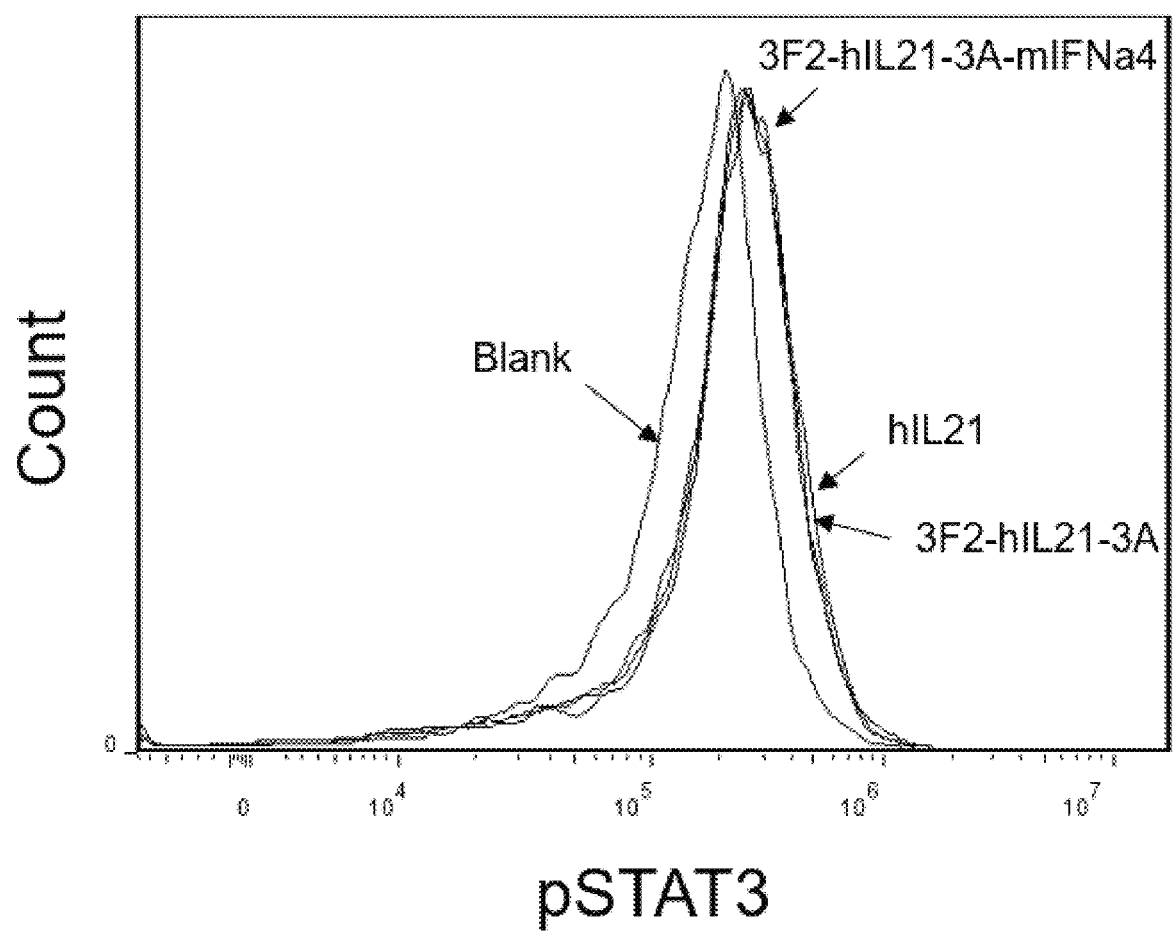
FIG. 17 shows pSTAT3 levels determined by flow cytometry in mouse spleen cells treated by PBS (blank), hIL21 protein, 3F2-hIL21-3A, or 3F2-hIL21-3A-mIFNa4.

The hIL21 activity was also measured using the mouse spleen cells. Specifically, the collected cells were first treated by PBS, hIL21 protein, 3F2-hIL21-3A, or 3F2-hIL21-3A-mIFNa4, and then stained with APC-labelled phospho-STAT3 monoclonal antibody and FITC-labelled anti-CD8a monoclonal antibody (53-6.7). After the staining step, the cells were washed by PBS and analyzed by flow cytometry. Because hIL21 can phosphorylate mouse spleen STAT3, the presence of hIL21 would be indicated by an increased APC signal. As shown in FIG. 17, the hIL21 protein, 3F2-hIL21-3A, and 3F2-hIL21-3A-mIFNa4 all exhibited an increased APC (Allophycocyanin) level, as compared to that of PBS-treated spleen cells (blank). The experiments above indicated that the inserted hIL21 preserved its bioactivity.

Example 7. PD-L1 Antibody Fused with TGFbR2

A PD-L1 antibody (PDL1-avelumab) was fused with the extracellular domain of human TGFbR2 (transforming growth factor, β receptor II) (SEQ ID NO: 13) at the heavy chain 3A site. The fusion protein, PDL1-TGFbR2-3A, was purified and analyzed by SEC-HPLC and gel electrophoresis. As shown in FIGS. 18A-18C, the fusion protein exhibited a clear major band in the native gel and a clear major peak in the SEC-HPLC result.

The binding affinity between TGFb1 and a purified M7824 (heavy chain: SEQ ID NO: 38; light chain: SEQ ID NO: 39), and the binding affinity between TGFb1 and PDL1-TGFbR2-3A was measured by SPR. M7824 is a bifunctional anti-PD-L1/TGFβ Trap fusion protein. The extracellular domain of TGFbR2 is linked at the C terminal of the Fc of the anti-PDL1 antibody in M7824. The results are shown in the table below.

TABLE 10

| Capture Solution | kon (1/Ms) | koff (1/s) | KD (M) |
| --- | --- | --- | --- |
| M7824 | 1.03E+05 | 0.008522 | 8.30E-08 |
| PDL1-TGFbR2-3A | 1.54E+05 | 0.005733 | 3.73E-08 |

The results indicated that the PD-L1 antibody with the extracellular domain of TGFbR2 fused to the 3A site had similar binding affinity to TGFb1 protein as compared to the M7824. The fusion did not affect the binding affinity of the modified proteins.

Example 8. PD-L1 Antibody Fused with Anti-CD40 scFv

Plasmids were designed to express a fusion protein with anti-CD40 single chain variable fragment (scFv) (SEQ ID NO: 16) fused at the heavy chain 3A site of a PD-L1 IgG1 antibody (PDL1-avelumab). The fusion protein is named as PDL1-C40-6A7-FV3A.

Experiments were performed to evaluate ADCC effects. The results indicated that the binding of the scFv at the 3A site to CD40 led to reduction or loss of affinity between IgG and Fc receptors due to steric effects.

In the experiment, the PD-L1 antibody PDL1-avelumab (G1) was used as the parent antibody. The hIL7 (PDL1-hIL7-3A; G2) and the scFV of an anti-CD40 antibody C40-6A7 (SEQ ID NO: 16) (PDL1-C40-6A7-FV3A; G3) were incorporated into the 3A site and were tested. The IgG4 subtype of the PDL1-C40-6A7-FV3A was also prepared. The IgG4 had limited ability to trigger effector functions, and it was used as a negative control (PDL1-C40-6A7-FV3A-IgG4; G5).

The PD-1 IgG4 antibody PD1-1A7 (1A7, or PD1-1A7-IgG4; VH SEQ ID NO: 40; VL SEQ ID NO: 41) was also used as the parent antibody. The scFV of the anti-PD-L1 antibody 3F2 (SEQ ID NO: 17) was fused at the 3A site of the IgG1 subtype of the PD-1 antibody (PD1-PL1-3F2-FV3A-IgG1; G4). The hCD16-expressing Jurkat cells and PD-L1-expressing CHO cells were used in the experiments. The hCD16-expressing Jurkat cells also included a Luc gene to express luciferase.

The experiment was performed as follows. The CHO cells expressing PD-L1 were recovered at 37° C. and added to a 96-well plate at $2 \times 10^4$ cells per well. The Jurkat cell suspension was then added to the 96-well plate at 25 μl per well (or $8 \times 10^4$ cells per well). Next, G1-G5 were diluted in 25 μl assay buffer at a dilution ratio of 1:3, then added to the 96-well plate at a final concentration of 100 nM. The 96-well plate was incubated at 37° C. for 6 hours. After incubation, a chromogenic reagent was added to each well and incubated for 5 minutes in dark. The plate was then placed in a luminescence detector to detect bioluminescence signal of each well.

Figure 19:
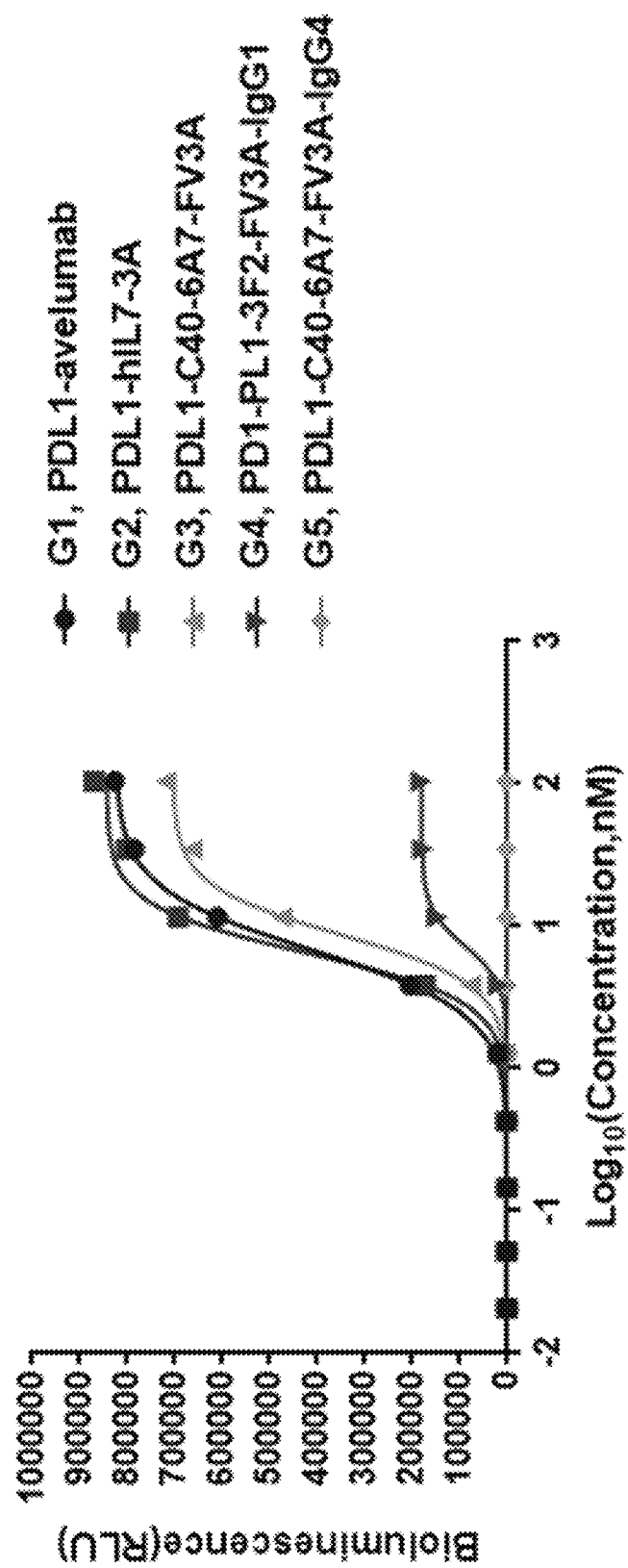
FIG. 19 shows the ADCC effects of several modified immunoglobulins.

As shown in FIG. 19, the results showed that the fusion of cytokines or scFV at 3A site did not affect the ADCC activity of the modified antibody. However, when the scFV inserted at the 3A site binds to the target protein (PD-L1 on CHO cells), the ADCC effect on the target cell was reduced or lost. In other words, when the scFV inserted at the 3A site bound to the target protein, the steric effect prevented Fc from binding to the Fc receptor to trigger ADCC effector function.

Example 9. Test of Amino Acid Replacement or Insertion Range within the 3A Site Antibody Fused with a Soluble Domain at the 3A, 3B, 3C, or 3D Sites A PD-L1 antibody (PDL1-avelumab) was fused with the extracellular domain of human TGFbR2 (transforming growth factor, β receptor II) at the heavy chain 3A site (amino acids from position 358 to position 362 according to EU numbering were replaced with the extracellular domain of human TGFbR2), 3B (amino acids from position 383-391 according to EU numbering were replaced with the extracellular domain of human TGFbR2), 3C (the extracellular domain of TGFbR2 was inserted between position 384 and position 385 according to EU numbering), or 3D sites (amino acids from position 413 to position 422 were replaced with the extracellular domain of human TGFbR2).

The corresponding fusion proteins, PDL1-TGFbR2-3A, PDL1-TGFbR2-3B, PDL1-TGFbR2-3C, and PDL1-TGFbR2-3D were purified and analyzed by gel electrophoresis. As shown in FIG. 22 and Table 11, only PDL1-TGFbR2-3A, PDL1-TGFbR2-3C, and PDL1-TGFbR2-3D showed a clear major band in the native gel. The expression level of each fusion protein was also determined. As shown in the table below, PDL1-TGFbR2-3A, PDL1-TGFbR2-3C, and PDL1-TGFbR2-3D, but not PDL1-TGFbR2-3B, were expressed.

TABLE 11

| Lane | Name | Concentration (μg/mL) |
|---|---|---|
| 1 | PDL1-TGFbR2-3A | 190.67 |
| 2 | PDL1-TGFbR2-3B | 0 |
| 3 | PDL1-TGFbR2-3C | 238 |
| 4 | PDL1-TGFbR2-3D | 164 |

Consistent with the results shown in Example 3, the fusion protein PDL1-TGFbR2-3A was stably expressed. As compared to the results in Example 3, fusion at the 3A site always provides stable expression.

Antibody Fused at the 3A Site with Various Starting and Ending Positions

A PD-L1 IgG1 antibody (PDL1-avelumab) was fused with the extracellular domain of human TGFbR2 at the 3A site with various starting and ending positions. Specifically, fusion protein PDL1-TGFbR2-3A was obtained by replacing amino acids from position 358-362 (according to EU numbering) with the extracellular domain of human TGFbR2, and fusion protein PDL1-TGFbR2-3A-IgG4 was obtained similarly using the PD-L1 IgG1 antibody with IgG4 subtype.

PDL1-avelumab was fused with the extracellular domain of human TGFbR2 at the 3A site with various starting positions and end positions. For example, fusion protein PDL1-TGFbR2-3AF1 was obtained by replacing amino acids from position 351-362 (according to EU numbering) with the extracellular domain of human TGFbR2. Fusion protein PDL1-TGFbR2-3AF2 was obtained by replacing amino acids from position 347-362 (according to EU numbering) with the extracellular domain of human TGFbR2. Fusion protein PDL1-TGFbR2-3AF3 was obtained by replacing amino acids from position 344-362 (according to EU numbering) with the extracellular domain of human TGFbR2. For example, fusion protein PDL1-TGFbR2-3AR1 was obtained by replacing amino acids from position 358-372 (according to EU numbering) with the extracellular domain of human TGFbR2. Fusion protein PDL1-TGFbR2-3AR2 was obtained by replacing amino acids from position 358-378 (according to EU numbering) with the extracellular domain of human TGFbR2. Fusion protein PDL1-TGFbR2-3AR3 was obtained by replacing amino acids from position 358-381 (according to EU numbering) with the extracellular domain of human TGFbR2. Fusion protein PDL1-TGFbR2-3AR4 was obtained by replacing amino acids from position 373-377 (according to EU numbering) with the extracellular domain of human TGFbR2.

The fusion proteins were purified and analyzed by gel electrophoresis. As shown in FIG. 23 and Table 12, fusion proteins PDL1-TGFbR2-3A (lane 1) and PDL1-TGFbR2-3A-IgG4 (lane 2) showed a clear major band in the native gel. The expression level of each fusion protein was also determined. As shown in the table below, expression of fusion proteins PDL1-TGFbR2-3A, PDL1-TGFbR2-3A-IgG4, and PDL1-TGFbR2-3AF1, but not the other tested fusion proteins, were detected. The results showed that IgG subtypes does not have effects on the expression of the fusion protein. In addition, amino acids from position 351-362 (according to EU numbering) can be used as the fusion site.

TABLE 12

| Lane | Name | Concentration (μg/mL) |
|---|---|---|
| 1 | PDL1-TGFbR2-3A (IgG1) | 190.67 |
| 2 | PDL1-TGFbR2-3A-IgG4 | 204.00 |
| 3 | PDL1-TGFbR2-3AF1 (IgG1) | 130.00 |
| 4 | PDL1-TGFbR2-3AF2 (IgG1) | 0 |
| 5 | PDL1-TGFbR2-3AF3 (IgG1) | 0 |
| 6 | PDL1-TGFbR2-3AR1 (IgG1) | 0 |
| 7 | PDL1-TGFbR2-3AR2 (IgG1) | 0 |
| 8 | PDL1-TGFbR2-3AR3 (IgG1) | 0 |
| 9 | PDL1-TGFbR2-3AR4 (IgG1) | 0 |

Antibody Fused at the 3A Site with Various Starting and Ending Positions

A PD-L1 IgG1 antibody (PDL1-avelumab) was fused with human IL21 (hIL21) at the 3A site with various starting and ending positions. Specifically, fusion protein PDL1-hIL21-3A-IgG4 was obtained by replacing amino acids from position 358-362 (according to EU numbering) within the CH3 domain of IgG4 with human IL21 using PDL1-avelumab with IgG4 subtype. PDL1-avelumab was fused with human IL21 at the 3A site with various starting positions and ending positions. For example, fusion protein PDL1-hIL21-3AF1 was obtained by replacing amino acids from position 351-362 (according to EU numbering) with human IL21. Fusion protein PDL1-hIL21-3AF2 was obtained by replacing amino acids from position 347-362 (according to EU numbering) with human IL21. Fusion protein PDL1-hIL21-3AF3 was obtained by replacing amino acids from position 344-362 (according to EU numbering) with human IL21. For example, fusion protein PDL1-hIL21-3AR1 was obtained by replacing amino acids from position 358-372 (according to EU numbering) with human IL21. Fusion protein PDL1-hIL21-3AR2 was obtained by replacing amino acids from position 358-378 (according to EU numbering) with human IL21. Fusion protein PDL1-hIL21-3AR3 was obtained by replacing amino acids from position 358-381 (according to EU numbering) with human IL21. Fusion protein PDL1-hIL21-3AR4 was obtained by replacing amino acids from position 373-377 (according to EU numbering) with human IL21.

The fusion proteins were purified and analyzed by gel electrophoresis. As shown in FIG. 24 and Table 13, fusion proteins PDL1-hIL21-3A-IgG4 (lane 1) and PDL1-hIL21-

3AF1 (lane 2) showed a clear major band in the native gel. The expression level of each fusion protein was also determined. As shown in the table below, expression of fusion proteins PDL1-hIL21-3A-IgG4 and PDL1-hIL21-3AF1, but not the other tested fusion proteins, were detected.

TABLE 13

| Lane | Name | Concentration (µg/mL) |
|---|---|---|
| 1 | PDL1-hL21-3A-IgG4 | 96 |
| 2 | PDL1-hL21-3AF1(IgG1) | 50.67 |
| 3 | PDL1-hL21-3AF2(IgG1) | 0 |
| 4 | PDL1-hL21-3AF3(IgG1) | 0 |
| 5 | PDL1-hL21-3AR1(IgG1) | 0 |
| 6 | PDL1-hL21-3AR2(IgG1) | 0 |
| 7 | PDL1-hL21-3AR3(IgG1) | 0 |
| 8 | PDL1-hL21-3AR4(IgG1) | 0 |

According to the above results, a non-native polypeptide can be fused to the 3A site of a PD-L1 antibody from position 351 to position 362, without interfering with the protein expression.

Insertion of Human TGFbR2 within the 3A Site

The extracellular domain of human TGFbR2 was inserted at the 3A site of an antibody (PDL1-avelumab). Specifically, fusion protein PDL1-TGFbR2-3A1 was obtained by inserting the extracellular domain of human TGFbR2 between position 358 and position 359 (according to EU numbering) within the 3A site. Fusion protein PDL1-TGFbR2-3A2 was obtained by inserting the extracellular domain of human TGFbR2 between position 359 and position 360 (according to EU numbering) within the 3A site. Fusion protein PDL1-TGFbR2-3A3 was obtained by inserting the extracellular domain of human TGFbR2 between position 360 and position 361 (according to EU numbering) within the 3A site. Fusion protein PDL1-TGFbR2-3A4 was obtained by inserting the extracellular domain of human TGFbR2 between position 361 and position 362 (according to EU numbering) within the 3A site.

Figure 25A:
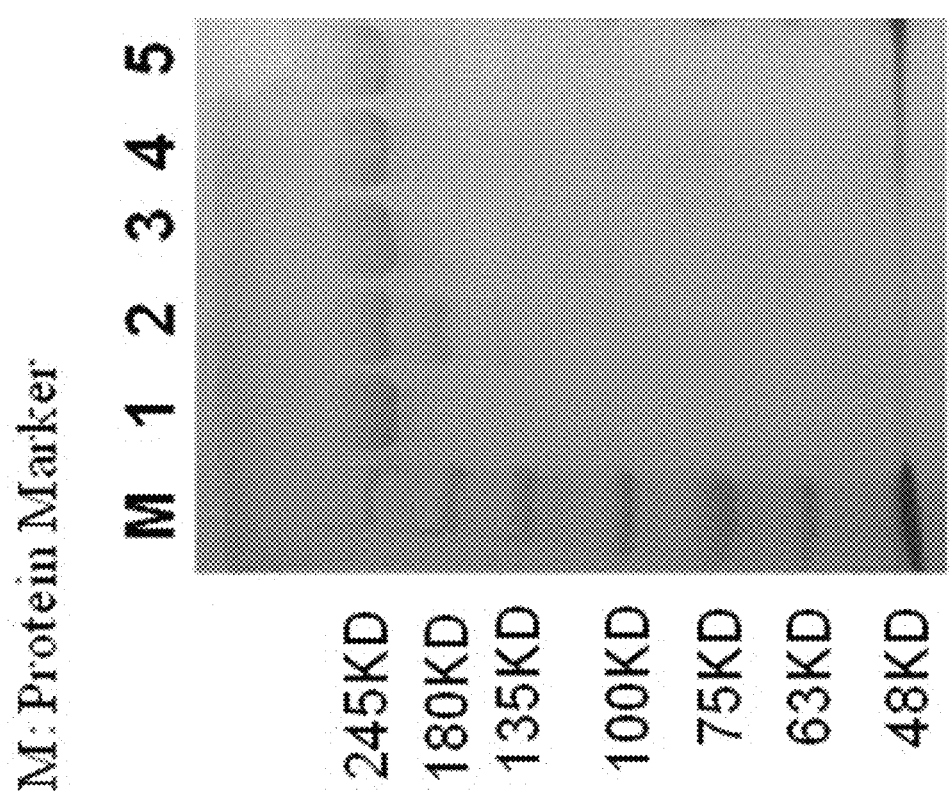
FIG. 25A is a gel image showing purified PDL1-TGFbR2-3A (lane 1), PDL1-TGFbR2-3A1 (lane 2), PDL1-TGFbR2-3A2 (lane 3), PDL1-TGFbR2-3A3 (lane 4), and PDL1-TGFbR2-3A4 (lane 5). M is protein marker.

The fusion proteins were purified and analyzed by gel electrophoresis and their expression levels were determined. As shown in FIGS. 25A and Table 14, all the fusion proteins showed a clear major band in the native gel. The expression level of each fusion protein was also determined. As shown in the table below, expression of all the tested fusion proteins was detected.

TABLE 14

| Lane | Name | Concentration (µg/mL) |
|---|---|---|
| 1 | PDL1-TGFbR2-3A | 190.67 |
| 2 | PDL1-TGFbR2-3A1 | 146.67 |
| 3 | PDL1-TGFbR2-3A2 | 166.67 |
| 4 | PDL1-TGFbR2-3A3 | 208.00 |
| 5 | PDL1-TGFbR2-3A4 | 144.00 |

Figure 25B:
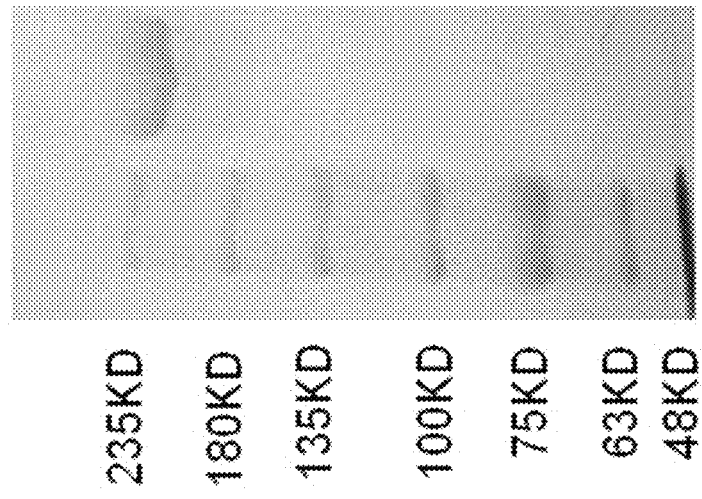
FIG. 25B is a gel image showing purified PDL1-TGFbR2-3A1 (new batch) in lane 1. M is protein marker.

Non-target bands were observed for PDL1-TGFbR2-3A1 (lane 2), which may be caused by protein degradation. To verify this, PDL1-TGFbR2-3A1 was purified from a new batch of cells, and immediately analyzed in a native gel. As shown in FIG. 25B and Table 15 below, non-target bands were not observed, indicating protein degradation occurred during storage of PDL1-TGFbR2-3A1.

TABLE 15

| Lane | Name | Concentration (µg/mL) |
|---|---|---|
| 1 | PDL1-TGFbR2-3A1 | 99.00 |

Figure 26:
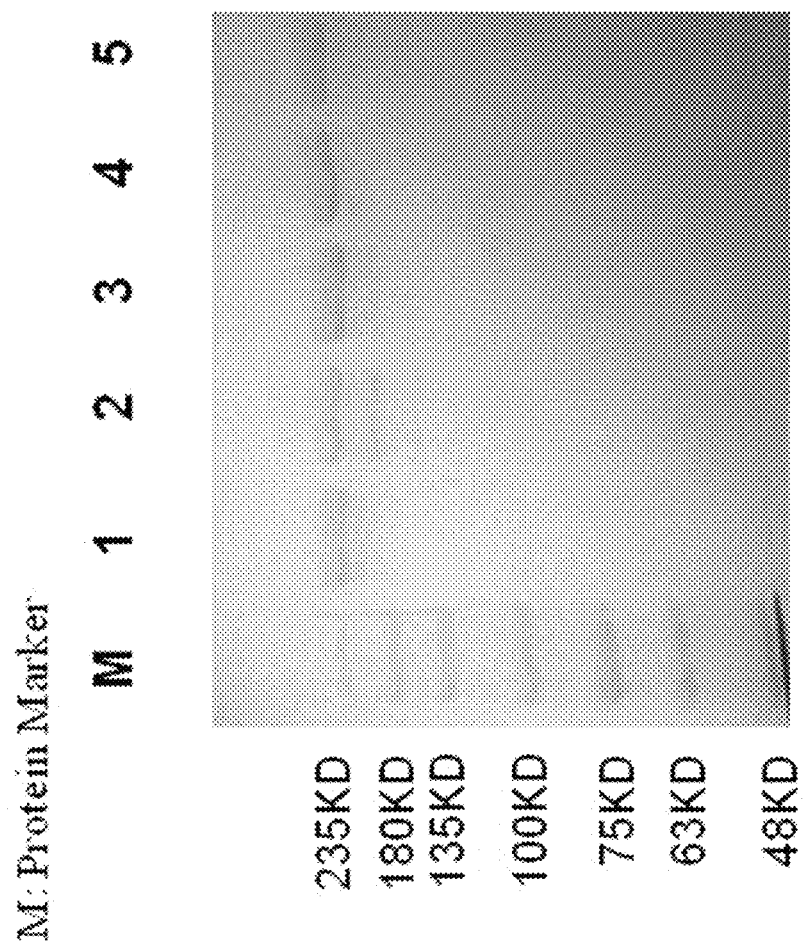
FIG. 26 is a gel image showing purified PDL1-TGFbR2-3A (lane 1), PDL1-TGFbR2-3A1 (lane 2), PDL1-TGFbR2-3A2 (lane 3), PDL1-TGFbR2-3A3 (lane 4), and PDL1-TGFbR2-3A4 (lane 5). M is protein marker.

The newly purified PDL1-TGFbR2-3A1 was kept for 10 days, and then loaded to the same native gel with the purified PDL1-TGFbR1-3A, PDL1-TGFbR1-3A2, PDL1-TGFbR1-3A3, PDL1-TGFbR1-3A4 in Table 14. The gel electrophoresis results in FIG. 26 showed non-target bands in the PDL1-TGFbR1-3A1 (lane 2), indicating that the non-target bands were caused by protein degradation.

The results above indicate that non-native polypeptides can be used to replace, or inserted between, any amino acids at position 351-362 (according to EU numbering), particularly, any amino acids at position 358-362 (according to EU numbering). However, insertion of the extracellular domain of human TGFbR2 between position 358 and position 359 (according to EU numbering) was not as stable as the other insertion sites. Antibodies with insertions at 359-360, 360-361, or 361-362 and antibodies with replacement at the 3A site were very stable.

Thermostability of Fusion Proteins

Thermostability of the obtained fusion proteins PDL1-TGFbR2-3A, PDL1-TGFbR2-3C, PDL1-TGFbR2-3D, PDL1-TGFbR2-3A1, PDL1-TGFbR2-3A2, PDL1-TGFbR2-3A3, and PDL1-TGFbR2-3A4 were determined by measuring the melting temperature (Tm). M7824 was used a control.

TABLE 16

| Name | Tm (° C.) |
|---|---|
| M7824 | 68.24 |
| PDL1-TGFbR2-3A | 67.61 |
| PDL1-TGFbR2-3C | 68.47 |
| PDL1-TGFbR2-3D | 66.51 |
| PDL1-TGFbR2-3A1 | 68.33 |
| PDL1-TGFbR2-3A2 | 68.55 |
| PDL1-TGFbR2-3A3 | 68.70 |
| PDL1-TGFbR2-3A4 | 68.74 |

In general, the results showed that Tm was minimally affected by amino acid replacement or insertion within the 3A or 3C site. PDL1-TGFbR2-3D exhibited a relatively low Tm as compared to M7824, probably due to low purity or the unstable structure.

Determination of Binding Affinity to TGFβ1

Binding affinity to human TGFβ1 of the obtained fusion proteins PDL1-TGFbR2-3A, PDL1-TGFbR2-3C, PDL1-TGFbR2-3D, PDL1-TGFbR2-3A1, PDL1-TGFbR2-3A2, PDL1-TGFbR2-3A3, and PDL1-TGFbR2-3A4 were determined by surface plasmon resonance (SPR) using Biacore™ T200 biosensor equipped with pre-immobilized protein A sensor chips. The results are shown in the table below.

TABLE 17

| Name | Target | kon (1/Ms) | koff (1/s) | KD (M) |
|---|---|---|---|---|
| PDL1-TGFbR2-3A | hTGF beta 1 | 3.76E+06 | 4.50E−03 | 1.20E−09 |
| PDL1-TGFbR2-3C | hTGF beta 1 | 5.00E+05 | 6.27E−04 | 1.25E−09 |
| PDL1-TGFbR2-3D | hTGF beta 1 | 5.80E+05 | 9.93E−04 | 1.71E−09 |
| PDL1-TGFbR2-3A1 | hTGF beta 1 | 3.97E+05 | 7.41E−04 | 1.87E−09 |
| PDL1-TGFbR2-3A2 | hTGF beta 1 | 4.39E+05 | 6.06E−04 | 1.38E−09 |
| PDL1-TGFbR2-3A3 | hTGF beta 1 | 2.45E+06 | 3.74E−03 | 1.53E−09 |
| PDL1-TGFbR2-3A4 | hTGF beta 1 | 4.06E+06 | 6.71E−03 | 1.65E−09 |

The results showed that all the tested fusion proteins exhibited specific binding to human TGFβ1 with high affinity. Thus, the results further indicated that inserted polypeptides at the 3A site can fold properly and are still functional.

Example 10. Antibody Fused with scFv at the 3A and 3C Sites

Expression Level and Purity

An antibody (PDL1-avelumab) was fused with anti-CD40 scFv at the heavy chain 3A site (amino acids from position 358 to position 362 according to EU numbering were replaced with anti-CD40 scFv), or 3C site (anti-CD40 scFv was inserted between position 384 and position 385 according to EU numbering), to generate fusion proteins PDL1-C40-6A7-FV3A and PDL1-C40-6A7-FV3C, respectively. PDL1-C40-6A7-FV3A-IgG4 was also obtained by replacing IgG1 with IgG4 subtype.

In addition, fusion protein PDL1-C40-6A7-FV3A1 was obtained by inserting anti-CD40 scFv between position 358 and position 359 (according to EU numbering) within the 3A site. Fusion protein PDL1-C40-6A7-FV3A2 was obtained by inserting anti-CD40 scFv between position 359 and position 360 (according to EU numbering) within the 3A site. Fusion protein PDL1-C40-6A7-FV3A3 was obtained by inserting anti-CD40 scFv between position 360 and position 361 (according to EU numbering) within the 3A site. The fusion proteins were purified and analyzed by gel electrophoresis. All the tested fusion proteins showed a clear major band in the native gel.

Determination of Binding Affinity to CD40

Binding affinity to human CD40 of the obtained fusion proteins PDL1-C40-6A7-FV3A (IgG1), PDL1-C40-6A7-FV3A-IgG4, PDL1-C40-6A7-FV3C (IgG1), PDL1-C40-6A7-FV3A1 (IgG1), PDL1-C40-6A7-FV3A2 (IgG1), and PDL1-C40-6A7-FV3A3 (IgG1) were determined by surface plasmon resonance (SPR) using Biacore™ T200 biosensor equipped with pre-immobilized protein A sensor chips. The original anti-CD40 monoclonal antibody C40-6A7 IgG2 (6A7, VH SEQ ID NO: 91, VL SEQ ID NO: 92), which the scFV was derived from, was used as a control. The results are shown in the table below.

TABLE 18

| Name | analysis | kon (1/Ms) | koff (1/s) | KD (M) |
|---|---|---|---|---|
| C40-6A7 (IgG2) | hCD40-his | 5.54E+05 | 1.71E-03 | 3.09E-09 |
| PDL1-C40-6A7-FV3A1 (IgG1) | hCD40-his | 6.16E+05 | 3.88E-04 | 6.30E-10 |
| PDL1-C40-6A7-FV3A2 (IgG1) | hCD40-his | 4.43E+05 | 3.75E-04 | 8.47E-10 |
| PDL1-C40-6A7-FV3A3 (IgG1) | hCD40-his | 3.64E+05 | 3.79E-04 | 1.04E-09 |
| PDL1-C40-6A7-FV3C (IgG1) | hCD40-his | 5.46E+05 | 4.72E-04 | 8.65E-10 |
| PDL1-C40-6A7-FV3A (IgG1) | hCD40-his | 3.91E+05 | 4.27E-04 | 1.09E-09 |
| PDL1-C40-6A7-FV3A-IgG4 | hCD40-his | 5.07E+05 | 4.32E-04 | 8.52E-10 |

The results showed that all the tested fusion proteins exhibited specific binding to human CD40 with high affinity.

Example 11. Determination of Binding Affinity to Fc Receptors

Binding affinities of the fusion proteins PDL1-TGFbR2-3A(IgG1) (or PDL1-TGFbR2-3A-IgG1) and PDL1-TGFbR2-3A-IgG4 to human Fc receptors were measured by surface plasmon resonance (SPR) using Biacore™ T200 biosensor equipped with pre-immobilized protein A sensor chips. The Fc receptors included FcγRI-Sino, FcγRIIA-R167-Sino, FcγRIIIA-F176-Sino, FcγRIIIB-Sino, and FcγRn. A humanized CTLA4 antibody CT4-4G12-IgG1 (CT4-4G12, or 4G12; VH SEQ ID NO: 44, VL SEQ ID NO: 45) was used as a control to test binding affinity to FcγRn. PDL1-avelumab was used as a control to test binding affinity to FcγRI-Sino, FcγRIIA-R167-Sino, FcγRIIIA-F176-Sino, and FcγRIIIB-Sino. The results are shown in the table below.

TABLE 19

| Capture 1 Solution | Analyte 1 Solution | KD (M) |
|---|---|---|
| PDL1-avelumab | FcγRI-Sino | 6.52E-09 |
| PDL1-TGFbR2-3A-IgG1 | FcγRI-Sino | 1.45E-08 |
| PDL1-TGFbR2-3A-IgG4 | FcγRI-Sino | 2.73E-07 |
| PDL1-avelumab | FcγRIIA-R167-Sino | 6.92E-07 |
| PDL1-TGFbR2-3A-IgG1 | FcγRIIA-R167-Sino | 8.44E-07 |
| PDL1-TGFbR2-3A-IgG4 | FcγRIIA-R167-Sino | 1.78E-06 |
| PDL1-avelumab | FcγRIIIA-F176-Sino | 5.63E-07 |
| PDL1-TGFbR2-3A-IgG1 | FcγRIIIA-F176-Sino | 3.77E-07 |
| PDL1-TGFbR2-3A-IgG4 | FcγRIIIA-F176-Sino | Negative |
| PDL1-avelumab | FcγRIIIB-Sino | 1.21E-06 |
| PDL1-TGFbR2-3A-IgG1 | FcγRIIIB-Sino | 1.33E-06 |
| PDL1-TGFbR2-3A-IgG4 | FcγRIIIB-Sino | 5.76E-07 |
| CT4-4G12 (IgG1) | FcγRn | 1.26E-07 |
| PDL1-TGFbR2-3A-IgG1 | FcγRn | 1.94E-08 |
| PDL1-TGFbR2-3A-IgG4 | FcγRn | 2.14E-07 |

The results showed that binding affinities to Fc receptors were not significantly affected when there is an insertion of a non-native polypeptide at the 3A site of the PD-L1 antibody.

Example 12. Replacement of Various Types of Molecules within the 3A Site

Various types of molecules, e.g., cytokine, receptor, scFv, ligand, nanobody, or fragment thereof, can be fused at the 3A site (e.g., amino acids from position 358 to position 362 according to EU numbering) of an antibody heavy chain, as shown in the table below. The antibody can be IgG1 or IgG4 subtype.

TABLE 20

| IgG subtype | Cytokine | Receptor | ScFv | Ligand | Nanobody |
|---|---|---|---|---|---|
| IgG1 | hIL21 | TGFβR2 | PDL1-3F2 | ATOR1015-CD86 | KN035-PDL1 |
| IgG4 | hIL21 | TGFβR2 | PDL1-3F2 | ATOR1015-CD86 | KN035-PDL1 |

The following sequences as shown in the table above were used as examples. For example, the cytokine can be derived from human IL21 (hIL21), with sequence set forth in SEQ ID NO: 12 (amino acids 25-162 of NP_068575.1). The receptor can be derived from TGFbR2, with sequence set forth in SEQ ID NO: 13 (amino acids 24-159 of NP_003233.4). The scFv can be derived from humanized anti-PD-L1 antibody PDL1-3F2, with sequence set forth in SEQ ID NO: 17. The ligand can be ATOR1015-CD86 (an optimized version of the Ig-like V-type domain of human CD86), with sequence set forth in SEQ ID NO: 14. Details of ATOR1015-CD86 can be found, e.g., in WO2018202649A1, which is incorporated herein by reference in its entirety. ATOR1015-CD86 is the CD86 portion of ATOR1015.

The nanobody can be KN035-PDL1 (or KN035), with variable region sequence set forth in SEQ ID NO: 15. Details of KN035 can be found, e.g., in US20180291103A1, which is incorporated herein by reference in its entirety.

Expression Level and Purity

The following fusion proteins were obtained by replacing amino acids corresponding to position 358-362 (according to EU numbering) of an antibody heavy chain with various non-native molecules. ATOR1015-CD86 was fused to a PD-L1 antibody (PDL1-avelumab) to generate PDL1-CD86-3A (or PDL1-CD86-3A-IgG1). PDL1-CD86-3A-IgG4 was obtained by replacing IgG1 with IgG4 subtype. KN035 was fused to a PD-1 antibody PD1-1A7-IgG4 to generate PD1-KN035-3A (or PD1-KN035-3A-IgG4). PD1-KN035-3A-IgG1 was obtained by replacing IgG4 with IgG1 subtype. An anti-PD-L1 scFv can be fused to PD1-1A7-IgG4 to generate PD1-PL1-3F2-FV3A (or PD1-PL1-3F2-FV3A-IgG4). PD1-PL1-3F2-FV3A-IgG1 was obtained by replacing IgG4 with IgG1 subtype. KN035 was fused to the CTLA4 antibody CT4-4G12-IgG1 (CT4) at the knob chain (structure shown in FIG. 20A as 3A-knob) to generate CT4-KN035-3A-knob (or CT4-KN035-3A-knob-IgG1). KN035 was fused to CT4-4G12-IgG1 at the hole chain (structure shown in FIG. 20A as 3A-hole) to generate CT4-KN035-3A-hole (or CT4-KN035-3A-hole-IgG1) (FIG. 20A).

Figure 27:
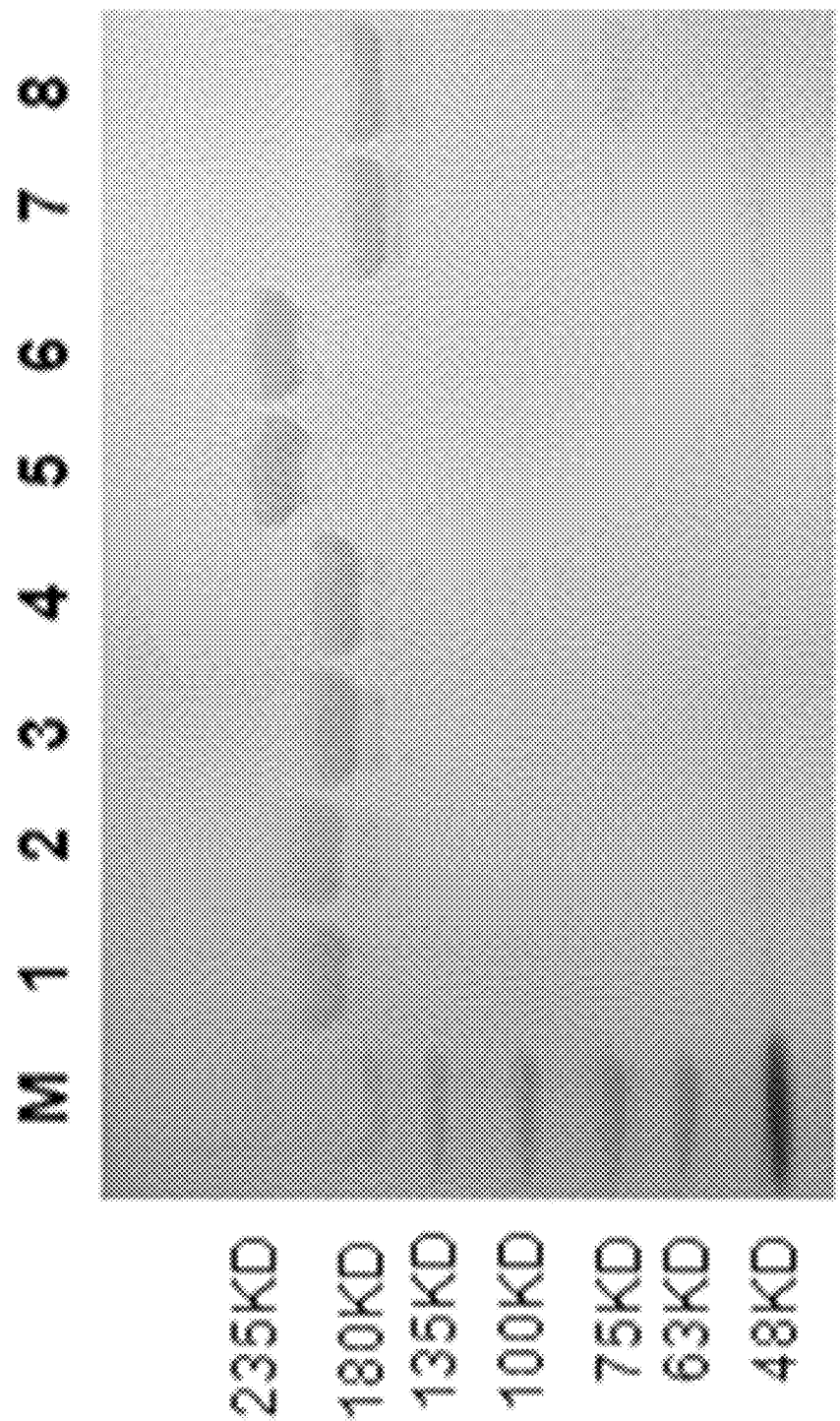
FIG. 27 is a gel image showing purified PDL1-CD86-3A (lane 1), PDL1-CD86-3A-IgG4 (lane 2), PD1-KN035-3A-IgG1 (lane 3), PD1-KN035-3A (lane 4), PD1-PL1-3F2-FV3A-IgG1 (lane 5), PD1-PL1-3F2-FV3A (lane 6), CT4-KN035-3A-knob (lane 7), and CT4-KN035-3A-kole (lane 8). M is protein marker.

As shown in FIG. 27 and Table 21, each fusion protein was loaded at 4 μg per lane in a 6% native gel. A clear major band was detected for all the fusion proteins. The expression level of each fusion protein was also determined. As shown in the table below, all the tested fusion proteins were stably expressed.

TABLE 21

| Lane | Name | Concentration (μg/mL) |
|---|---|---|
| 1 | PDL1-CD86-3A-IgG1 | 266 |
| 2 | PDL1-CD86-3A-IgG4 | 308 |
| 3 | PD1-KN035-3A-IgG1 | 88 |
| 4 | PD1-KN035-3A-IgG4 | 124 |
| 5 | PD1-PL1-3F2-FV3A-IgG1 | 29 |
| 6 | PD1-PL1-3F2-FV3A-IgG4 | 34 |
| 7 | CT4-KN035-3A-knob-IgG1 | 175 |
| 8 | CT4-KN035-3A-kole-IgG1 | 136 |

Determination of Binding Affinities

Binding affinities of the fusion proteins against human CTLA4 (hCTLA4-His) or human PD-L1 (hPDL1) were measured by surface plasmon resonance (SPR) using Biacore™ T200 biosensor equipped with pre-immobilized protein A sensor chips. The results are shown in the table below. A CTLA4 antibody CT4-4G12-IgG1 (CT4) was used as a control. ATOR1015-CD86 (CD86) and KN035-IgG1 (with D265A mutation in heavy chain constant domain) were also used as controls.

TABLE 22

| Capture 1 Solution | Analyte 1 Solution | kon (1/Ms) | koff (1/s) | KD (M) |
|---|---|---|---|---|
| CT4 | hCTLA4-His | 2.56E+05 | 1.51E−03 | 5.91E−09 |
| CD86 | hCTLA4-His | 2.91E+05 | 2.97E−04 | 1.02E−09 |
| PDL1-CD86-3A-IgG1 | hCTLA4-His | 3.97E+05 | 6.93E−04 | 1.74E−09 |
| PDL1-CD86-3A-IgG4 | hCTLA4-His | 3.64E+05 | 6.84E−04 | 1.88E−09 |
| PD1-KN035-3A-IgG1 | hPDL1 | 4.87E+05 | 6.87E−03 | 1.41E−08 |
| PD1-KN035-3A-IgG4 | hPDL1 | 4.25E+05 | 7.42E−03 | 1.74E−08 |
| CT4-KN035-3A-knob-IgG1 | hPDL1 | 1.97E+05 | 2.31E−03 | 1.17E−08 |
| CT4-KN035-3A-kole-IgG1 | hPDL1 | 9.27E+04 | 1.90E−03 | 2.04E−08 |
| KN035-IgG1 (D265A) | hPDL1 | 1.78E+06 | 2.04E−02 | 1.15E−08 |
| PD1-PL1-3F2-FV3A-IgG1 | hPDL1 | 4.29E+05 | 1.03E−03 | 2.41E−09 |
| PD1-PL1-3F2-FV3A-IgG4 | hPDL1 | 3.58E+05 | 1.06E−03 | 2.97E−09 |

The results showed that the ATOR1015-CD86 maintained its binding affinity to human CTLA4 after being fused to the PD-L1 antibody. In addition, the results showed that KN035 maintained its binding affinity to human PD-L1 after being fused to the PD-1 or CTLA4 antibodies. The anti-PD-L1 scFv also maintained a high binding affinity to PD-L1 after being fused to the PD-1 antibody. Further, the subtype of IgG (e.g., IgG1 or IgG4) did not affect the binding affinity of the fused molecule.

Example 13. Expression and Purification of Fusion Proteins with 3A-HC, or 3A Structure The extracellular domain of TGFβR2 was linked to the C-terminus of PDL1-CD86-3A-IgG1 heavy chain (structure shown in FIG. 20A as 3A-HC) to generate PDL1-CD86-3A-TGFbR2.

Figure 28:
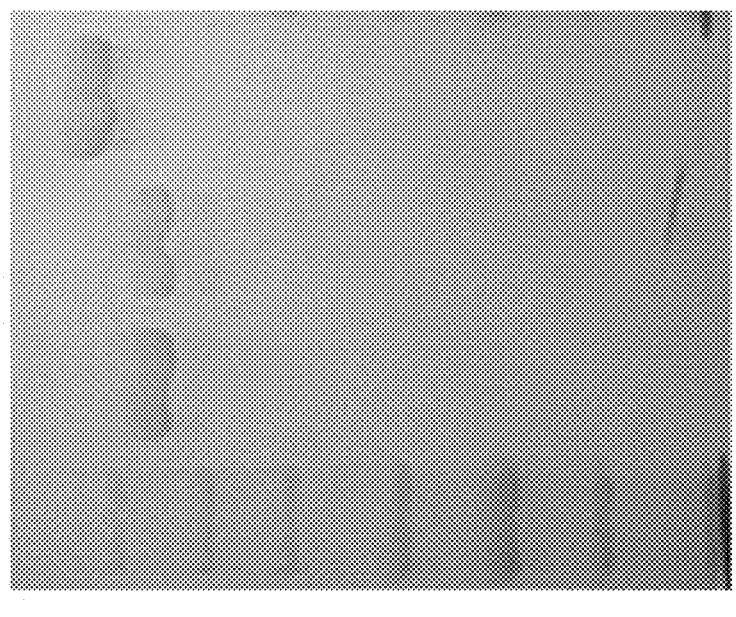
FIG. 28 is a gel image showing purified PDL1-CD86-3A-IgG1 (lane 1), PDL1-CD86-3A-IgG4 (lane 2), and PDL1-CD86-3A-TGFbR2 (lane 3). M is protein marker.

The fusion proteins PDL1-CD86-3A-IgG1, PDL1-CD86-3A-IgG4 and PDL1-CD86-3A-TGFbR2 were purified and analyzed by gel electrophoresis. As shown in FIG. 28 and Table 23, all the fusion proteins showed a clear major band in the native gel. The expression level of each fusion protein was also determined. As shown in the table below, expression of all the tested fusion proteins was detected. The results indicate that fusion proteins with 3A-HC structure can be expressed and purified.

TABLE 23

| Lane | Name | Concentration (μg/mL) |
|---|---|---|
| 1 | PDL1-CD86-3A-IgG1 | 266.67 |
| 2 | PDL1-CD86-3A-IgG4 | 308.00 |
| 3 | PDL1-CD86-3A-TGFbR2 | 80.67 |

Example 14. CTLA4 Antibody Fused with Anti-OX40 scFv

Plasmids were designed to express a fusion protein with anti-OX40 single chain variable fragment (scFv) linked at the heavy chain C-terminus, or fused at the 3A site of a CTLA4 antibody CT4-4G12-IgG1. The fusion proteins were named as CT4-O40-SCFV-HC and CT4-O40-FV3A, with corresponding heavy chain sequences set forth in SEQ ID NO: 46 and SEQ ID NO: 47, respectively.

Experiments were performed to evaluate ADCC effects. The results indicated that the binding of the scFv at the heavy chain C-terminus or the 3A site to OX40 maintained the affinity between IgG and Fc receptors.

In the experiment, the CTLA4 antibody CT4-4G12-IgG1 (CT4) was used as the parent antibody. The scFV was derived from a humanized anti-OX40 antibody OX40-9H3 (VH SEQ ID NO: 48; VL SEQ ID NO: 49). The OX40 antibody OX40-9H3-IgG1 (O40) was also used a control.

The experiment was performed as described in Example 8 using hCD16-expressing Jurkat cells and OX40-expressing CHO cells. The hCD16-expressing Jurkat cells also included a Luc gene to express luciferase.

Figure 29:
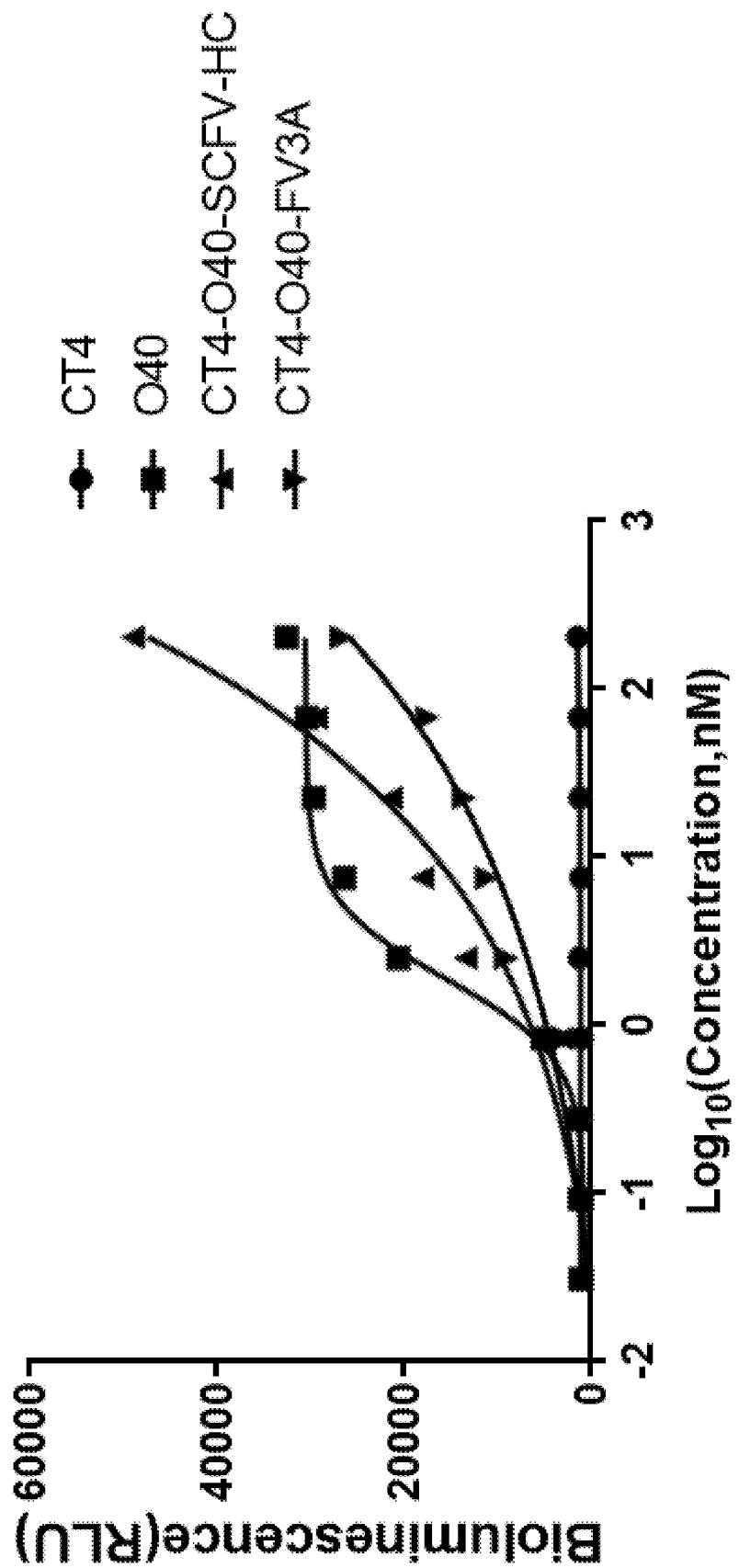
FIG. 29 shows the ADCC effect of several modified immunoglobulins.

As shown in FIG. 29, the results showed that when the scFv linked to the heavy chain C-terminus or fused at the 3A site, binds to the target protein (OX40 on CHO cells), the ADCC effect on the target cell can be maintained. The reduction of ADCC effect as compared to the parent antibody may be caused by steric effects.

Example 15. PD-L1 Antibody Fused with Different Cytokine

As discussed herein, cytokines (e.g., IL7 or IL21) can be fused to the 3A site to generate multifunctional fusion proteins that are easy to express, stable, and functional. The fused cytokines were shown to exhibit similar functions as compared to that of the soluble ones. In addition, cytokine fusion did not affect the binding affinities of the parent antibody to specific antigens or Fc receptors (e.g., FCRn). In this Example, more cytokines were selected to generate fusion proteins, and the protein expression was detected.

The following sequences were used. For example, the cytokine can be derived from human IL3 (hIL3), with sequence set forth in SEQ ID NO: 93; human IL4 (hIL4), with sequence set forth in SEQ ID NO: 94; human IL5 (hIL5), with sequence set forth in SEQ ID NO: 95; human IL6 (hIL6), with sequence set forth in SEQ ID NO: 96; human IL8 (hIL8), with sequence set forth in SEQ ID NO: 97; human IL9 (hIL9), with sequence set forth in SEQ ID NO: 98; human IL13 (hIL13), with sequence set forth in SEQ ID NO: 99; and human IL15 (hIL15), with sequence set forth in SEQ ID NO: 100.

PDL1-3F2-IgG1 was selected as a parent antibody. The following fusion proteins were obtained by replacing amino acids corresponding to position 358-362 (according to EU numbering) of PDL1-3F2-IgG1 antibody heavy chain with cytokine molecules: 3F2-hIL3-3A; 3F2-hIL4-3A; 3F2-hIL5-3A; 3F2-hIL6-3A; 3F2-hIL8-3A; 3F2-hIL9-3A; 3F2-hIL13-3A; and 3F2-hIL15-3A.

In addition, cytokines were connected to the C-terminus of the parent antibody heavy chain through a linker sequence (SEQ ID NO: 9) (structure shown in FIG. 20A as HC). The following fusion proteins were obtained: 3F2-hIL3-HC; 3F2-hIL4-HC; 3F2-hIL5-HC; 3F2-hIL6-HC; 3F2-hIL8-HC; 3F2-hIL9-HC; 3F2-hIL13-HC; and 3F2-hIL15-HC.

Figure 30A:
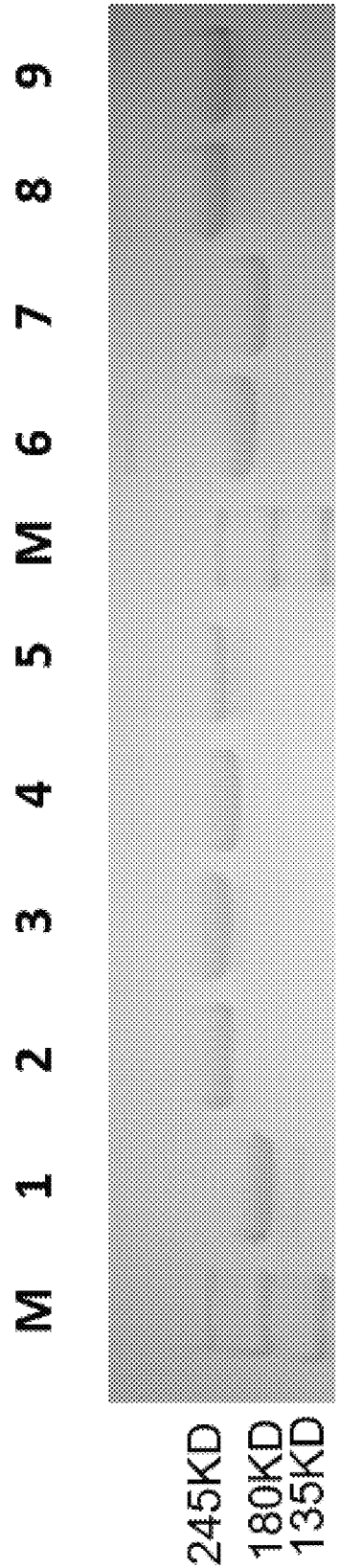
FIG. 30A is a native gel image showing purified PDL1-3F2 (lane 1), 3F2-hIL3-3A (lane 2), 3F2-hIL3-HC (lane 3), 3F2-hIL4-3A (lane 4), 3F2-hIL4-HC (lane 5), 3F2-hIL5-3A (lane 6), 3F2-hIL5-HC (lane 7), 3F2-hIL6-3A (lane 8), and 3F2-hIL6-HC (lane 9). M is protein marker.
Figure 30B:
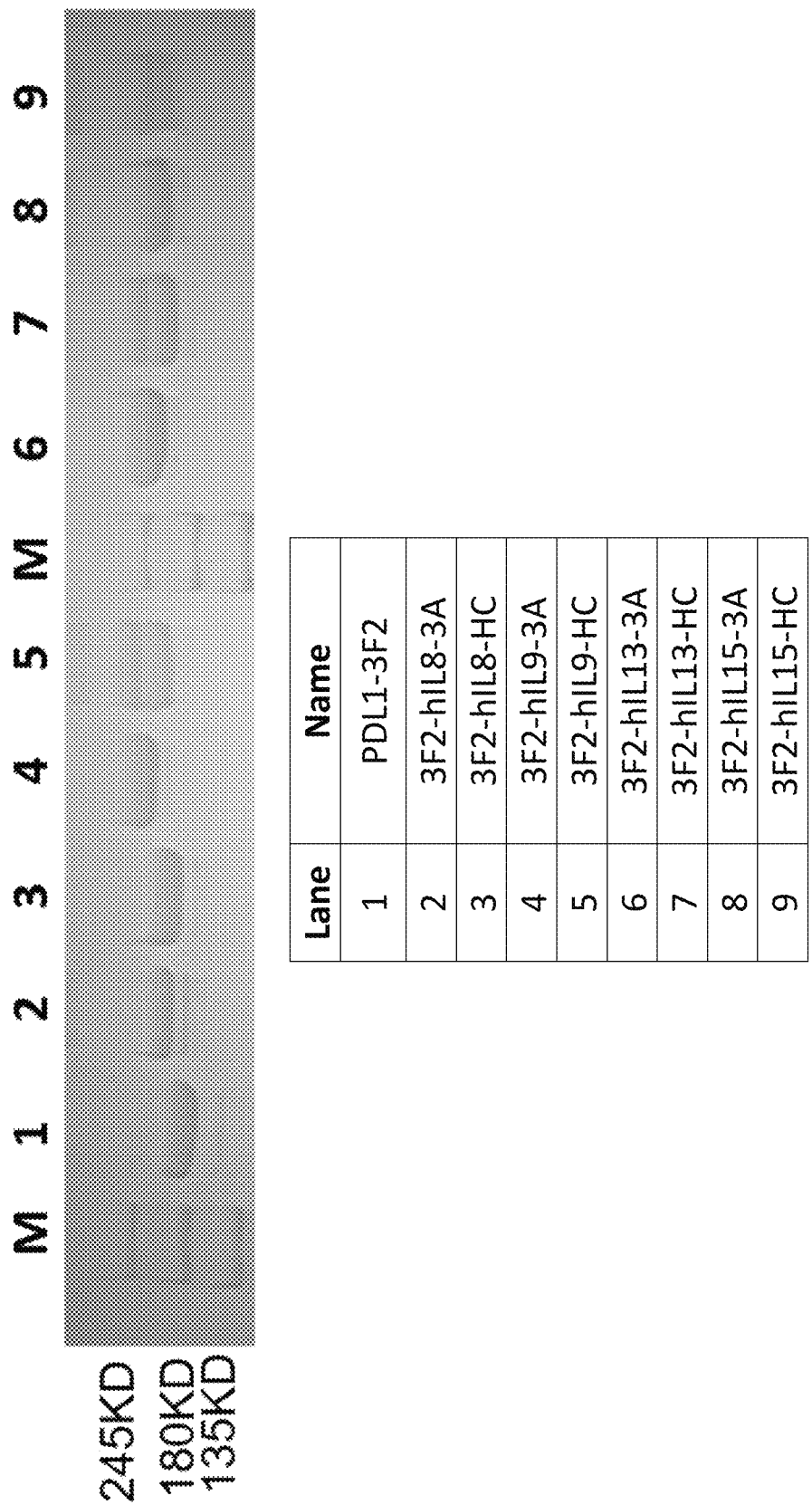
FIG. 30B is a native gel image showing purified PDL1-3F2 (lane 1), 3F2-hIL8-3A (lane 2), 3F2-hIL8-HC (lane 3), 3F2-hIL9-3A (lane 4), 3F2-hIL9-HC (lane 5), 3F2-hIL13-3A (lane 6), 3F2-hIL13-HC (lane 7), 3F2-hIL15-3A (lane 8), and 3F2-hIL15-HC (lane 9). M is protein marker.
Figure 31A:
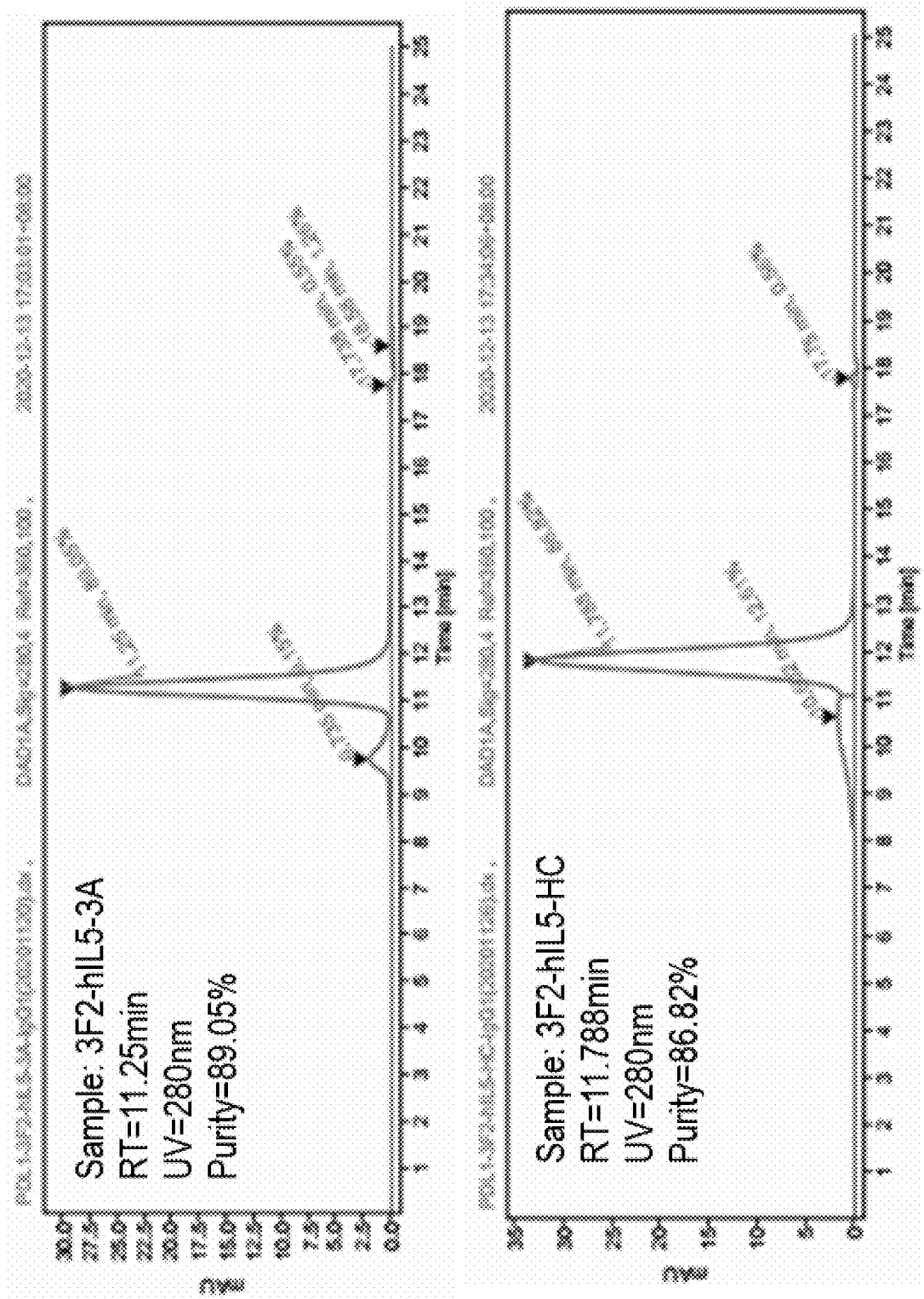
FIG. 31A shows SEC-HPLC results of 3F2-hIL5-3A and 3F2-hIL5-HC.
Figure 31B:
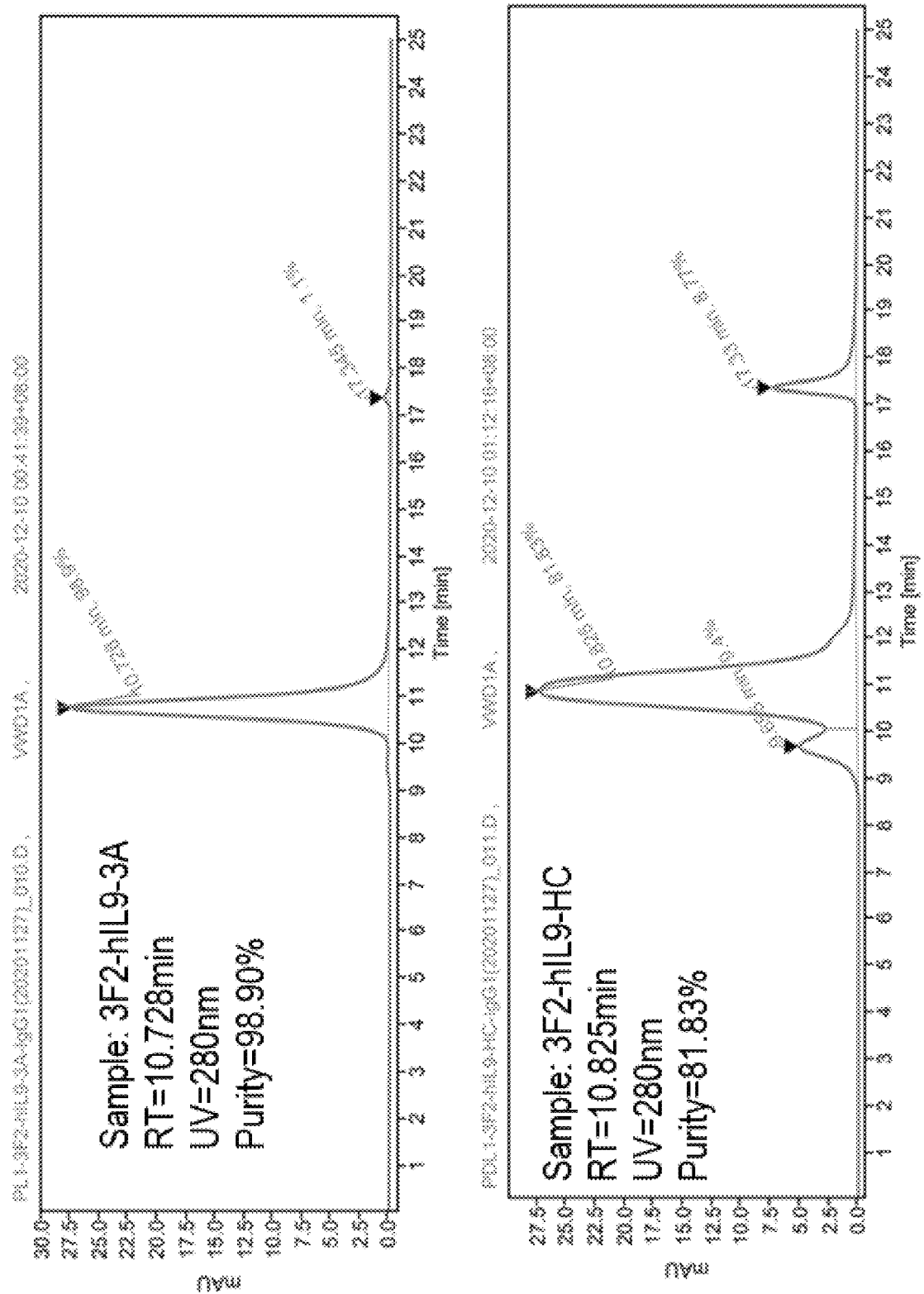
FIG. 31B shows SEC-HPLC results of 3F2-hIL9-3A and 3F2-hIL9-HC.
Figure 31C:
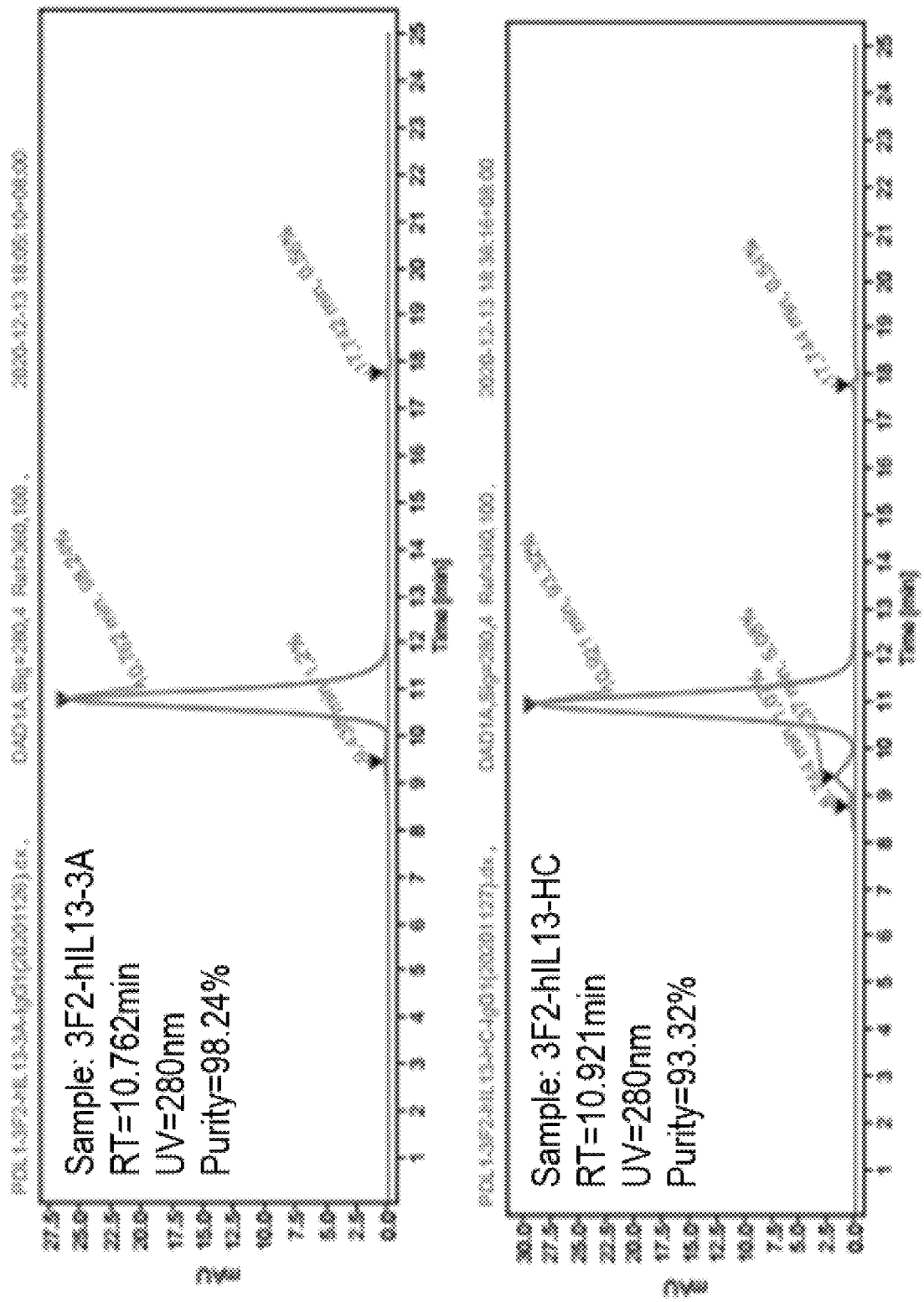
FIG. 31C shows SEC-HPLC results of 3F2-hIL13-3A and 3F2-hIL13-HC.
Figure 31D:
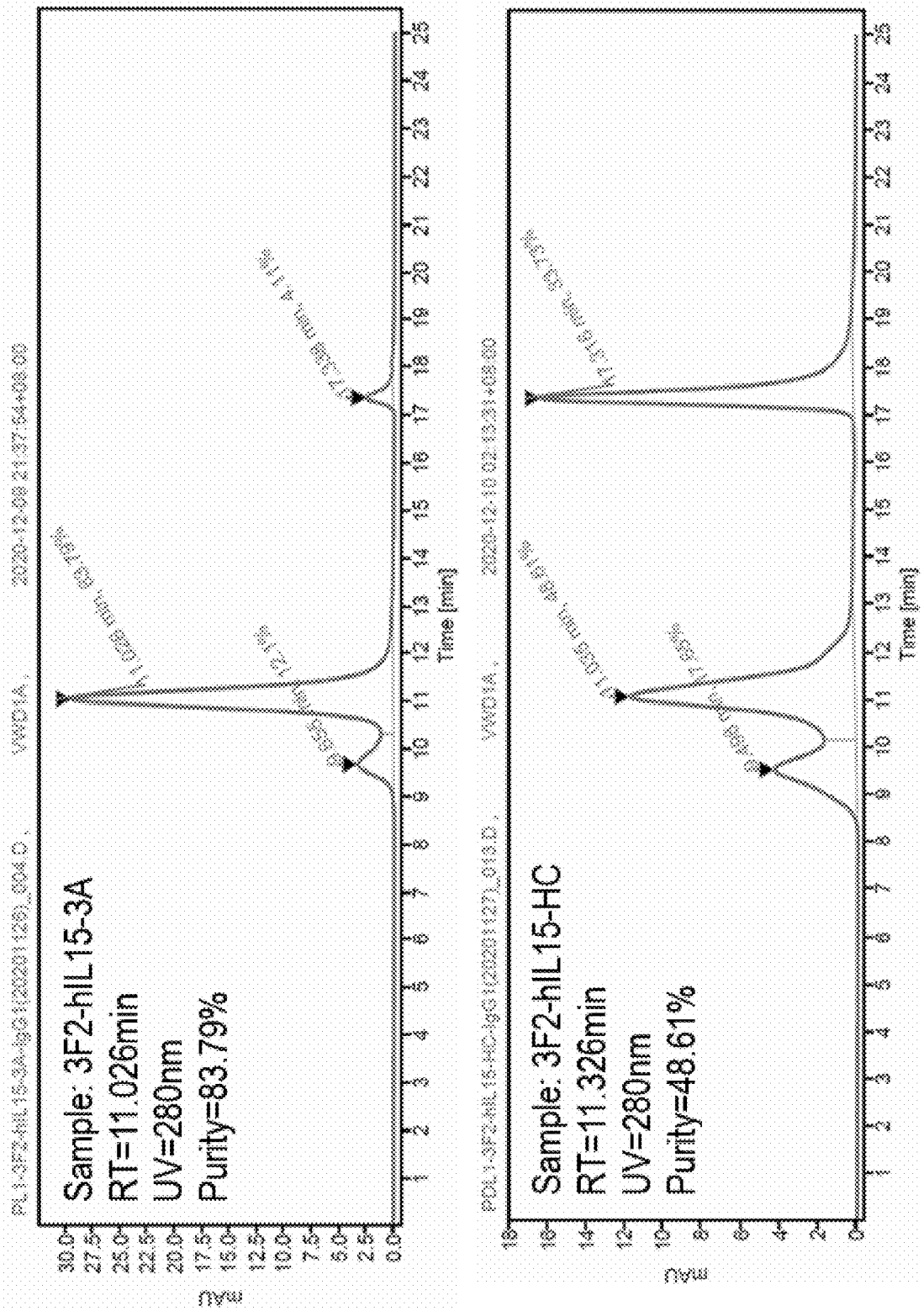
FIG. 31D shows SEC-HPLC results of 3F2-hIL15-3A and 3F2-hIL15-HC.

The fusion proteins were purified by protein A chromatography and then analyzed by gel electrophoresis (using a native gel). Results are shown in FIGS. 30A-30B. As shown in FIG. 30A, all the tested fusion proteins exhibited relatively high purity. However, in FIG. 30B, some fusion proteins with HC structure showed multiple bands (e.g., lane 5, lane 7, and lane 9), whereas the corresponding fusion proteins with 3A structure showed a single band (e.g., lane 4, lane 6, and lane 8).

In addition, the theoretical molecular weights of antibodies with 3A structure and antibodies with HC structure are similar. However, the band representing 3F2-hIL5-3A (lane 6 in FIG. 30A) was higher than the band representing 3F2-hIL5-HC (lane 7 in FIG. 30A), indicating that 3F2-hIL5-3A had a higher molecular weight than that of 3F2-hIL5-HC.

The fusion proteins described above were subjected to further analysis. SEC-HPLC was used to measure protein purity and the results are shown in FIGS. 31A-31D. Specifically, 3F2-hIL5-3A (purity: 89.05%) had a slightly higher purity as compared to 3F-hIL5-HC (purity: 86.82%). In other tested fusion proteins, the 3A structure showed a higher purity than the corresponding HC structure. For example, 3F2-hIL9-3A (purity: 98.90%) had a higher purity than 3F2-hIL9-HC (purity: 81.83%), 3F2-hIL13-3A (purity: 98.24%) had a higher purity than 3F2-hIL13-HC (purity: 93.32%); 3F2-hIL15-3A (purity: 83.79%) had a higher purity than 3F2-hIL15-HC (purity: 48.61%).

Figure 32A:
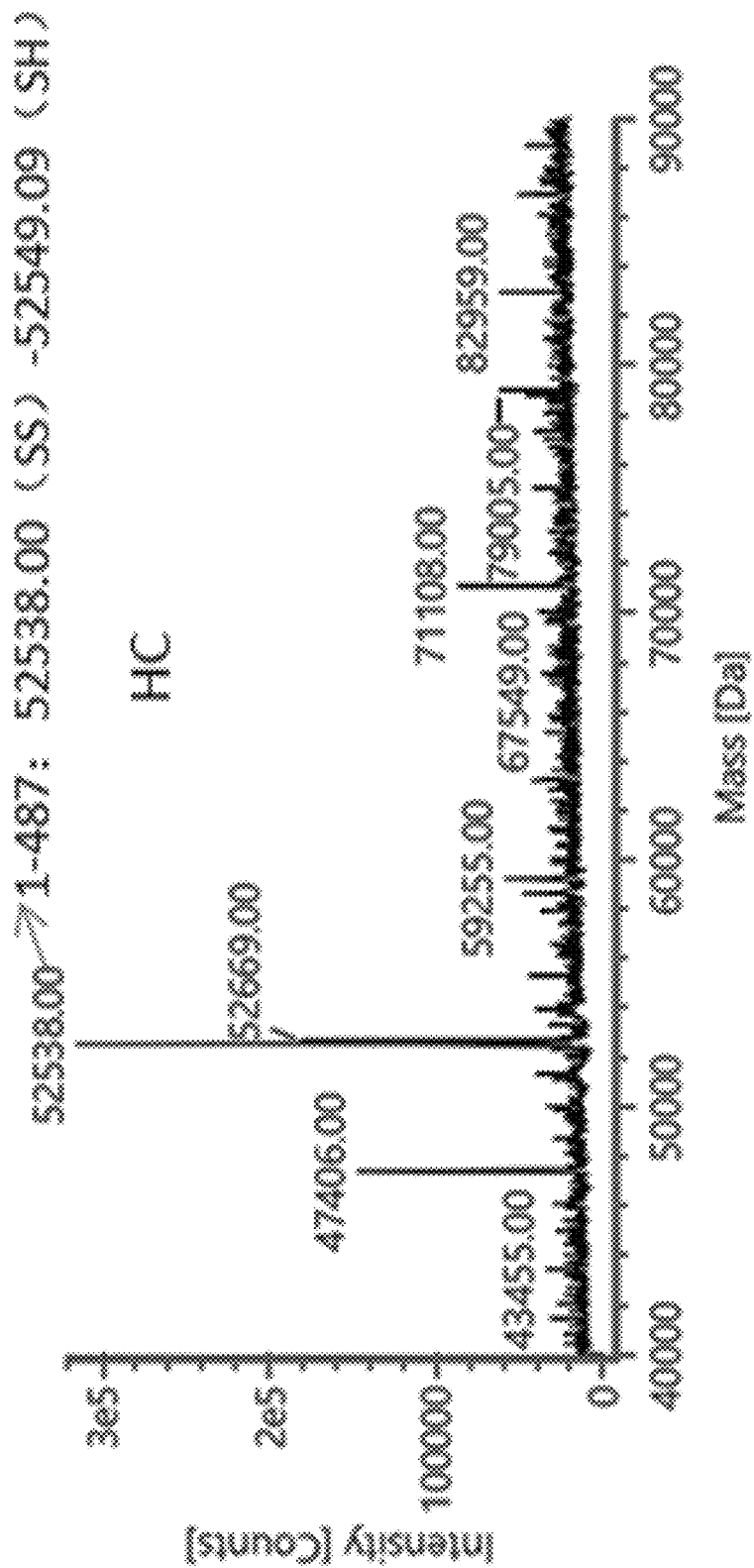
FIG. 32A shows mass spectrometry result of 3F2-hIL5-HC.
Figure 32B:
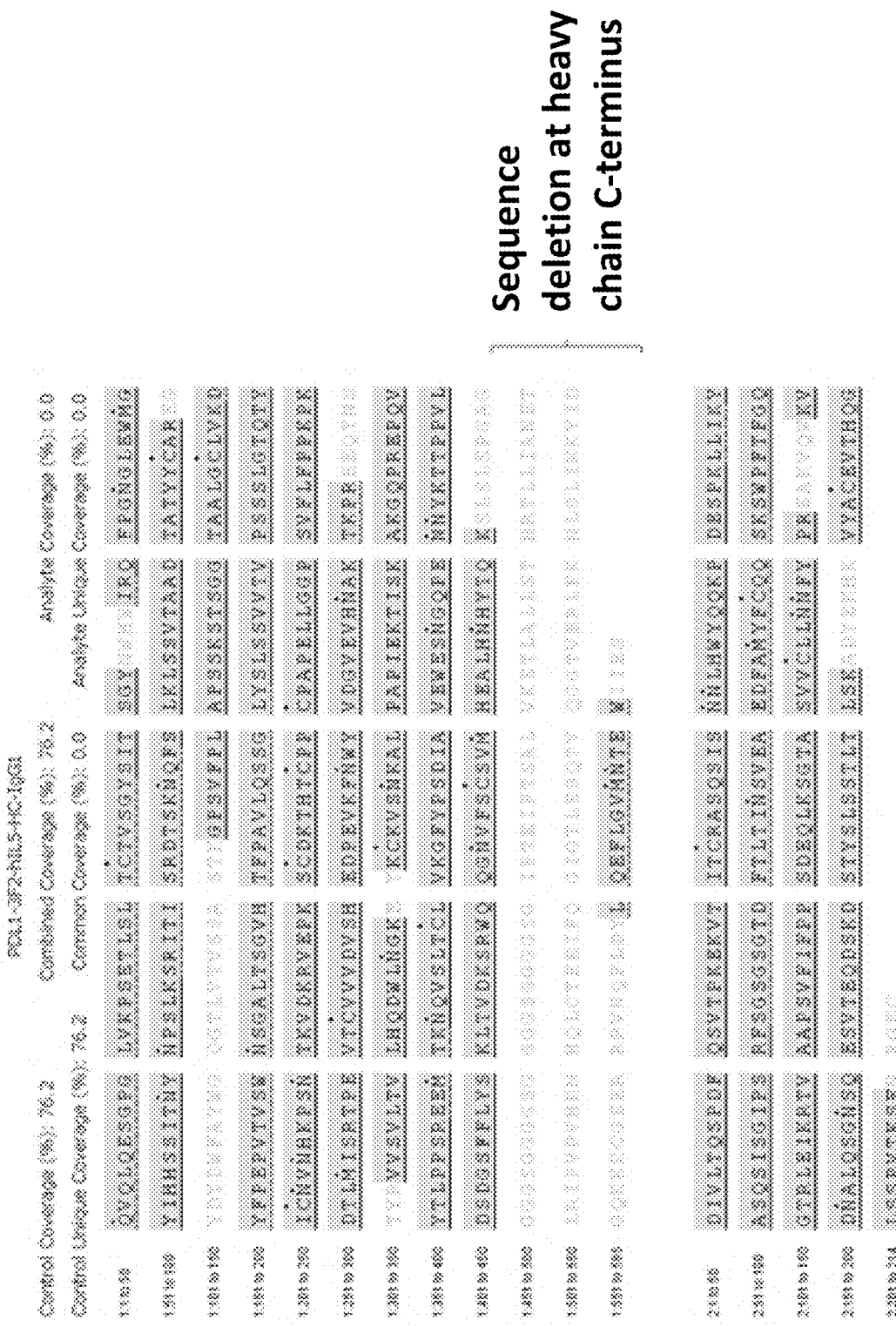
FIG. 32B shows antibody secondary peptide coverage mapping results of 3F2-hIL5-HC. The bracketed region shows deleted sequence at heavy chain C-terminus of 3F-hIL5-HC.

Because the retention time (RT) of 3F2-hIL5-HC on SEC-HPLC was later than that of 3F2-hIL5-3A (see FIG. 31A), it was confirmed that the molecular weight of 3F2-hIL5-HC was less than the theoretical value. Therefore, mass spectrometry (MS) was used to measure the molecular weight of 3F2-hIL5-HC, and the results confirmed that (FIG. 32A) the molecular weight of 3F2-hIL5-HC was less than the theoretical value. It is possible that expression of 3F2-hIL5-HC was incomplete. In addition, the secondary peptide coverage mapping results (FIG. 32B) showed that there was a sequence deletion at the C-terminus of the heavy chain.

Example 16. IL12a Fused at 3A Site of PD-L1 Antibody

Figure 38A:
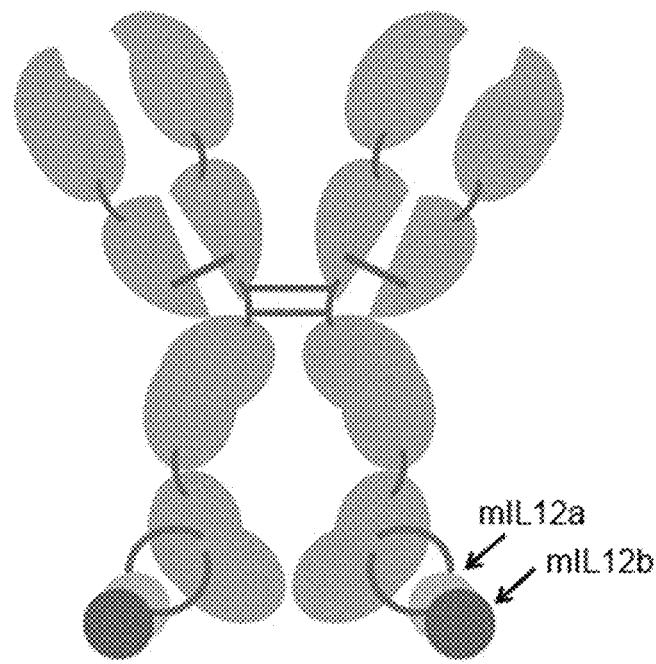
FIG. 38A shows a schematic structure of 3F2-mIL12-3A.

Plasmids were constructed to express a fusion protein that comprises a mouse interleukin 12 alpha subunit (IL12a, or P35), fused at the 3A site (position 358 to position 362 according to EU numbering) of each of the two heavy chains of a humanized anti-PD-L1 antibody PDL1-3F2, as shown in FIG. 38A. The PDL1-3F2 IgG1 antibody comprises a heavy chain variable region (VH) with sequence set forth in SEQ ID NO: 36, and a light chain variable region (VL) with sequence set forth in SEQ ID NO: 37. Specifically, the N-terminus of IL12a was linked to position 357 (according to EU numbering) of PDL1-3F2 IgG1 heavy chains via GGGGSGGGGS (SEQ ID NO: 30), and the C-terminus of IL12a was linked to position 363 (according to EU numbering) of PDL1-3F2 IgG1 heavy chains via GGGGSGGGGS (SEQ ID NO: 30).

Figure 38B:
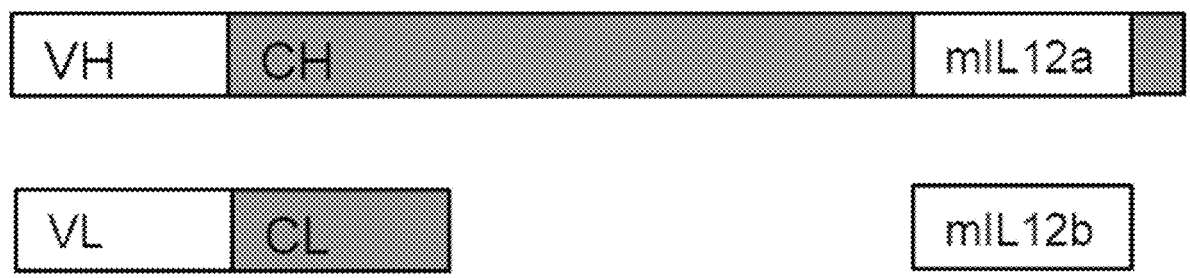
FIG. 38B shows schematic diagrams of plasmids encoding the modified heavy chain, light chain and IL12b of 3F2-mIL12-3A.

A mouse interleukin 12 beta subunit (IL12b, or P40) and the PDL1-3F2 IgG1 light chains were encoded by separate plasmids. Schematic diagrams of the plasmids are shown in FIG. 38B. The modified PDL1-3F2 IgG1 antibody fused with IL12 (including IL12a and IL12b) was named 3F2-mIL12-3A (or 3F2-mIL12-3A-IgG1).

Example 17. IFNa4 Linked at Heavy Chain C-Terminus of PD-L1 Antibody

Plasmids were constructed to express a fusion protein that further comprises a mouse interferon alpha 4 (IFNa4) (SEQ ID NO: 10), linked to each of the two heavy chain C-terminus of 3F2-mIL12-3A through a linker sequence (SEQ ID NO: 9). As shown in FIG. 39A, the modified PDL1-3F2 IgG1 antibody fused with IL12 (including IL12a and IL12b) and IFNa4 was named 3F2-mIL12-3A-mIFNa4. Similar to 3F2-mIL12-3A, the IL12b and light chains were encoded by separate plasmids. Schematic diagrams of the plasmids are shown in FIG. 39B.

Example 18. Fusion Proteins with Diverse Structures

Plasmids were also constructed to express fusion proteins as described below.
1) 3F2-mIL12-3A-Knob
3F2-mIL12-3A-knob is a fusion protein that comprises an IL12a fused at the 3A site (position 358 to position 362 according to EU numbering) of the knob heavy chain of PDL1-3F2 IgG1 with knobs-into-holes (KIH) mutations. Specifically, the N-terminus of IL12a was linked to position 357 (according to EU numbering) of the knob heavy chain via GGGGSGGGGS (SEQ ID NO: 30), and the C-terminus of IL12a was linked to position 363 (according to EU numbering) of the knob heavy chain via GGGGSGGGGS (SEQ ID NO: 30). The IL12b and light chains were encoded by separate plasmids.
2) 3F2-mIL12-3A-Hole
3F2-mIL12-3A-hole is a fusion protein that comprises an IL12a fused at the 3A site (position 358 to position 362 according to EU numbering) of the hole heavy chain of PDL1-3F2 IgG1 with knobs-into-holes (KIH) mutations. Specifically, the N-terminus of IL12a was linked to position 357 (according to EU numbering) of the hole heavy chain via GGGGSGGGGS (SEQ ID NO: 30), and the C-terminus of IL12a was linked to position 363 (according to EU numbering) of the hole heavy chain via GGGGSGGGGS (SEQ ID NO: 30). The IL12b and light chains were encoded by separate plasmids.
3) 3F2-mIL12-3A-IgG4
3F2-mIL12-3A-IgG4 is a fusion protein that comprises the same overall structure and sequences as 3F2-mIL12-3A, except that the IgG1 constant regions are replaced by IgG4 constant regions.

Example 19. Purification of 3F2-mIL12-3A and 3F2-mIL12-3A-mIFNa4

The fusion proteins 3F2-mIL12-3A and 3F2-mIL12-3A-mIFNa4 were purified and analyzed by sodium dodecyl sulphate-polyacrylamide gel electrophoresis (SDS-PAGE) and size-exclusive chromatography (SEC). Specifically, plasmids expressing the fusion proteins were constructed and used to transiently transform CHO cells. The transfected CHO cells were then cultured at 37° C. for 6-7 days. Afterwards, the culture supernatant was collected by centrifugation, and the fusion protein was first purified by a Protein A affinity column and then analyzed by SDS-PAGE. Protein purity was further measured by SEC.

Figure 40:
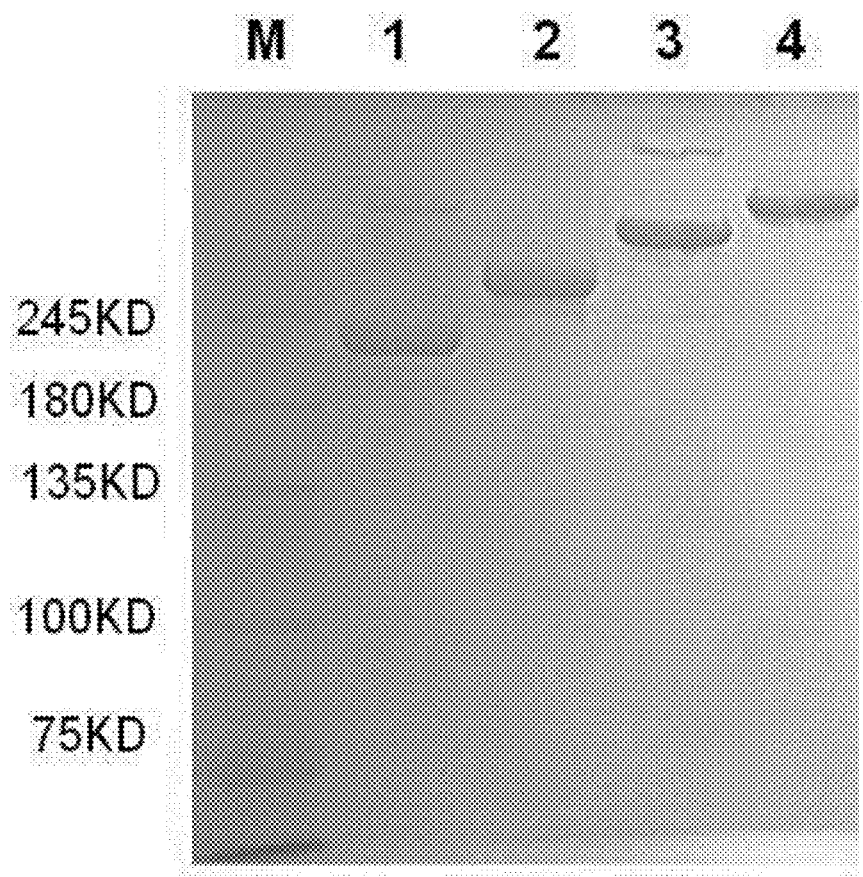
FIG. 40 shows non-reducing SDS-PAGE results of 3F2-mIL12-3A and 3F2-mIL12-3A-mIFNa4.

Non-reducing SDS-PAGE was performed using a 6% acrylamide gel. The protein samples were prepared as follows. First, the protein samples were diluted to 1 mg/ml. 2.4 µl of the diluted protein sample was mixed with 6 µl Tris-Glycine SDS Sample Buffer (2×) and 3.6 µl distilled water. The mixture was then boiled for 2 minutes and instantly centrifuged before loading. As shown in FIG. 40, both 3F2-mIL12-3A and 3F2-mIL12-3A-mIFNa4 showed a single band with correct molecular weight.

Figure 41A:
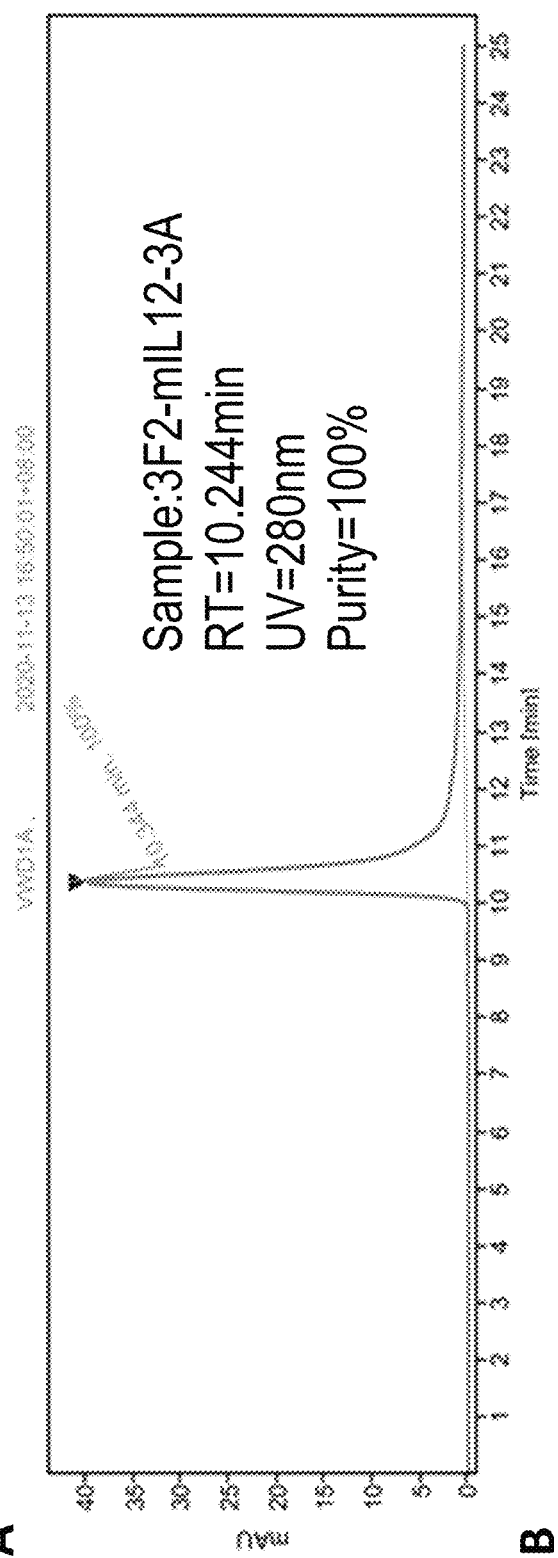
FIG. 41A shows SEC result of 3F2-mIL12-3A.
Figure 41B:
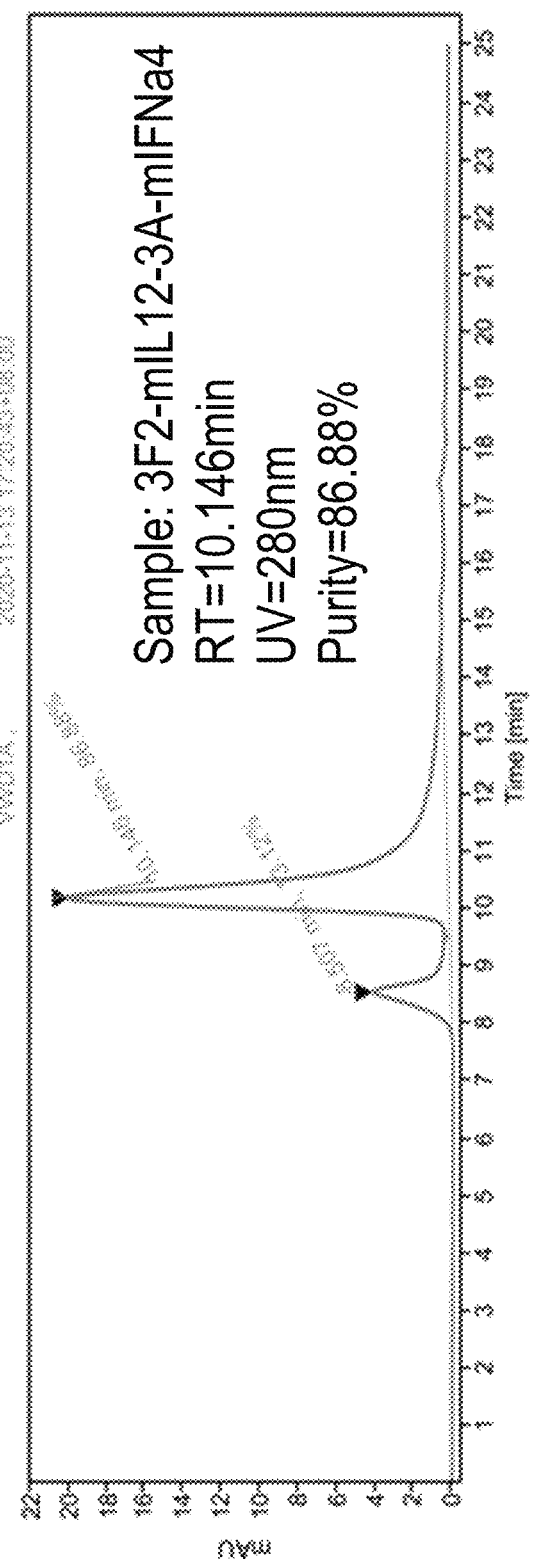
FIG. 41B shows SEC result of 3F2-mIL12-3A-mIFNa4.

Protein purity was further measured by SEC using the TSKgel® G3000SW$_{XL}$ HPLC Column (Tosoh Bioscience LLC) connected to Agilent 1260 series HPCL system. The protein A purified fusion protein samples were analyzed by SEC-HPLC. Before injection, the samples were diluted to 1 mg/ml and then filtered with a 0.22 µm filter. The experimental parameters were set up as: flow rate: 0.7 mL/min; time: 30 minutes; and detection wavelength: 280 nm. Agilent liquid chromatography analysis software was used to analyze the data. Chromatographic curves of the tested fusion proteins were obtained. As shown in FIGS. 41A-41B, the total detected peak area percentage and retention time (RT) were recorded. In general, the purity of the protein A-purified fusion protein 3F2-mIL12-3A was slightly higher than that of 3F2-mIL12-3A-mIFNa4 (86.88% purity, with a small amount of impurities).

Example 20. Determination of Binding Affinity to PD-L1

The binding affinity between purified His-tagged human PD-L1 (hPL1-His; ACRO Biosystems) and PDL1-3F2 IgG1, 3F2-mIL12-3A, 3F2-mIL12-3A-mIFNa4 were measured by surface plasmon resonance (SPR) using Biacore™ (Biacore Inc., Piscataway N.J.) T200 biosensor equipped with pre-immobilized protein A sensor chips.

The fusion proteins 3F2-mIL12-3A and 3F2-mIL12-3A-mIFNa4 (1 µg/mL) were injected into Biacore™ T200 biosensor at 10 µL/min for 30 seconds to achieve to a desired protein density (about 67 RU). His-tagged human PD-L1 (hPL1-His) at concentrations of 200 nM, 100 nM, 50 nM, 25 nM, 12.5 nM, 6.25 nM, 3.125 nM, and 1.5625 nM were then injected at 30 µL/min for 100 seconds. Dissociation was monitored for 400 seconds. The chip was regenerated after the last injection of each titration with Glycine (pH 2.0, 30 µL/min for 12 seconds). As a person of ordinary skill in the art would understand, the same method with appropriate adjustments for parameters (e.g., fusion protein concentration) was performed for each tested fusion protein. The results for the tested fusion proteins are shown in the table below.

TABLE 24

| Ligand | Analysis | kon (1/Ms) | koff (1/s) | KD (M) | Rmax (RU) |
|---|---|---|---|---|---|
| PDL1-3F2 IgG1 | hPL1-His | 2.32E+06 | 1.30E−03 | 5.59E−10 | 32.37 |
| 3F2-mIL12-3A | hPL1-His | 2.49E+06 | 9.52E−04 | 3.82E−10 | 16.5 |
| 3F2-mIL12-3A-mIFNa4 | hPL1-His | 2.33E+06 | 9.22E−04 | 3.96E−10 | 14.86 |

Kinetic association rates (kon) and dissociation rates (koff) were obtained simultaneously by fitting the data globally to a 1:1 Langmuir binding model (Karlsson, R. Roos, H. Fagerstam, L. Petersson, B., 1994. Methods Enzymology 6. 99-110) using Biacore™ T200 Evaluation Software 3.0. Affinities were calculated from the quotient of the kinetic rate constants (KD=koff/kon). The results showed that all three tested fusion proteins PDL1-3F2 IgG1, 3F2-mIL12-3A, and 3F2-mIL12-3A-mIFNa4 can bind to hPL1-His with comparable binding affinities. Non-specific effects were not observed.

Example 21. Determination of Binding Affinity to IL12

The binding affinity between purified His-tagged recombinant mouse IL12RB2 protein (mIL12R-B2-His; Sino Biological Inc., Cat #: 50099-M08H) and 3F2-mIL12-3A, 3F2-mIL12-3A-mIFNa4 were measured by SPR using Biacore™ (Biacore Inc., Piscataway N.J.) T200 biosensor equipped with pre-immobilized protein A sensor chips. The experiment was performed by a similar method as described in Example 5. The results for the tested fusion proteins are shown in the table below.

TABLE 25

| Ligand | Analysis | kon (1/Ms) | koff (1/s) | KD (M) | Rmax (RU) |
|---|---|---|---|---|---|
| 3F2-mIL12-3A | mIL12R-B2-His | 5.73E+04 | 3.35e−03 | 5.85E−08 | 56.2 |
| 3F2-mIL12-3A-mIFNa4 | mIL12R-B2-His | 5.29E+04 | 2.99e−03 | 5.65E−08 | 42.3 |

The results showed that both tested fusion proteins 3F2-mIL12-3A and 3F2-mIL12-3A-mIFNa4 can bind to mIL12R-B2-His with comparable binding affinities. Non-specific effects were not observed.

Example 22. In Vivo Pharmacological Validation

A hPD-1/hPD-L1 mouse model (obtained from Biocytogen Pharmaceuticals (Beijing) Co., Ltd., Cat #120522) was engineered to express a chimeric PD-1 protein and a chimeric PD-L1 protein. The chimeric PD-1 protein includes a replacement of a part of the extracellular region of the mouse PD-1 protein with the corresponding human PD-1 extracellular region. The chimeric PD-L1 protein includes a replacement of a part of the extracellular region of the mouse PD-L1 protein with the corresponding human PD-L1 extracellular region.

The humanized mouse model (hPD-1/hPD-L1) provides a tool for testing new therapeutic treatments in a clinical setting by significantly decreasing the difference between clinical outcome in human and in ordinary mice expressing mouse PD-1 or PD-L1. A detailed description regarding humanized PD-1 mouse, PD-L1 mouse and hPD-1/hPD-L1 mouse model can be found in PCT/CN2017/090320, PCT/CN2017/099574, CN Application No. 201710505554.0 and CN Application No. 201710757022.6, each of which is incorporated herein by reference in its entirety.

PD-1/PD-L1 double humanized mice (5-8 weeks) were subcutaneously injected with mouse colon cancer cell MC38 ($5 \times 10^5$/100 μl PBS), and when the tumor volume grew to about 100-150 mm$^3$, the mice were divided to a control group and six treatment groups based on tumor size (n=7/group). The treatment groups were randomly selected for humanized anti-human PD-L1 antibody PDL1-3F2 IgG1 treatment (1 mg/kg or 3 mg/kg), fusion protein 3F2-mIL12-3A treatment (1.82 mg/kg or 5.46 mg/kg), or fusion protein 3F2-mIL12-3A-mIFNa4 treatment (2.11 mg/kg or 6.34 mg/kg). The molar dosages (e.g., mole/kg) of 3F2-mIL12-3A and 3F2-mIL12-3A-mIFNa4 were equal to that of PDL1-3F2 IgG1. The control group mice were injected with an equal volume of physiological saline (PS). The frequency of administration was twice a week (6 times of administrations in total). The tumor volume was measured twice a week and the body weight of the mice was weighed as well. Euthanasia was performed when the tumor volume of the mouse reached 3000 mm$^3$.

TABLE 26

| Group | No. of mice | Antibodies | Dosage (mg/kg) | Route | Frequency | Total No. of administration |
|---|---|---|---|---|---|---|
| G1 | 7 | PS | — | i.p. | BIW | 6 |
| G2 | 7 | PDL1-3F2 IgG1 | 1 mg/kg | i.p. | BIW | 6 |
| G3 | 7 | PDL1-3F2 IgG1 | 3 mg/kg | i.p. | BIW | 6 |
| G4 | 7 | 3F2-mIL12-3A | 1.82 mg/kg | i.p. | BIW | 6 |
| G5 | 7 | 3F2-mIL12-3A | 5.46 mg/kg | i.p. | BIW | 6 |
| G6 | 7 | 3F2-mIL12-3A-mIFNa4 | 2.11 mg/kg | i.p. | BIW | 6 |
| G7 | 7 | 3F2-mIL12-3A-mIFNa4 | 6.34 mg/kg | i.p. | BIW | 6 |

Figure 42:
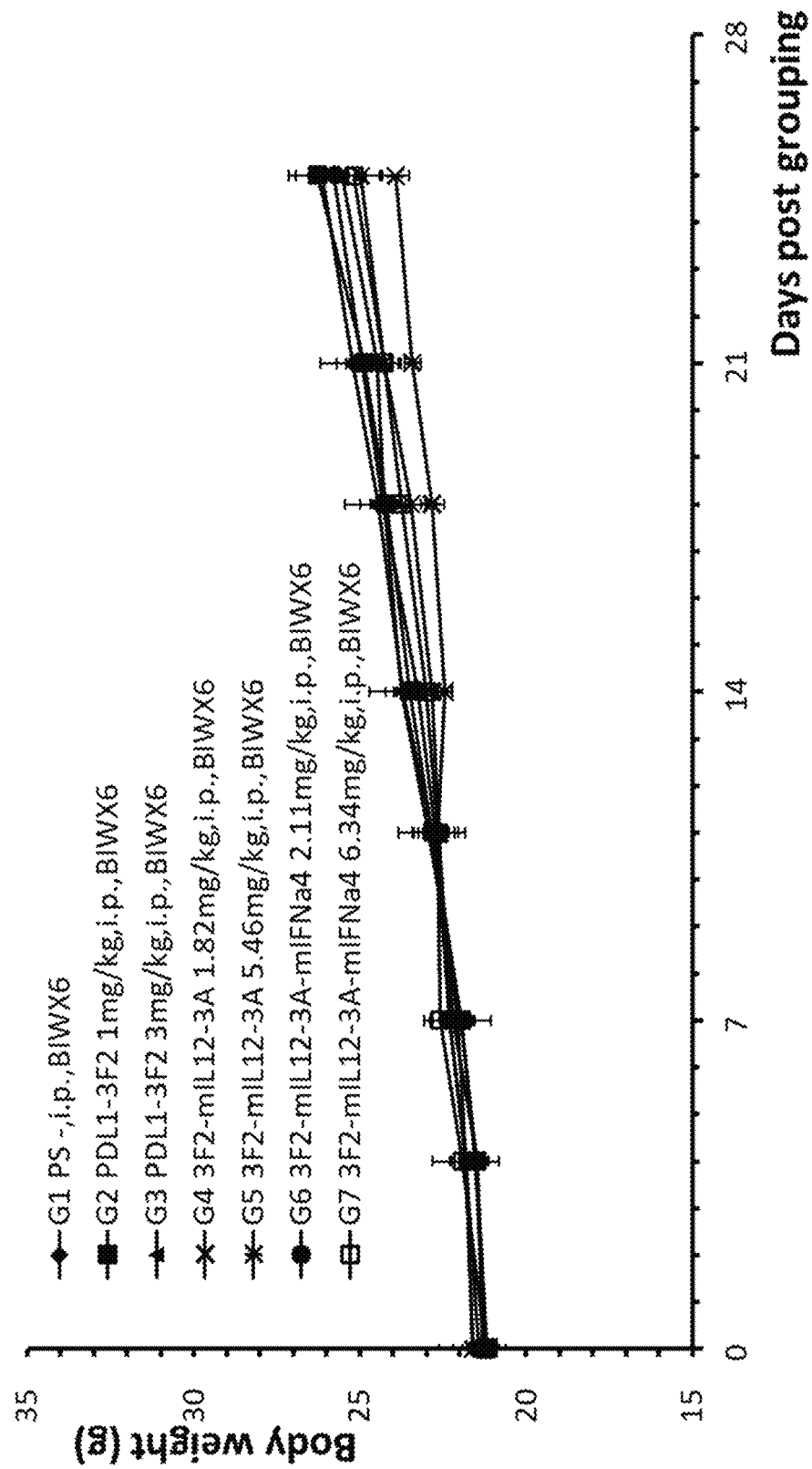
FIG. 42 is a graph showing body weight over time of double humanized hPD-1/hPD-L1 mice that were injected with mouse colon cancer cells MC38, and were treated with PDL1-3F2, 3F2-mIL12-3A, or 3F2-mIL12-3A-mIFNa4. Saline solution was injected as a control.
Figure 43:
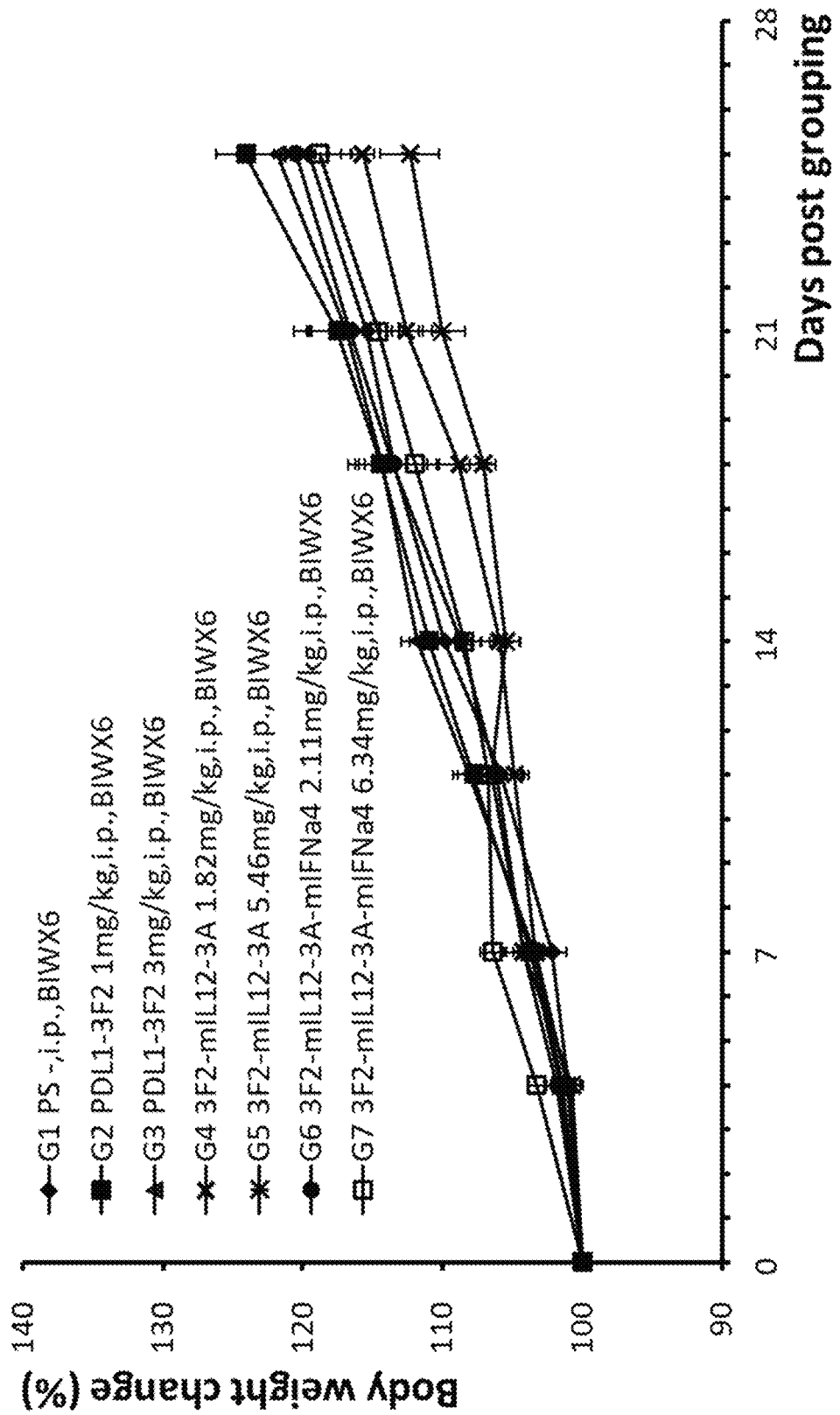
FIG. 43 is a graph showing body weight change over time of double humanized hPD-1/hPD-L1 mice that were injected with mouse colon cancer cells MC38, and were treated with PDL1-3F2, 3F2-mIL12-3A, or 3F2-mIL12-3A-mIFNa4. Saline solution was injected as a control.
Figure 44:
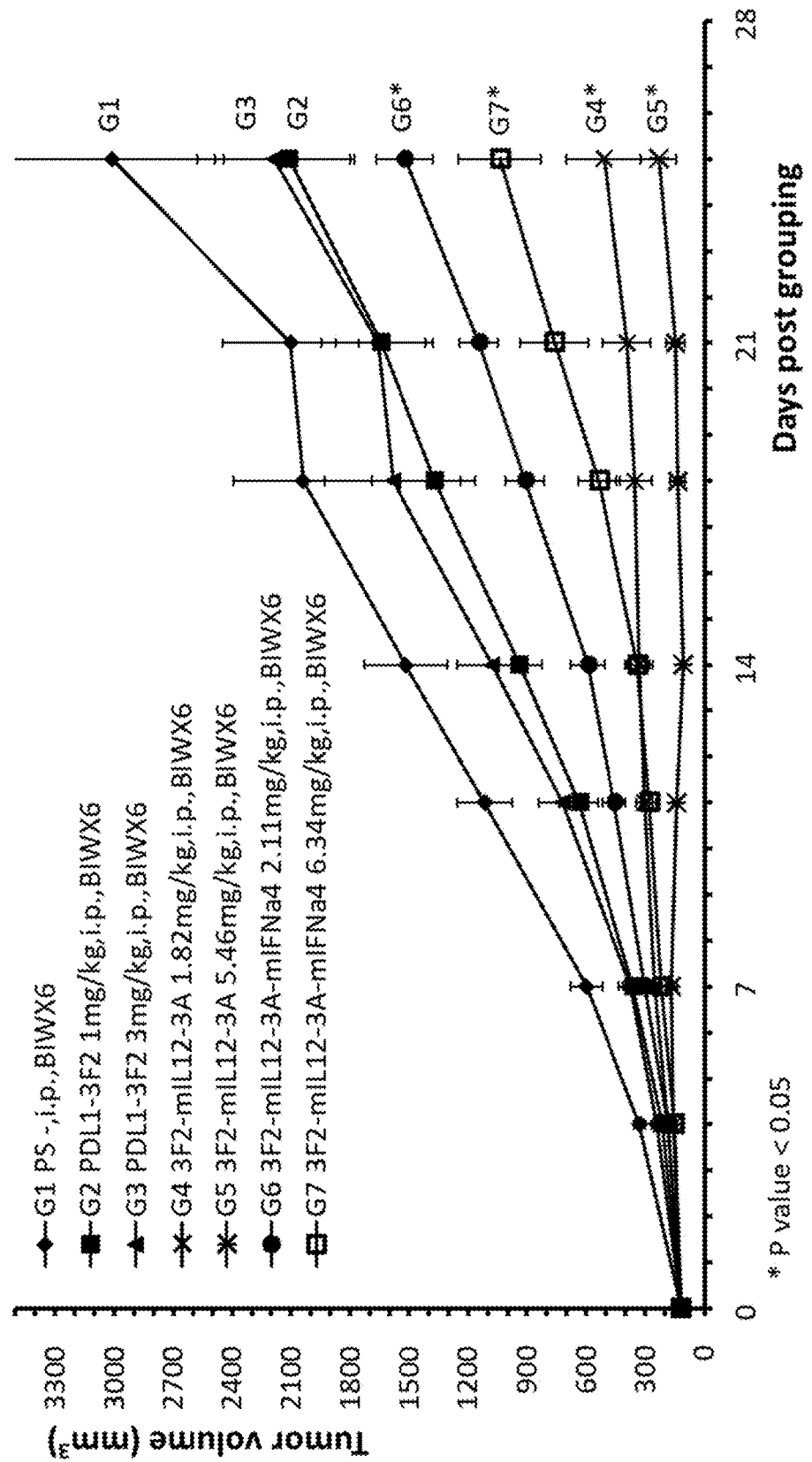
FIG. 44 is a graph showing average tumor volume in different groups of double humanized hPD-1/hPD-L1 mice that were injected with mouse colon cancer cells MC38, and were treated with PDL1-3F2, 3F2-mIL12-3A, or 3F2-mIL12-3A-mIFNa4. Saline solution was injected as a control.

Overall, the mice in each group were healthy. The body weight of all the treatment and control group mice increased, and the body weight were not obviously different from each other (FIGS. 42 and 43). As shown in FIG. 44, the tumor in the control group continued growing during the experimental period. When compared with the control group mice, the tumor volumes in the treatment groups were smaller than the control group. Thus, the anti-human PD-L1 antibody PDL1-3F2 IgG1 and the two fusion proteins 3F2-mIL12-3A, 3F2-mIL12-3A-mIFNa4 were well tolerated, and inhibited the tumor growth in mice.

The table below summarizes the results for this experiment, including the tumor volumes on the day of grouping (day 0), 14 days after the grouping (day 14), and at the end of the experiment (day 25); number of tumor-free mice; the survival rate of the mice; the Tumor Growth Inhibition value (TGI$_{TV}$); and the statistical differences (P value) of mouse tumor volume between the treatment and control groups.

TABLE 27

| | | Tumor volume (mm$^3$) | | | | | | P value |
|---|---|---|---|---|---|---|---|---|
| | | Day 0 | Day 14 | Day 25 | Tumor-free | Survival | TGI$_{TV}$% | Tumor Volume |
| Control | G1 | 120 ± 4 | 1517 ± 210 | 3014 ± 526 | 0 | 6/7 | N/A | N/A |
| Treatment groups | G2 | 120 ± 4 | 941 ± 118 | 2110 ± 334 | 0 | 7/7 | 31.2 | 0.163 |
| | G3 | 120 ± 4 | 1081 ± 174 | 2190 ± 387 | 0 | 6/7 | 28.5 | 0.236 |

TABLE 27-continued

| | Tumor volume (mm³) | | | | | P value |
|---|---|---|---|---|---|---|
| | Day 0 | Day 14 | Day 25 | Tumor-free | Survival | TGI$_{TV}$% Tumor Volume |
| G4 | 120 ± 5 | 328 ± 67 | 512 ± 189 | 0 | 7/7 | 86.5 0.001 |
| G5 | 120 ± 4 | 109 ± 12 | 233 ± 92 | 2 | 7/7 | 96.1 <0.001 |
| G6 | 120 ± 4 | 592 ± 85 | 1522 ± 145 | 0 | 7/7 | 51.6 0.014 |
| G7 | 120 ± 3 | 340 ± 62 | 1038 ± 208 | 0 | 7/7 | 68.3 0.003 |

At the end of the experiment (day 25), the body weight of each group increased and there was no significant difference between the treatment group (except G5) and control group mice. Although the body weight of the G5 group mice was lower than that of the G1 group mice, the G5 group mice continued to gain weight throughout the experimental period, and the body weight increased by about 10% at the end of the experiment. No obvious difference in body weight change was observed. Considering that the mice in the G5 group had a lower tumor volume at the end of the experiment, the difference in body weight between the G5 group and the G1 group was mainly caused by the tumor weight. The results indicate that the anti-human PD-L1 antibody PDL1-3F2 IgG1 and the two fusion proteins 3F2-mIL12-3A, 3F2-mIL12-3A-mIFNa4 were well tolerated by mice.

The tumor volumes in all treatment groups (G2-G7) were smaller than those in the control group (G1). The results also showed that anti-human PD-L1 antibody PDL1-3F2 IgG1 and the two fusion proteins 3F2-mIL12-3A, 3F2-mIL12-3A-mIFNa4 had different tumor inhibitory effects, which was dosage-dependent. Under the same condition (e.g., administration dosage and frequency), the inhibitory effects of the fusion proteins (G4-G7) were better than other the anti-PD-L1 antibody (G2 and G3). This indicate that fusion of IL12 to PD-L1 antibody can improve the in vivo efficacy of PD-L1 antibody. In addition, at the same dosage, the effect of 3F2-mIL12-3A was slightly better than that of 3F2-mIL12-3A-mIFNa4, indicating that fusion of interferon alpha (e.g., IFNa4) may not further promote the tumor inhibitory effect of 3F2-mIL12-3A.

The above results showed that the two fusion proteins (3F2-mIL12-3A, 3F2-mIL12-3A-mIFNa4) exhibited significantly better tumor growth inhibitory effect as compared to that of PDL1-3F2 IgG1, in PD-1/PD-L1 double humanized mice. In addition, these fusion proteins had no obvious toxic effects in mice.

Example 23. In Vivo Results for PD-1/CD40 BsAB

CD40 is a key immune co-stimulatory pathway receptor, which exists on the surface of antigen-presenting cells (APC) in the immune system, and plays a key role in the activation of the innate and adaptive immune system mechanisms. Anti-CD40 antibodies that are currently under development include, e.g., APX005M developed by Apexigen, RG7876 (selicrelumab) developed by Roche, VIB4920 developed by Viela Bio, and ADC-1013 developed by Alligator Biosciences. In this experiment, anti-CD40 monoclonal antibody selicrelumab (VH SEQ ID NO: 130; VL SEQ ID NO: 131; scFV SEQ ID NO: 132) was selected to generate bispecific antibodies in combination with anti-PD-1 monoclonal antibody 1A7-H2K3-IgG4 at the heavy chain 3A site and heavy chain C-terminus. The resulting antibodies were named as 1A7-selicrelumab-FV3A-IgG4 (with heavy chain sequence set forth in SEQ ID NO: 133 and light chain sequence set forth in SEQ ID NO: 134) and 1A7-selicrelumab-FVHC-IgG4 (with heavy chain sequence set forth in SEQ ID NO: 135 and light chain sequence set forth in SEQ ID NO: 136).

A hPD-1/hCD40 mouse model (obtained from Biocytogen Pharmaceuticals (Beijing) Co., Ltd., Cat #120526) was engineered to express a chimeric PD-1 protein and a chimeric CD40 protein. The chimeric PD-1 protein includes a replacement of a part of the extracellular region of the mouse PD-1 protein with the corresponding human PD-1 extracellular region. The chimeric CD40 protein includes a replacement of a part of the extracellular region of the mouse CD40 protein with the corresponding human CD40 extracellular region.

The humanized mouse models (e.g., B-hCD40 mice, or double humanized CD40/PD-1 mice (B-hPD-1/hCD40 mice) provide a new tool for testing new therapeutic treatments in a clinical setting by significantly decreasing the difference between clinical outcome in human and in ordinary mice expressing mouse CD40 or PD-1. A detailed description regarding humanized CD40, humanized PD-1 and double humanized CD40/PD-1 mouse models can be found in PCT/CN2018/091845 and PCT/CN2017/090320; each of which is incorporated herein by reference in its entirety.

Similar to the previous in vivo drug efficacy experiments, the antibodies were tested for their effect on tumor growth in vivo in a mouse model of colon carcinoma. MC-38 cancer tumor cells (colon adenocarcinoma cell) expressing human PD-L1 (MC38-hPD-L1) were injected subcutaneously in double humanized CD40/PD-1 mice (B-hPD-1/hCD40 mice). When the tumors in the mice reached a volume of about 400 mm³, the mice were randomly placed into different groups (8 mice per group) based on the tumor volume.

In each group, B-hPD-1/hCD40 mice were injected with phosphate-buffered saline (PBS, G1), 1 mg/kg anti-CD40 monoclonal antibody Selicrelumab (Selicrelumab-IgG2, G2), 1 mg/kg anti-PD-1 monoclonal antibody 1A7-H2K3-IgG4 (G3), 1 mg/kg Selicrelumab in combination with 1 mg/kg 1A7-H2K3-IgG4 (G4), 1.35 mg/kg 1A7-selicrelumab-FV3A-IgG4 (G5), or 1.35 mg/kg 1A7-selicrelumab-FVHC-IgG4 (G6) by intraperitoneal (i.p.) administration. The frequency of administration was twice a week (6 administrations in total). Details are shown in the table below.

TABLE 28

| Group | Antibodies | Dosage (mg/kg) | Route | Frequency | Total No. of administration |
|---|---|---|---|---|---|
| G1 | PBS | — | i.p. | BIW | 6 |
| G2 | Selicrelumab | 1 mg/kg | i.p. | BIW | 6 |
| G3 | 1A7-H2K3-IgG4 | 1 mg/kg | i.p. | BIW | 6 |
| G4 | Selicrelumab + 1A7-H2K3-IgG4 | 1 + 1 mg/kg | i.p. | BIW | 6 |

TABLE 28-continued

| Group | Antibodies | Dosage (mg/kg) | Route | Frequency | Total No. of administration |
|---|---|---|---|---|---|
| G5 | 1A7-selicrelumab-FV3A-IgG4 | 1.35 mg/kg | i.p. | BIW | 6 |
| G6 | 1A7-selicrelumab-FVHC-IgG4 | 1.35 mg/kg | i.p. | BIW | 6 |

Figure 45A:
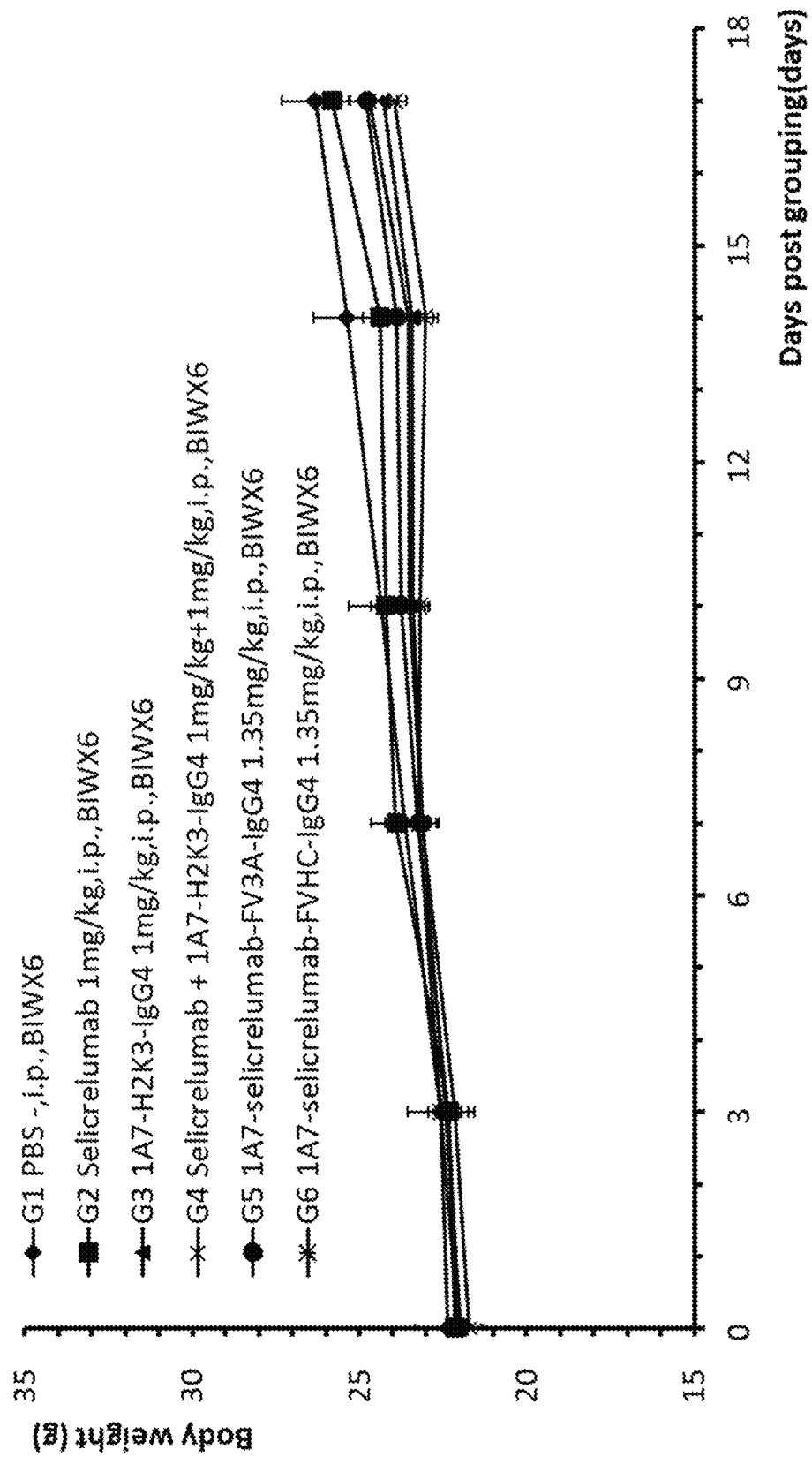
FIG. 45A is a graph showing body weight over time of B-hPD-1/hCD40 mice that were injected with MC38-hPD-L1 cells, and were treated with monoclonal antibodies (G2 and G3), combination of monospecific antibodies (G4), or bispecific antibodies (G5 and G6). PBS solution was administered as a control (G1).
Figure 45B:
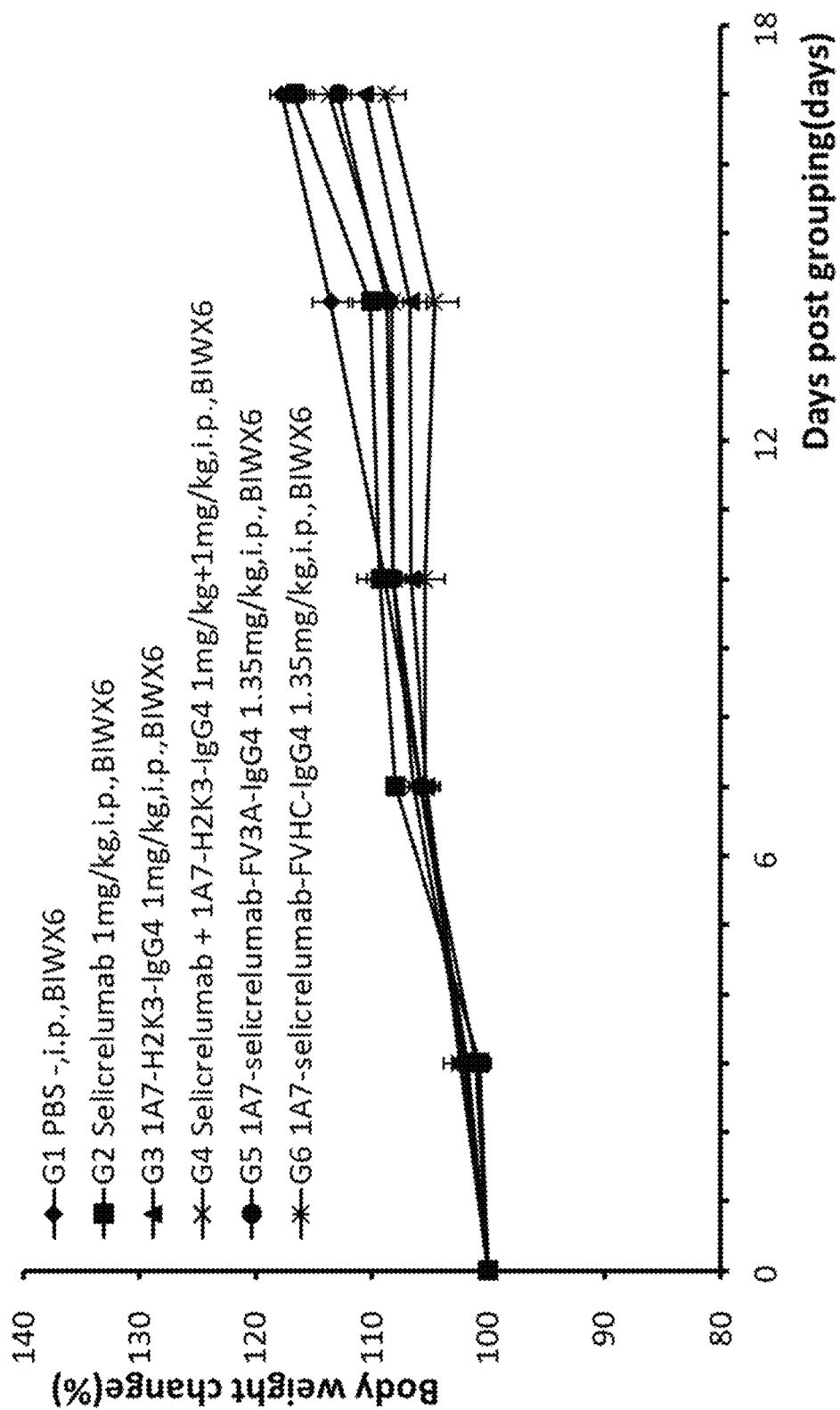
FIG. 45B is a graph showing body weight change over time of B-hPD-1/hCD40 mice that were injected with MC38-hPD-L1 cells, and were treated with monoclonal antibodies (G2 and G3), combination of monospecific antibodies (G4), or bispecific antibodies (G5 and G6). PBS solution was injected as a control (G1).

The weight of the mice was monitored during the entire treatment period. The average weight of mice in different groups all increased to different extents (FIG. 45A, and FIG. 45B). All the mice gained weight among different groups at the end of the treatment period.

Figure 45C:
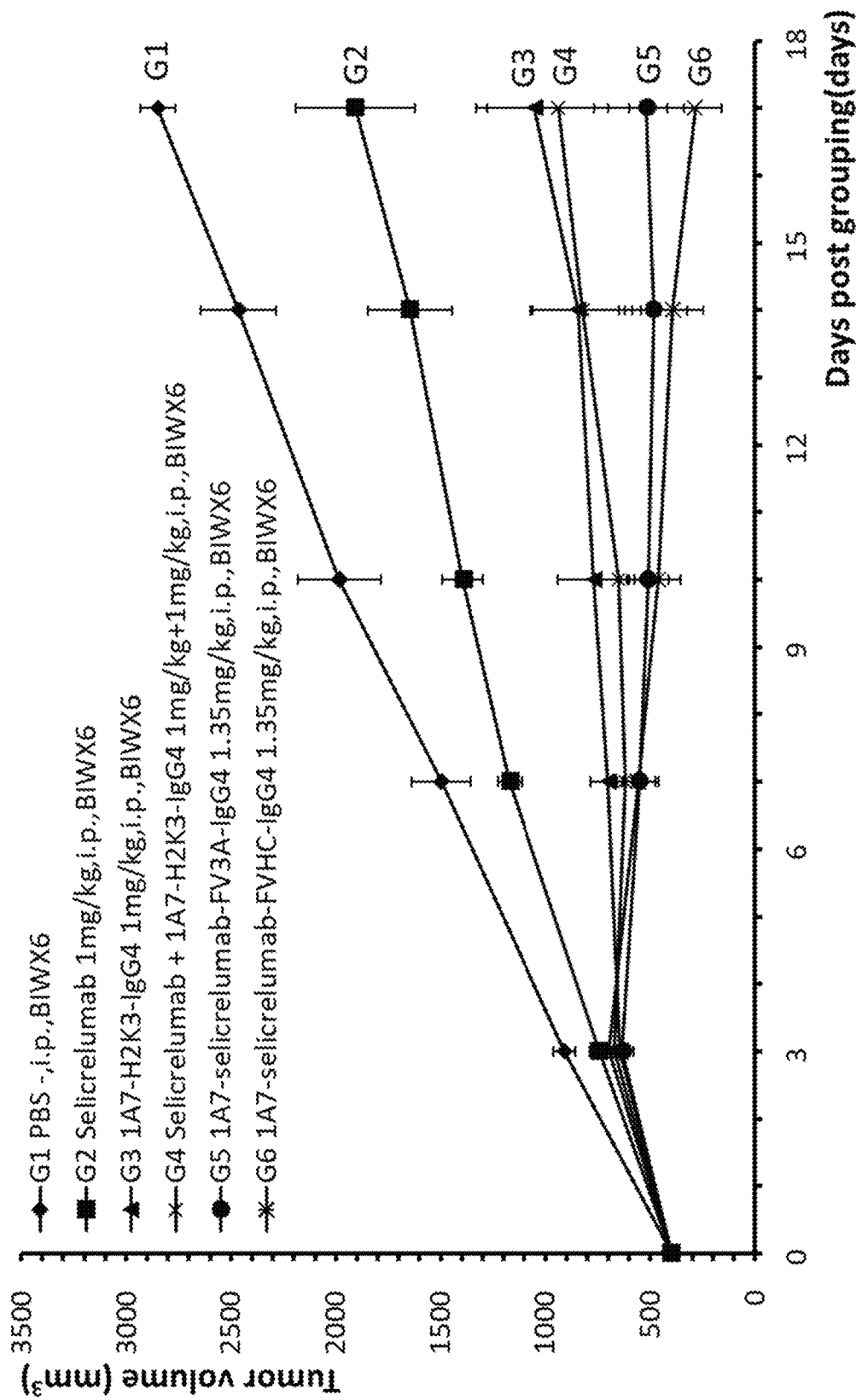
FIG. 45C is a graph showing tumor volume over time of B-hPD-1/hCD40 mice that were injected with MC38-hPD-L1 cells, and were treated with monoclonal antibodies (G2 and G3), combination of monospecific antibodies (G4), or bispecific antibodies (G5 and G6). PBS solution was injected as a control (G1).

The tumor size in groups treated with the antibodies is shown in FIG. 45C. The $TGI_{TV}$% at Day 17 (17 days after grouping) was calculated as shown in the table below. P values in the following table was calculated based on the data on Day 17.

TABLE 29

| | | Tumor volume (mm³) | | | Survival at Day 17 | $TGI_{TV}$% at Day 17 | P value for Day 17 Body weight | P value for Day 17 Tumor Volume |
|---|---|---|---|---|---|---|---|---|
| | | Day 0 | Day 14 | Day 17 | | | | |
| Control | G1 | 402 ± 14 | 2464 ± 444 | 2849 ± 183 | 5/6 | n.a. | n.a. | n.a. |
| Treat | G2 | 402 ± 14 | 1647 ± 495 | 1907 ± 701 | 6/6 | 38.5% | 0.573 | 0.018 |
| | G3 | 402 ± 18 | 845 ± 545 | 1051 ± 689 | 6/6 | 73.5% | 0.007 | 3.25E−04 |
| | G4 | 402 ± 19 | 822 ± 578 | 939 ± 826 | 6/6 | 78.1% | 0.106 | 0.001 |
| | G5 | 402 ± 25 | 485 ± 396 | 519 ± 438 | 6/6 | 95.2% | 0.088 | 1.56E−06 |
| | G6 | 402 ± 18 | 394 ± 363 | 288 ± 320 | 6/6 | 104.7% | 0.002 | 7.22E−08 |

The results showed that both 1A7-selicrelumab-FV3A-IgG4 (G5) and 1A7-selicrelumab-FVHC-IgG4 (G6) inhibited tumor growth with a higher $TGI_{TV}$ % (e.g., on Day 17) than that of the monoclonal antibodies (G2 and G3) and the antibody combinations (G4). The results indicate that fusion proteins of PD-1/CD40 bispecific antibodies 1A7-selicrelumab-FV3A-IgG4 and 1A7-selicrelumab-FVHC-IgG4 can significantly inhibit tumor growth with superior efficacy.

In another experiment, the toxicity of PD-1/CD40 bispecific antibody was tested in mice. Double humanized CD40/PD-1 mice (about 7-week old) were randomly placed into different groups (3 mice per group) according to their body weight. One of the following antibodies was randomly selected and administered on the day of grouping and every 3 days thereafter: anti-CD40 monoclonal antibody Selicrelumab (G2), anti-PD-1 monoclonal antibody 1A7-H2K3-IgG4 (G3), 1A7-selicrelumab-FVHC-IgG4 (G4) and 1A7-selicrelumab-FV3A-IgG4 (G5). The control group (G1) was injected with PBS.

TABLE 30

| Group | Antibodies | Dosage (mg/kg) | Route | Frequency | Total No. of administration |
|---|---|---|---|---|---|
| G1 | PBS (control) | — | i.p. | Day 0, Day 3, Day 6 | 3 |

TABLE 30-continued

| Group | Antibodies | Dosage (mg/kg) | Route | Frequency | Total No. of administration |
|---|---|---|---|---|---|
| G2 | Selicrelumab | 10 mg/kg | i.p. | Day 0, Day 3, Day 6 | 3 |
| G3 | 1A7-H2K3-IgG4 | 10 mg/kg | i.p. | Day 0, Day 3, Day 6 | 3 |
| G4 | 1A7-selicrelumab-FVHC-IgG4 | 13 mg/kg | i.p. | Day 0, Day 3, Day 6 | 3 |
| G5 | 1A7-selicrelumab-FV3A-IgG4 | 13 mg/kg | i.p. | Day 0, Day 3, Day 6 | 3 |

Figure 46A:
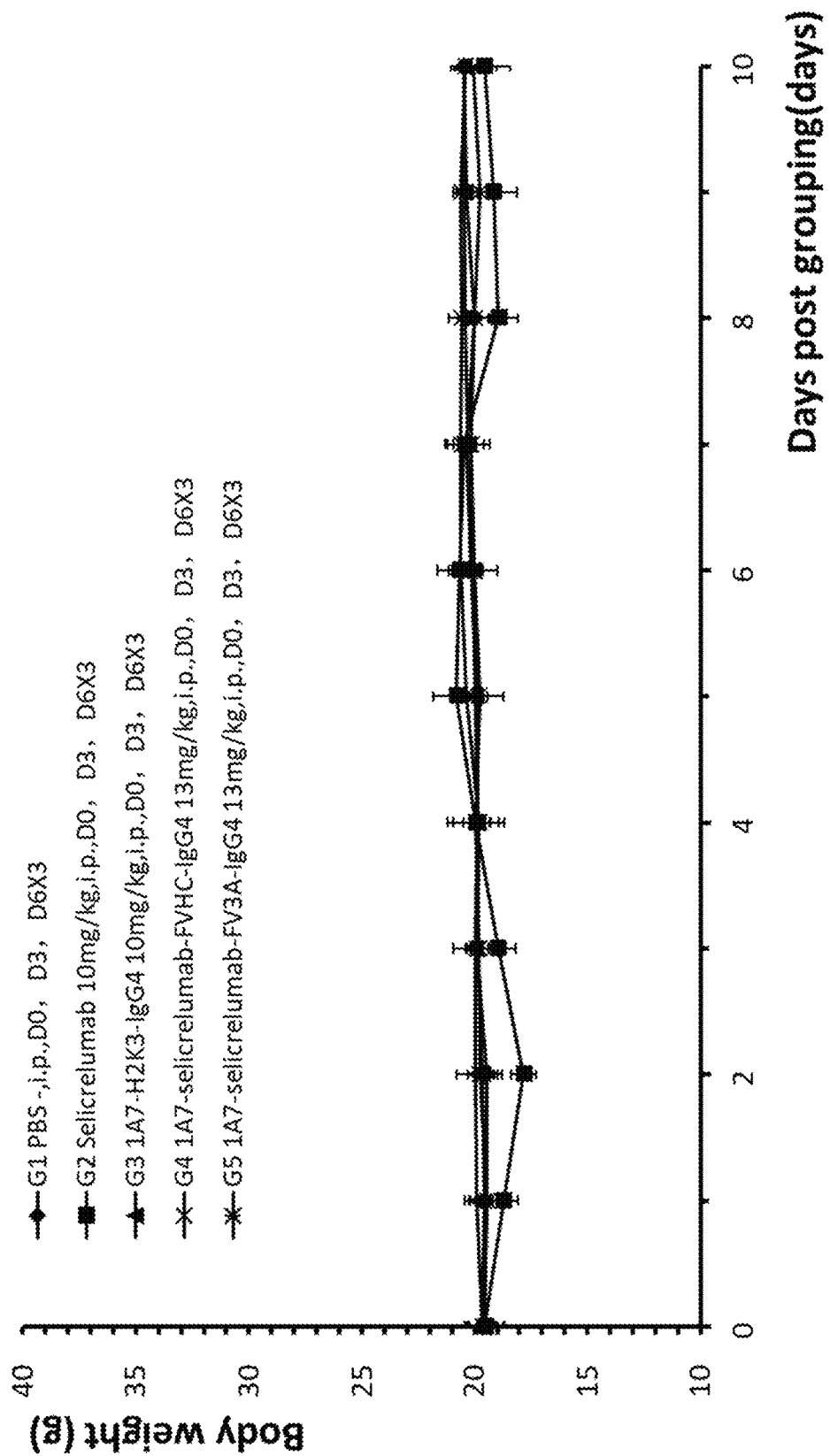
FIG. 46A is a graph showing body weight over time of B-hPD-1/hCD40 mice that were injected with monoclonal antibodies (G2 and G3), bispecific antibody 1A7-selicrelumab-FVHC-IgG4 (G4) or 1A7-selicrelumab-FV3A-IgG4 (G5). PBS solution was injected as a control (G1).
Figure 46B:
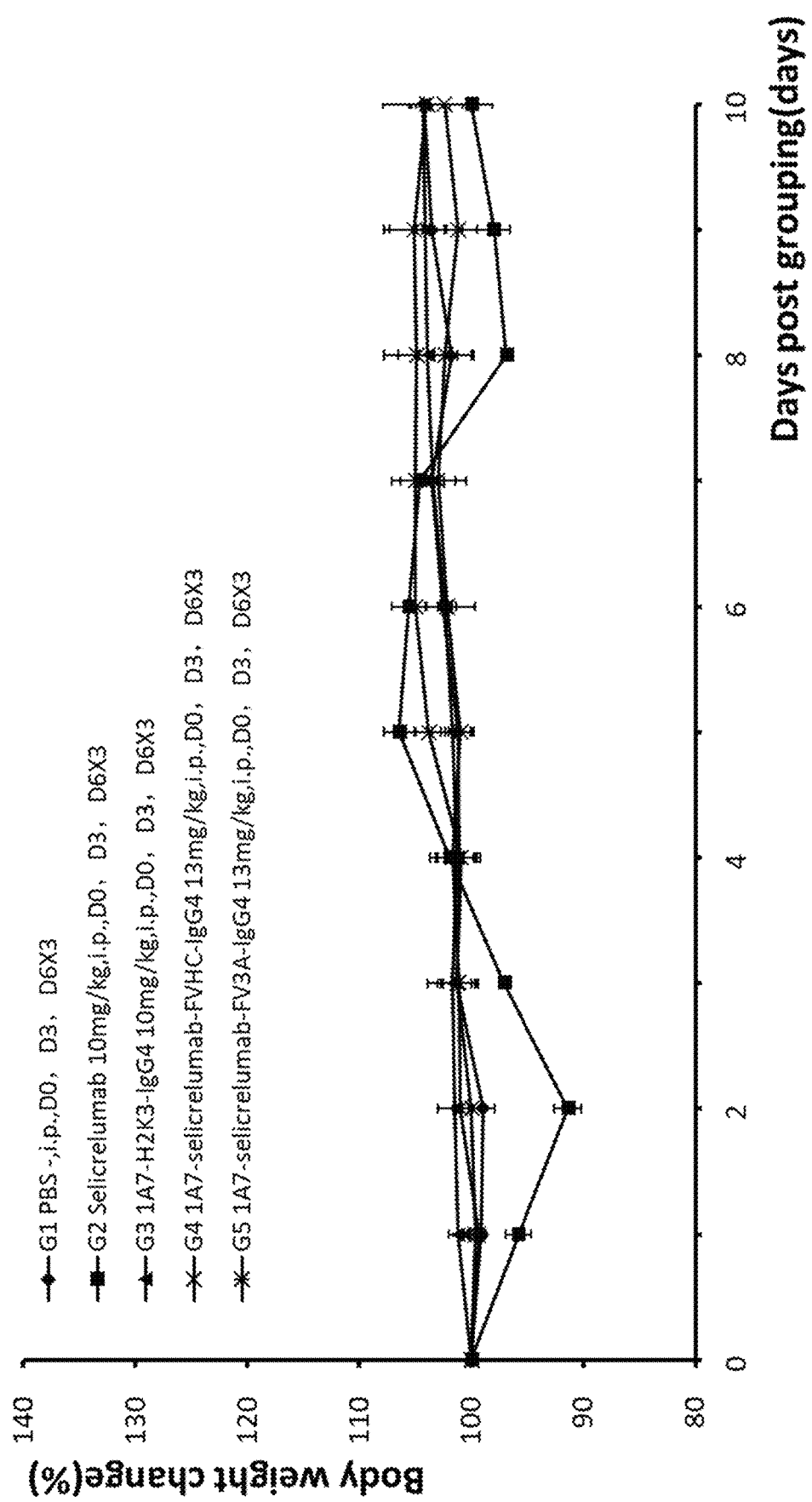
FIG. 46B is a graph showing body weight change over time of B-hPD-1/hCD40 mice that were injected with monoclonal antibodies (G2 and G3), bispecific antibody 1A7-selicrelumab-FVHC-IgG4 (G4) or 1A7-selicrelumab-FV3A-IgG4 (G5). PBS solution was injected as a control (G1).

As shown in FIGS. 46A-46B, the experimental results showed that only the G2 group mice showed significant weight loss, and the body weight of mice in other treatment groups showed no significant difference as compared with the control group mice.

Figure 47B:
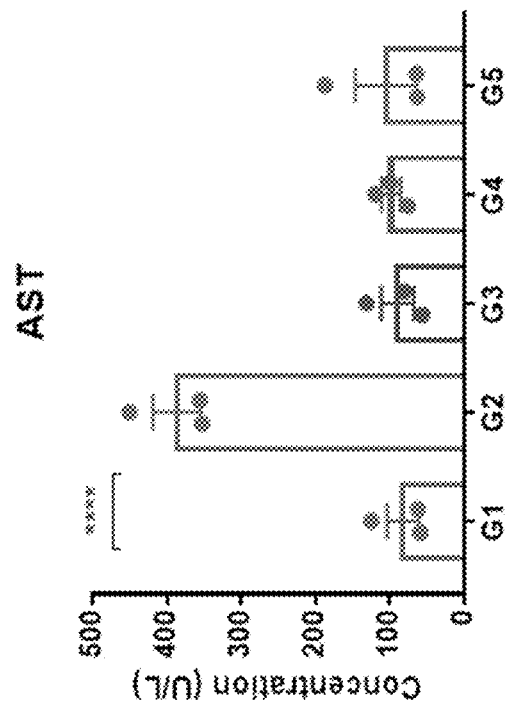
FIG. 47B shows mouse blood AST level on Day 7 post grouping in different groups of B-hPD-1/hCD40 mice that were injected with PBS (G1), monoclonal antibodies (G2 and G3), bispecific antibody 1A7-selicrelumab-FVHC-IgG4 (G4) or 1A7-selicrelumab-FV3A-IgG4 (G5).
Figure 47A:
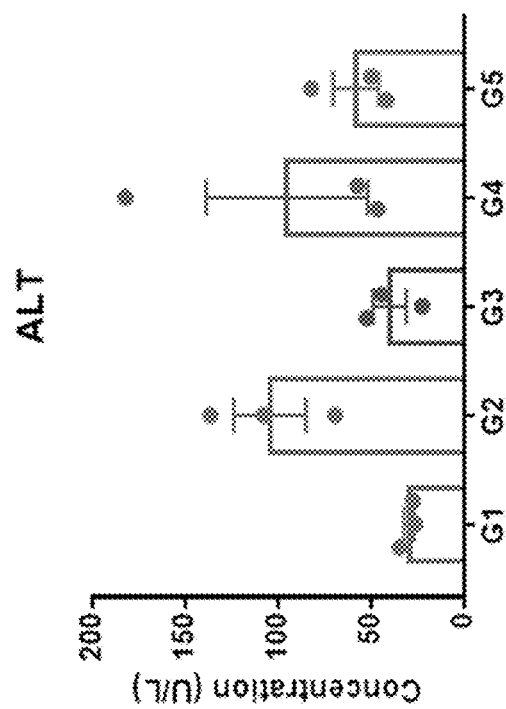
FIG. 47A shows mouse blood ALT level on Day 7 post grouping in different groups of B-hPD-1/hCD40 mice that were injected with PBS (G1), monoclonal antibodies (G2 and G3), bispecific antibody 1A7-selicrelumab-FVHC-IgG4 (G4) or 1A7-selicrelumab-FV3A-IgG4 (G5).

On Day 7 post grouping, peripheral blood was collected to detect the concentration of asparagine aminotransferase (AST) and alanine aminotransferase (ALT). As shown in FIGS. 47A-47B, the ALT and AST detection results showed that the G2 group mice (administered with anti-CD40 monoclonal antibody selicrelumab) had the highest concentration of both ALT and AST aminotransferases. The aminotransferase concentrations in the bispecific antibodies groups (G4-G5) were lower than that in the G2 group.

On Day 10 post grouping, the mouse liver was isolated and examined under microscope. The results are shown in the table below, which showed that the toxicity of the bispecific antibody 1A7-selicrelumab-FV3A-IgG4 (G5) was lower than that of the monoclonal antibodies (G2-G3) and 1A7-selicrelumab-FVHC-IgG4 (G4).

The results indicate that 3A structure format of PD-1/CD40 bispecific antibody can significantly reduce toxicity of anti-CD40 antibody. In addition, the results indicate that the 3A structure format of PD-1/CD40 bispecific antibody exhibited a lower toxicity than that of the HC structure format of PD-1/CD40 bispecific antibody.

TABLE 31

| Group | Mouse ID | RESULT |
|---|---|---|
| G1 | 110643 | NVL* |
| | 110660 | NVL |
| | 110656 | NVL |

TABLE 31-continued

| Group | Mouse ID | RESULT |
|---|---|---|
| G2 | 110650 | Chronic inflammation (+++) |
|  | 110658 | Chronic inflammation (++) |
|  | 110645 | Chronic inflammation (+++) |
| G3 | 110661 | NVL |
|  | 110641 | Inflammatory cell infiltration (+) |
|  | 110663 | NVL |
| G4 | 110651 | Chronic inflammation (++) |
|  | 110647 | Chronic inflammation (++) |
|  | 110657 | Inflammatory cell infiltration (+) |
| G5 | 110659 | Inflammatory cell infiltration (+) |
|  | 110642 | NVL |
|  | 110653 | Inflammatory cell infiltration (+) |

*non-visible lesion

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A nucleic acid encoding a polypeptide complex comprising:
a first polypeptide comprising a first CH3 domain,
a second polypeptide comprising a second CH3 domain;
wherein a third polypeptide is linked to a first amino acid residue and a second amino acid residue of the first CH3 domain, wherein:
(1) the first amino acid residue is at position 358 of the first CH3 domain according to EU numbering, and the second amino acid residue is at position 359 of the first CH3 domain according to EU numbering,
(2) the first amino acid residue is at position 359 of the first CH3 domain according to EU numbering, and the second amino acid residue is at position 360 of the first CH3 domain according to EU numbering,
(3) the first amino acid residue is at position 360 of the first CH3 domain according to EU numbering, and the second amino acid residue is at position 361 of the first CH3 domain according to EU numbering, or
(4) the first amino acid residue is at position 361 of the first CH3 domain according to EU numbering, and the second amino acid residue is at position 362 of the first CH3 domain according to EU numbering.

2. The nucleic acid of claim 1, wherein the third polypeptide is a cytokine, a soluble polypeptide, a single chain antigen-binding polypeptide, a scFv, a single-domain antibody, a soluble portion of a transmembrane protein, a secretory protein, a ligand, or a VHH.

3. The nucleic acid of claim 1, wherein the polypeptide complex comprises two light chain polypeptides.

4. The nucleic acid of claim 1, wherein the polypeptide complex further comprises:
a fourth polypeptide, wherein the fourth polypeptide is fused to the second CH3 domain at a region from position 344 to position 382 of the second CH3 domain according to EU numbering.

5. A host cell comprising the nucleic acid of claim 1.

6. A method for producing a polypeptide complex, the method comprising culturing the host cell of claim 5 under conditions suitable to produce the polypeptide complex.

7. The nucleic acid of claim 4, wherein the polypeptide complex further comprises:
a fifth polypeptide, wherein the fifth polypeptide is fused to the C-terminus of the first polypeptide.

8. The nucleic acid of claim 7, wherein the polypeptide complex further comprises:
a sixth polypeptide, wherein the sixth polypeptide is fused to the C-terminus of the second polypeptide.

9. The nucleic acid of claim 1, wherein the third polypeptide is a cytokine.

10. The nucleic acid of claim 1, wherein the third polypeptide is a soluble polypeptide.

11. The nucleic acid of claim 1, wherein the third polypeptide is a single chain antigen-binding polypeptide.

12. The nucleic acid of claim 1, wherein the third polypeptide is a scFv.

13. The nucleic acid of claim 1, wherein the third polypeptide is a single-domain antibody.

14. The nucleic acid of claim 1, wherein the third polypeptide is a soluble portion of a transmembrane protein.

15. The nucleic acid of claim 1, wherein the third polypeptide is a secretory protein.

16. The nucleic acid of claim 1, wherein the third polypeptide is a ligand.

17. The nucleic acid of claim 1, wherein the third polypeptide is a VHH.

* * * * *